United States Patent
Ebetino et al.

(10) Patent No.: US 10,865,220 B2
(45) Date of Patent: Dec. 15, 2020

(54) BISPHOSPHONATE QUINOLONE CONJUGATES AND USES THEREOF

(71) Applicants: BIOVINC, LLC, Pasadena, CA (US); UNIVERSITY OF SOUTHERN CALIFORNIA, Los Angeles, CA (US)

(72) Inventors: Frank H. Ebetino, Pasadena, CA (US); Shuting Sun, Pasadena, CA (US); Mark W. Lundy, Pasadena, CA (US); Charles E. McKenna, Pasadena, CA (US); Eric Richard, Pasadena, CA (US); Parish Sedghizadeh, Los Angeles, CA (US); Keivan Sadrerafi, Pasadena, CA (US); Philip T. Cherian, Pasadena, CA (US)

(73) Assignees: BIOVINC, LLC, Pasadena, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 16/207,465

(22) Filed: Dec. 3, 2018

(65) Prior Publication Data
US 2019/0169214 A1 Jun. 6, 2019

Related U.S. Application Data

(63) Continuation-in-part of application No. PCT/US2017/035764, filed on Jun. 2, 2017.
(Continued)

(51) Int. Cl.
*C07F 9/6558* (2006.01)
*C07F 9/6561* (2006.01)
(Continued)

(52) U.S. Cl.
CPC ........ *C07F 9/65583* (2013.01); *A61K 47/548* (2017.08); *A61K 47/55* (2017.08);
(Continued)

(58) Field of Classification Search
CPC .... C07F 9/65583; C07F 9/6561; A61K 47/55; A61P 31/04; A61P 19/10
(Continued)

(56) References Cited

U.S. PATENT DOCUMENTS

| | | | | |
|---|---|---|---|---|
| 5,854,227 | A | * 12/1998 | Hartmann | A61B 5/0422 514/79 |
| 5,856,314 | A | 1/1999 | Kaas et al. | |

(Continued)

FOREIGN PATENT DOCUMENTS

| | | | |
|---|---|---|---|
| DE | 19532235 | * | 3/1997 |
| WO | 98/15560 A1 | | 4/1998 |
| WO | 2007/017762 A2 | | 2/2007 |

OTHER PUBLICATIONS

Herczegh; J. Med. Chem. 2002, 45, 2338-2341. DOI:10.1021/jm0105326 (Year: 2002).*
(Continued)

*Primary Examiner* — Daniel R Carcanague
(74) *Attorney, Agent, or Firm* — Thomas|Horstemeyer, LLP

(57) ABSTRACT

Described herein are bisphosphonate quinolone compounds, conjugates and pharmaceutical formulations thereof that can include a bisphosphonate and a quinolone, where the quinolone can be releasably coupled to the bisphosphonate. Also provided herein are methods of making and methods of using the bisphosphonate quinolone compounds, conjugates and pharmaceutical formulations thereof.

10 Claims, 58 Drawing Sheets

Related U.S. Application Data

(60) Provisional application No. 62/345,370, filed on Jun. 3, 2016, provisional application No. 62/357,727, filed on Jul. 1, 2016, provisional application No. 62/448,060, filed on Jan. 19, 2017, provisional application No. 62/695,583, filed on Jul. 9, 2018.

(51) Int. Cl.
*A61P 31/04* (2006.01)
*A61P 19/10* (2006.01)
*A61K 47/55* (2017.01)
*A61K 47/54* (2017.01)

(52) U.S. Cl.
CPC ............ *A61K 47/552* (2017.08); *A61P 19/10* (2018.01); *A61P 31/04* (2018.01); *C07F 9/6561* (2013.01)

(58) Field of Classification Search
USPC ......................................................... 544/359
See application file for complete search history.

(56) References Cited

U.S. PATENT DOCUMENTS

| | | | | |
|---|---|---|---|---|
| 5,880,111 | A * | 3/1999 | Farcasiu | C07D 499/00 514/100 |
| 6,333,424 | B1 * | 12/2001 | Herczegh | C07F 9/3865 544/337 |
| 7,300,924 | B2 * | 11/2007 | Boojamra | C07F 9/4006 514/80 |
| 2008/0287396 | A1 * | 11/2008 | Delorme | C07F 9/65583 514/81 |
| 2010/0113333 | A1 * | 5/2010 | Tanaka | C07F 9/6561 514/2.9 |
| 2011/0178001 | A1 * | 7/2011 | Dietrich | A61K 31/675 514/2.9 |
| 2012/0046246 | A1 * | 2/2012 | Holliday | A61K 31/00 514/81 |
| 2014/0051625 | A1 | 2/2014 | Karpeisky et al. | |
| 2018/0362559 | A1 * | 12/2018 | McKenna | C07F 9/58 |
| 2019/0030172 | A1 * | 1/2019 | McKenna | C12N 15/11 |

OTHER PUBLICATIONS

Houghton,; J. Med. Chem. 2008, 51, 6955-6969. DOI:10.1021/jm801007z (Year: 2008).*
McPherson; European Journal of Medicinal Chemistry 2012, 47, 615-618. DOI:10.1016/j.ejmech.2011.10.049 (Year: 2012).*
Pieper; Phosphorus, Sulfur and Silicon and the Related Elements 2001, 170, 5-14. DOI:10.1080/10426500108040581 (Year: 2001).*
Tanaka; Bioorg Med Chem. 2008, 16, 9217-9229. DOI:10.1016/j.bmc.2008.09.010 (Year: 2008).*
Sedghizadeh; J. Med. Chem. 2017, 60, 2326-2343. DOI:10.1021/acs.jmedchem.6b01615 (Year: 2017).*
Huttunen; Pharmacol Rev 2011, 63, 750-771. doi:10.1124/pr.110.003459 (Year: 2011).*
Herczegh et al., "Osteoadsorptive Bisphosphonate Derivatives of Fluoroquinolone Antibacterials", J. Med. Chem. 2002, vol. 45, pp. 2338-2341.
International Search Report & Written Opinion, PCT/US2017/035764, dated Sep. 6, 2017, pp. 1-8.
International Preliminary Report on Patentability, PCT/US2017/035764, dated Dec. 4, 2018, pp. 1-6.
Tom J. Houghton et al: "Linking Bisphosphonates to the Free Amino Groups in Fluoroquinolones: Preparation of Osteotropic Prodrugs for the Prevention of Osteomyelitis", Journal of Medicinal Chemistry, vol. 51, No. 21, Nov. 13, 2008 (Nov. 13, 2008), pp. 6955-6969.
Supplementary European Search Report for EP 17 80 760.5 (PCT/US2017/035764), dated Sep. 19, 2019, pp. 1-7.
Parish P. Sedghizadeh et al: "Design, Synthesis, and Antimicrobial Evaluation of a Novel Bone-Targeting Bisphosphonate-Ciprofloxacin Conjugate for the Treatment of Osteomyelitis Biofilms", Journal of Medicinal Chemistry, vol. 60, No. 6, Mar. 23, 2017 (Mar. 23, 2017), pp. 2326-2343.

* cited by examiner

| Staphylococcus aureus strain # | *Sensitivity (S) or Resistance (R) | MIC for ciprofloxacin (mcg/mL) | MIC for BP-ciprofloxacin (mcg/mL) |
| --- | --- | --- | --- |
| 1 | S | 1 | 3.9 |
| 2 | S | 0.25 | 0.49 |
| 3 | S | 0.25 | 0.49 |
| 4 | S | 1 | 3.9 |
| 5 | S | 0.5 | 1.9 |
| 6 | S | 1 | 7.8 |
| 7 | S | 0.5 | 0.98 |
| 8 | S | 1 | 3.9 |
| 9 | S | 1 | 3.9 |
| 10 | S | 0.75 | 1.9 |
| 11 | S | 0.5 | 1.9 |
| 12 | S | 1 | 7.8 |
| ATCC-6538 | S | 1 | 31.2 |
| MR4-CIPS | S | 1 | 15.6 |

* According to EUCAST references from disc diffusion inhibition zone assays

FIG. 3

| Compound | Concentration [µg/mL] | | | | | | | | |
|---|---|---|---|---|---|---|---|---|---|
| | 1 | 5 | 10 | 25 | 50 | 100 | 200 | 400 | 0 (Control discs in DMSO) | 0 (Control discs in PBS) |
| 6 | 7.1x10$^{10}$ | 3.3x10$^9$ | No growth | No growth | No growth | No growth | No growth | No growth | Not applicable | 4.5x10$^{10}$ |
| Ciprofloxacin | 5.5x10$^{10}$ | 9.2x10$^{10}$ | 3.7x10$^9$ | 8.9x10$^7$ | No growth | No growth | No growth | No growth | 8.1x10$^{10}$ | Not applicable |

FIG. 11

| Sample strain | Antibiotic sensitivity (S) or resistance (R) | MIC for ciprofloxacin (mcg/mL) | MIC for BCC (mcg/mL) | MIC for BAC (mcg/mL) |
|---|---|---|---|---|
| MSSA 1 | S | 1 | 3.9 | 31.2 |
| MSSA 2 | S | 0.25 | 0.49 | 31.2 |
| MSSA 3 | S | 0.25 | 0.49 | 15.6 |
| MSSA 4 | S | 1 | 3.9 | 62.5 |
| MSSA 5 | S | 0.5 | 1.9 | 7.8 |
| MSSA 6 | S | 1 | 7.8 | 15.6 |
| MSSA: ATCC-6538 | S | 1 | 31.2 | 62.5 |
| MRSA: MR4-CIPS | S | 1 | 15.6 | Not tested |

FIG. 17

| S. aureus strain | antibiotic sensitivity (S) or resistance (R) | MIC for ciprofloxacin [μg/mL] | MIC for 6 [μg/mL] | MIC for 11 [μg/mL] |
|---|---|---|---|---|
| MSSA1 | S | 1 | 3.9 | 31.2 |
| MSSA2 | S | 0.25 | 0.49 | 31.2 |
| MSSA3 | S | 0.25 | 0.49 | 15.6 |
| MSSA4 | S | 1 | 3.9 | 62.5 |
| MSSA5 | S | 0.5 | 1.9 | 7.8 |
| MSSA6 | S | 1 | 7.8 | 15.6 |
| MSSA-ATCC-6538 | S | 1 | 31.2 | 62.5 |
| MRSA-MR4-CIPS | S | 1 | 15.6 | Not tested |

*MSSA = methicillin-susceptible S. aureus; MRSA = methicillin-resistant S. aureus.

FIG. 32

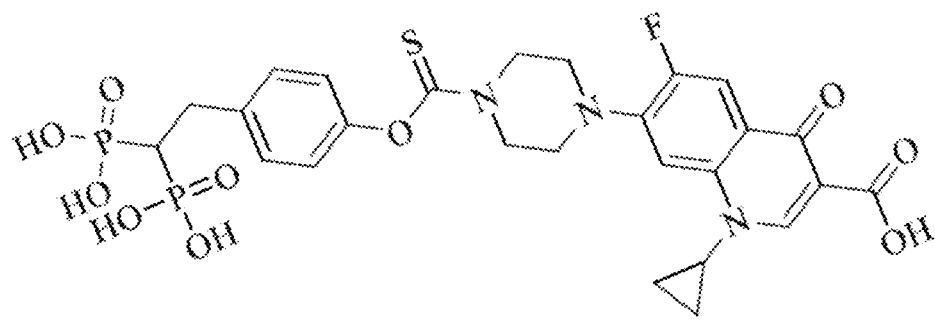
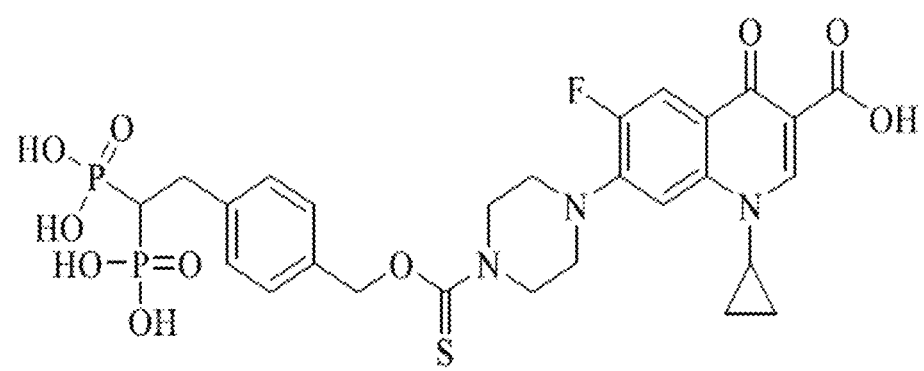
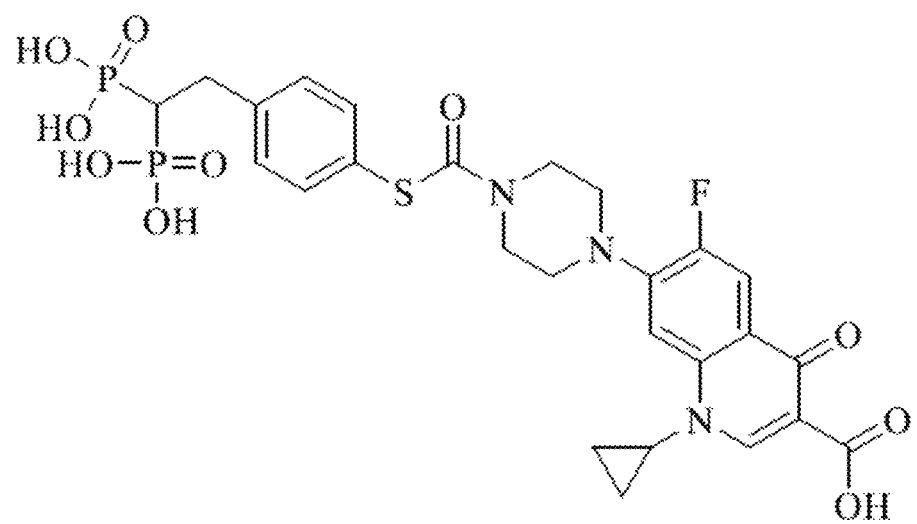
FIG. 47 ctd.

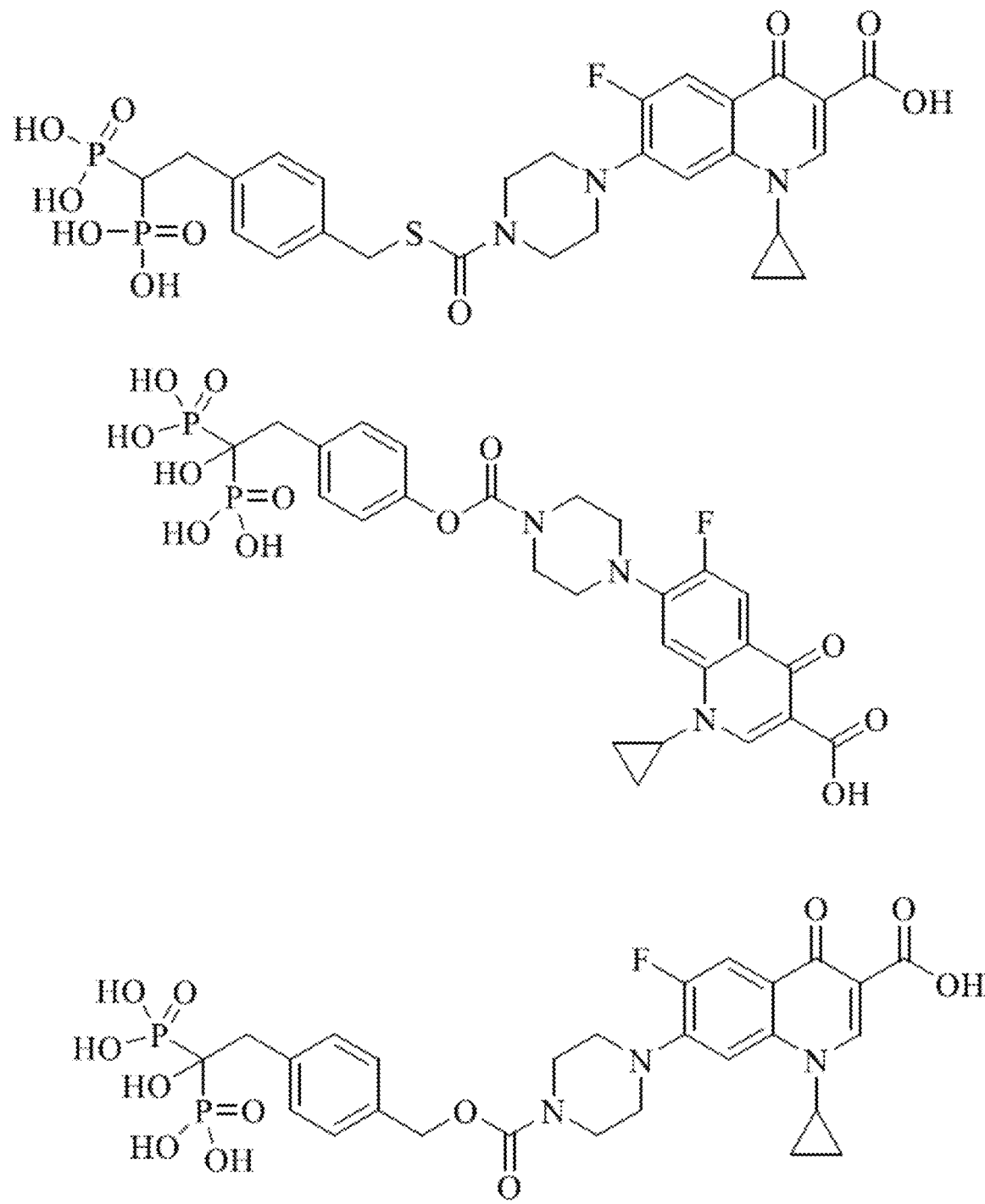
FIG. 47 ctd.

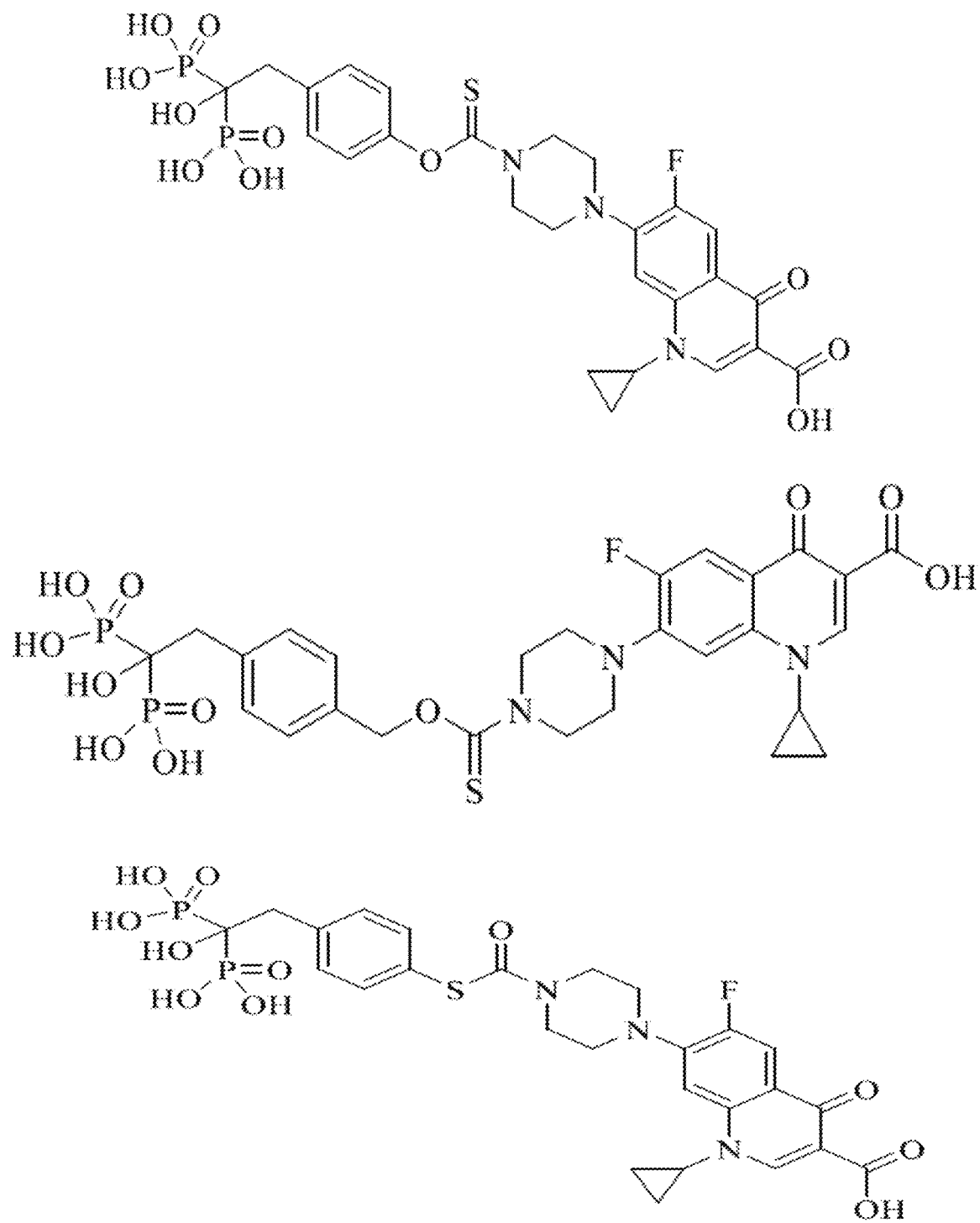
FIG. 47 ctd.

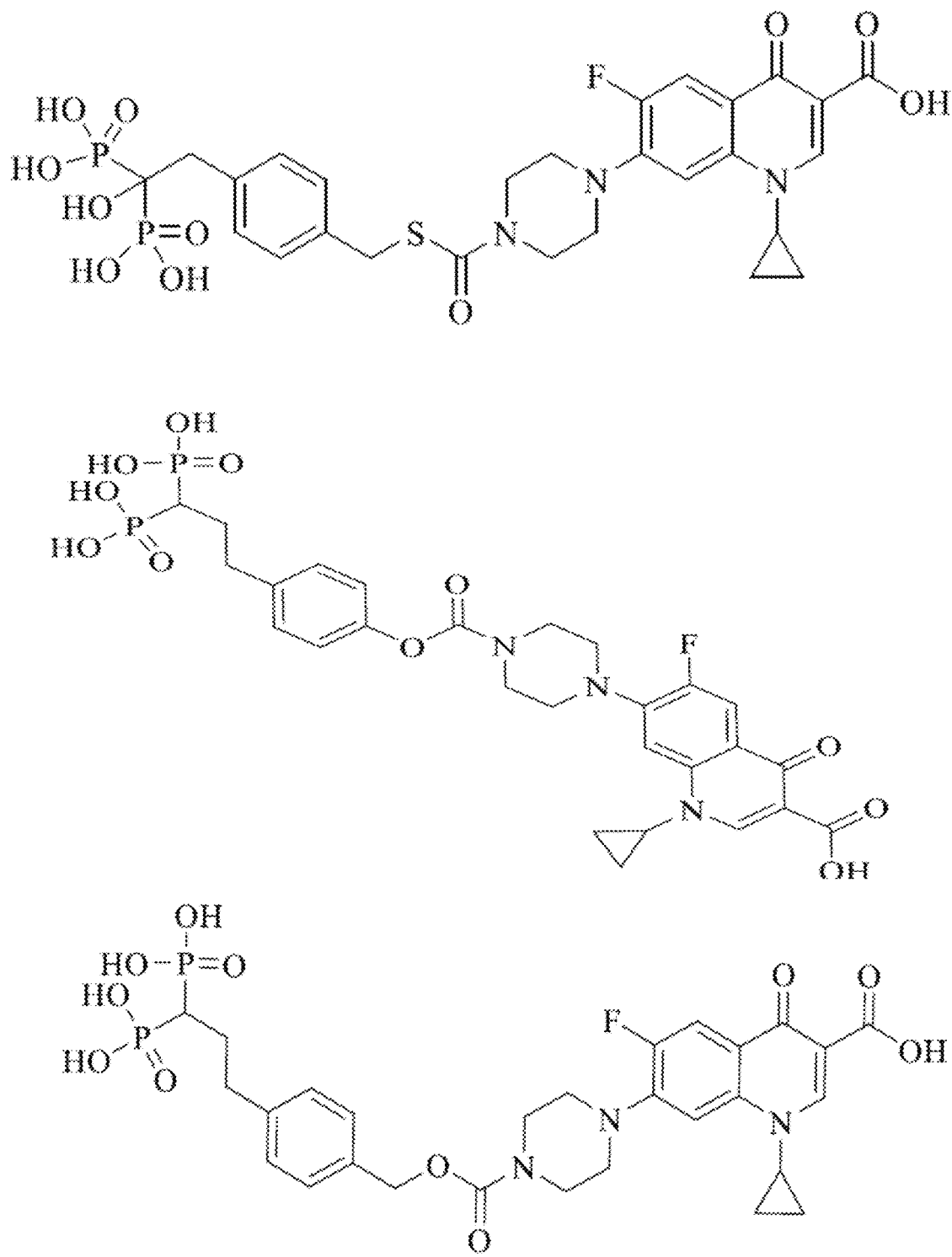
FIG. 47 ctd.

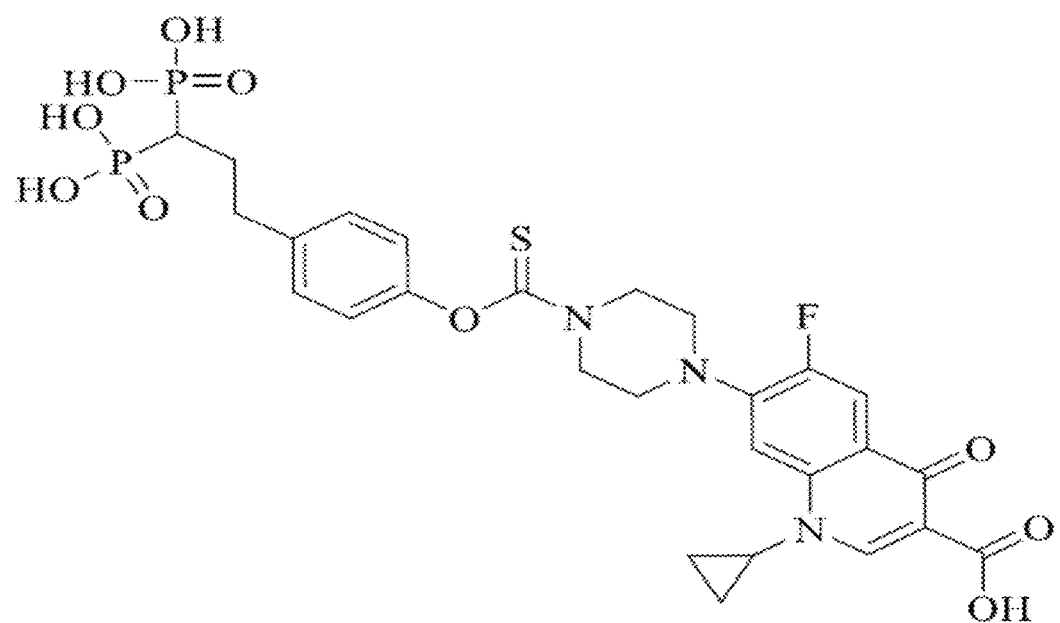
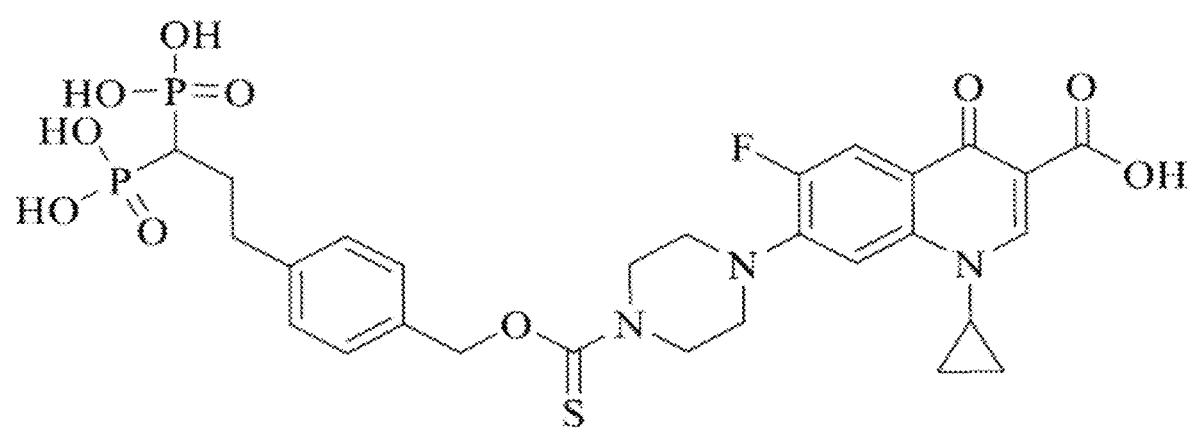
FIG. 47 ctd.

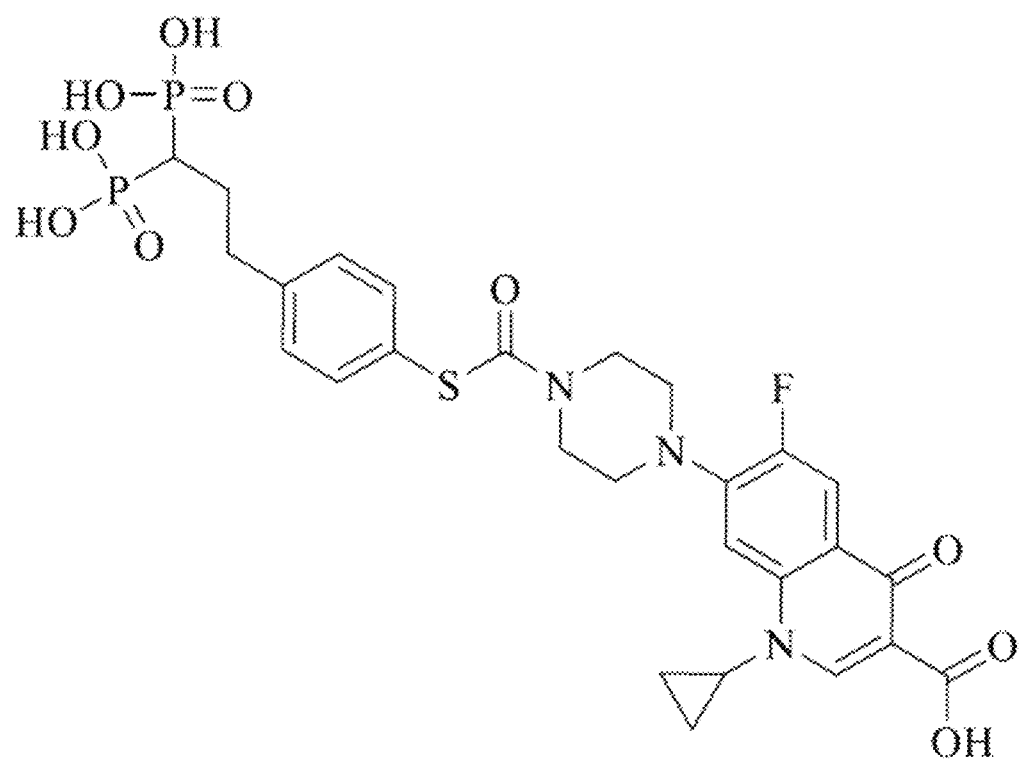
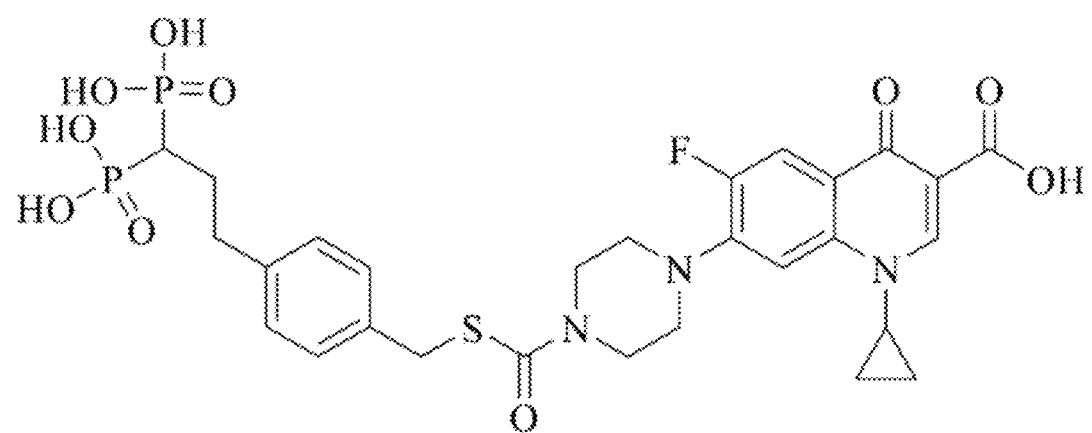
FIG. 47 ctd.

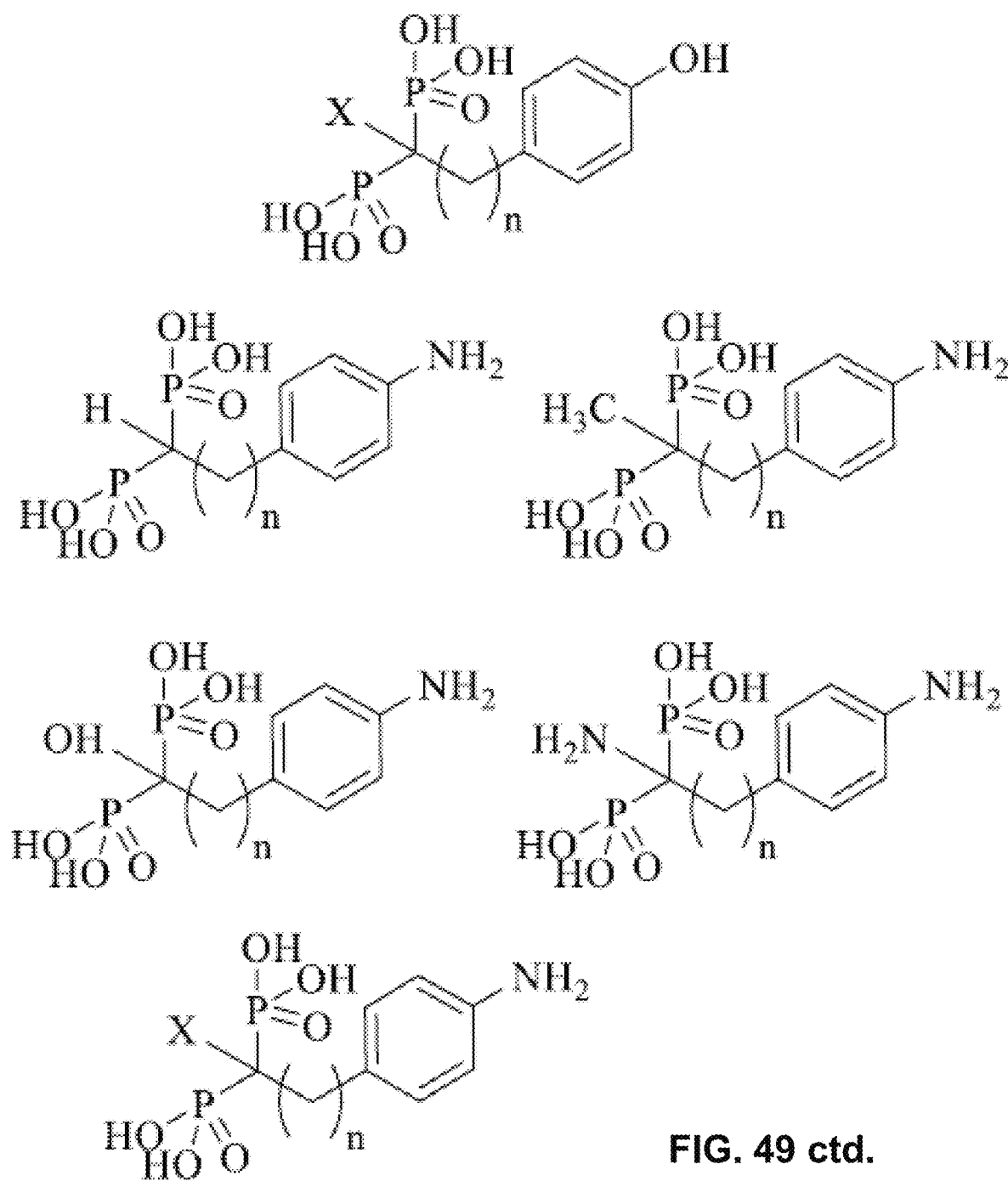
FIG. 49 ctd.

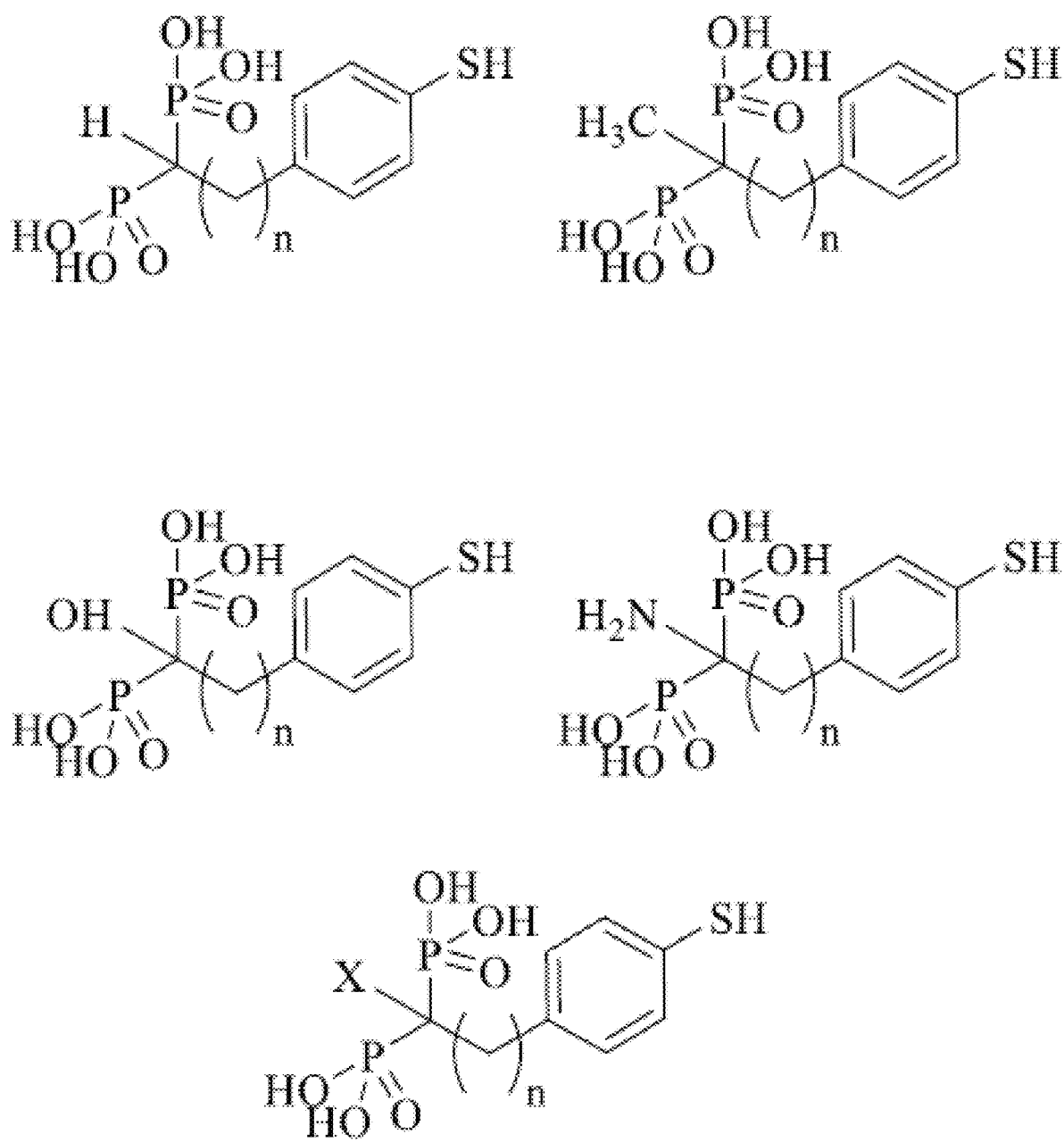
FIG. 49 ctd.

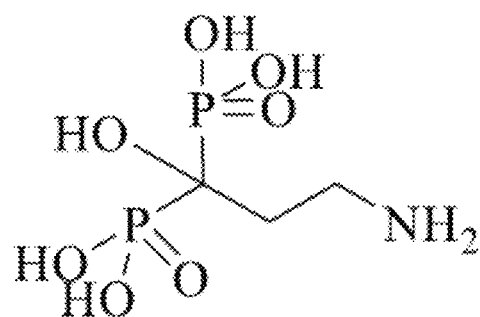
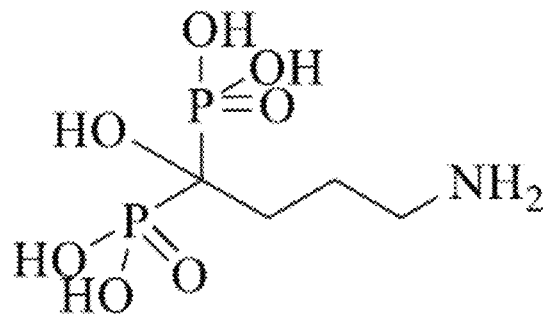
Pamidronate · · · · · · · · · · · · · · · · · · · · · · · · Alendronate
FIG. 50
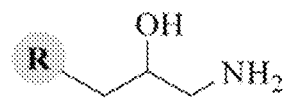
R =
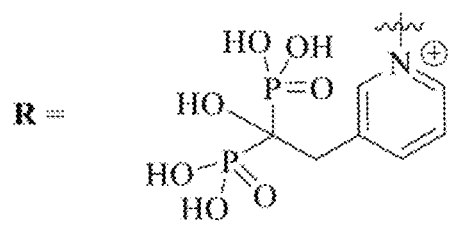 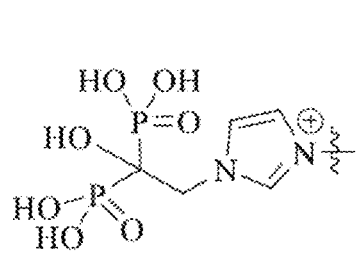 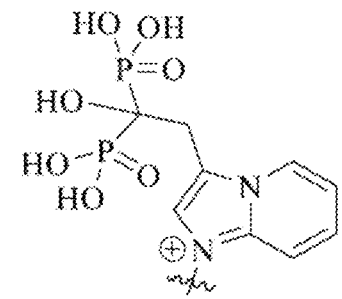
Risedronate · · · · · · · Zoledronate · · · · · · · Minodronate
FIG. 51
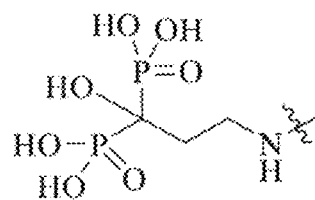 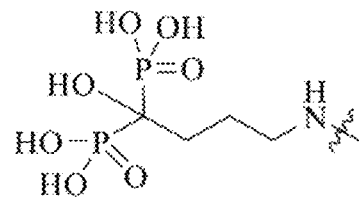
Pamidronate · · · · · · · · · · · · · · · · · · · · · · · · Alendronate

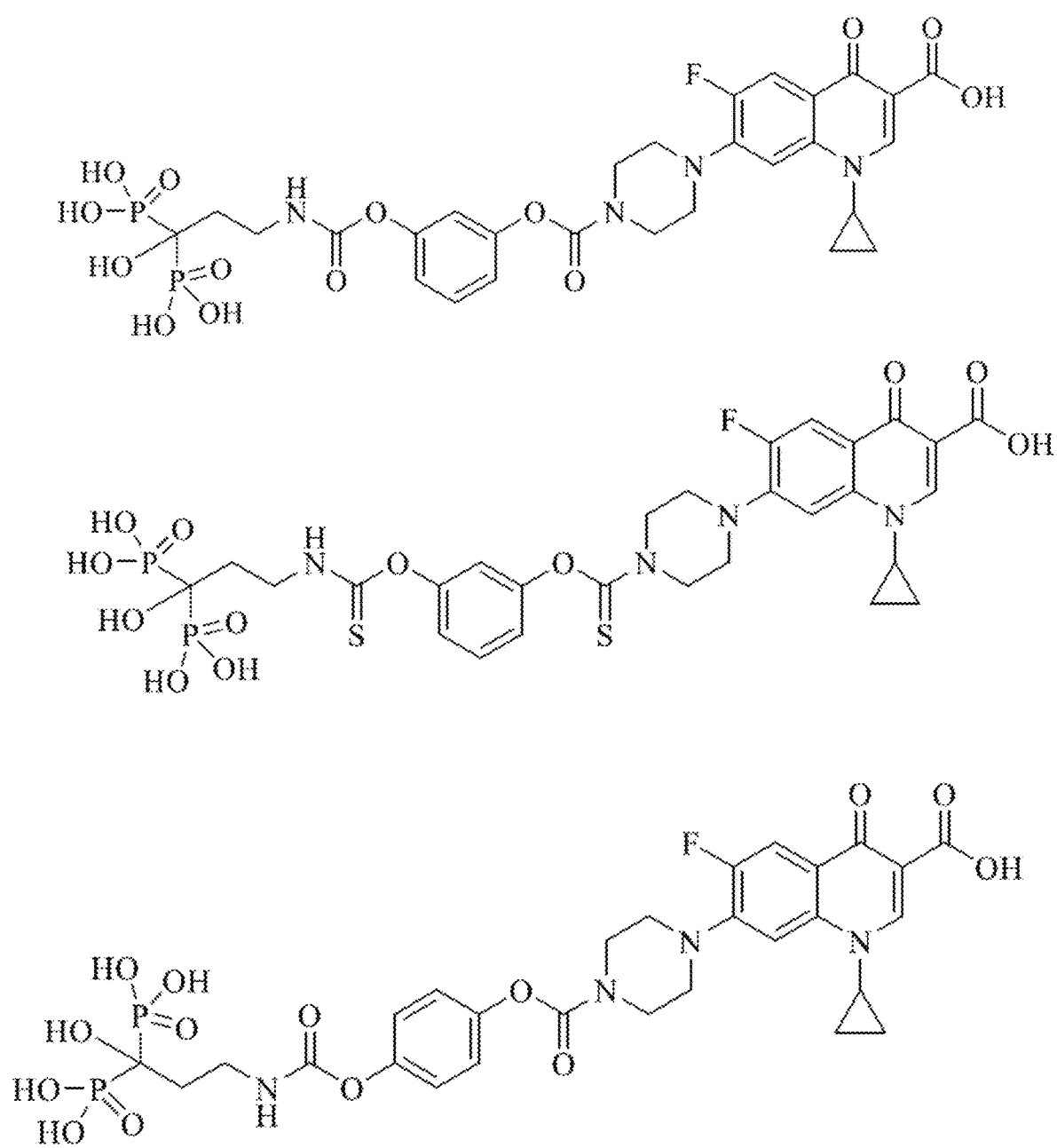
FIG. 52 ctd.

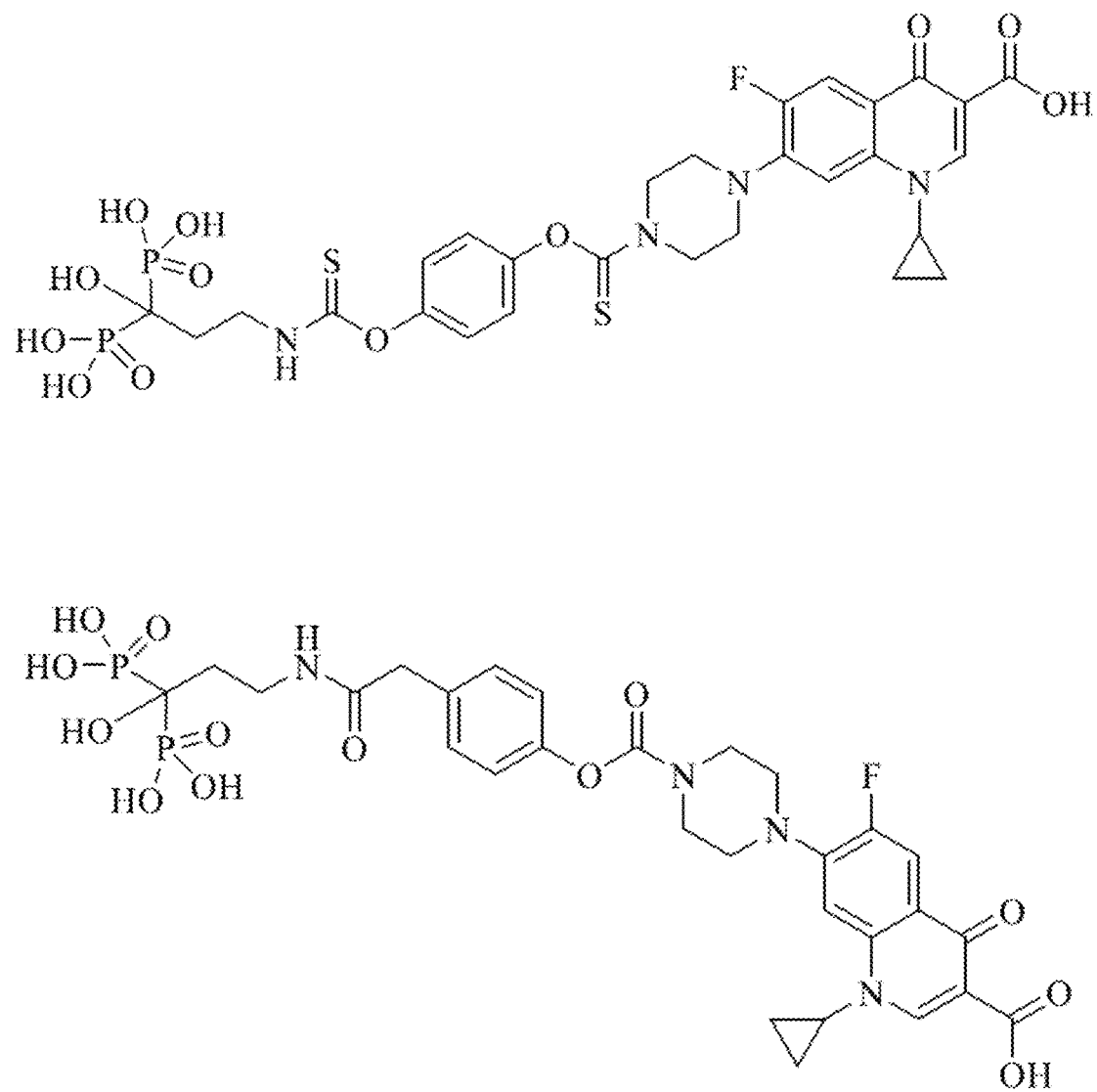
FIG. 52 ctd.

BISPHOSPHONATE QUINOLONE CONJUGATES AND USES THEREOF

CROSS-REFERENCE TO RELATED APPLICATIONS

This application is a continuation-in-part of PCT/US2017/035764, filed Jun. 2, 2017, that claims the benefit of and priority to: U.S. Provisional Patent Application No. 62/345,370, filed on Jun. 3, 2016, entitled "BONE TARGETED THERAPEUTICS AND DIAGNOSTICS;" U.S. Provisional Patent Application No. 62/357,727, filed on Jul. 1, 2016, entitled "BISPHOSPHONATE QUINOLONE BIOCONJUGATES AND USES THEREOF;" and U.S. Provisional Patent Application No. 62/448,060, filed on Jan. 19, 2017, entitled "BISPHOSPHONATE QUINOLONE BIOCONJUGATES AND USES THEREOF," the contents of all of which are incorporated by reference herein in their entirety.

This application also claims the benefit of and priority to U.S. Provisional Patent Application No. 62/695,583, filed Jul. 9, 2018, entitled "BISPHOSPHONATE QUINOLONE CONJUGATES AND USES THEREOF," the contents of which are incorporated by reference herein in its entirety.

STATEMENT REGARDING FEDERALLY SPONSORED RESEARCH OR DEVELOPMENT

This invention was made with government support under grant number 1R41DE025789-01 awarded by the NIH/NIDCR. The government has certain rights in the invention.

BACKGROUND

Infectious bone disease, also referred to as osteomyelitis, jawbone infections, and other bone infections, is a significant problem in human and animal health and can have devastating consequences from limb loss to fatality. Due to the inherent difficulties bone presents, treatment of osteomyelitis and other bone infections is typically long and difficult and often requires surgical intervention. Therefore, there exists a long-felt and unmet need for improved treatments for osteomyelitis in all its forms or clinical subtypes and other bone infections.

SUMMARY

Provided herein, in some aspects, are BP quinolone compounds and conjugates that can contain a bisphosphonate (BP) that can be releasably conjugated to a quinolone, such as ciprofloxacin or moxifloxacin. In embodiments, the BP quinolone conjugate can selectively deliver a quinolone to bone, bone grafts, and or bone graft substitutes (i.e. can target bone, bone grafts, or bone graft substitutes) in a subject. In some embodiments, the BP quinolone conjugate can release the quinolone. Also provided herein are methods of synthesizing BP quinolone conjugates and methods of killing or inhibiting bacteria growth and of treating or preventing bone diseases with abnormal bone resorption, osteoporosis, osteomyelitis, osteonecrosis, peri-implantitis, periodontis, and/or other bone infections with one or more of the BP quinolone compounds and conjugates provided herein.

In some aspects the conjugate can be a compound according to Formula (6)

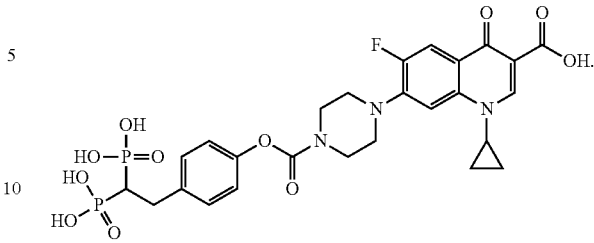

Formula (6)

Also provided herein are pharmaceutical compositions containing a compound according to Formula (6) and a pharmaceutically acceptable carrier.

Also provided herein are methods of treating a bone infection in a subject in need thereof that can include the step of administering an amount of the compound according to Formula (6) or a pharmaceutical formulation containing a compound according to Formula (6) to a subject in need thereof.

Also provided herein are compounds and conjugates containing a bisphosphonate (BP) and a quinolone compound, wherein the quinolone compound is releasably coupled to the bisphosphonate via a linker. The BP can be selected from the group of: hydroxyl phenyl alkyl or aryl bisphosphonates, hydroxyl phenyl (or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxyl alkyl phenyl(or aryl) alkyl bisphosphonates, hydroxyl phenyl(or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxypyridyl alkyl bisphosphonates, pyridyl alkyl bisphosphonates, hydroxyl imadazoyl alkyl bisphosphonates, imidazoyl alkyl bisphosphonates, etidronate, pamidronate, neridronate, olpadronate, alendronate, ibandronate, risedronate, zoledronate, minodronate and combinations thereof, wherein all the compounds can be optionally further substituted or are unsubstituted. The quinolone compound can be a fluoroquinolone. The quinolone compound can be selected from the group of: alatrofloxacin, amifloxacin, balofloxacin, besifloxacin, cadazolid, ciprofloxacin, clinafloxacin, danofloxacin, delafloxacin, difloxacin, enoxacin, enrofloxacin, finafloxacin, flerofloxacin, flumequine, gatifloxacin, gemifloxacin, grepafloxacin, ibafloxacin, JNJ-Q2, levofloxacin, lomefloxacin, marbofloxacin, moxifloxacin, nadifloxacin, norfloxacin, ofloxacin, orbifloxacin, pazufloxacin, pefloxacin, pradofloxacin, prulifloxacin, rufloxacin, sarafloxacin, sitafloxacin, sparfloxacin, temafloxacin, tosufloxacin, trvafloxacin, zabofloxacin, nemonoxacin and combinations thereof.

The quinolone compound can have a structure according to Formula A,

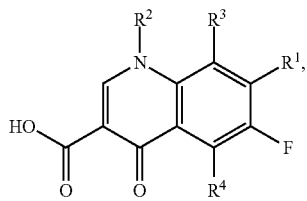

Formula (A)

where R¹ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, where R² can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, where R³ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, and where R⁴ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

In any one or more aspects, the linker can be a carbamate linker. The linker can be an aryl carbamate linker. The linker can be an O-thioaryl carbamate linker. The linker can be an S-thioaryl carbamate linker. The linker can be a phenyl carbamate linker (either substituted or unsubstituted). The linker can be a thiocarbamate linker. The linker can be a O-thiocarbamate linker. The linker can be an S-thiocarbamate linker. The linker can be an O-carbamate linker. The linker can be an activated carbamate, for example a phosphonyl carbamate such as in Formula (41) and Formula (43) herein. The activated carbamate can be an aryl or a phosphonyl substituted carbamate. The linker can be attached to the R¹ group of Formula A.

In any one or more aspects, the alpha position of the ethylidenebisphosphonate can be substituted by hydroxy, fluoro, chloro, bromo or iodo. In some aspects, the bisphosphonate can include a para-hydroxyphenylethylidene group or derivative thereof. In some aspects, ethylidenebisphosphonate does not contain an alpha-hydroxy at the alpha position.

In some aspects, the compound has a formula according to Formula (12):

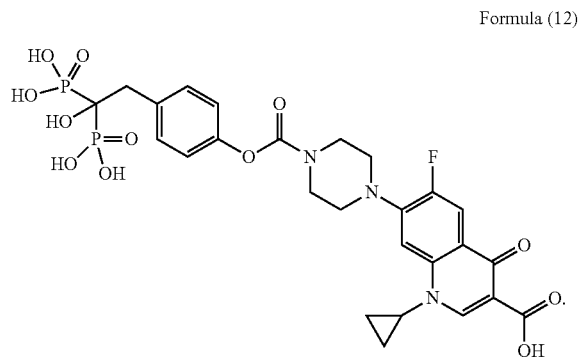 [SMILES: O=C(O)c1cn(C2CC2)c2cc(N3CCN(C(=O)Oc4ccc(CC(O)(P(=O)(O)O)P(=O)(O)O)cc4)CC3)c(F)cc2c1=O]

Formula (12)

In some aspects, the compound has a formula according to Formula (13),

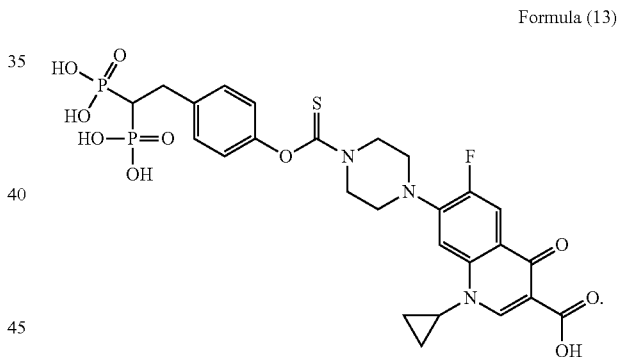

Formula (13)

In some aspects, the compound has a formula according to Formula (15),

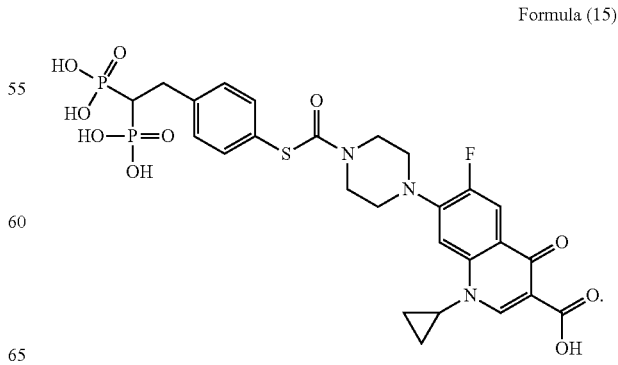

Formula (15)

In some aspects, the compound has a formula according to Formula (41) or Formula (43),

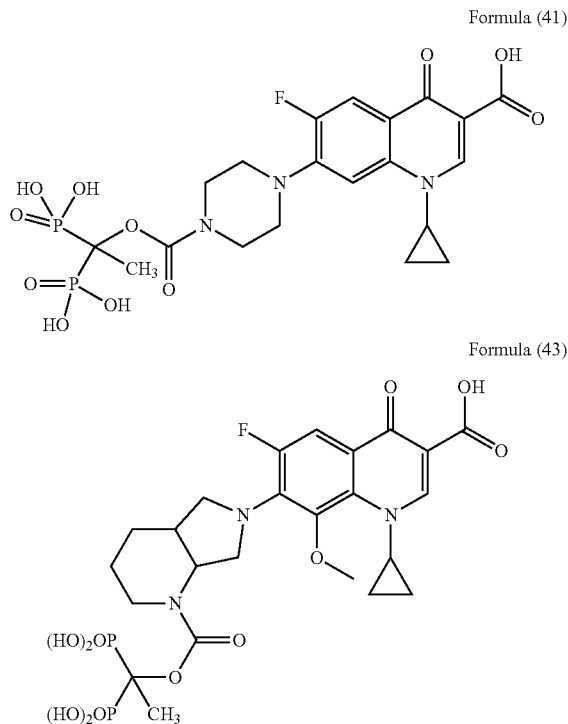

Formula (41)

Formula (43)

Also provided herein are pharmaceutical formulations that can contain a bisphosphonate and a quinolone compound, wherein the quinolone compound is releasably coupled to the bisphosphonate via a linker; and a pharmaceutically acceptable carrier. The bisphosphonate can be selected from the group of: hydroxyl phenyl alkyl or aryl bisphosphonates, hydroxyl phenyl (or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxyl alkyl phenyl(or aryl) alkyl bisphosphonates, hydroxyl phenyl(or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxypyridyl alkyl bisphosphonates, pyridyl alkyl bisphosphonates, hydroxyl imadazoyl alkyl bisphosphonates, imidazoyl alkyl bisphosphonates, etidronate, pamidronate, neridronate, olpadronate, alendronate, ibandronate, risedronate, zoledronate, minodronate, methylenehydroxy bisphosphonate, ethylidene bisphosphonate, and combinations thereof, wherein all the compounds can be optionally further substituted or are unsubstituted.

The quinolone compound can be a fluoroquinolone. The quinolone compound can be selected from the group of: alatrofloxacin, amifloxacin, balofloxacin, besifloxacin, cadazolid, ciprofloxacin, clinafloxacin, danofloxacin, delafloxacin, difloxacin, enoxacin, enrofloxacin, finafloxacin, flerofloxacin, flumequine, gatifloxacin, gemifloxacin, grepafloxacin, ibafloxacin, JNJ-Q2, levofloxacin, lomefloxacin, marbofloxacin, moxifloxacin, nadifloxacin, norfloxacin, ofloxacin, orbifloxacin, pazufloxacin, pefloxacin, pradofloxacin, prulifloxacin, rufloxacin, sarafloxacin, sitafloxacin, sparfloxacin, temafloxacin, tosufloxacin, trvafloxacin, zabofloxacin, nemonoxacin and combinations thereof.

In some aspects, the BP is etidronate. In some aspects, the quinolone is ciprofloxacin or moxifloxacin. In other aspects, the BP can be another BP described herein, such as pamidronate, neridronate, olpadronate, alendronate, ibandronate, minodronate, risedronate, zoledronate, hydroxymethylenebisphosphonate, and combinations thereof. In some aspects, the quinolone is ciprofloxacin or moxifloxacin.

The quinolone compound can have a structure according to Formula A,

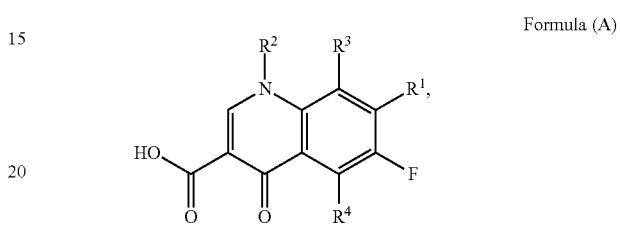

Formula (A)

where $R^1$ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, where $R^2$ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, where $R^3$ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, and where $R^4$ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

In any one or more aspects, the linker can be a carbamate linker. The linker can be an aryl carbamate linker. The linker can be an O-thioaryl carbamate linker. The linker can be an S-thioaryl carbamate linker. The linker can be a phenyl carbamate linker (either substituted or unsubstituted). The linker can be a thiocarbamate linker. The linker is can be a O-thiocarbamate linker. The linker can be an S-thiocarbamate linker. The linker can be an O-carbamate linker. The linker can be an activated carbamate, for example a phosphonyl carbamate such as in Formula (41) and Formula (43) herein. The activated carbamate can be an aryl or a phosphonyl substituted carbamate. The linker can be attached to the $R^1$ group of Formula A.

In some aspects, the alpha position of the ethylidenebisphosphonate can be substituted by hydroxy, fluoro, chloro, bromo or iodo. In some aspects, the bisphosphonate can include a para-hydroxyphenylethylidene group or derivative thereof. In some aspects, ethylidenebisphosphonate does not contain an alpha-hydroxy at the alpha position.

In some aspects, the compound has a formula according to Formula (12):

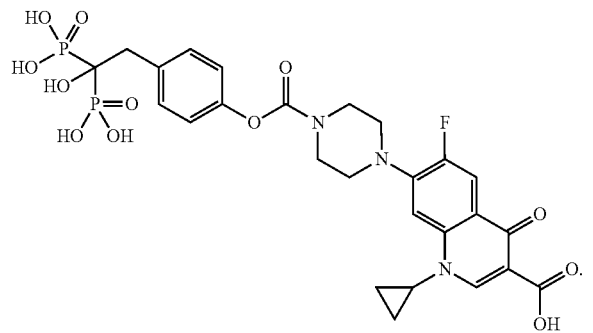

Formula (12)

In some aspects, the compound has a formula according to Formula (13),

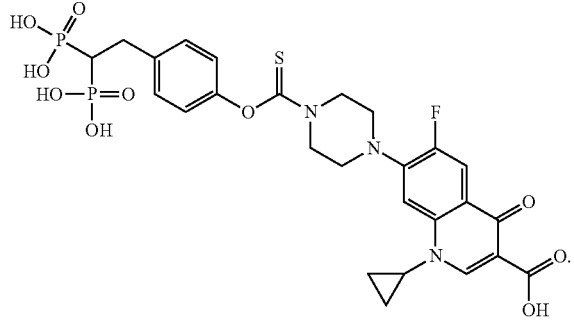

Formula (13)

In some aspects, the compound has a formula according to Formula (15),

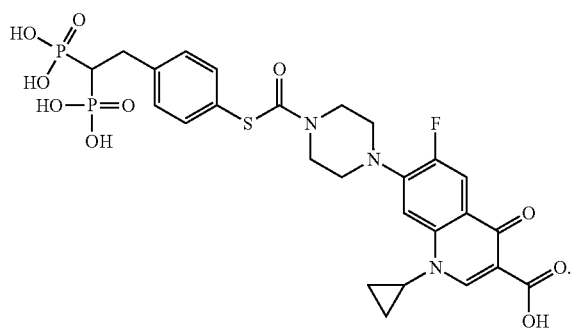

Formula (15)

In some aspects, the compound has a formula according to Formula (41) or Formula (43),

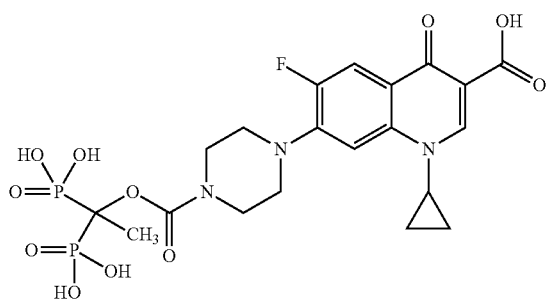

Formula (41)

Formula (43)

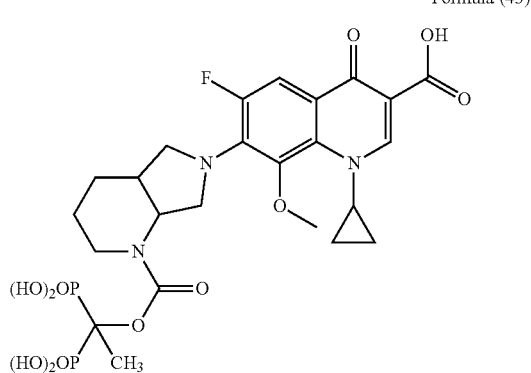

In various aspects, a compound or a conjugate is provided that comprises: a bisphosphonate (BP); and a quinolone compound; wherein the quinolone compound is releasably coupled to the bisphosphonate via a linker. The linker can be a carbamate linker, as described herein. The linker can be an aryl carbamate, an aryl thiocarbamate, an O-thioaryl carbamate, an S-thioaryl carbamate, a thiocarbamate (such as an O-thiocarbamate or an S-thiocarbamate), a phenyl carbamate (either substituted or unsubstituted), an O-carbamate, or a phosphonyl carbamate (such as in Formula (41) and Formula (43) herein). The linker can be an activated carbamate, such as an aryl or a phosphonyl substituted carbamate. The bisphosphonate, quinolone compound and linker can be any of those provided herein. In an aspect, the compound can comprise a bisphosphonate (BP), quinolone and a linker, wherein the BP is an alpha-OH containing BP and the quinolone is indirectly conjugated to the BP at the geminal end of the P by the linker. A pharmaceutical composition is also provided comprising an amount of the compound or conjugate as set forth in any one or more of the aspects provided herein, and a pharmaceutically acceptable carrier.

In various aspects, a method is provided comprising: administering an amount of the compound or conjugate as set forth in any one or more aspects provided herein, or a pharmaceutical formulation thereof, to a subject.

The amount of the compound in the pharmaceutical formulation can be an amount effective to kill or inhibit bacteria growth. The amount of the compound in the pharmaceutical formulation can be an amount effective to treat or prevent bone diseases with abnormal bone resorption, osteoporosis, osteomyelitis, osteonecrosis, peri-implantitis, and/or periodontitis.

Also provided herein are methods of treating or preventing osteomyelitis in a subject in need thereof that can include the step of administering an amount of a compound as provided herein or pharmaceutical formulation thereof to the subject in need thereof.

Also provided herein are methods of treating or preventing peri-implantitis or periodontitis in a subject in need thereof, the method comprising administering an amount of administering an amount of a compound as provided herein or pharmaceutical formulation thereof to the subject in need thereof.

Also provided herein are methods of treating or preventing diabetic foot in a subject in need thereof, the method comprising administering an amount of administering an amount of a compound as provided herein or pharmaceutical formulation thereof to the subject in need thereof.

Also provided herein are bone graft compositions that can include a bone graft material and a compound as described herein or a pharmaceutical formulation thereof, wherein the compound or pharmaceutical formulation thereof is attached to, integrated with, chemisorbed to, or mixed with the bone graft material. The bone graft material can be autograft bone material, allograft bone material, xenograft bone material, a synthetic bone graft material, or any combination thereof.

Also provided herein are methods that can include the step of implanting the bone graft composition as described herein in a subject in need thereof.

Also provided herein are methods of treating or preventing biofilm infection at an osseous or implant surgical site, or at a surgical site where bone grafting is performed, where the methods can include the step of administering a compound as described herein to a subject in need thereof.

Also provided herein are methods of treating or preventing biofilm infection at an osseous or implant surgical site, or at a surgical site where bone grafting is performed, where the method can include the step of implanting a bone graft composition as described herein to a subject in need thereof.

Other compounds, compositions, formulations, methods, features, and advantages of the present disclosure of a fabrication system for nanowire template synthesis, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 3 shows a table demonstrating the AST and MIC results for ciprofloxacin and BP-ciprofloxacin against a panel of clinical S. aureus osteomyelitis pathogens.

FIG. 11 shows a table demonstrating the survival of biofilm bacteria after 24 hr incubation in presence of BP-ciprofloxacin coated HA discs.

FIG. 17 shows antimicrobial susceptibility testing results for ciprofloxacin, BCC (compound 6) and BP-Amide-Ciprofloxacin (BAC, compound 11) tested against a panel of clinically relevant S. aureus osteomyelitis pathogens. (MSSA=methicillin-susceptible S. aureus; MRSA=methicillin-resistant S. aureus).

FIG. 32 shows a graph demonst the results of a minimal inhibitory concentration (MIC) assay for 6 and 11 against eight S. aureus strains using microdilution methodology.

FIG. 50 shows various BP's with terminal primary amines.

FIG. 51 shows various BPs coupled to a linker containing a terminal hydroxyl and amine functional groups where R can be Risedronate, Zoledronate, Minodronate, Pamidronate, or Alendronate.

DETAILED DESCRIPTION

Figure 1:
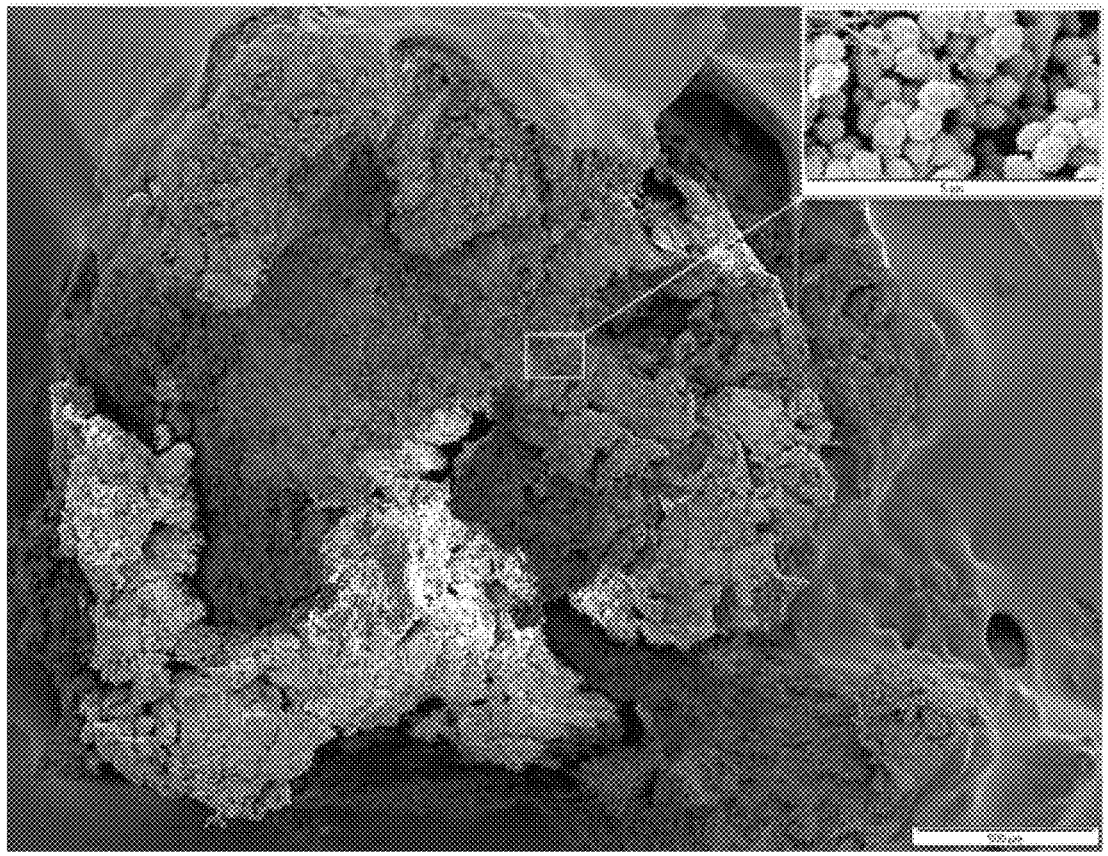
FIG. 1 shows a scanning electron micrograph (SEM; 100× magnification) of a surgical specimen from a patient with chronic osteomyelitis showing characteristic multi-layered and matrix-enclosed biofilms colonizing bone surfaces internally and externally; inset top right shows high-power view (5000× magnification) of the causative staphylococcal biofilm pathogens. [The sample was processed for SEM, sputter coated with platinum and imaged with an XL 30S SEM (FEG, FEI Co., Hillsboro, Oreg.) operating at 5 kV in the secondary electron mode].

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, pharmacology, organic chemistry, biochemistry, botany and the like, which are within the skill of the art. Such techniques are explained fully in the literature.

Definitions

Unless otherwise specified herein, the following definitions are provided.

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term "farm animal" includes a horse, sheep, goat, chicken, pig, cow, donkey, llama, alpaca, turkey, and the like.

As used herein, "control" can refer to an alternative subject or sample used in an experiment for comparison purposes and included to minimize or distinguish the effect of variables other than an independent variable.

As used herein, "analogue," such as an analogue of a bisphosphonate described herein, can refer to a structurally close member of the parent molecule or an appended parent molecule such as a bisphosphonate.

As used herein, "conjugated" can refer to direct attachment of two or more compounds to one another via one or more covalent or non-covalent bonds. The term "conjugated" as used herein can also refer to indirect attachment of two or more compounds to one another through an intermediate compound, such as a linker.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "active agent" or "active ingredient" refers to a component or components of a composition to which the whole or part of the effect of the composition is attributed.

As used herein, "dose," "unit dose," or "dosage" refers to physically discrete units suitable for use in a subject, each unit containing a predetermined quantity of a BP conjugate, such as a BP quinolone conjugate, composition or formulation described herein calculated to produce the desired response or responses in association with its administration.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters, amides, hydroxamic acids, or hydrazides. Derivatives include compounds in which hydroxyl groups in the parent compound have been derivatized to form O-acyl, O-carbamoyl, or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring, as an example, with saturated or unsaturated cyclohexane or other more complex, e.g., nitrogen-containing rings, and extensions of these rings with various groups.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats.

Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

As used herein, "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl) $C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl) amino, carbamoyl, ($C_1$-$C_6$ alkyl)carbonyl, ($C_1$-$C_6$ alkoxy) carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl) sulfonyl, and arylsulfonyl. The groups listed above as suitable substituents are as defined hereinafter except that a suitable substituent may not be further optionally substituted.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl can have 30 or fewer carbon atoms in its backbone (e.g., $C_1$-$C_{30}$ for straight chains, and $C_3$-$C_{30}$ for branched chains). In other embodiments, a straight chain or branched chain alkyl can contain 20 or fewer, 15 or fewer, or 10 or fewer carbon atoms in its backbone. Likewise, in some embodiments cycloalkyls can have 3-10 carbon atoms in their ring structure. In some of these embodiments, the cycloalkyl can have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom.

Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O—alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

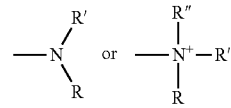

wherein R, R', and R" each independently represent a hydrogen, an alkyl, an alkenyl, —(CH$_2$)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

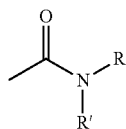

wherein R and R' are as defined above.

As used herein, "Aryl" refers to $C_5$-$C_{10}$-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof. The term "aryl" includes phenyl.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. The terms "heterocycle" or "heterocyclic" can be used to describe a compound that can include a heterocycle or heterocyclic ring.

The term "carbonyl" is art-recognized and includes such moieties as can be represented by the general formula:

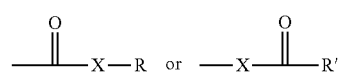

wherein X is a bond or represents an oxygen or a sulfur, and R and R' are as defined above. Where X is an oxygen and R or R' is not hydrogen, the formula represents an "ester".

Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium. Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, the term "nitro" refers to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

As used herein, "carbamate" can be used to refer to a compound derived from carbamic acid ($NH_2COOH$) and can include carbamate esters. "Carbamates" can have the general structure of:

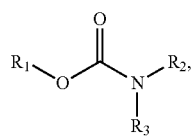

Where $R^1$, $R^2$, and $R^3$ can be any permissible substituent.

As used herein, "effective amount" can refer to the amount of a composition described herein or pharmaceutical formulation described herein that will elicit a desired biological or medical response of a tissue, system, animal, plant, protozoan, bacteria, yeast or human that is being sought by the researcher, veterinarian, medical doctor or other clinician. The desired biological response can be modulation of bone formation and/or remodeling, including but not limited to modulation of bone resorption and/or uptake of the BP conjugates, such as the BP quinolone conjugates, described herein. The effective amount will vary depending on the exact chemical structure of the composition or pharmaceutical formulation, the causative agent and/or severity of the infection, disease, disorder, syndrome, or symptom thereof being treated or prevented, the route of administration, the time of administration, the rate of excretion, the drug combination, the judgment of the treating physician, the dosage form, and the age, weight, general health, sex and/or diet of the subject to be treated. "Effective amount" can refer to the amount of a compositions described herein that is effective to inhibit the growth of or reproduction of a microorganism, including but not limited to a bacterium or population thereof. "Effective amount" can refer to the amount of a compositions described herein that is kill a microorganism, including but not limited to a bacterium or population thereof. "Effective amount" can refer to the amount of a compositions described herein that is effective to treat and/or prevent osteomyelitis in a subject in need thereof.

As used herein, "therapeutic" generally can refer to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof.

As used herein, the terms "treating" and "treatment" can refer generally to obtaining a desired pharmacological and/or physiological effect. The effect may be prophylactic in terms of preventing or partially preventing a disease, symptom or condition thereof.

As used herein, "synergistic effect," "synergism," or "synergy" refers to an effect arising between two or more molecules, compounds, substances, factors, or compositions that is greater than or different from the sum of their individual effects.

As used herein, "additive effect" refers to an effect arising between two or more molecules, compounds, substances, factors, or compositions that is equal to or the same as the sum of their individual effects.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein, the term osteomyelitis can refer to acute or chronic osteomyelitis, and/or diabetic foot osteomyelitis, diabetic chronic osteomyelitis, prosthetic joint infections, periodontitis, peri-implantitis, osteonecrosis, and/or hematogenous osteomyelitis and/or other bone infections.

Discussion

Infectious bone disease, or osteomyelitis, is a major problem worldwide in human and veterinary medicine and can be devastating due to the potential for limb-threatening sequelae and mortality. The treatment approach to osteomyelitis is mainly antimicrobial, and often long-term, with surgical intervention in many cases to control infection. The causative pathogens in most cases of long bone osteomyelitis are biofilms of *Staphylococcus aureus*, which are bound to bone in contrast to their planktonic (free-floating) counterparts. Other bone infections are known to arise from a broad spectrum of both gram positive and gram negative bacteria.

The biofilm-mediated nature of osteomyelitis is important in clinical and experimental settings because many biofilm pathogens are uncultivable and exhibit an altered phenotype with respect to growth rate and antimicrobial resistance (as compared to their planktonic counterparts). The difficulty in eradicating biofilms with conventional antibiotics partly explains why the higher success rates of antimicrobial therapy in general have not yet been realized for orthopedic infections, along with the development of resistant biofilm pathogens, the poor penetration of antimicrobial agents in bone, and adverse events related to systemic toxicity.

To overcome the many challenges associated with osteomyelitis treatment, there is increasing interest in drug delivery approaches using bone-targeting conjugates to achieve higher or more sustained local therapeutic concentrations of antibiotic in bone while minimizing systemic exposure. Fluoroquinolone and non-fluoroquinolone antibiotics conjugated to bisphosphonates (BPs), for example osteoadsorptive BPs, represents a promising approach because of the long clinical track-record of safety of each constituent, and their advantageous biochemical properties. In early investigations of the fluoroquinolone family in this context, ciprofloxacin demonstrated the best binding and microbiological properties when bound to a BP. Ciprofloxacin has several advantages for repurposing in this context: it can be administered orally or intravenously with relative bioequivalence, it has broad spectrum antimicrobial activity that includes the most commonly encountered osteomyelitis pathogens, it demonstrates bactericidal activity in clinically achievable doses, and it is the least expensive drug in the fluoroquinolone family.

The specific bone-targeting properties of the BP family makes them ideal carriers for introducing antibiotics to bone in osteomyelitis pharmacotherapy. BPs form strong bidentate and tridentate bonds with calcium and as a result concentrate in hydroxyapatite (HA), particularly at sites of active metabolism or infection and inflammation. BPs also exhibit exceptional stability against both chemical and biological degradation. The concept of targeting ciprofloxacin to bone via conjugation with a BP has been discussed in a number of reports over the years.

Despite these positive attributes of BPs and fluoroquinolones, such as ciprofloxacin, current attempts at generating prodrugs containing BPs and fluoroquinolones, such as ciprofloxacin, have been unsuccessful. Most attempts resulted in either systemically unstable prodrugs or non-cleavable conjugates that were found to mostly inactivate either component of the conjugate by interfering with the pharmacophoric requirements.

With the deficiencies of current BP fluoroquinolone conjugates in mind, described herein are BP quinolone conjugates that can contain a BP that can be releasably conjugated to a quinolone, such as ciprofloxacin. In embodiments, the BP quinolone conjugate can selectively deliver a quinolone to bone, bone grafts, and or bone graft substitutes (i.e. can target bone, bone grafts, or bone graft substitutes) in a subject. In some embodiments, the BP quinolone conjugate can release the quinolone. Also provided herein are methods of synthesizing BP quinolone conjugates and methods of treating or preventing osteomyelitis or other bone infections with one or more of the BP quinolone conjugates provided herein.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Bisphosphonate (BP) Quinolone Conjugates and Formulations Thereof

BP Quinolone Conjugates

Figure 13:
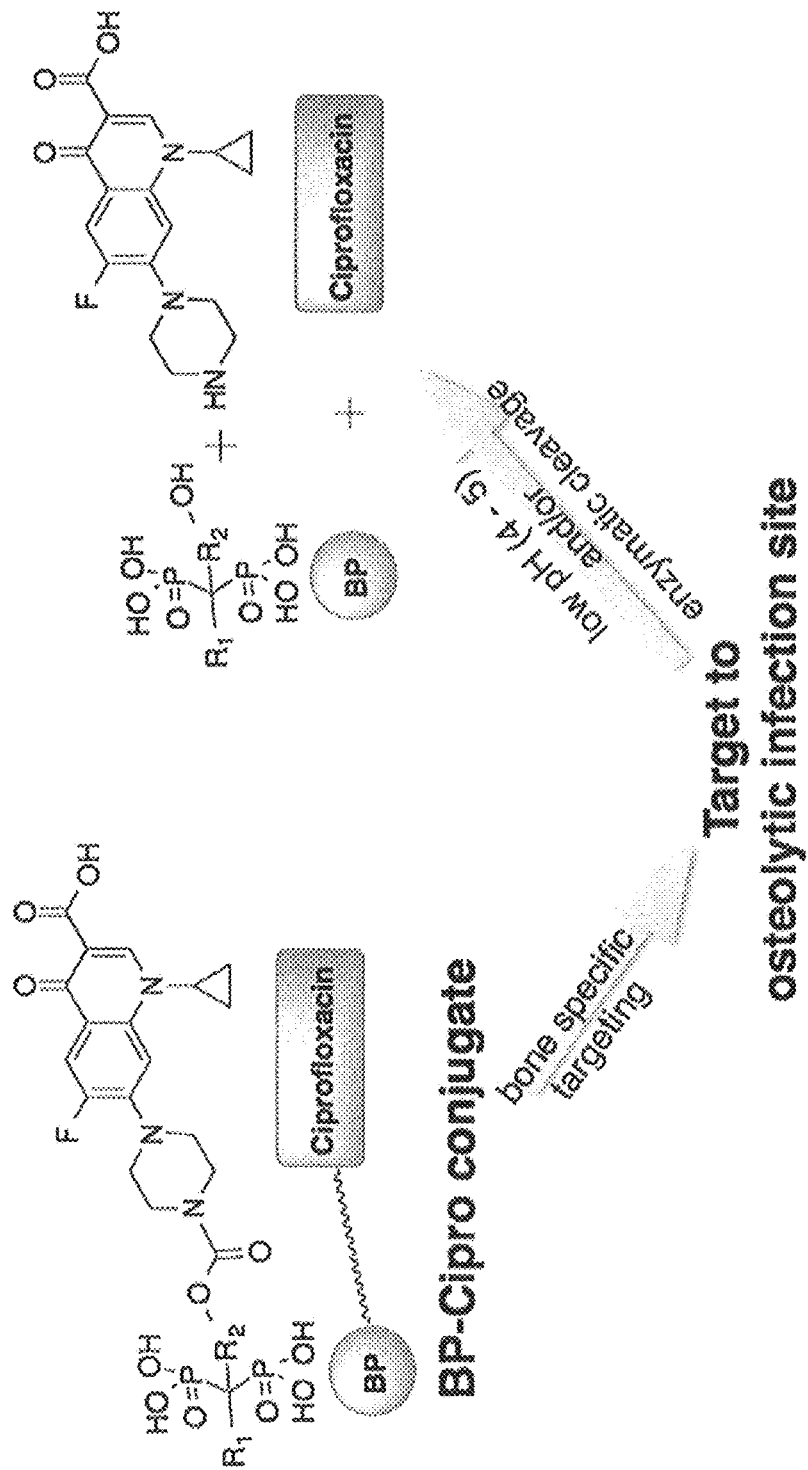
FIG. 13 demonstrates the general BP quinolone conjugate targeting strategy.

Provided herein are BP quinolone conjugates and formulations thereof. A BP can be conjugated to a quinolone via a linker. In embodiments, the linker is a releasable linker. The quinolone can be releasably attached via a linker to the BP. Thus, in some embodiments, the BP quinolone conjugate can selectively deliver and release the quinolone at or near bone, bone grafts, or bone graft substitutes (FIG. 13). In other words, the BP fluoroquinolone conjugate can provide targeted delivery of fluoroquinolones to bone and/or the areas proximate to bone The BP of the BP quinolone conjugates provided herein can be any BP including but not limited to, hydroxyl phenyl alkyl or aryl bisphosphonates, hydroxyl phenyl (or aryl) alkyl hydroxyl bisphosphonates, amino phenyl(or aryl) alkyl bisphosphonates, amino phenyl (or aryl) alkyl hydroxyl bisphosphonates, hydroxyl alkyl bisphosphonates, hydroxyl alkyl hydroxyl bisphosphonates hydroxyl alkyl phenyl(or aryl) alkyl bisphosphonates, hydroxyl phenyl(or aryl) alkyl hydroxyl bisphosphonates, amino phenyl(or aryl) alkyl bisphosphonates, amino phenyl (or aryl) alkyl hydroxyl bisphosphonates, hydroxyl alkyl bisphosphonates, hydroxyl alkyl hydroxyl bisphosphonates (all of the former being further unsubstituted or substituted, etidronate, pamidronate, neridronate, olpadronate, alendronate, ibandronate, risedronate, zoledronate, hydroxymethylenebisphosphonate, and combinations thereof. Bisphosphonate may also be substituted for phosphono phosphinic acid or phosphono carboxylic acid. In embodiments, the BP can be pamidronate, alendronate, risedronate, zoledronate, minodronate, neridronate, etidronate, which can be unmodified or modified as described herein.

Figure 29:
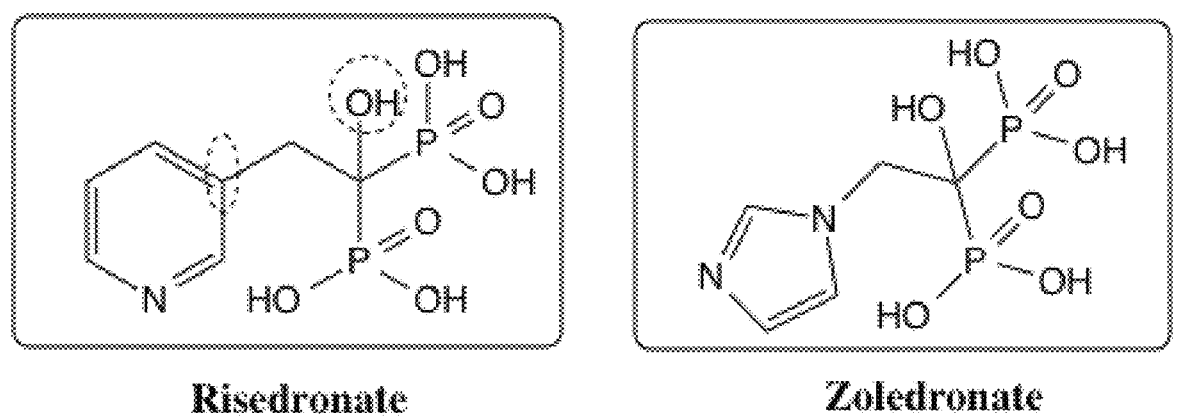
FIG. 29 shows an alpha-hydroxy modified risedronate and zoledronate.
Figure 30:
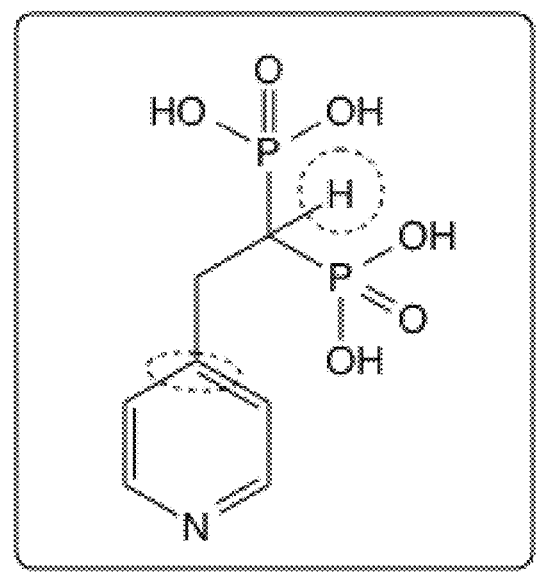
FIG. 30 shows 1) a BP modified by substituting or removing the alpha-hydroxy group (p-PyrEBP); 2) a BP modified by substituting at the para-position of pyridine ring (p-RIS). The circled H is attached to the alpha carbon of the bisphosphonate substituted carbon chain.
Figure 30:
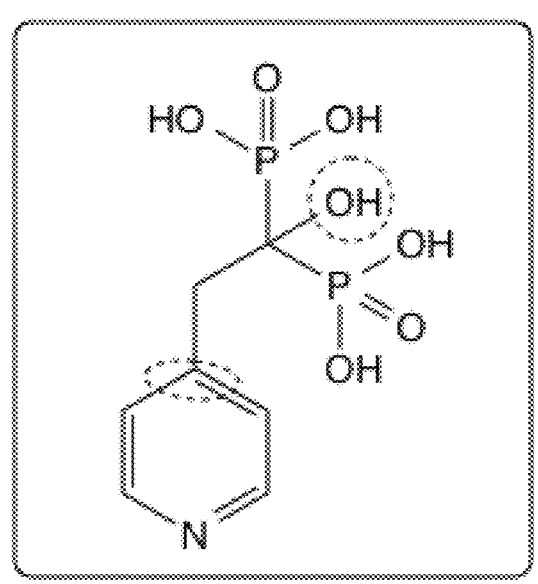

The BP can be modified to contain an alpha-hydroxy group (e.g. alpha-hydroxy modified risedronate and zoledronate, FIG. 29) Other BPs can be modified in the same way. In some embodiments, the BP can be modified by substituting or removing the alpha-hydroxy group. (FIG. 30, e.g. p-PyrEBP). Removal or substitution of the alpha-hydroxyl group can reduce or eliminate the anti-resorptive effect of the BP as compared to an unmodified equivalent BP. As such, in some embodiments, the BP conjugates provided herein can contain a BP that lacks the alpha-hydroxy group or has a substituted alpha-hydroxy group. Suitable substitutions for the alpha-hydroxy group can include, but are not limited to, H, alkyl, aryl, alkyl aryl. Further additional molecules conjugated to the BP can also affect the anti-resorptive effect. For example, when the quinolone and/or linker is coupled to the BP having a para-substituted side change, the anti-resorptive effect can be significantly reduced or eliminated. In some embodiments, the BP can be modified to include both an alpha hydroxyl deletion or substitution and a para-substituted side chain.

In BPs containing an aryl or phenyl, the aryl or phenyl can be substituted with a suitable substitutent at any position on the ring. In some embodiments, the aryl or phenyl ring of the BP is substituted with one or more electron donating species (e.g. F, N, and Cl).

Non-pharmacologically active BP variants may also be used for the purpose of fluoroquinolone delivery absent BP action.

The quinolone can be any quinolone, including but not limited to alatrofloxacin, amifloxacin, balofloxacin, besifloxacin, cadazolid, ciprofloxacin, clinafloxacin, danofloxacin, delafloxacin, difloxacin, enoxacin, enrofloxacin, finafloxacin, flerofloxacin, flumequine, gatifloxacin, gemifloxacin, grepafloxacin, ibafloxacin, JNJ-Q2, levofloxacin, lomefloxacin, marbofloxacin, moxifloxacin, nadifloxacin, norfloxacin, ofloxacin, orbifloxacin, pazufloxacin, pefloxacin, pradofloxacin, prulifloxacin, rufloxacin, sarafloxacin, sitafloxacin, sparfloxacin, temafloxacin, tosufloxacin, trvafloxacin, zabofloxacin, nemonoxacin and any combination thereof. The quinolone can be a fluoroquinolone.

The quinolone can have a generic structure according to Formula 1, where R¹ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, where R² can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, where R³ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups, and where R⁴ can be substituents including alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

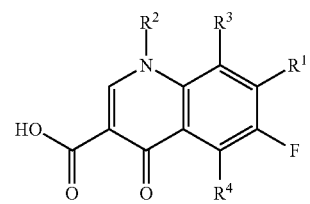

Formula (A)

The BP can be conjugated to the fluoroquinolone via a releasable linker. In some embodiments the releasable linker can be a phenyl carbamate linker. The releasable linker can be an aryl carbamate linker. In some embodiments the linker can be an aryl thiocarbamate linker. In some embodiments the linker can be a phenyl thiocarbamate linker. In some embodiments the thiocarbamate linker can be an O-thiocarbamate linker. In some embodiments, the thiocarbamate linker can be an S-thiocarbamate linker. In some embodiments, the linker can be a carbonate linker. In some embodiments the linker can be a urea linker. In some embodiments, the linker can be an aryl dithiocarbamate linker.

In various aspects, an alpha-OH containing BP can be conjugated to the quinolone, such as a quinolone (including any fluoroquinolone), at a geminal OH group on the BP as shown below. In some aspects the quinolone, such as a fluoroquinolone or other quinolone as described herein, can be indirectly conjugated via a linker, such as described herein, at the geminal OH group of the BP.

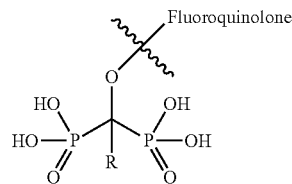

conjugates between alpha-OH containing BP and fluoroquinolone

In some aspects, the compound can have a formula according to Formula (41) or Formula (43)

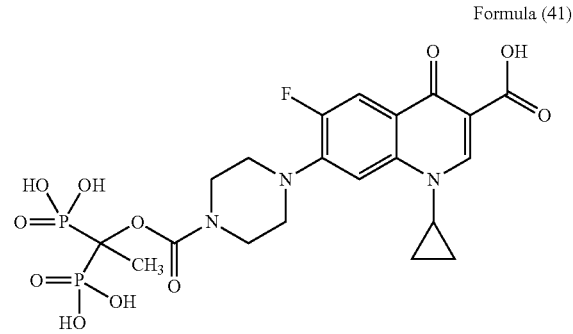

Formula (41)

-continued

Formula (43)

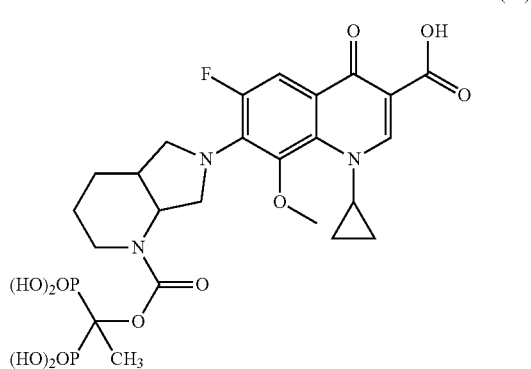

BP Quinolone Conjugate Pharmaceutical Formulations

Also described herein are formulations, including pharmaceutical formulations, which can contain an amount of a BP quinolone conjugate described elsewhere herein. The amount can be an effective amount. The amount can be effective to inhibit the growth and/or reproduction of a bacterium. The amount can be effective to kill a bacterium. Formulations, including pharmaceutical formulations can be formulated for delivery via a variety of routes and can contain a pharmaceutically acceptable carrier. Techniques and formulations generally can be found in *Remington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the BP quinolone conjugates and/or components thereof can be formulated in solid form and redissolved or suspended immediately prior to use. Lyophilized forms are also included. Formulations, including pharmaceutical formulations, of the BP quinolone conjugates can be characterized as being at least sterile and pyrogen-free. These formulations include formulations for human and veterinary use.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with BP quinolone conjugate.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the BP quinolone conjugate.

Another formulation includes the addition of BP quinolone conjugates to bone graft material or bone void fillers for the prevention or treatment of osteomyelitis, peri-implantitis or peri-prosthetic infections, and for socket preservation after dental extractions.

The pharmaceutical formulations can be formulated to be compatible with their intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Formulations, including pharmaceutical formulations, suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it can be useful to include isotonic agents, for example, sugars, polyalcohols such as mannitol, sorbitol, and sodium chloride in the composition.

Sterile injectable solutions can be prepared by incorporating any of BP quinolone conjugates described herein in an amount in an appropriate solvent with one or a combination of ingredients enumerated herein, as required, followed by filtered sterilization. Generally, dispersions can be prepared by incorporating BP quinolone conjugate into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents, bile salts, and fluidic acid derivatives. Transmucosal administration can be accomplished through the use of nasal sprays or suppositories. For transdermal administration, the BP quinolone conjugates can be formulated into ointments, salves, gels, or creams as generally known in the art. In some embodiments, the BP quinolone conjugates can be applied via transdermal delivery systems, which can slowly release the BP quinolone conjugates for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

For oral administration, a formulation as described herein can be presented as capsules, tablets, powders, granules, or as a suspension or solution. The formulation can contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration through a route other than the alimentary canal), the formulations described herein can be combined with a sterile aqueous solution that is isotonic with the blood of the subject. Such a formulation can be prepared by dissolving the active ingredient (e.g. the BP quinolone conjugate) in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulations described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

For inclusion in bone graft substitutes or bone void fillers to prevent local post-operative infection or graft failure after surgery, and to provide sustained local release of antibiotic at the graft site, the formulations described herein can be combined with any xenograft (bovine), autograft (self) or allograft (cadaver) material or synthetic bone substitute. For example, a powder formulation can be premixed by the treating surgeon or clinician bedside/chairside with any existing bone graft substitute on the market or with an autologous graft. This formulation can be further combined with any previously described formulation, and can be combined with products containing hydroxyapatites, tricalcium phosphates, collagen, aliphatic polyesters (poly(lactic) acids (PLA), poly(glycolic) acids (PGA), and polycaprolactone (PCL), polyhydroxybutyrate (PHB), methacrylates, polymethylmethacrylates, resins, monomers, polymers, cancellous bone allografts, human fibrin, platelet rich plasma, platelet rich fibrin, plaster of Paris, apatite, synthetic hydroxyapatite, coralline hydroxyapatite, wollastonite (calcium silicate), calcium sulfate, bioactive glasses, ceramics, titanium, devitalized bone matrix, non-collagenous proteins, collagen, and autolyzed antigen extracted allogenic bone. In this embodiment the bone graft material combined with BP quinolone conjugate can be in the formulation of a paste, powder, putty, gel, hydrogel, matrix, granules, particles, freeze-dried powder, freeze-dried bone, demineralized freeze-dried bone, fresh or fresh-frozen bone, corticocancellous mix, pellets, strips, plugs, membranes, lyophilized powder reconstituted to form wet paste, spherules, sponges, blocks, morsels, sticks, wedges, cements, or amorphous particles; many of these may also be in injectable formulations or as a combination of two or more aforementioned formulations (e.g. injectable paste with sponge).

In another embodiment, BP-quinolone conjugate can be combined with factor-based bone grafts containing natural or recombinant growth factors, such as transforming growth factor-beta (TGF-beta), platelet-derived growth factor (PDGF), fibroblast growth factors (FGF), and/or bone morphogenic protein (BMP). In another embodiment, BP quinolone conjugate can be combined with cell-based bone grafts used in regenerative medicine and dentistry including embryonic stem cells and/or adults stem cells, tissue-specific stem cells, hematopoietic stem cells, epidermal stem cells, epithelial stem cells, gingival stem cells, periodontal ligament stem cells, adipose stem cells, bone marrow stem cells, and blood stem cells. Therefore, a bone graft with the property of osteoconduction, osteoinduction, osteopromotion, osteogenesis, or any combination thereof can be combined with BP quinolone conjugate for clinical or therapeutic use.

Dosage Forms

The BP quinolone conjugates, compounds, and formulations thereof, described herein can be provided in unit dose form such as a tablet, capsule, single-dose injection or infusion vial, or as a predetermined dose for mixing with bone graft material as in formulations described above. Where appropriate, the dosage forms described herein can be microencapsulated. The dosage form can also be prepared to prolong or sustain the release of any ingredient. In some embodiments, the complexed active agent can be the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Coatings may be formed with a different ratio of water soluble polymer, water insoluble polymers, and/or pH dependent polymers, with or without water insoluble/water soluble non polymeric excipient, to produce the desired release profile. The coatings can be either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Effective Amounts

The formulations can contain an effective amount of a BP quinolone conjugate or compound (effective for inhibiting and/or killing a bacterium) described herein. In some embodiments, the effective amount ranges from about 0.001 pg to about 1,000 g or more of the BP quinolone conjugate described herein. In some embodiments, the effective amount of the BP quinolone conjugate described herein can range from about 0.001 mg/kg body weight to about 1,000 mg/kg body weight. In yet other embodiments, the effective amount of the BP quinolone conjugate can range from about 1% w/w to about 99% or more w/w, w/v, or v/v of the total formulation. In some embodiments, the effective amount of the BP quinolone conjugate is effective at killing a bacterium that is the causative agent of osteomyelitis and all its subtypes (e.g. diabetic foot osteomyelitis), jaw osteonecrosis, and periodontitis including, but not limited to any strain or species of *Staphylococcus, Pseudomonas, Aggregatibacter, Actinomyces, Streptococcus, Haemophilus, Salmonella, Serratia, Enterobacter, Fusobacterium, Bacteroides, Porphyromonas, Prevotella, Veillonella, Campylobacter, Peptostreptococcus, Eikenella, Treponema, Dialister, Micromonas, Yersinia, Tannerella*, and *Escherichia*.

Methods of Using the BP Quinolone Conjugates

An amount, including an effective amount, of the BP quinolone conjugates, compounds, and formulations thereof, described herein can be administered to a subject in need thereof. In some embodiments the subject in need thereof can have a bone infection, disease, disorder, or a symptom thereof. In some embodiments, the subject in need thereof can be suspected of having or is otherwise predisposed to having a bone infection, disease, disorder, or a symptom thereof. In some embodiments, the subject in need thereof may be at risk for developing an osteomyelitis, osteonecrosis, peri-prosthetic infection, and/or peri-implantitis. In embodiments, the disease or disorder can be osteomyelitis and all its subtypes, osteonecrosis, peri-implantitis or periodontitis. In some embodiments the subject in need thereof has a bone that is infected with a microorganism, such as a bacteria. In some embodiments, the bacteria can be any strain or species of *Staphylococcus, Pseudomonas, Aggregatibacter, Actinomyces, Streptococcus, Haemophilus, Salmonella, Serratia, Enterobacter, Fusobacterium, Bacteroides, Porphyromonas, Prevotella, Veillonella, Campylobacter, Peptostreptococcus, Eikenella, Treponema, Dialister, Micromonas, Yersinia, Tannerella*, and *Escherichia*. In some embodiments, the bacteria can form biofilms. In some embodiments, osteomyelitis can be treated in a subject in need thereof by administering an amount, such as an effective amount, of BP quinolone conjugate or formulation thereof described herein to the subject in need thereof. In some embodiments, the compositions and compounds provided herein can be used in osteonecrosis treatment and/or prevention, distraction osteogenesis, cleft repair, repair of critical supra-alveolar defects, jawbone reconstruction, and any other reconstructions or repair of a bone and/or joint.

Administration of the BP quinolone conjugates is not restricted to a single route, but can encompass administration by multiple routes. For instance, exemplary administrations by multiple routes include, among others, a combination of intradermal and intramuscular administration, or intradermal and subcutaneous administration. Multiple administrations can be sequential or concurrent. Other modes of application by multiple routes will be apparent to the skilled artisan.

The pharmaceutical formulations can be administered to a subject by any suitable method that allows the agent to exert its effect on the subject in vivo. For example, the formulations and other compositions described herein can be administered to the subject by known procedures including, but not limited to, by oral administration, sublingual or buccal administration, parenteral administration, transdermal administration, via inhalation, via nasal delivery, vaginally, rectally, and intramuscularly. The formulations or other compositions described herein can be administered parenterally, by epifascial, intracapsular, intracutaneous, subcutaneous, intradermal, intrathecal, intramuscular, intraperitoneal, intrasternal, intravascular, intravenous, parenchymatous, and/or sublingual delivery. Delivery can be by injection, infusion, catheter delivery, or some other means, such as by tablet or spray. Delivery can also be by a carrier such as hydroxyapatite or bone in the case of anti-infective bone graft material at a surgical site. Delivery can be via attachment or other association with a bone graft material.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Infectious bone disease, or osteomyelitis, is a major problem worldwide in human and veterinary medicine and can be devastating due to the potential for limb-threatening sequelae and mortality (Lew, et al., Osteomyelitis. Lancet 2004; 364:369-79; Desrochers, et al, Limb amputation and prosthesis. Vet Clin North Am Food Anim Pract 2014; 30:143-55; Stoodley, et al., Orthopaedic biofilm infections. Curr Orthop Pract 2011; 22:558-63; Huang, et al., Chronic osteomyelitis increases long-term mortality risk in the elderly: a nationwide population-based cohort study. BMC Geriatr 2016; 16:72). The treatment approach to osteomyelitis is mainly antimicrobial, and often long-term, with surgical intervention in many cases to control infection. The causative pathogens in most cases of long bone osteomyelitis are biofilms of *Staphylococcus aureus*; by definition these microbes are bound to bone (FIG. 1) in contrast to their planktonic (free-floating) counterparts (Wolcott, et al., Biofilms and chronic infections. J Am Med Assoc 2008; 299: 2682-2684).

The biofilm-mediated nature of osteomyelitis is important in clinical and experimental settings because many biofilm pathogens are uncultivable and exhibit an altered phenotype with respect to growth rate and antimicrobial resistance (as compared to their planktonic counterparts) (Junka, et al., Microbial biofilms are able to destroy hydroxyapatite in the absence of host immunity in vitro. J Oral Maxillofac Surg 2015; 73:451-64; Herczegh, et al., Osteoadsorptive bisphosphonate derivatives of fluoroquinolone antibacterials. J Med Chem 2002; 45:2338-41). The difficulty in eradicating biofilms with conventional antibiotics partly explains why the higher success rates of antimicrobial therapy in general have not yet been realized for orthopedic infections, along with the development of resistant biofilm pathogens, the poor penetration of antimicrobial agents in bone, and adverse events related to systemic toxicity (Buxton, et al., Bisphosphonate-ciprofloxacin bound to Skelite is a prototype for enhancing experimental local antibiotic delivery to injured bone. Br J Surg 2004; 91:1192-6).

To overcome the many challenges associated with osteomyelitis treatment, there is increasing interest in drug delivery approaches using bone-targeting conjugates to achieve higher or more sustained local therapeutic concentrations of antibiotic in bone while minimizing systemic exposure (Panagopoulos, et al., Local Antibiotic Delivery Systems in Diabetic Foot Osteomyelitis: Time for One Step Beyond? Int J Low Extrem Wounds 2015; 14:87-91; Puga, et al., Hot melt poly-epsilon-caprolactone/poloxamine implantable matrices for sustained delivery of ciprofloxacin. Acta biomaterialia 2012; 8:1507-18). Fluoroquinolone antibiotics conjugated to osteoadsorptive bisphosphonates (BPs) represents a promising approach because of the long clinical track-record of safety of each constituent, and their advantageous biochemical properties (Buxton, et al., Bisphosphonate-ciprofloxacin bound to Skelite is a prototype for enhancing experimental local antibiotic delivery to injured bone. Br J Surg 2004; 91:1192-6). In early investigations of the fluoroquinolone family in this context, ciprofloxacin demonstrated the best binding and microbiological properties when bound to BP (Herczegh, et al., Osteoadsorptive bisphosphonate derivatives of fluoroquinolone antibacterials. J Med Chem 2002; 45:2338-41). Ciprofloxacin has several advantages for repurposing in this context: it can be administered orally or intravenously with relative bioequivalence, it has broad spectrum antimicrobial activity that includes the most commonly encountered osteomyelitis pathogens, it demonstrates bactericidal activity in clinically achievable doses, and it is the least expensive drug in the fluoroquinolone family (Houghton, et al., Linking bisphosphonates to the free amino groups in fluoroquinolones: preparation of osteotropic prodrugs for the prevention of osteomyelitis. J Med Chem 2008; 51:6955-69).

The specific bone-targeting properties of the BP family makes them ideal carriers for introducing antibiotics to bone in osteomyelitis pharmacotherapy (Zhang S, et al., 'Magic bullets' for bone diseases: progress in rational design of bone-seeking medicinal agents. Chem Soc Rev 2007; 36:507-31). BPs form strong bidentate and tridentate bonds with calcium and as a result concentrate in hydroxyapatite (HA), particularly at sites of active metabolism or infection and inflammation (Cheong, et al., Bisphosphonate uptake in areas of tooth extraction or periapical disease. J Oral Maxillofac Surg 2014; 72:2461-8). BPs also exhibit exceptional stability against both chemical and biological degradation (Russell, et al., Mechanisms of action of bisphosphonates: similarities and differences and their potential influence on clinical efficacy. Osteoporos Int 2008; 19:733-59). The concept of targeting ciprofloxacin to bone via conjugation with BP has been discussed in a number of reports over the years (David, et al., Methylene-bis[(aminomethyl)phosphinic acids]: synthesis, acid-base and coordination properties. Dalton Trans 2013; 42:2414-22; Fardeau, et al., Synthesis and antibacterial activity of catecholate-ciprofloxacin conjugates. Bioorg Med Chem 2014; 22:4049-60; EUCAST: European Committee on Antimicrobial Susceptibility Testing breakpoint tables for interpretation of MICs and zone diameters. 2015. http://www.eucast.org/fileadmin/src/media/PDFs/EUC; CLSI. M100-S25 performance standards for antimicrobial susceptibility testing, Twenty-fifth informational supplement, 2015; Tanaka, et al., Bisphosphonated fluoroquinolone esters as osteotropic prodrugs for the prevention of osteomyelitis. Bioorg Med Chem 2008; 16:9217-29; McPherson, et al., Synthesis of osteotropic hydroxybisphosphonate derivatives of fluoroquinolone antibacterials. Eur J Med Chem 2012; 47:615-8). However, early attempts resulted in either systemically unstable prodrugs or non-cleavable conjugates that were found to mostly inactivate either component of the conjugate by interfering with the pharmacophoric requirements. In the fluoroquinolone field a prominent example was described by Herczegh et al where significant gram-positive antibacterial properties of the ciprofloxacin constituent were lost on conjugation with a stable BP-linked congener (Herczegh, et al., Osteoadsorptive bisphosphonate derivatives of fluoroquinolone antibacterials. J. Med. Chem 2002; 45:2338-41). Subsequent investigations in this field have elucidated that these conjugates alone cannot exert significant antimicrobial effects without cleavage of the parent antibiotic (Herczegh, et al., Osteoadsorptive bisphosphonate derivatives of fluoroquinolone antibacterials. J. Med. Chem 2002; 45:2338-41; Houghton, et al., Linking bisphosphonates to the free amino groups in fluoroquinolones: preparation of osteotropic prodrugs for the prevention of osteomyelitis. J. Med. Chem 2008; 51:6955-69). Houghton et al, for example, synthesized and tested various BP-fluoroquinolone conjugates and found that phenylpropanone and acyloxyalkyl carbamate gatifloxacin prodrugs were possibly able to regenerate the parent drug once bound to bone, and thus demonstrated greater antimicrobial activity than simple conjugates such as bisphosphonoethyl, bisphosphonopropionyl and amide derivatives which were unable to release the antibiotic (Houghton, et al., Linking bisphosphonates to the free amino groups in fluoroquinolones: preparation of osteotropic prodrugs for the prevention of osteomyelitis. J. Med. Chem 2008; 51:6955-69).

Taken together, the research findings in this field to date indicate that BP-fluoroquinolone antimicrobial activity is complex and is related to the specific strain of pathogen tested, the choice of antibiotic and covalently bound BP moiety, the tether length between the two constituents, the bone binding affinity of the BP, the adsorption-desorption equilibria of the BP, and the stability/lability and kinetics of the linkage scheme used for conjugation (Herczegh, et al., Osteoadsorptive bisphosphonate derivatives of fluoroquinolone antibacterials. J. Med. Chem 2002; 45:2338-41; Houghton, et al., Linking bisphosphonates to the free amino groups in fluoroquinolones: preparation of osteotropic prodrugs for the prevention of osteomyelitis. J. Med. Chem 2008; 51:6955-69; Tanaka, et al., Bisphosphonated fluoroquinolone esters as osteotropic prodrugs for the prevention of osteomyelitis. Bioorg Med Chem 2008; 16:9217-29; McPherson, et al., Synthesis of osteotropic hydroxybisphosphonate derivatives of fluoroquinolone antibacterials. Eur J. Med Chem 2012:47:615-8). Therefore, accumulating evidence suggests that a 'target and release' linker strategy may offer more opportunities for optimization and success in this context. We thus hypothesized that conjugation of ciprofloxacin to a phenyl BP moiety, through metabolically hydrolyzable carbamate linkers, should mitigate the problems seen with antibiotic bone dosing in osteomyelitis pharmacotherapy. The cleavable carbamate linkage and structural motif is a key functionality in many drugs designed for target and release in specific tissues, and confers pharmacokinetic advantages such as stability in serum and lability at infected bone surfaces in the presence of an acidic and enzymatic environment (Ossipov, et al., Bisphosphonate-modified biomaterials for drug delivery and bone tissue engineering. Expert Opin Drug Deliv 2015; 12:1443-58; Guo, et al., pH-triggered intracellular release from actively targeting polymer micelles. Biomaterials 2013; 34:4544-54; Ghosh, et al., Organic carbamates in drug design and medicinal chemistry. J Med Chem 2015; 58:2895-940).

One recent apparent success utilizing a bone-targeting and release strategy has been observed where Morioka et al designed an estradiol analog to target and release at bone, using a cleavable variant (carbamate) of the more stable amide peptide bond (Morioka, et al., Design, synthesis, and biological evaluation of novel estradiol-bisphosphonate conjugates as bone-specific estrogens. Bioorg Med Chem 2010; 18:1143-8). Several versions of this linkage were attempted before the identification of a pharmacologically active variant (phenyl carbamate). Importantly, they demonstrated that a 1000× lower single dose of a similarly linked BP-estradiol conjugate produced a similar effect on bone to that of estradiol dosed alone (Morioka, et al., Design, synthesis, and biological evaluation of novel estradiol-bisphosphonate conjugates as bone-specific estrogens. Bioorg Med Chem 2010; 18:1143-8). The conjugate also provided a larger therapeutic index or improved safety, as there were minimal effects in uterine tissue. Pharmacokinetic studies completed by Arns et al are in agreement with this dramatic enhancement of potency with a phenyl carbamate linked BP-prostaglandin (Arns, et al., Design and synthesis of novel bone-targeting dual-action pro-drugs for the treatment and reversal of osteoporosis. Bioorg Med Chem 2012; 20:2131-40). A synthetic example of this approach in the antimicrobial field is reported for the macrolide class; however, only alkyl carbamates were explored and lack of further success suggests that target and release strategies are likely chemical class-dependent (taking into consideration compatibilities of the functional groups of each component) as well as biochemical target-dependent, and the design for any particular chemical class must be customized for its use (Tanaka, et al., Synthesis and in vitro evaluation of bisphosphonated glycopeptide prodrugs for the treatment of osteomyelitis. Bioorg Med Chem Lett 2010; 20:1355-9).

This Example demonstrates a phenyl carbamate BP-ciprofloxacin conjugate and systematical evaluation of its antimicrobial activity in vitro against common osteomyelitis pathogens, and assessed in vivo safety and efficacy in an animal model of peri-implant osteomyelitis. Importantly, the in vitro and in vivo studies presented herein are predicated on biofilm models and methodology in addition to planktonic cultures, which has not been performed to date in this field and which should provide for greater clinical relevance. The present study specifically addresses an unmet medical need in the treatment of infectious bone disease, and thus has been designed for translational significance.

Results and Discussion

Figure 2A:
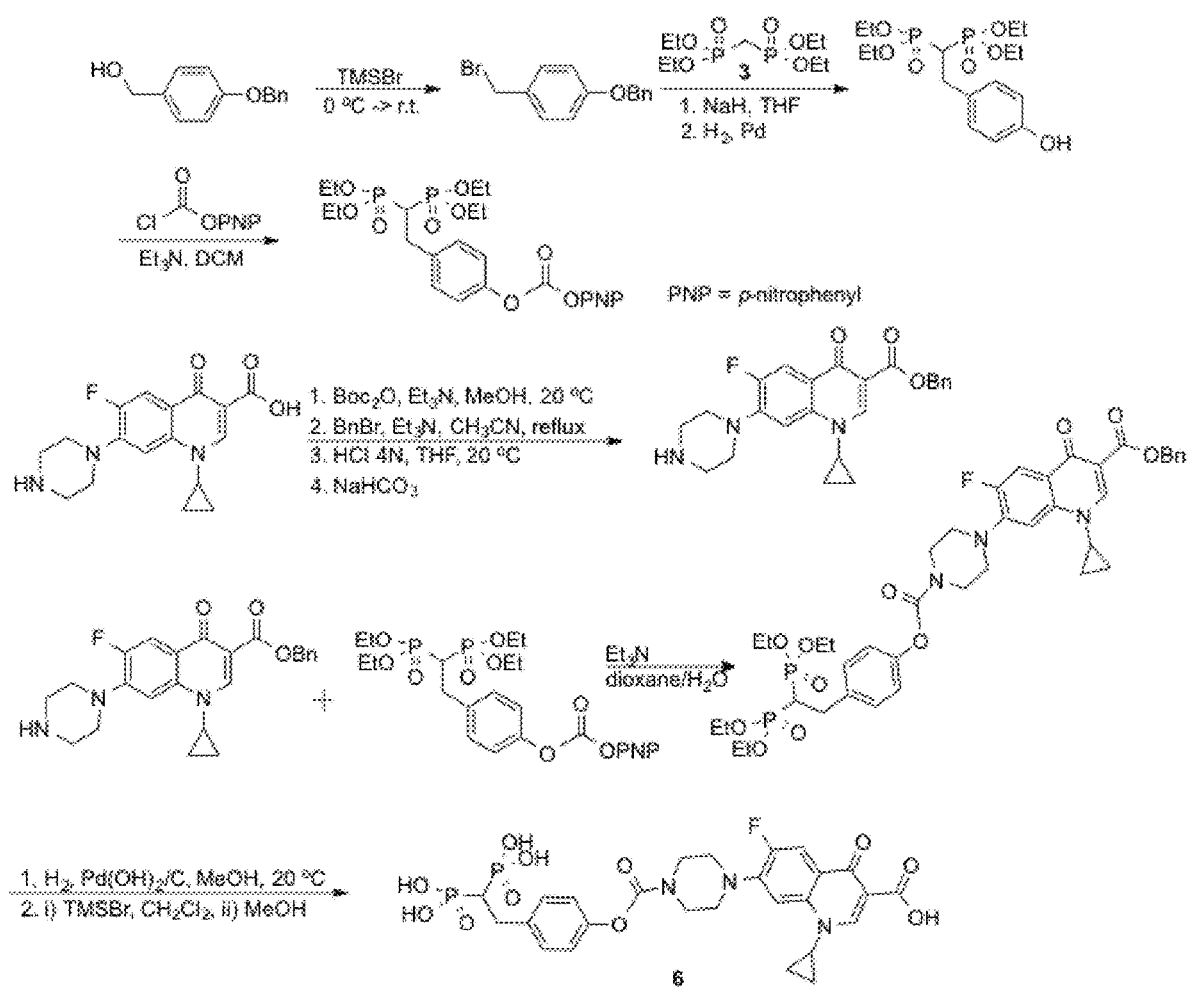
FIGS. 2A-2B shows general synthesis schemes of a phenyl carbamate BP-ciprofloxacin conjugate.
Figure 2B:
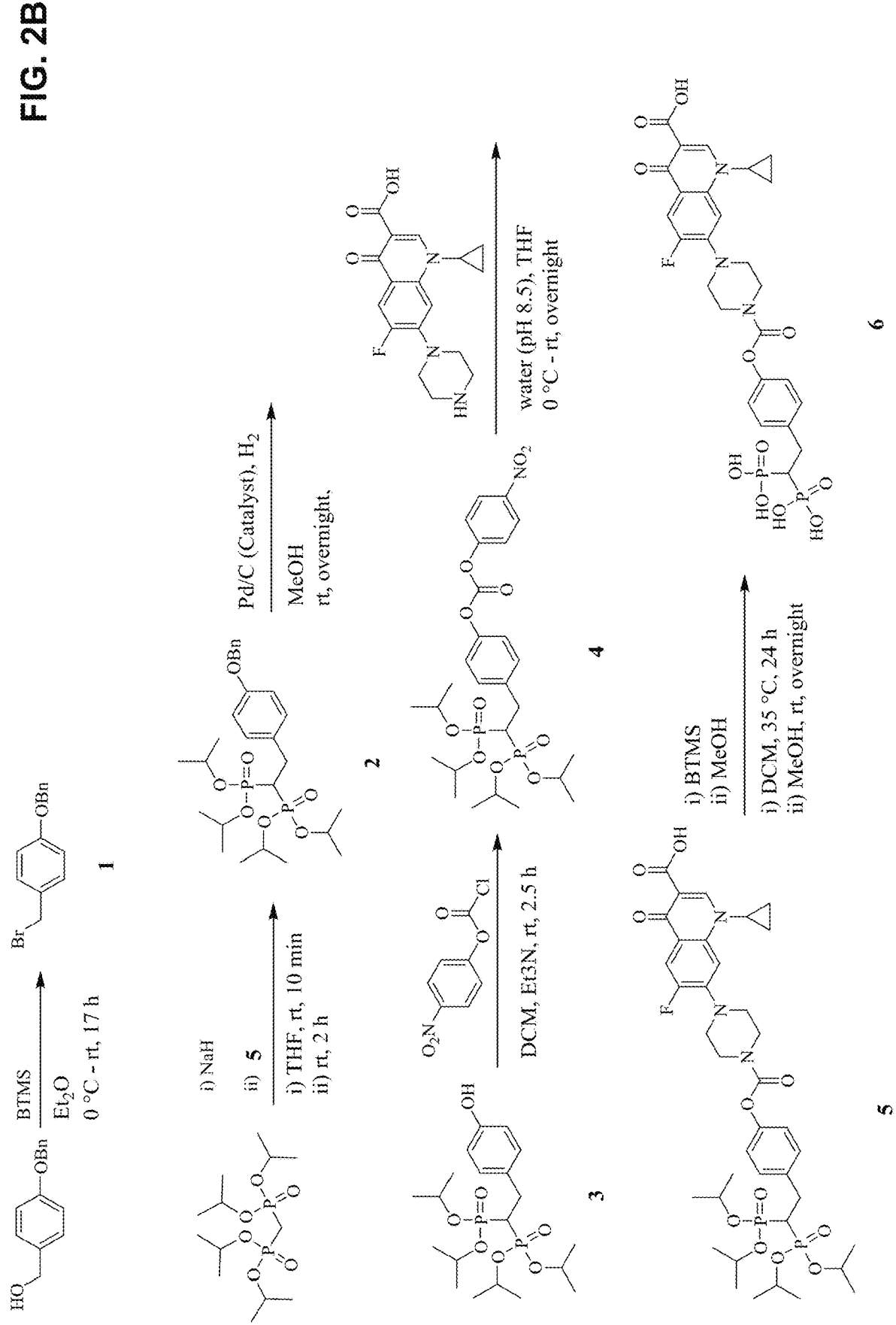

Chemistry:

The overall synthetic route for the one BP-ciprofloxacin conjugate (BCC, compound 6) is shown in Schemes in FIGS. 2A-2B. As a starting point our project team identified the inert 4-hydroxyphenylethylidene BP for this conjugation. The rationale for this BP design was to retain the bone-seeking ability of the BP moiety while suppressing its unneeded antiresorptive activity, enabling us to minimize confounders and focus uniquely on evaluating the antimicrobial effect due to the parent ciprofloxacin compound. BP ligands can be designed to have antiresorptive functionality (of varying potency) if needed to provide a dual-action effect of bone tissue protection in addition to antimicrobial effects at the anatomic site of infection. We also chose this phenyl BP with consideration to bone binding affinity and tether length, as previous studies have demonstrated that weak binding affinity decreases targeting efficiency and that lengthening the distance between the fluoroquinolone and the BP functionality can decrease the rate of hydrolysis and regeneration of the parent compound (Houghton, et al., Linking bisphosphonates to the free amino groups in fluoroquinolones: preparation of osteotropic prodrugs for the prevention of osteomyelitis. J. Med. Chem. 2008; 51:6955-69; Tanaka, et al., Bisphosphonated fluoroquinolone esters as osteotropic prodrugs for the prevention of osteomyelitis, Bioorg Med Chem 2008, 16:9217-29; McPherson, et al., Synthesis of osteotropic hydroxybisphosphonate derivatives of fluoroquinolone antibacterials, Eur J Med Chem 2012, 47:615-8). Most importantly, we believed the use of an aryl carbamate as a linker might offer optimized stability in plasma and adequate release on bone for this biochemical target relative to previous BP-F quinolone conjugates. Accordingly, the tetraethyl ester of 4-hydroxyphenylethylidene BP (4) was prepared as described previously (David, et al., Methylene-bis[(aminomethyl)phosphinic acids]: synthesis, acid-base and coordination properties. Dalton Trans 2013; 42:2414-22). The phenol group of BP (4) was then activated with p-nitrophenyl chloroformate to form compound (5) for conjugation with protected ciprofloxacin (7) (Fardeau, et al., Synthesis and antibacterial activity of catecholate-ciprofloxacin conjugates. Bioorg Med Chem 2014; 22:4049-60). Ciprofloxacin (6) was protected with a benzyl (Bn) group via a Di-t-butyl dicarbonate ($Boc_2O$) reaction. Final deprotection of the conjugate (8) with hydrogenolysis and bromotrimethylsilane (TMSBr) lead to our first fluoroquinolone phenyl carbamate BP-ciprofloxacin prodrug (9) ready for biochemical and antimicrobial evaluations.

Microbiology:

The first set of investigations we undertook were aimed at evaluating the antimicrobial activity of the conjugate in standard laboratory planktonic culture systems against a panel of 14 S. aureus clinical strains associated with bone infections (methicillin-sensitive: MSSA and methicillin-resistant: MRSA). Following EUCAST (European Committee on Antimicrobial Susceptibility Testing) guidelines, results from disc diffusion inhibition zone assays revealed diameters ranging from 25-40 mm (mean 31.5, SD±5), and every strain demonstrated antimicrobial sensitivity according to EUCAST breakpoints (EUCAST: European Committee on Antimicrobial Susceptibility Testing breakpoint tables for interpretation of MICs and zone diameters. 2015. http://www.eucast.org/fileadmin/src/media/PDFs/EUC). MIC results for BP-ciprofloxacin tested against all 14 strains using microdilution methodology are shown in FIG. 3. MICs for the parent compound ciprofloxacin alone were determined concurrently for reference (which shows Table 1) and were found to be consistent with established clinical breakpoints.[26] It has already been established that prodrugs in this class lack significant antibacterial activity of their own, and that any BP-related antimicrobial effect is negligible, therefore release of the parent drug is a prerequisite for observing any appreciable antimicrobial activity such as that reported here (Houghton, et al., Linking bisphosphonates to the free amino groups in fluoroquinolones: preparation of osteotropic prodrugs for the prevention of osteomyelitis. J. Med. Chem. 2008, 51:6955-69).

The AST and MIC data indicate that against planktonic *S. aureus* pathogens both the conjugate and ciprofloxacin have bactericidal activity, and that conjugation impacts ciprofloxacin antimicrobial activity in vitro with slightly greater concentrations of conjugate required to reach MIC than ciprofloxacin alone. This is anticipated since it is well-established that conjugation is based on chemical modification of both BP and the antibiotic that has to be delivered to bone; as a result, properties of the parent drug including its therapeutic effect can be altered by such modification. Our results are also consistent with previous literature in this field indicating that successful and functional conjugates retain the antibacterial activity of the parent compound, albeit at a slightly lower level (Herczegh, et al., Osteoadsorptive bisphosphonate derivatives of fluoroquinolone antibacterials. J. Med. Chem 2002, 45:2338-41; Houghton, et al., Linking bisphosphonates to the free amino groups in fluoroquinolones: preparation of osteotropic prodrugs for the prevention of osteomyelitis. J. Med. Chem 2008, 51: 6955-69; Zhang, et al., 'Magic Bullets' for bone diseases: progress in rational design of bone-seeking medicinal agents). Importantly, in the therapeutic context of osteomyelitis the pathogens are not planktonic (as in these standard assays) but rather biofilm, and bound to bone as a substrate, so the enhanced bone targeting property of the BP-ciprofloxacin conjugate should provide more than adequate concentrations of antibiotic for antimicrobial effect at bone and thus greater efficacy (as forthcoming biofilm-relevant in vitro and in vivo data support).

Figure 4:
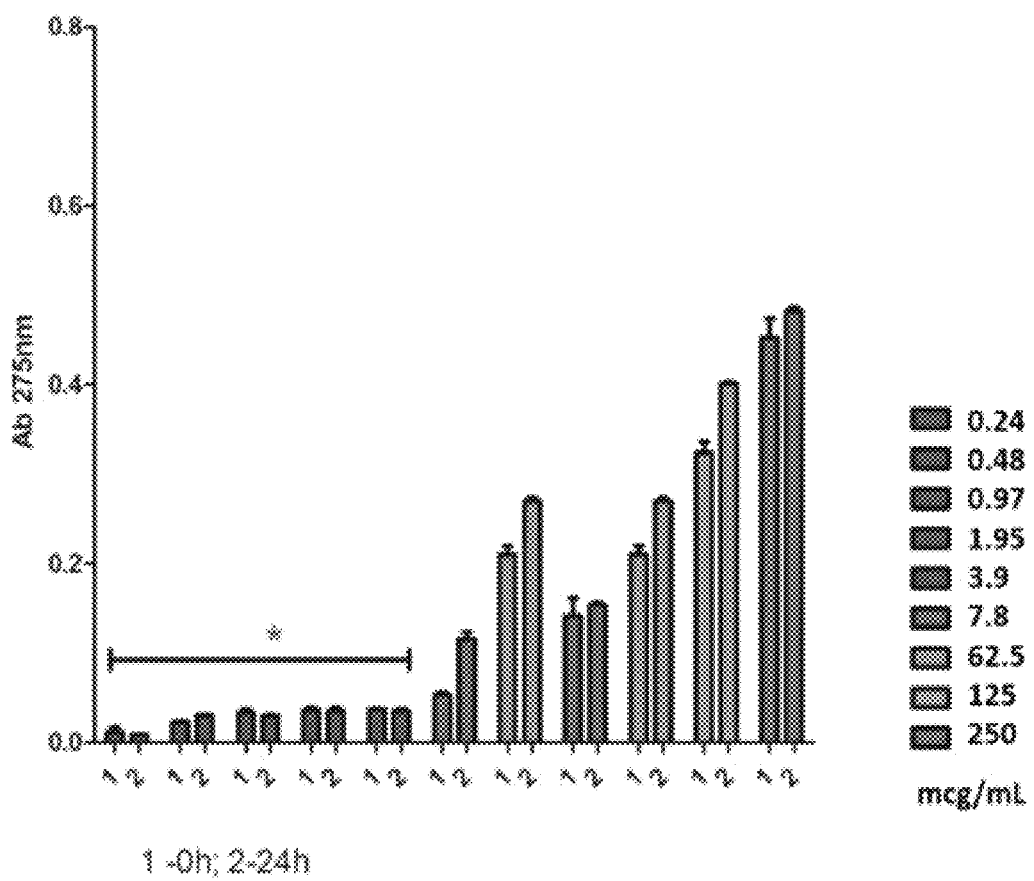
FIG. 4 shows a graph demonstrating the results from a spectroscopic analysis of BP-ciprofloxacin conjugate in trypticase soy broth microbiological media at 0 hr and at 24 hrs for the various concentrations of the conjugate used in antimicrobial susceptibility testing in vitro; no degradation is observed after 24 hrs, which is the typical length of an experimental period for in vitro antimicrobial testing, indicating excellent stability of the antimicrobial. [*results for 0.24-3.9 mcg/mL (red bars) are inconclusive because of a high value of "blank" measurements]

Because microbiological media used for in vitro antimicrobial testing has proteins, carbohydrates, enzymes and salts/metals, the potential exists for degradation, denaturation or chelation of BP-ciprofloxacin during antimicrobial testing. This could adversely impact antibiotic activity and be unrelated to the chemical conjugation itself. Based on our AST and MIC results and demonstrable antimicrobial efficacy of the conjugate this is highly unlikely to any significant extent. Nonetheless, we sought to objectively assess BP-ciprofloxacin stability by introducing the conjugate to trypticase soy broth microbiological media and conducting quantitative spectroscopic analysis as shown in FIG. 4. Results indicated excellent stability of the antimicrobial with no evidence of degradation or denaturation in microbiological media after 24 hrs. Therefore, microbiological media likely has little to no adverse effect on conjugate activity and efficacy.

Figure 5:
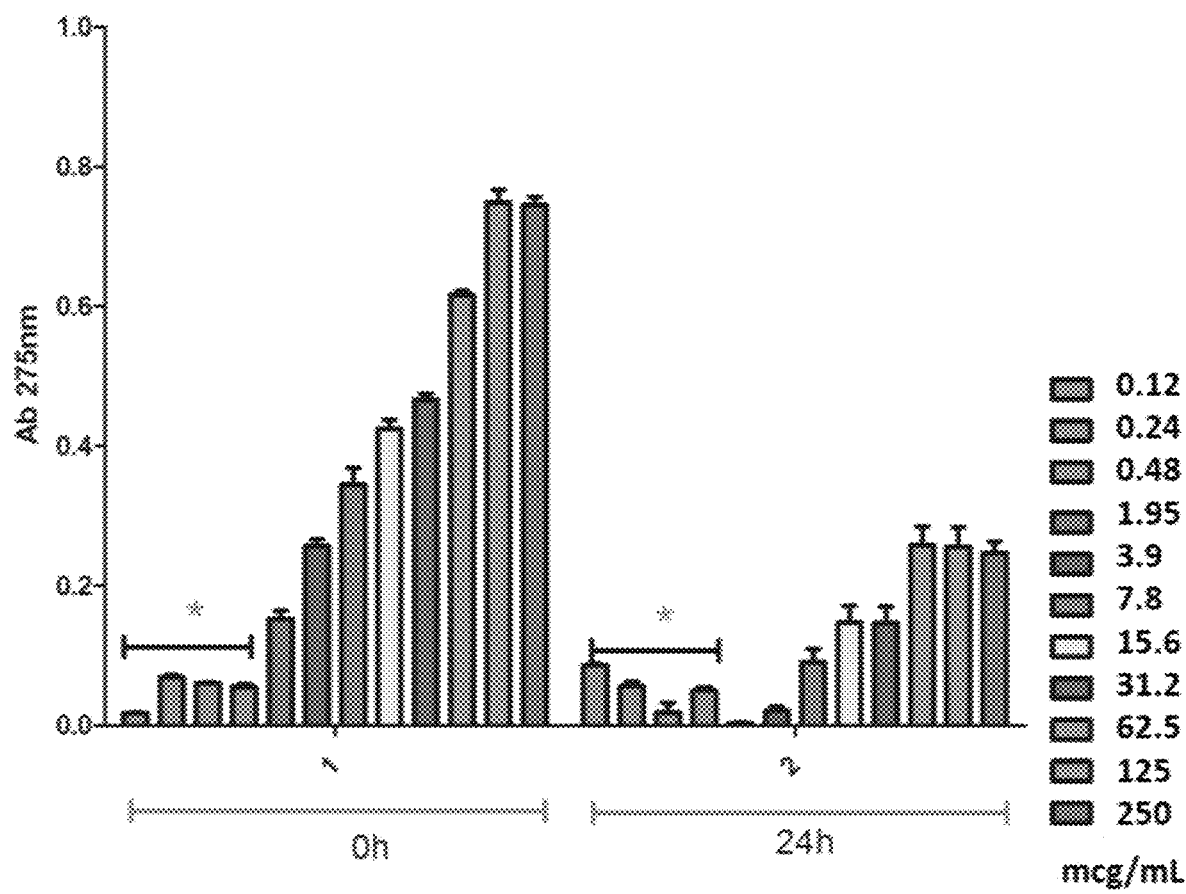
FIG. 5 shows a graph demonstrating the results of a spectroscopic analysis of one BP-ciprofloxacin conjugate (BP-carbamate-Ciprofloxacin, BCC, compound 6) in trypticase soy broth microbiological media with the addition of HA spherules; the significant decreases from 0 hr to 24 hrs confirms conjugate adsorption to HA since only the supernatant is measured absent the HA spherules with adsorbed conjugate. [results for 1.95-250 mcg/mL are all statistically significant: p<0.05, ANOVA; triplicate; *results for 0.12-0.48 mcg/mL (red bars) are inconclusive because of a high value of "blank" measurements].

Having established the antimicrobial efficacy and chemical stability of the conjugate, we next sought to evaluate HA binding ability. When we added HA spherules to our microbiological media and then introduced BP-ciprofloxacin at various concentrations similar to those used in our antimicrobial testing, quantitative spectroscopic analysis of supernatant (without HA spherules) confirmed significant adsorption and retention of the conjugate by HA (FIG. 5). These results are consistent with previously reported analogs in this class containing BP moieties with similar bone affinities (Tanaka, et al., Bisphosphonated fluoroquinolone esters as osteotropic prodrugs for the prevention of osteomyelitis. Bioorg Med Chem 2008; 16:9217-29; McPherson, et al., Synthesis of osteotropic hydroxybisphosphonate derivatives of fluoroquinolone antibacterials. Eur J Med Chem 2012; 47:615-8). Bone adsorption also appeared to be a concentration-dependent phenomenon.

Figure 6:
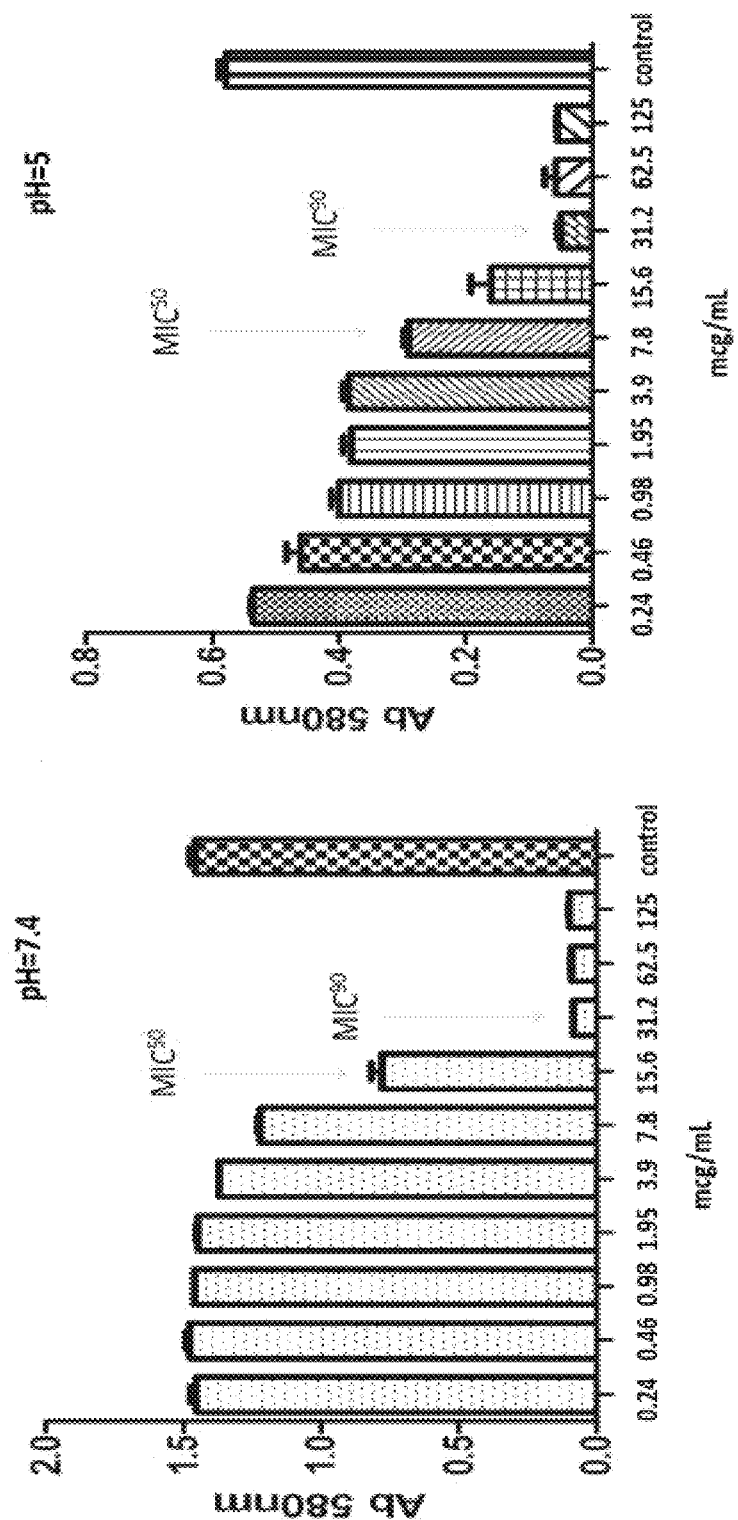
FIG. 6 shows graphs demonstrating the results from antimicrobial susceptibility testing of BP-ciprofloxacin against planktonic cultures of S. aureus strain ATCC-6538 shows an improved bactericidal profile in acidic (right graph) versus basic (left graph) pH.

We then selected the *S. aureus* strain ATCC-6538 for further testing because it demonstrated the least susceptibility and poorest MIC profile to both ciprofloxacin and the conjugate (FIG. 3) as compared to other tested strains. This strain is also a well-known and robust biofilm forming pathogen as compared to other tested strains. Consequently, we could test and optimize our conjugate against the most virulent pathogen to limit bias and overestimated results, while also facilitating the testing of antimicrobial activity in biofilm-based and clinically relevant models. So, we performed AST on planktonic *S. aureus* strain ATCC-6538 with BP-ciprofloxacin under both acidic and basic conditions to assess the effect of pH on conjugate activity. Quantitative results from standard microdilution methodology indicated that under acidic conditions antimicrobial activity was improved overall, and the $MIC^{50}$ was reached at half the conjugate concentration required to reach $MIC^{50}$ under basic conditions (FIG. 6). This could be useful for clinical osteomyelitis applications where biofilm pathogens along with host inflammation and osteoclastogenesis produce an acidic local milieu. Other investigators have suggested, however, that although the local acidity brought on by infecting organisms and inflammation might be associated with some drug release in bone, the efficiency of such a process in providing a sufficient concentration of the antimicrobial agent is doubtful, and that prodrug design and conjugation scheme likely play a greater role (Houghton, et al., Linking bisphosphonates to the free amino groups in fluoroquinolones: preparation of osteotropic prodrugs for the prevention of osteomyelitis. J. Med. Chem 2008; 51:6955-69). Finally, AST data also indicated that MICs for ciprofloxacin and the conjugate were equivalent to their mean bactericidal concentrations (MBCs), respectively.

Next, time-kill assays were performed with the conjugate according to CLSI (Clinical Laboratory Standards Institute) methods and results indicated that the conjugate was bactericidal at the previously established MIC for methicillin-susceptible (ATCC-6538) and methicillin-resistant (MR4-CIPS) isolates of planktonic *S. aureus* within 1 hr and up to 24 hrs, preventing 100% of growth; these kinetic studies indicated that half the MIC was bactericidal within 1 hr and also inhibited growth (50%) up to 24 hrs as compared to controls (FIG. 7) (CLSI. M100-S25 performance standards for antimicrobial susceptibility testing; Twenty-fifth informational supplement; 2015). Kinetic results demonstrate the time efficacy of the conjugate against tested bacteria and the sustained bactericidal activity over 24 hrs, supporting cleavage activity in the presence of tested bacteria.

Figure 8:
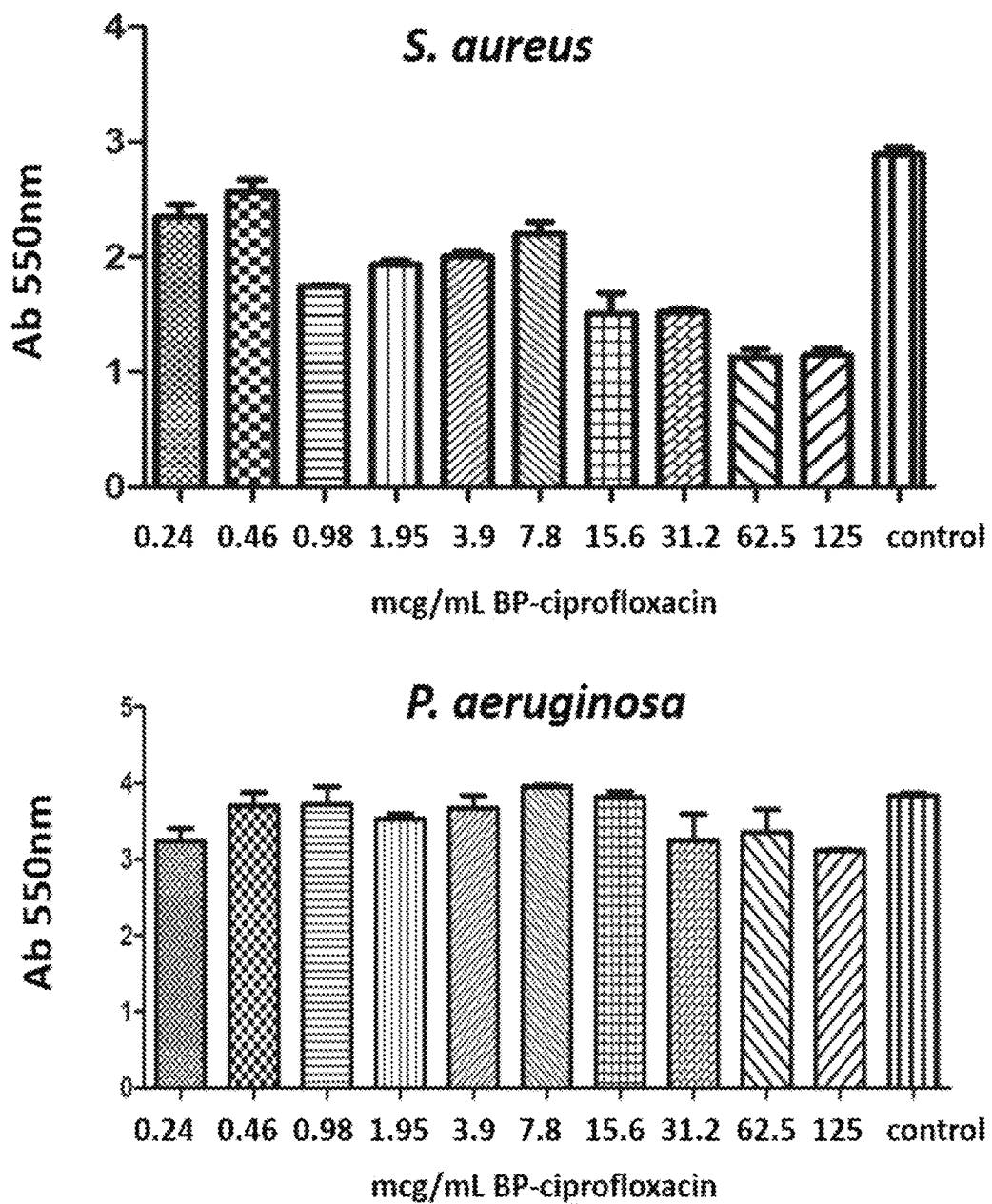
FIG. 8 shows graphs demonstrating results from antimicrobial susceptibility testing of BP-ciprofloxacin against biofilms of S. aureus strain ATCC-6538 (top graph) and P. aeruginosa strain ATCC-15442 (bottom graph) formed on polystyrene as a substrate.

Next, we tested the conjugate against pre-formed bacterial biofilms on two different substrates (polystyrene and HA discs) to evaluate antimicrobial efficacy against biofilms for the first time in this context, and to also determine if substrate specificity plays a role. Biofilms of *S. aureus* (ATCC-6538), and additionally biofilms of *Pseudomonas aeruginosa* (ATCC-15442), were subjected to BP-ciprofloxacin and antimicrobial activity was assessed. We also tested *P. aeruginosa* here because it is the second most common clinical pathogen in osteomyelitis, though far less frequent in prevalence than *S. aureus* cases. FIG. 8 shows results for polystyrene as the substrate for biofilm growth, and the minimal biofilm inhibitory concentration ($MBIC^{50}$) of BP-ciprofloxacin was 15.6-31.2 mcg/mL for *S. aureus* ATCC-6538, which was comparable to the MIC for this strain in planktonic cultures; no $MBIC^{50}$ was observed for *P. aeruginosa* ATCC-15442 in the tested range of concentrations.

Figure 9:
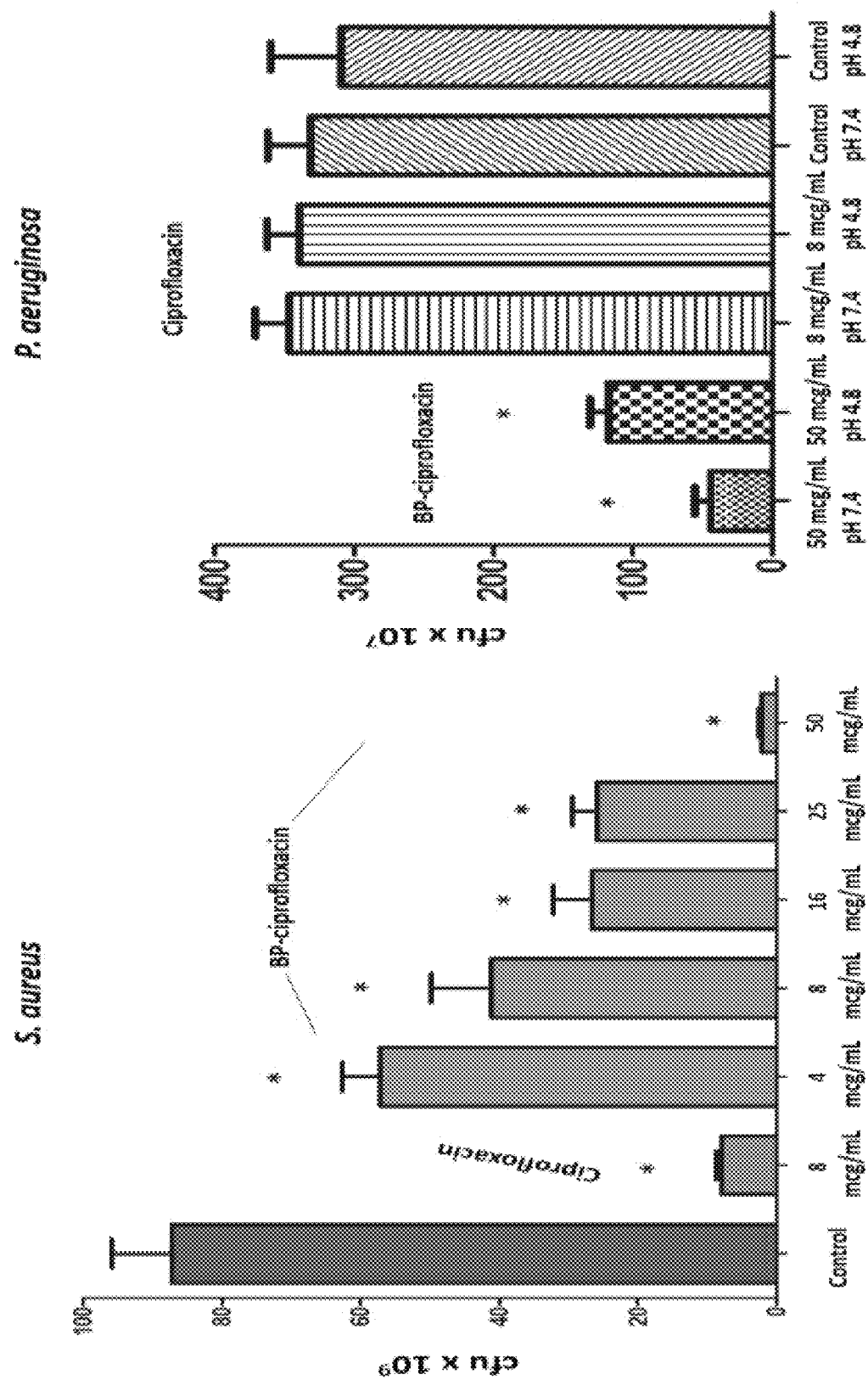
FIG. 9 shows graphs demonstrating results from antimicrobial susceptibility testing of BP-ciprofloxacin against biofilms of S. aureus strain ATCC-6538 (left graph) and P. aeruginosa strain ATCC-15442 (right graph) formed on HA discs as the substrate. All tested concentrations of the conjugate (orange bars) resulted in statistically significant bactericidal activity against S. aureus including ciprofloxacin alone (red bar). [*p<0.05, Kruskal-Wallis test; triplicate].

However, when HA discs were used as the biofilm substrate, markedly improved bactericidal activity was observed as shown in FIG. 9, and all tested concentrations of the conjugate resulted in statistically significant bactericidal activity and reduction of colony forming units (CFUs). The $MBIC^{50}$ of the conjugate was 8 mcg/mL and the $MBIC^{90}$ was 50 mcg/mL against *S. aureus* strain ATCC-6538; the $MBIC^{90}$ for the parent drug ciprofloxacin was 8 mcg/mL against this pathogen. However, against *P. aeruginosa* strain ATCC-15442 ciprofloxacin had no inhibitory or bactericidal activity while the conjugate was bactericidal in acidic and basic conditions at 50 mcg/mL, and showed improved bactericidal activity in basic conditions as compared to *S. aureus* where improved antimicrobial activity was observed in acidic conditions. Overall, these results suggest that the conjugate is more effective against biofilm pathogens in the presence of HA versus polystyrene as a substrate, and that substrate specificity plays a role in antimicrobial activity in addition to factors like strain of pathogen tested and mode of bacterial growth (planktonic versus biofilm). This has not been demonstrated previously and adds insight into antimicrobial potential of these compounds for clinical applications against biofilm pathogens.

Figure 10:
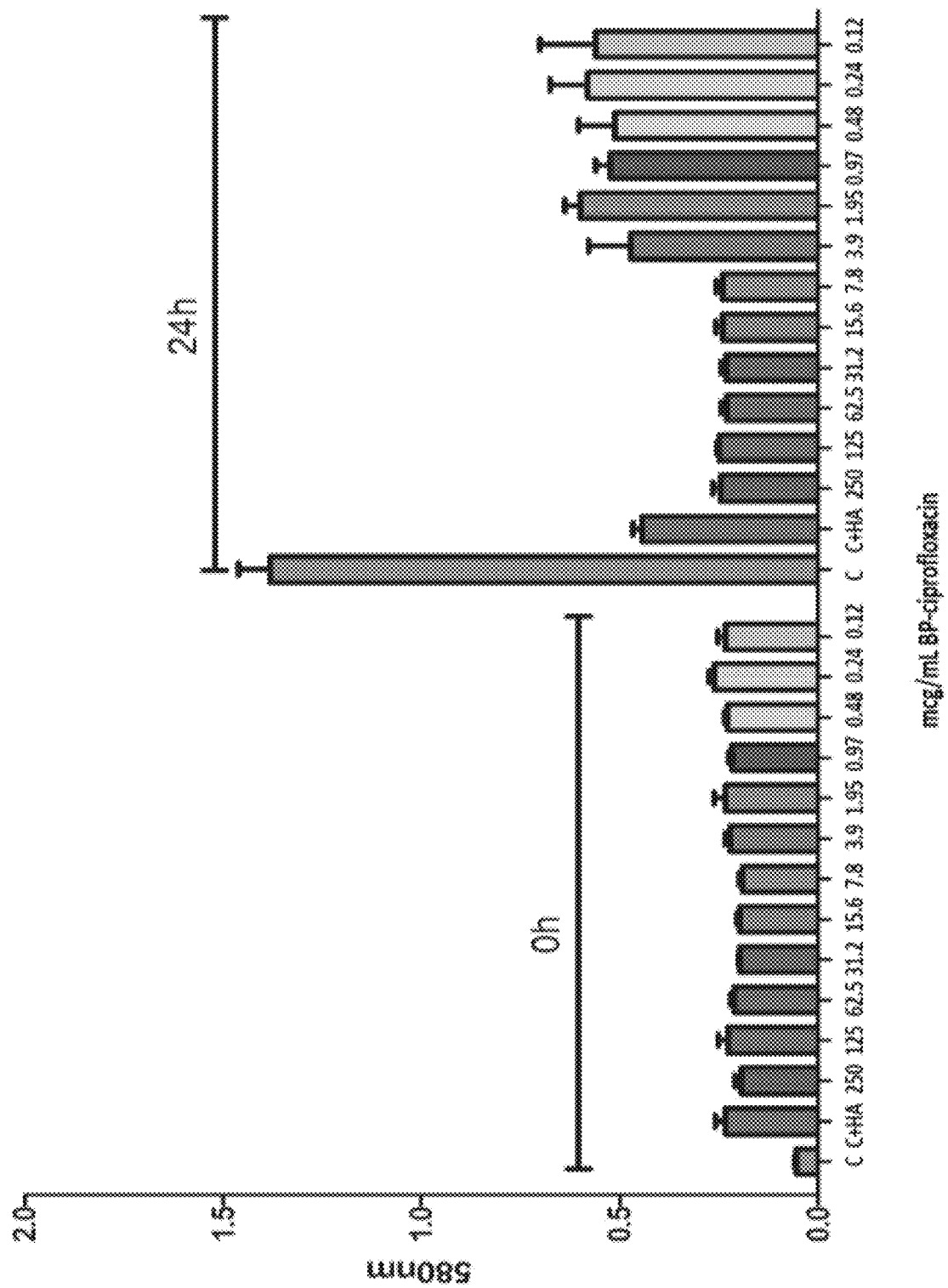
FIG. 10 shows a graph demonstrating results from preventative experiments where HA spherules are pre-coated with BP-ciprofloxacin and then inoculated with S. aureus. Control (C: red bar) represents cultured bacteria without HA and not treated with conjugate, and after 24 hrs an expected significant increase in planktonic growth is observed when the supernatant is measured. Control+HA (C+HA bar) represents cultured bacteria with HA, but still no treatment, and after 24 hrs some bacterial growth is observed but not as much as the HA negative control (red bar) because bacteria bind to HA and form biofilms which are not measured in the HA free supernatant. Comparing these controls to the treatments we can see that at 7.8 to 250 mcg/mL of the conjugate there is complete bacterial inhibition after 24 h. At lower concentrations ranging from 0.12 to 3.9 mcg/mL bacteria grew slightly but were still strongly inhibited.

Lastly, we performed antimicrobial tests with the conjugate in a preventative type of experimental setting with planktonic and biofilm cultures, which could also have clinical relevance in antibiotic prophylactic scenarios for osteomyelitis. Here HA spherules were introduced to varying concentrations of BP-ciprofloxacin and then inoculated with *S. aureus* for 24 hrs, and quantitative assessments indicated no bacterial growth at concentrations as low as 7.8 mcg/mL and up to 250 mcg/mL of the conjugate, and minimal bacterial growth with strong inhibition at conjugate concentrations ranging from 0.12 to 3.9 mcg/mL as shown in FIG. 10.

We then used HA discs as substrates for growing *S. aureus* biofilms again, but this time the discs were rinsed with media after incubation of either BP-ciprofloxacin or ciprofloxacin prior to inoculation and biofilm growth. FIG. 11 shows results of quantitative biofilm cultures and CFUs after 24 hrs of growth, and at 100 mcg/mL ciprofloxacin inhibited all biofilm growth whereas at 10 mcg/mL BP-ciprofloxacin inhibited all growth. Since the molecular mass of ciprofloxacin is approximately half that of the conjugate, the conjugate was 20× more active in achieving complete bactericidal action as compared to ciprofloxacin alone. These findings support an efficient mechanism of enzymatic cleavage and release over time of the parent drug ciprofloxacin from the prodrug. Efficient binding to HA and cleavage or regeneration of the parent antibiotic is requisite for conjugates in this class to demonstrate substantial antimicrobial efficacy comparable or better than the parent antibiotic alone (Houghton, et al., Linking bisphosphonates to the free amino groups in fluoroquinolones: preparation of osteotropic prodrugs for the prevention of osteomyelitis. J. Med. Chem 2008; 51:6955-69; (Tanaka, et al., Bisphosphonated fluoroquinolone esters as osteotropic prodrugs for the prevention of osteomyelitis. Bioorg Med Chem 2008; 16:9217-29; McPherson, et al., Synthesis of osteotropic hydroxybiphosphonate derivatives of fluoroquinolone anti bacterials).

In Vivo Safety and Efficacy:

Since this BP-ciprofloxacin conjugate is novel and has not been tested in vivo, we performed an initial safety and efficacy study in an animal model of peri-implant osteomyelitis. This model is a unique in-house jawbone peri-implant osteomyelitis model that was developed specifically for translational value to study biofilm-mediated disease and host response in vivo (Freire, et al, Development of animal model for *Aggregatibacter actinomycetemcomitans* biofilm-mediated oral osteolytic infection: a preliminary study. J Periodontol 2011; 82:778-89). Briefly, biofilms of the jawbone osteomyelitis pathogen *Aggregatibacter actinomycetemcomitans* (Aa; wild-type rough strain D7S-1; serotype a), which is not indigenous to rat normal flora, are pre-inoculated on miniature titanium implants at $10^9$ CFU. To confirm Aa sensitivity to the parent drug ciprofloxacin prior to our animal studies, we performed AST and MIC assays as performed for the long bone osteomyelitis pathogens described previously. Disc diffusion inhibition zone assays revealed diameters >40 mm, and the $MIC^{90}$ was 2 mcg/mL, indicating strong susceptibility of this microbe to the parent drug ciprofloxacin. Aa has also been tested previously for susceptibility to a pH-sensitive biotinylated ciprofloxacin prodrug and was found to be sensitive to the parent antibiotic (Manrique, et al., Perturbation of the indigenous rat oral microbiome by ciprofloxacin dosing. Mol Oral Microbiol 2013; 28:404-14). After biofilms are established on the implants in vitro, they are surgically transferred to the jawbone of each rat. Animals are anesthetized, the cheeks are retracted and a transmucosal osteotomy is performed so implants can be manually inserted into the osteotomy and secured. Two biofilm-inoculated implants are placed in each rat (n=12 rats and 24 implants) in the palatal bone bilaterally. This model allows standardized and reproducible quantities of viable bacteria to be formed as well-established biofilms on each implant, which we have previously demonstrated persists in vivo for several weeks after placement and causes infection, inflammation and bone destruction locally (Freire, et al, Development of animal model for *Aggregatibacter actinomycetemcomitans* biofilm-mediated oral osteolytic infection: a preliminary study. J Periodontol 2011; 82:778-89).

Once peri-implant infection is established 1 week postoperatively, the animals are dosed with BP-ciprofloxacin, ciprofloxacin alone as a positive control, and sterile endotoxin-free saline as a negative control at the dosing regimens specified in the experimental section. To determine appropriate dosing concentrations, we calculated approximate initial doses for the conjugate based on previous studies and pharmacokinetic data using similar target and release strategies and also rodents (Houghton, et al., Linking bisphosphonates to the free amino groups in fluoroquinolones: preparation of osteotropic prodrugs for the prevention of osteomyelitis. J Med Chem 2008; 51:6955-69; Morioka, et al., Design, synthesis, and biological evaluation of novel estradiol-bisphosphonate conjugates as bone-specific estrogens. Bioorg Med Chem 2010; 18:1143-8). We expected that increasing doses of 0.1, 1 and 10 mg/kg BP-ciprofloxacin molar equivalents will allow us to determine antimicrobial activity in 2 test animals per group based on sample size estimations and previous experience with the animal model (Freire, et al, Development of animal model for *Aggregatibacter actinomycetemcomitans* biofilm-mediated oral osteolytic infection: a preliminary study. J Periodontol 2011; 82:778-89). Animals were dosed via intraperitoneal injection under general anesthesia, and all compounds were constituted in sterile physiological injectable saline at appropriate pH. One week after pharmacotherapy, all animals were sacrificed and resection of peri-implant tissues was performed, and tissues were immediately homogenized and processed for quantitative assessment of microbial load.

Animals were monitored throughout the study period for local or systemic adverse effects of pharmacotherapy.

Figure 12:
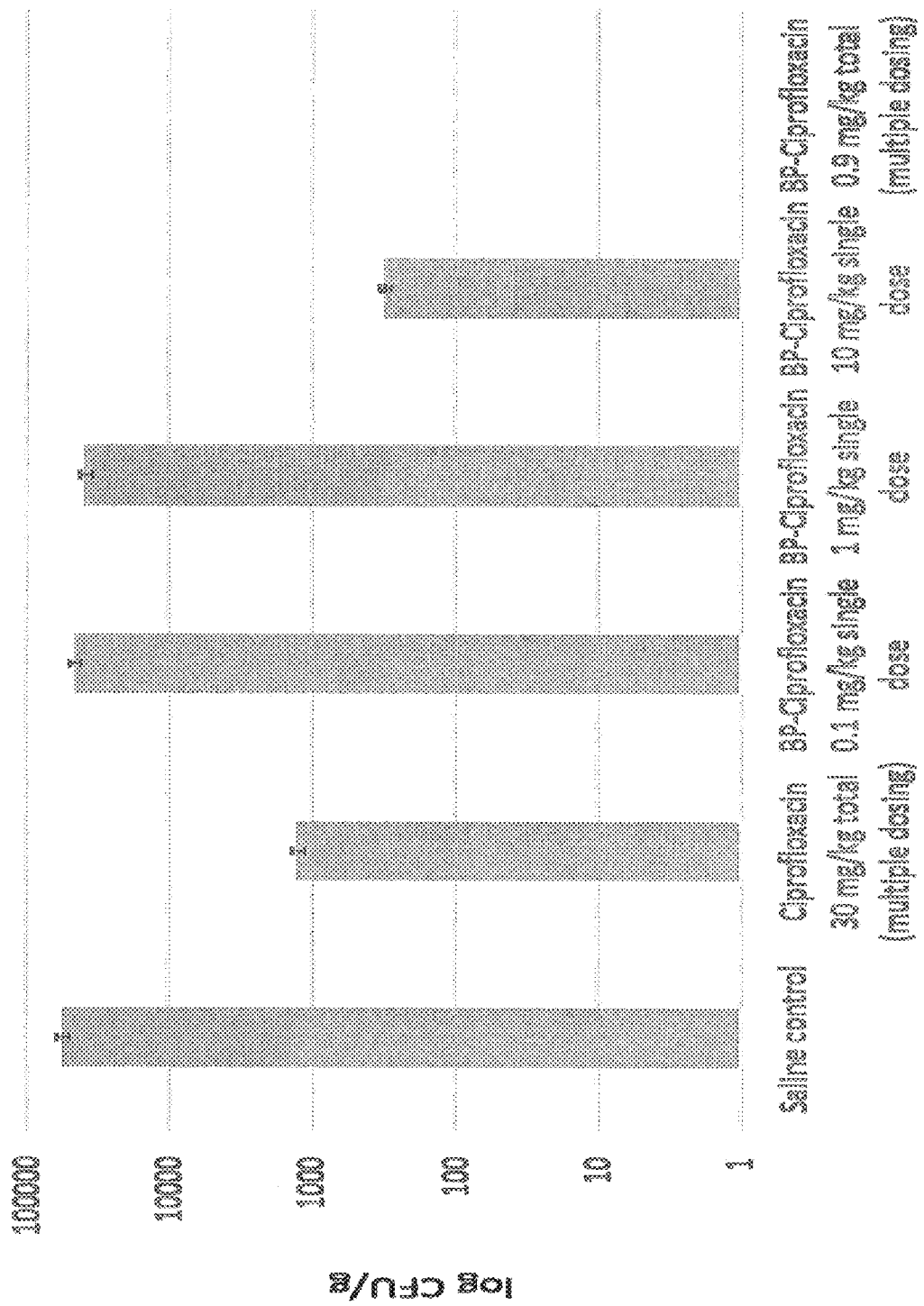
FIG. 12 shows a graph demonstrating the antimicrobial results from in vivo animal testing showing efficacy of tested compounds for reducing bacterial load. The conjugate showed the greatest efficacy at 0.9 mg/kg total given in multiple doses, with no recoverable bacteria. Next a single dose of 10 mg/kg of the conjugate demonstrated 2 log reduction (99% bactericidal activity) as compared to the negative control, and nearly 1 log greater bactericidal activity as compared to the multiple dosing regimen of ciprofloxacin alone which demonstrated a 1 log reduction.

All animals tolerated the pharmacotherapy well with no cutaneous injection-site reactions or inflammation, and no systemic adverse events were reported by managing veterinarians throughout the study period. Treatment efficacy was quantitatively measured in terms of the logarithm of the amount of viable bacteria (average log CFU per gram of tissue) as shown in FIG. 12.

In vivo, the animals dosed with the conjugate at 0.3 mg/kg in multiple doses (×3) over the course of a week demonstrated no recovery of Aa or 100% killing. A single dose of BP-ciprofloxacin at 10 mg/kg also showed high efficacy with 2 log reduction or 99% bacterial killing and more than an order of magnitude greater activity than ciprofloxacin alone at the same total concentration but in multiple doses. Ciprofloxacin alone in a multiple dosing regimen resulted in 1 log reduction or 90% bacterial killing, which was expected and why we chose it as the positive control given the known efficacy of this compound, its antimicrobial activity, and the fact that it represents the parent drug of the conjugate. Conjugate concentrations of 0.1 and 1 mg/kg had little effect, suggesting that further optimization is possible in this context. Nonetheless, given the targeting and release ability of the prodrug, effective doses can be reasonably achieved in a clinical setting given the safety profile of constituent compounds and the ability to dose orally or intravenously. Interestingly, in the conjugate multiple dosing group our cultures showed evidence of yeast morphology and no recoverable Aa. One explanation for this phenomenon could be contamination, although this is highly unlikely since methodology was performed similarly and simultaneously, yeast is not cultured in our laboratory, the only animal samples where Aa was not recovered were in this same multiple dosing group and in two separate animals. Therefore, a more likely explanation is that killing and resolution of Aa occurred in vivo and that another organism less sensitive to the parent drug ciprofloxacin grew in our cultures, such as yeast. In fact rats are used as a well-established model for oral candidiasis and their equivalent to normal human oral flora yeast is *Candida pintolopessi*, which can cause unexpected disease in antibiotic-treated or immune-compromised rodents (Junqueira. Models hosts for the study of oral candidiasis. Adv Exp Med Biol. 2012; 710:95-105). This is also a well-known phenomenon in human patients treated with antibiotics, namely yeast overgrowth or candidiasis due to suppression of bacterial flora that normally competes with yeast in vivo.

The resolution of infection over time in vivo with the conjugate as compared to negative controls, and also as compared to the positive control parent drug, further supports that the conjugate binds effectively to bone and releases the parent antibacterial agent. Lack of efficacy in this model would suggest either that the prodrug is not binding to or that it is not releasing the parent drug. This provides at least an indirect way to understand the pharmacokinetics of the prodrug in vivo (Houghton, et al., Linking bisphosphonates to the free amino groups in fluoroquinolones: preparation of osteotropic prodrugs for the prevention of osteomyelitis. J. Med. Chem. 2008; 51:6955-69). A similar study but in a rat tibia osteomyelitis model tested the activity of BP-fluoroquinolones and found similar efficacy and evidence of greatly enhanced antimicrobial activity of tested conjugates, but in a preventative context where a single intravenous injection of the prodrug was administered 1-2 days before an infection of the bone (Houghton, et al., Linking bisphosphonates to the free amino groups in fluoroquinolones: preparation of osteotropic prodrugs for the prevention of osteomyelitis. J. Med. Chem. 2008; 51:6955-69). The infection in this model was created by injecting a bolus of planktonic bacteria in the surgically exposed tibia and the animals were sacrificed 24 h after infection. This study was not a biofilm-mediated osteomyelitis treatment study, but is consistent with in vitro data presented herein demonstrating that biofilm growth can be prevented with pre-treatment of BP-ciprofloxacin (Houghton, et al., Linking bisphosphonates to the free amino groups in fluoroquinolones: preparation of osteotropic prodrugs for the prevention of osteomyelitis. J. Med. Chem. 2008; 51:6955-69). Our experiment confirms the ability of a BP-ciprofloxacin prodrug at safe and adequate single dose produces a sufficient concentration of the parent drug to maintain bactericidal activity against established biofilms when the activity of the parent antibiotic alone has already diminished. This conjugate will be further evaluated for the ability to treat long bone osteomyelitis in an animal model, and comprehensive pharmacokinetic and pharmacodynamic studies will also be performed in vivo; the results of these examinations will be presented in due course.

Discussion

This Example demonstrates successful design and synthesis of a phenyl carbamate BP-ciprofloxacin conjugate utilizing a target and release strategy, and systematically evaluated functionality of each constituent of this compound (as well as the conjugate as a whole) in vitro and in vivo. In vitro antimicrobial investigations of BP-ciprofloxacin tested against common osteomyelitis pathogens revealed a strong bactericidal profile, and safety and efficacy was demonstrated in vivo in an animal model of peri-prosthetic osteomyelitis. In vivo, the animals dosed with the conjugate at 0.3 mg/kg in multiple doses (0.9 mg/kg total) over the course of a week demonstrated optimal efficacy with no recoverable bacteria. A single dose of 10 mg/kg of conjugate (5 mg ciprofloxacin considering the molecular mass of the conjugate is twice that of the parent drug) also showed strong antimicrobial activity and resulted in 99% killing of bacteria. The multiple dosing of the conjugate and the highest single dose of the conjugate were superior to multiple dosing of the parent antibiotic ciprofloxacin at 30 mg/kg. Lower single dose concentrations (0.1 and 1 mg/kg) of the conjugate were not efficacious.

These findings indicate a minimum dose is necessary for in vivo efficacy of the conjugate when given as a single dose, but that a much lower concentration of the conjugate when dosed regularly can provide greatest efficacy and at $<\!\!\frac{1}{10}^{th}$ the concentration of the parent antibiotic. For translation to practice this targeting strategy could prove useful by reducing dosing concentrations for patients and improving therapeutic index, and also by limiting systemic exposure. Importantly, these results along with other studies in this field are indicating that direct comparisons between these prodrugs and their parent compound are somewhat arbitrary as conjugates have unique pharmacometric parameters. Any future pharmacokinetic modeling for conjugates in this class would have to include a skeletal compartment of distribution mathematically, which is not generally done with antibiotic pharmacokinetic studies. This would provide for novel pharmacological data and also has in vivo implications.

BP-ciprofloxacin was also tested against clinically relevant biofilms for the first time here, and demonstrated strong antimicrobial activity when biofilms were attached to bone as a substrate both in vitro and in vivo. Antimicrobial activity of the conjugate appears to be associated with many parameters, including the species and strain of pathogen tested, its mode of growth (biofilm versus planktonic), substrate for biofilm colonization, pH, concentration, bone binding affinity and release kinetics. Optimization of this class of conjugates using BPs as biochemical vectors for the delivery of antimicrobial agents to bone (where biofilm pathogens reside) through a target and release strategy should represent an advantageous approach to the treatment of osteomyelitis and provide for improved pharmacokinetics while minimizing systemic toxicity.

Materials and Methods
Chemistry:

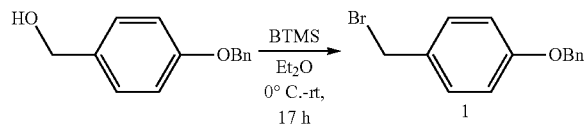 [SMILES: OCc1ccc(OCc2ccccc2)cc1 ; BrCc1ccc(OCc2ccccc2)cc1]

1-(benzyloxy)-4-(bromomethyl)benzene (1)

4-Benzyloxy benzyl alcohol (1.00 g, 4.67 mmol) was dissolved in anhydrous diethyl ether (25 ml) in an oven-dried flask under nitrogen. The flask was cooled in an ice bath. Bromotrimethylsilane (BTMS, 1.26 ml, 9.52 mmol) was added by syringe. The flask was allowed to slowly warm to room temperature. After 17 h of stirring, the reaction mixture was poured into water (50 ml) and the organic phase was separated. The aqueous phase was washed with diethyl ether (2×20 ml) then the combined organic phase was washed with brine (2×20 ml) and dried over sodium sulfate. Evaporation of the ether gave the product as a white crystalline solid (1.23 g, 95% yield) $^1$H NMR (400 MHz, Chloroform-d) δ 7.47-7.28 (m, 7H), 6.98-6.90 (m, 2H), 5.07 (s, 2H), 4.50 (s, 2H).

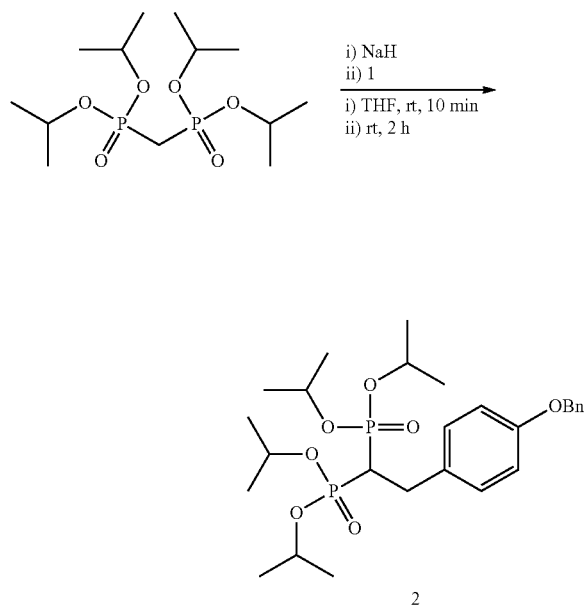

Tetraisopropyl (2-(4-(benzyloxy)phenyl)ethane-1,1-diyl)bis(phosphonate) (2)

Under nitrogen protection, anhydrous THF (2 ml) was added to sodium hydride 57-63% dispersion in mineral oil. Tetraisopropyl methylene diphosphonate (0.57 ml, 1.8 mmol) was added dropwise with stirring at room temperature. Gas was evolved and the grey suspended solid was consumed leaving a mostly clear solution. The mixture was stirred a further 10 min. Solid 1 was added in one portion under nitrogen counterflow. Solution remained clear for 1 min and then became cloudy. Stirring was maintained for 2 h then the reaction was checked by TLC (100% EtOAc visualized by UV or cerium ammonium molybdate (CAM) stain) two new spots were apparent at RF=0.37 and 0.58. Some 1 (RF>0.9) remained, reaction was heated to 50° C. for 30 min, little progress was apparent by TLC) Reaction mixture was poured into 5% aqueous citric acid and extracted with ether (2×30 ml), washed with brine and evaporated. The residue was purified by flash chromatography using 230-400 mesh silica using 10% EtOAc in hexane increasing to 100% EtOAc as eluent. Desired compound was obtained as a colorless oil (0.508 g, 52% yield)

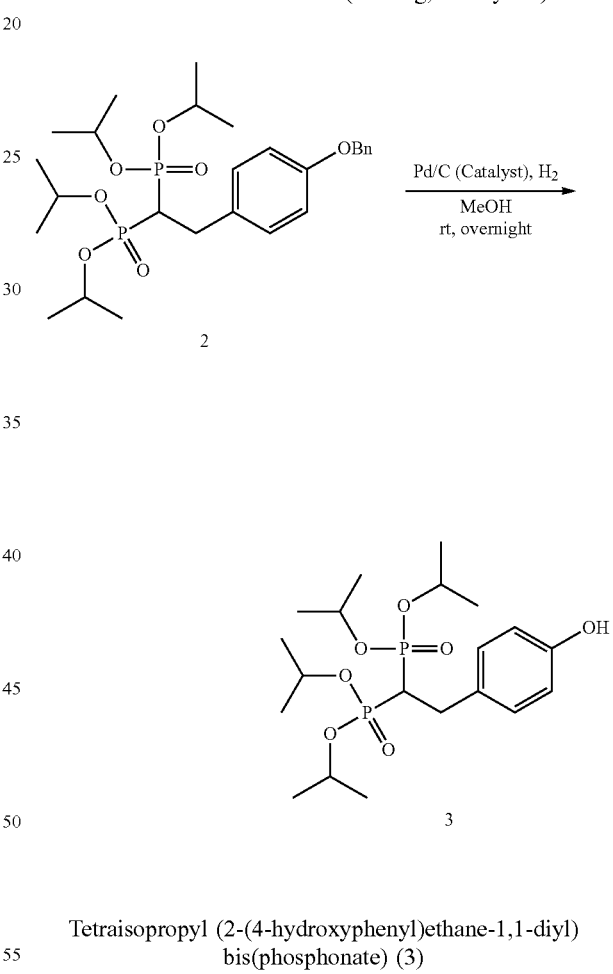

Tetraisopropyl (2-(4-hydroxyphenyl)ethane-1,1-diyl)bis(phosphonate) (3)

Compound 2 (0.508 g, 0.925 mmol) was dissolved in 13 ml of methanol and 70 mg of 10% palladium on carbon was added. The flask was flushed with nitrogen, then hydrogen and stirred overnight with a hydrogen balloon in place. TLC (10% MeOH in EtOAc, vis. w/ UV or CAM stain) showed disappearance of the starting material (RF=0.63) and appearance of a new spot with RF=0.49. The reaction mix was filtered through celite with 100 ml of methanol. Evaporation of the filtrate gave the desired compound as a slightly yellow oil (0.368 g, 88% yield) that was used without further purification. ¹H NMR (400 MHz, Chloroform-d) δ 7.07 (d, 21.06. J=8.2 Hz, 2H), 6.69 (d, J=8.2 Hz, 2H), 4.71 (m, 4H), 3.11 (td, J=16.9, 6.0 Hz, 2H), 2.47 (tt, J=24.4, 6.0 Hz, 1H), 1.32-1.21 (m, 24H). 31P NMR (162 MHz, Chloroform-d) δ

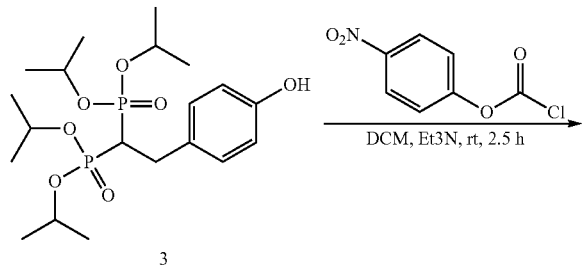

4-(2,2-bis(diisopropoxyphosphoryl)ethyl)phenyl (4-nitrophenyl) carbonate (4)

Compound 3 (0.171 g, 0.380 mmol) was dissolved in 8 ml of dichloromethane then triethylamine (159 μl, 1.14 mmol) was added followed by p-nitrophenyl chloroformate (0.086 g, 0.418 mmol) in one portion. The solution turned from colorless to yellow immediately. After stirring for 2.5 h, TLC (5% MeOH in EtOAc, UV visualization) showed only a trace of starting material (RF=0.31) and appearance of a strong spot at RF=0.59. The compound was purified by flash chromatography using 1:1 ethyl acetate:hexane as eluent to remove one impurity (RF=0.88) before eluting the product with pure ethyl acetate. ¹H NMR (400 MHz, Chloroform-d) δ 8.29 (d, J=9.1 Hz, 2H), 7.46 (d, J=9.1 Hz, 2H), 7.33 (d, J=8.5 Hz, 2H), 7.15 (d, J=8.6 Hz, 2H), 4.84-4.58 (m, 4H), 3.22 (td, J=16.5, 6.2 Hz, 2H), 2.47 (tt, J=24.1, 6.2 Hz, 1H), 1.33-1.14 (m, 24H).

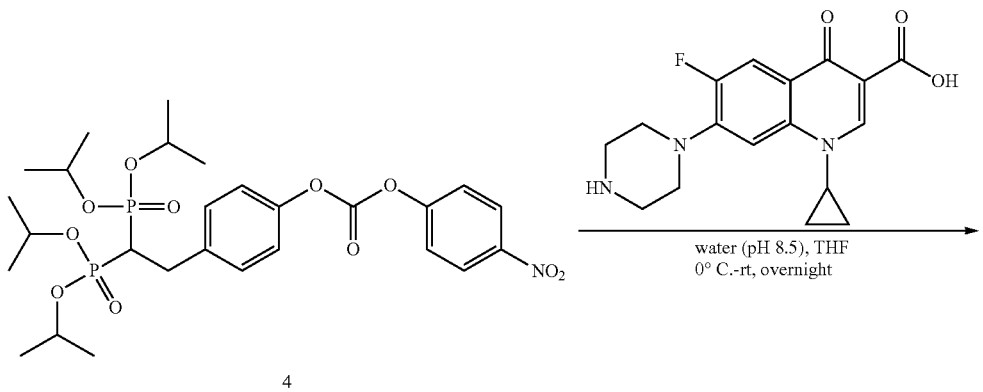

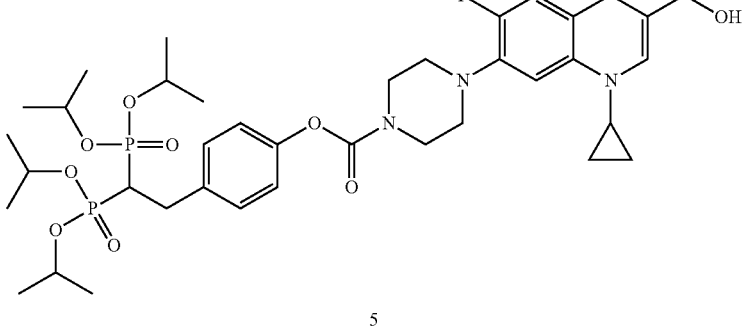

-continued

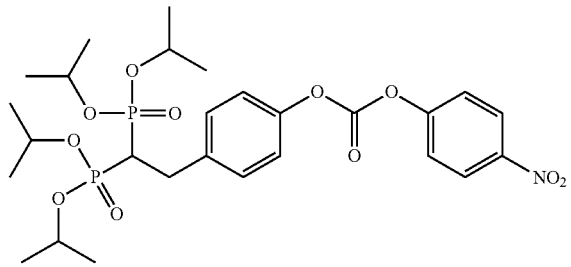

7-(4-((4-(2,2-bis(diisopropoxyphosphoryl)ethyl) phenoxy)carbonyl)piperazin-1-yl)-1-cyclopropyl-6-fluoro-4-oxo-1,4-dihydroquinoline-3-carboxylic Acid (5)

Ciprofloxacin (46.5 mg, 0.140 mmol) was suspended in 1.4 ml of water in a plastic vial. 151 μl of 1 M HCl was added and the vial was vortexed to dissolve ciprofloxacin giving a clear colorless solution. Na₂CO₃ was added to adjust the pH to 8.5 and a thick white precipitate formed. The vial was placed in an ice bath and Compound 4 (71.9 mg, 0.117 mmol) dissolved in 1.4 ml of THF was added dropwise over about 5 min. The vial was then removed from the ice bath, protected from light and stirred overnight at room temperature. The reaction mixture turned bright yellow with suspended solid. TLC (5% MeOH in EtOAc) showed disappearance of the starting material 4 and appearance of a fluorescent blue spot (RF=0.51) and a visible yellow spot (RF=0.816) attributed to p-nitro phenol byproduct. The reaction mixture was diluted with 10 ml of water and filtered through a fine glass frit. The retained solid was washed with water until no yellow color remained. The solids were then dissolved and washed from the frit with DCM and the solution was loaded onto a flash silica column and eluted with DCM increasing MeOH concentration to 5% to elute a band with light blue fluorescence. Combined fractions were evaporated to give the title compound as a white solid. $^1$H NMR (400 MHz, Methanol-d4) $^1$H NMR (400 MHz, Methanol-d4) δ 8.79 (s, 1H), 7.93 (d, J=13.3 Hz, 1H), 7.54 (s, 1H), 7.30 (d, J=8.4 Hz, 2H), 7.05 (d, J=8.5 Hz, 2H), 4.70 (dpd, J=7.4, 6.2, 1.3 Hz, 4H), 3.90 (s, 5H), 3.75 (s, 3H), 3.39 (s, 4H), 3.18 (td, J=16.6, 6.4 Hz, 2H), 2.65 (tt, J=24.3, 6.3 Hz, 1H), 1.43-1.34 (m, 1H), 1.34-1.19 (m, 24H), 1.18-1.10 (m, 2H).

with blue fluorescence. HPLC analysis (Luna $C_{18}$, buffer system 0.1 M $NH_4OAc$ buffer pH 7.1; A: 20% acetonitrile, B: 70% acetonitrile. 0-7 min: 100% A, 7-25 min gradient 0-100% B) showed major peak at RT=14.8 min and minor peaks at 5.76 min (assigned to ciprofloxacin) and 18.8 min. Ciprofloxacin standard (saturated solution in buffer A diluted 2×, 5 μl injection) gave an RT of 5.68 min.

Microbiology:

Experimental strains: Twelve *S. aureus* clinical osteomyelitis strains of methicillin-susceptible profile and one clinical methicillin-resistant strain (MR-CIPS) were tested. These pathogens are part of the strain collection of the Department of Pharmaceutical Microbiology and Parasitology Wroclaw Medical University, Poland. Additionally, the following ATCC collection strains were chosen for experimental purposes: *S. aureus* 6538 and *P. aeruginosa* 15442.

HA discs: For custom disc manufacturing, commercially available HA powder was used. Powder pellets of 9.6 mm in diameter were pressed without a binder. Sintering was performed at 900° C. The tablets were compressed using the

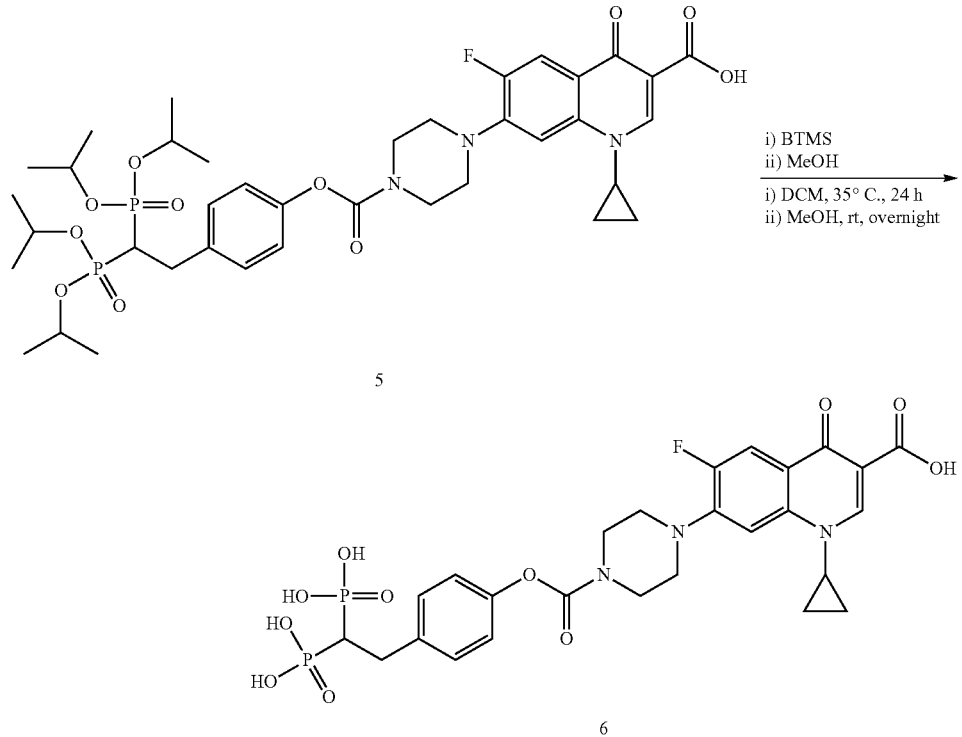

1-cyclopropyl-7-(4-((4-(2,2-diphosphonoethyl)phenoxy)carbonyl)piperazin-1-yl)-6-fluoro-4-oxo-1,4-dihydroquinoline-3-carboxylic Acid (6), Also Referred to Herein as Formula 2

Compound 5 (10.0 mg, 0.0124 mmol) was dissolved in DCM (0.2 ml) in a 1.5 ml vial and bromotrimethylsilane (BTMS) (0.2 ml) was added and the vial was quickly capped and immersed in a 35° C. oil bath. After stirring for 24 h, solvent and BTMS were removed by evaporation and 1 ml of MeOH was added and the vial stirred overnight. Evaporation of solvent left 6.82 mg (0.107 mmol) of pale yellow solid with green fluorescence. A sample ~0.2 mg was taken for HPLC analysis. Suspended in water, pH was measured at 2.5 then adjusted to 6.7 to give a slightly yellow solution Universal Testing System for static tensile, compression, and bending tests (Instron model 3384; Instron, Norwood, Mass.). The quality of the manufactured HA discs was checked by means of confocal microscopy and microcomputed tomography (micro-CT) using an LEXT OLS4000 microscope (Olympus, Center Valley, Pa.) and Metrotom 1500 microtomograph (Carl Zeiss, Oberkochen, Germany), respectively.

Disc diffusion test to evaluate sensitivity of tested strains to ciprofloxacin: This procedure was performed according to EUCAST guidelines. Briefly, 0.5 McFarland (MF) of bacterial dilution was spread on Mueller-Hinton (MH) agar plate. The discs containing 5 mg of ciprofloxacin were introduced and the plate was subjected to incubation at 37° C./24 h. Next, inhibition zones were recorded using a ruler.

Obtained values (mm) were compared to appropriate values of inhibition zone from EUCAST tables.

Evaluation of MIC of tested compounds against planktonic forms of clinical staphylococcal strains analyzed: To assess the impact of BP-ciprofloxacin and ciprofloxacin on microbial growth, 100 μl of microbial solutions of density of $1\times10^5$ cfu/ml were placed into wells of 96-well test plate together with appropriate concentrations of tested compounds. Immediately after that, the absorbance of solutions was measured using a spectrometer (Thermo Scientific Multiscan GO) at 580 nm wavelength. Subsequently, the plate was incubated for 24 h/37° C. in a shaker to obtain optimal conditions for microbial growth and to prevent bacteria from forming biofilms. After incubation, the absorbance was measured once again. The following control samples were established: negative control sample one: sterile medium without microbes; negative control sample two: sterile medium without microbes implemented with DMSO (dimethyl sulfoxide, Sigma-Aldrich) to final concentration of 1% (v/v); positive control sample one: medium+microbes with no compound tested; positive control sample two: medium+microbes with no compound tested but implemented with DMSO to final concentration of 1% (v/v). Rationale for use of 1% DMSO was that ciprofloxacin dissolves efficiently in this solvent, however, concentrations of DMSO>1% might be detrimental for microbial cells. To assess relative number of cells, the following calculations were performed. The value of absorbance of control samples (medium+microbes in case of BP-ciprofloxacin, medium+microbes+DMSO for ciprofloxacin) was estimated at 100%. Next, the relative number of cells subjected to incubation with tested compounds were counted as follows: value of control sample absorbance/value of tested sample*100%.

Spectroscopic analysis of BP-ciprofloxacin conjugate in trypticase soy broth (TSB) microbiological media to test stability: BP-ciprofloxacin in final concentrations of 0.24-250 mg/L in TSB microbiological medium was introduced to wells of 96-well plate. Immediately afterwards the absorbance of solutions was measured using a spectrometer (Thermo Scientific Multiscan GO) at 275 nm wavelength. Next, solutions were left for 24 h/37° C./shaking. After incubation, absorbance was measured once again. To assess for degradation of conjugate, values of absorbance taken at 0 hr and 24 hrs were compared.

Spectroscopic analysis of BP-ciprofloxacin conjugate in trypticase soy broth microbiological media with the addition of HA spherules: Various BP-ciprofloxacin concentrations were introduced to HA powder (spherules) suspended in TSB microbiological medium. Solutions containing BP-ciprofloxacin and HA spherules were introduced to wells of 24-well plate. Final concentration of powder was 10 mg/1 mL, while final concentration of conjugate was 0.24-250 mg/L. Immediately afterwards the absorbance of solutions was measured using a spectrometer (Thermo Scientific Multiscan GO) at 275 nm wavelength. Plates were shaken automatically in the spectrometer prior to assessment. Next, plates were left for 24 h/37° C./shaking. After 24 hours, absorbance was measured once again. To assess the relative concentration of the conjugate at 0 hr and 24 hrs, values of absorbance taken in the beginning and at the end of experiment were compared.

Antimicrobial susceptibility testing of BP-ciprofloxacin against planktonic cultures of S. aureus strain ATCC-6538 in acidic versus basic pH: This experimental setting was performed in the same manner as described previously for disc diffusion testing, but microbiological media was adjusted to pH 7.4 and pH 5 using KOH or HCL solution and measured using a universal pH-indicator (Merck, Poland).

Time-kill assay for BP-ciprofloxacin conjugate against S. aureus strain ATCC-6538 (MSSA) and clinical MRSA strain MR4-CIPS: This experiment was performed in the same manner as described previously under the subheading: "Evaluation of MIC of tested compounds against planktonic forms of clinical staphylococcal strains analyzed", but absorbance assays (at 580 nm wavelength) were taken in hour: 0, 1, 2, 4, 8, 16, 24.

Antimicrobial susceptibility testing of BP-ciprofloxacin against preformed biofilms of S. aureus strain ATCC-6538 and P. aeruginosa strain ATCC-15442: Strains cultured on appropriate agar plates (Columbia agar plate for S. aureus; MacConkey agar plate for P. aeruginosa) were transferred to liquid microbiological media and incubated for 24 h/37° C. under aerobic conditions. After incubation, strains were diluted to the density of 1 MF. The microbial dilutions were introduced to wells of 24-well plates containing HA discs as a substrate, or simply to polystyrene wells where the bottom surface of the wells served as the substrate for biofilm development. Strains were incubated at 37° C. for 4 hrs. Next, the microbe-containing solutions were removed from the wells. The surfaces, HA discs and polystyrene plates, were gently rinsed to leave adhered cells and to remove planktonic or loosely-bound microbes. Surfaces prepared in this manner were immersed in fresh TSB medium containing 0.24-125 mg/L of BP-ciprofloxacin conjugate. After 24 hrs of incubation at 37° C. the surfaces were rinsed using physiological saline solution and transferred to 1 mL of 0.5% saponin (Sigma-Aldrich, St Louis, Mo.). The surfaces were vortex-mixed vigorously for 1 minute to detach cells. Subsequently, all microbial suspensions were diluted 10 to $10^9$ times. Each dilution (100 mL) was cultured on the appropriate stable medium (MacConkey, Columbia for P. aeruginosa and S. aureus, respectively) and incubated at 37° C. for 24 hours. After this time, the microbial colonies were counted and the number of cells forming biofilm was assessed. Results were presented as the mean number of CFU per square millimeter surface ±standard error of the mean. To estimate the exact surface area of HA discs, x-ray tomographic analysis was applied. For estimation of the area of test plate bottoms, the equation for circle area: πr2 was applied.

Preventative ability of BP-ciprofloxacin conjugate to inhibit S. aureus 6538 adherence to HA spherules: Various BP-ciprofloxacin concentrations were introduced to HA powder (spherules) suspended in TSB microbiological medium. Solutions containing conjugate and HA spherules were introduced to wells of 24-well plates. Final concentrations of powder were 10 mg/1 mL, while final concentrations of the conjugate were 0.12-250 mg/L. Suspensions were left for 24 h/37° C./shaking. After 24 h, suspensions were removed from the wells and impulse-centrifuged to precipitate HA powder. Next, supernatant was very gently discarded and a fresh 1 mL of S. aureus of density $10^5$ cfu/mL was introduced to the HA spherules. Subsequently, this solution was shaken, absorbance was measured using 580 nm wavelength and left for 24 h/37° C./shaking. After incubation absorbance was measured again and values from 0 hr and 24 hrs were compared to assess reduction of bacterial growth with regard to control sample one (bacterial suspension but no spherules) and control sample two (bacterial suspension+spherules) but with no conjugate added). Additionally, solutions were impulse-centrifuged, supernatant was gently discarded, while bacteria-containing HA spherules were culture plated as before and quantitatively assessed.

Survival of *S. aureus* after 24 hrs of incubation in presence of conjugate-coated HA discs: HA discs were immersed in 2 mL of solution containing various concentrations of BP-ciprofloxacin or ciprofloxacin alone and left for 24 h/37° C. HA discs incubated in DMSO or phosphate buffer served as control samples. Next, discs were rinsed 3 times with sterile water. After rinsing, 2 mL of 0.5 MF of. *S. aureus* ATCC6538 were introduced to wells containing HA discs as a substrate for biofilm development and biofilms were formed as before.

Animal Study:

All animal protocols and procedures were approved and performed in accordance with the Institutional Animal Care and Use Committee (IACUC) of the University of Southern California (USC), and in accordance with the Panel on Euthanasia of the American Veterinary Medical Association. USC is registered with the United States Department of Agriculture (USDA), has a fully approved Letter of Assurance (#A3518-01) on file with the National Institutes of Health (NIH) and is accredited by the American Association for the Accreditation of Laboratory Animal Care (AAALAC). USC's animal welfare assurance number is A3518-01. The title of our IACUC approved protocol is: "Bone targeted antimicrobials for biofilm-mediated osteolytic infection treatment", and the protocol number is 20474. For this study 12 five-month-old, virgin, female Sprague-Dawley rats weighing approximately 200 g each were used in this study. Two animals were housed per cage in a vivarium at 22° C. under a 12-h light/12-h dark cycle and fed ad libitum with a soft diet (Purina Laboratory Rodent Chow). All animals were treated according to the guidelines and regulations for the use and care of animals at USC. Animals were under the supervision of full-time veterinarians on call 24 hrs/day who evaluate the animals personally on a daily basis. All animal experiments are described using the ARRIVE guidelines for reporting on animal research to ensure the quality, reliability, validity and reproducibility of results (Kilkenny, et al., Improving bioscience research reporting: the ARRIVE guidelines for reporting animal research. Vet Clin Pathol 2012; 41:27-31).

This animal model is an in-house jawbone peri-implant osteomyelitis model designed specifically to study biofilm-mediated disease and host response in vivo (Freire, et al, Development of animal model for *Aggregatibacter actinomycetemcomitans* biofilm-mediated oral osteolytic infection: a preliminary study. J Periodontol 2011; 82:778-89). Biofilms of the jawbone osteomyelitis pathogen Aa were pre-formed on miniature titanium implants at $10^9$ CFU. To confirm Aa sensitivity to the parent drug ciprofloxacin prior to our animal studies, we performed AST and MIC assays as performed for the long bone osteomyelitis pathogens described previously. After biofilms were established on the implants in vitro, they were surgically transferred to the jawbone of each rat. For surgery, animals were anesthetized with 4% isoflurane inhalant initially followed by intraperitoneal injection of ketamine (80-90 mg/kg) plus xylazine (5-10 mg/kg). Then local anesthesia was given via infiltration injection of bupivicaine 0.25% at the surgical site. Buprenorphine sustained release (1.0-1.2 mg/kg) was then given subcutaneously as preemptive analgesia before making initial incisions. Once anesthetized, the buccal mucosa of each rat was retracted and a transmucosal osteotomy was performed with a pilot drill into the alveolar ridge in the natural diastema of the anterior palate. Implants were then manually inserted into the osteotomy and secured into the bone until the platform is at mucosal level. Two biofilm-inoculated implants were placed in each rat in the palatal bone bilaterally.

One week post-operatively isoflurane 4% was given again to briefly anesthetize the rats and check implant stability and document clinical findings at the implant and infection site. The animals were then dosed via intraperitoneal injection with BP-ciprofloxacin (0.1 mg/kg, 1 mg/kg, or 10 mg/kg as a single dose, and at 0.3 mg/kg 3×/week for a multiple dosing group) or ciprofloxacin alone (10 mg/kg 3×/week also as a multiple dosing group) as a positive control, and sterile endotoxin-free saline as a negative control. Allocation of animals to treatment and control groups was done through a randomization process. The multiple dosing group animals were anesthetized as before prior to each additional injection over the course of the week. All compounds were pharmacological grade and constituted in sterile physiological injectable saline at appropriate pH. One week after pharmacotherapy, all animals were euthanized in a $CO_2$ chamber (60-70% concentration) for five minutes, followed by cervical dislocation. Resection of peri-implant tissues (1 $cm^2$) was performed en bloc and implants were removed. Peri-implant tissues were immediately homogenized and processed for quantitative assessment of microbial load. Rat allocations to treatment and control groups were de-identified and concealed from subsequent investigators analyzing the microbial data. For microbial analysis, peri-implant soft tissue and bone was processed by placement in 1 mL of 0.5% saponine and vortexed for 1 minute before being transferred directly to agar plates and cultured. The medium for culturing Aa consisted of modified TSB and frozen stocks were maintained at –80° C. in 20% glycerol, 80% modified TSB. All culturing was performed at 37° C. in 5% $CO_2$. The numbers of CFU in the homogenate (numbers of CFU per gram) was determined by plating aliquots of the serially diluted homogenate onto TSA plates. The reduction in the mean log 10 number of CFU per gram as a function of treatment was recorded.

Statistical Analysis:

Statistical calculations were performed with the SigmaStat package, version 2.0 (SPSS, Chicago, Ill.). Power analyses were performed to determine sample size estimation for in vitro and in vivo studies prior to experimentation using G Power 3 software (Faul F, Erdfelder E, Buchner A, Lang A G. Statistical power analyses using G*Power 3.1: tests for correlation and regression analyses. Behav Res Meth 2009; 41:1149-60). Quantitative data from experimental results was analyzed using the Kruskall-Wallis test or one-way ANOVA and statistical significance was accepted at $p<0.05$ when comparing treatments to controls.

Example 2

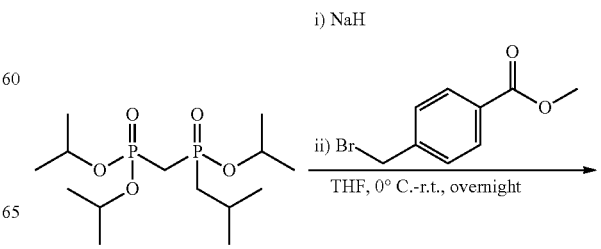

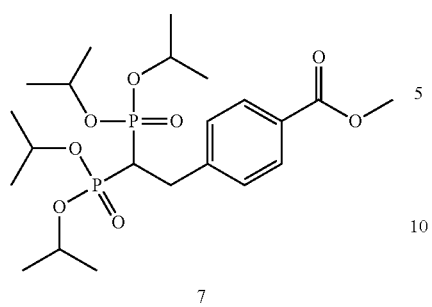

7 methyl 4-(2,2-bis(diisopropoxyphosphoryl)ethyl)benzoate (7)

Under nitrogen atmosphere, in a 50 mL 2-neck round bottom flask, THF (3 mL) was added to 60% dispersion of NaH in mineral oil (0.122 g, 3.05 mmol). The suspension was cooled to 0° C., while stirring, and tetraisopropyl methylenediphosphonate (0.69 mL, 2.18 mmol) was added gradually. The reaction was allowed to reach ambient temperature and once hydrogen gas stopped bubbling out of the reaction mixture, the solution was cooled to 0° C. again. Methyl 4-(bromomethyl)benzoate (0.5 g, 2.18 mmol) was dissolved in THF (2 mL) and added to the reaction dropwise. The resulting solution was allowed to stir overnight while slowly reaching ambient temperature. Reaction mixture was then cooled to 0° C. and quenched with H$_2$O (1 mL). 5% aqueous solution of citric acid in water (30 mL) and extracted with Et$_2$O (3×30 mL) combined organics were washed with brine (50 mL), dried on Na$_2$SO$_4$, filtered, concentrated under reduced pressure and purified by silica gel column chromatography using a EtOAc:Hex gradient (10-100%) to afford 7 as a faint yellow oil (0.323 g, 30% yield). $^1$H NMR (400 MHz, CDCl$_3$) δ 7.93 (d, J=8.0 Hz, 2H), 7.33 (d, J=8.4, 6.0 Hz, 2H), 4.79-4.683 (m, 4H), 3.88 (s, 3H), 3.24 (td, J=16.0, 6.4 Hz, 2H), 2.50 (tt, J=24.0, 6.2 Hz, 1H), 1.34-1.24 (m, 24H). $^{31}$P NMR (162 MHz, Chloroform-d) δ 20.57.

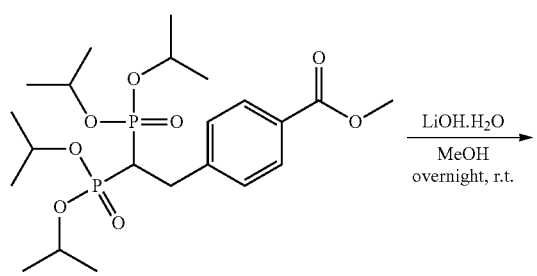

7 → (LiOH.H$_2$O, MeOH, overnight, r.t.)

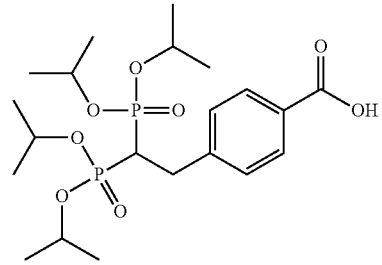

8

4-(2,2-bis(diisopropoxyphosphoryl)ethyl)benzoic Acid (8)

To a solution of 7 (0.278 g, 0.583 mmol) in MeOH (3 mL) in a 8 Dr glass vial, LiOH.H$_2$O (0.122 g, 2.914 mmol) was added and the resulting solution was stirred at room temperature overnight. The reaction mixture was evaporated to dryness, the residue was dissolved in water (30 mL), and HCl$_{(aq)}$ (1 M) was added slowly to reach pH 3. The resulting mixture was extracted with CHCl$_3$ (3×30 mL). Combined organics were dried on MgSO$_4$ and concentrated under reduced pressure to afford a thick clear oil. Yield: quantitative. $^1$H NMR (400 MHz, CDCl$_3$): δ=7.96 (d, J 6.4, 2H), 7.36 (d, J 6.4, 2H), 4.78 (sex, J 5.0, 4H), 3.27 (td, J 14.0, 4.8, 2H), 2.60 (tt, J 20.0, 4.8, 1H), 1.43-1.26 (m, 24H). $^{31}$P NMR (162 MHz, Chloroform-d) δ 20.57.

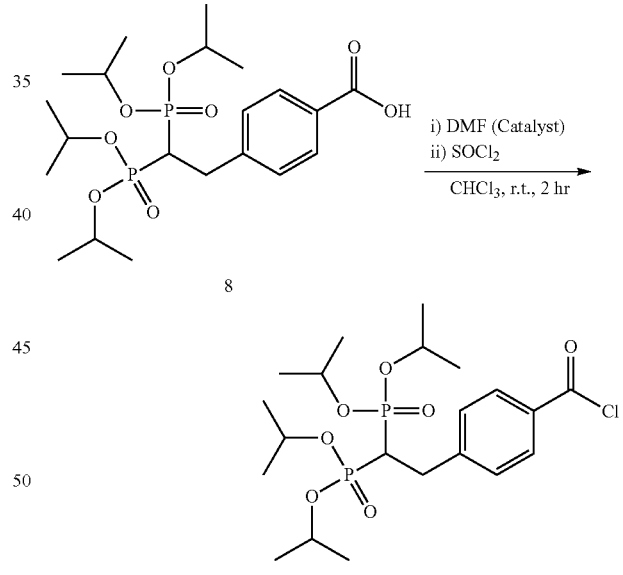

tetraisopropyl (2-(4-(chlorocarbonyl)phenyl)ethane-1,1-diyl)bis(phosphonate) (9)

Under nitrogen atmosphere, Compound 8 (0.162 g, 0.339 mmol) was dissolved in chloroform (1 ml) and catalytic amount of DMF (1.3 μL, 0.017 mmol) was added. Thionyl chloride (49.2 μL, 0.678 mmol) was added slowly and the reaction was allowed to stir for 2 hours at room temperature. Solvents were removed under vacuum to afford a clear oil. The product was immediately used in the next step without further manipulation. Yield: quantitative.

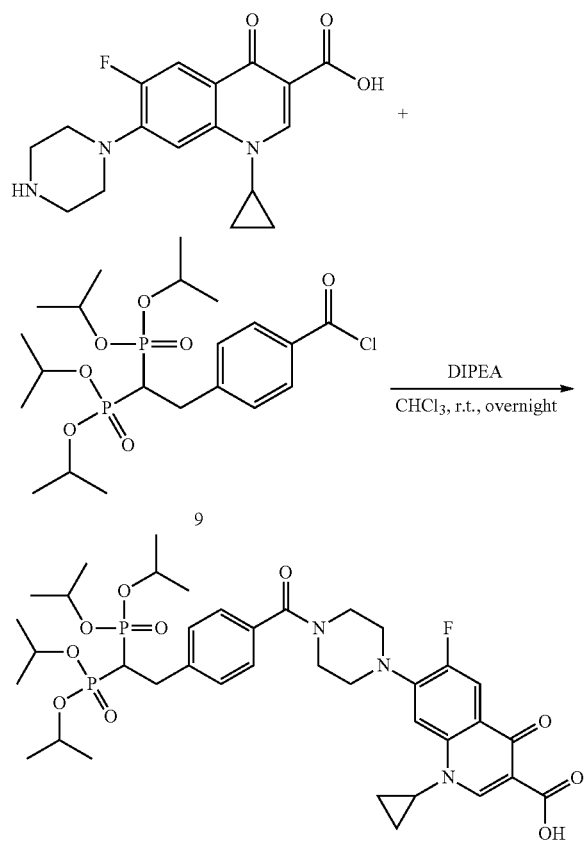

7-(4-(4-(2,2-bis(diisopropoxyphosphoryl)ethyl)benzoyl)piperazin-1-yl)-1-cyclopropyl-6-fluoro-4-oxo-1,4-dihydroquinoline-3-carboxylate (10)

Ciprofloxacin (0.112 g, 0.339 mmol) was suspended in chloroform (1 ml) and N,N-diisopropylethylamine (DIPEA) (354.3 μL, 2.034 mmol) was added. Freshly made compound 9 was dissolved in chloroform (1 mL) and gradually added to the Ciprofloxacin:DIPEA suspension. Reaction mixture was covered with foil and allowed to stir at room temperature overnight. The following day, solvents were removed under vacuum and the resulting crude was dissolved in DCM (5 mL) and filtered through a medium frit funnel and washed with more DCM (3×5 mL). The filtrate was concentrated under vacuum and further purified by silica gel column chromatography using a MeOH:DCM gradient (0-10%) to afford 10 as a viscous oil that gradually solidified (0.226 g, 84% yield, 1.8 eq DIPEA salt). $^1$H NMR (400 MHz, CDCl$_3$) δ=8.79 (s, 1H), 8.06 (d, J 12.8, 1H), 7.38 (m, 5H), 4.80-4.73 (m, 4H), 4.00 (s, br, 4H), 3.56-3.53 (m, 1H), 3.33-3.20 (m, 6H) 2.50 (m, 1H), 1.45-1.38 (m, 2H), 1.32-1.25 (m, 24H), 1.23-1.19 (m, 2H). $^{31}$P NMR (162 MHz, Chloroform-d) δ 20.77.

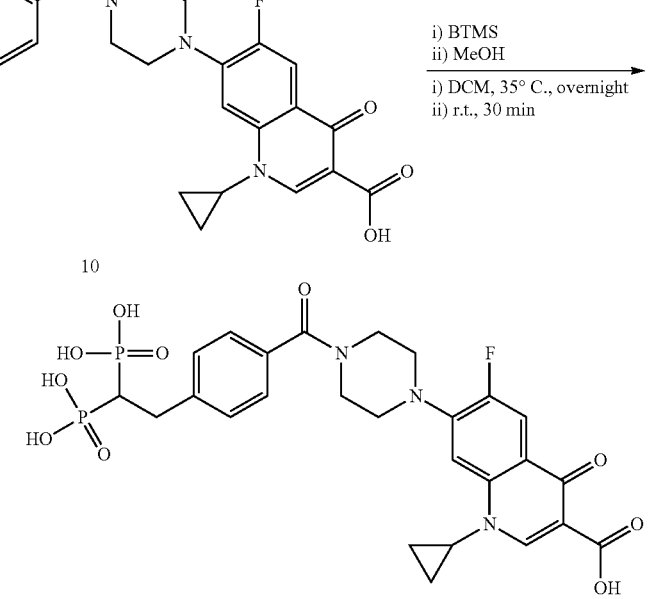

1-cyclopropyl-7-(4-(4-(2,2-diphosphonoethyl)benzoyl)piperazin-1-yl)-6-fluoro-4-oxo-1,4-dihydroquinoline-3-carboxylic Acid (11)

In a 8 Dr glass vial, compound 10 (0.108 g, 0.136 mmol) was dissolved in DCM (700 μL) and BTMS (686.0 μL, 5.200 mmol) was added. The vial was capped and heated overnight at 35° C. while covered with foil and stirring. The following day, solvent was removed under vacuum and the crude was quenched with MeOH (2 mL). The resulting solution was stirred at room temperature for 30 minutes. Solvent was removed under vacuum to afford an orange oil. A few drops of water was added to ppt a yellow solid. More MeOH (2 mL) was added and the resulting suspension was filtered using a medium fritted glass funnel. The resulting solid was further washed with MeOH to afford a yellow powder (0.070 g, 82% yield). $^1$H NMR (400 MHz, D$_2$O, pH 7.5): δ=8.54 (s, br, 1H), 7.89 (m, 1H), 7.64 (m, 1H), 7.54 (d, J 8.0, 2H), 7.44 (d, J 8.0, 2H), 4.79 (m, overlap with D$_2$O, 4H), 4.00 (s, br, 2H), 3.79 (s, br, 2H), 3.47 (s, br, 2H), 3.34 (s, br, 2H), 3.21 (td, J 14.0, 6.4, 2H), 2.30 (tt, J 22.0, 6.6, 1H). $^{31}$P NMR (162 MHz, Chloroform-d) δ 19.12. ESI-MS m/z (−): 622.24 [M−H].

Example 3

Non-limiting examples of quinolones that can be included in the BP conjugates.

Fluorinated Quinolones

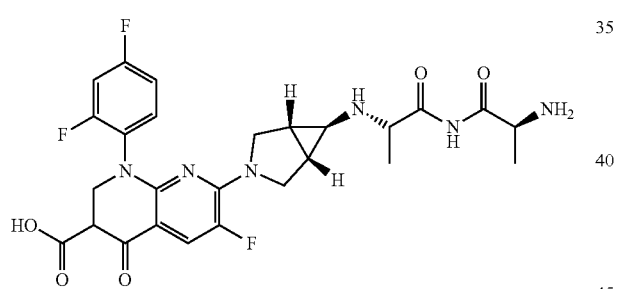
Alatrofloxacin

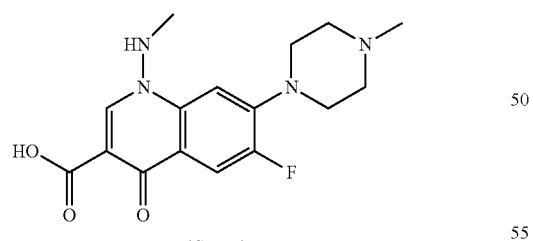
Amifloxacin

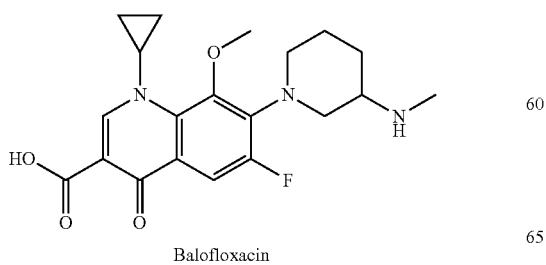
Balofloxacin

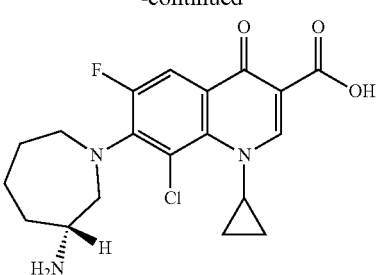
Besifloxacin

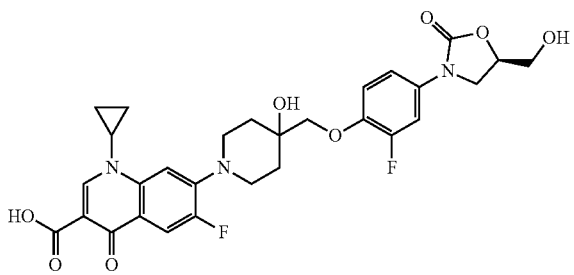
Cadazolid

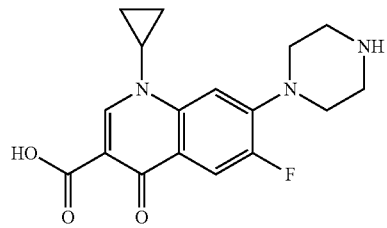
Ciprofloxacin

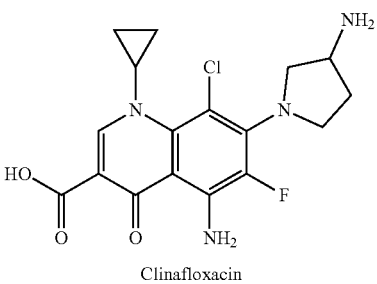
Clinafloxacin

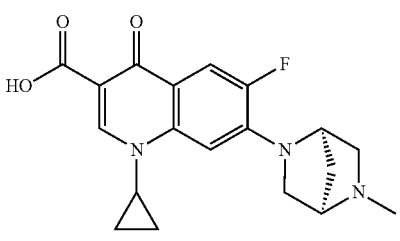
Danofloxacin

-continued
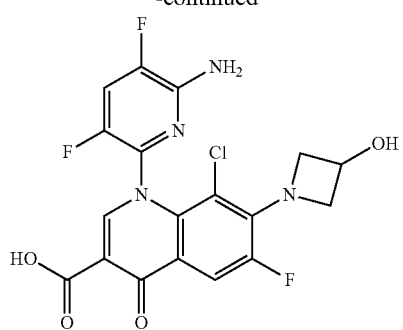
Delafloxacin
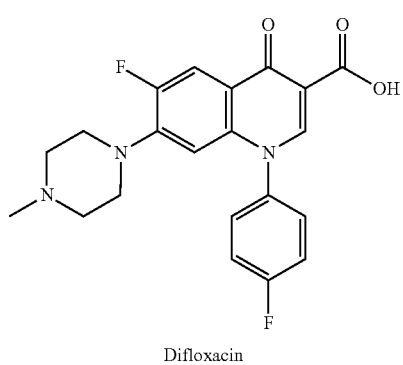
Difloxacin
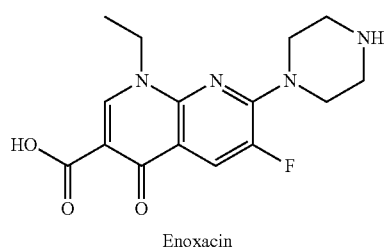
Enoxacin
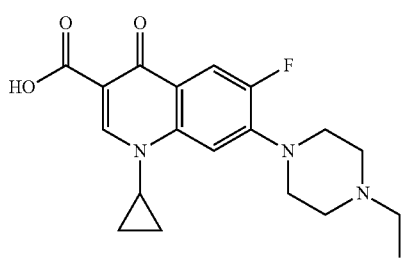
Enrofloxacin
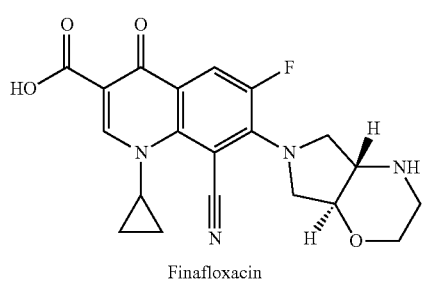
Finafloxacin
-continued
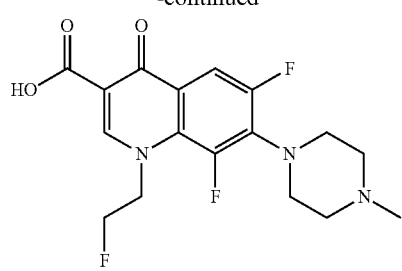
Flerofloxacin
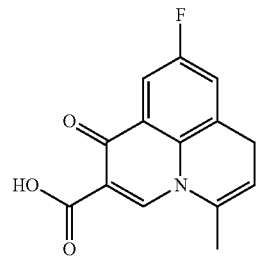
Flumequine
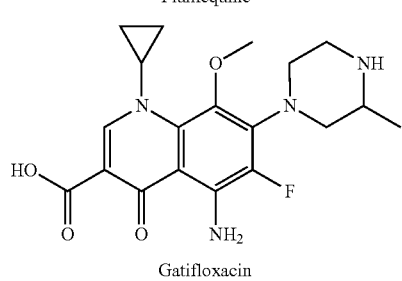
Gatifloxacin
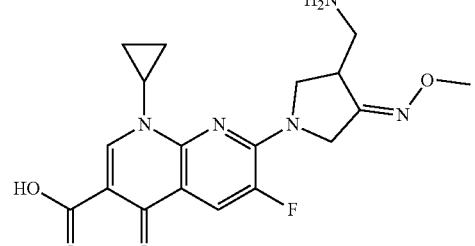
Gemifloxacin
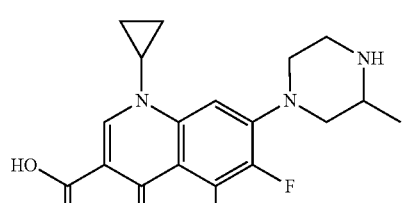
Grepafloxacin
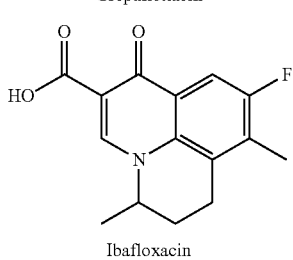
Ibafloxacin

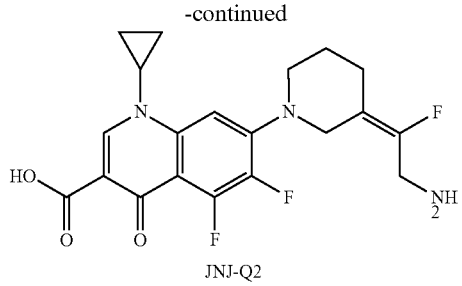
JNJ-Q2
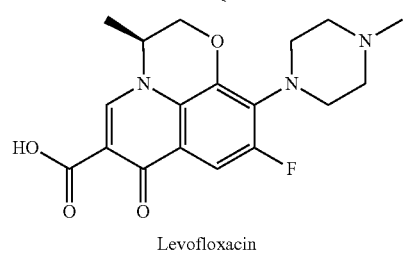
Levofloxacin
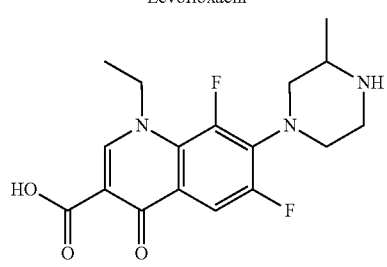
Lomefloxacin
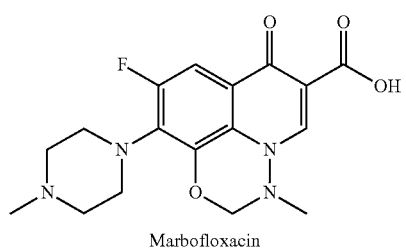
Marbofloxacin
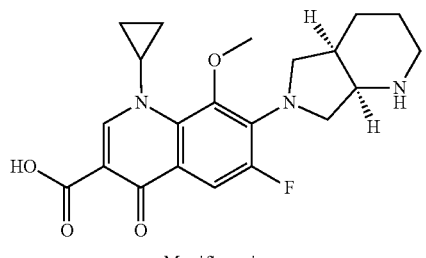
Moxifloxacin
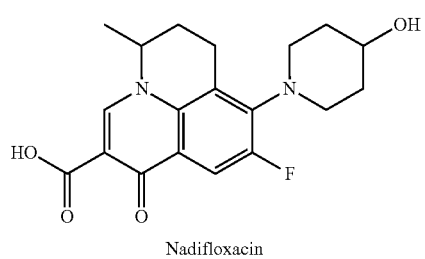
Nadifloxacin
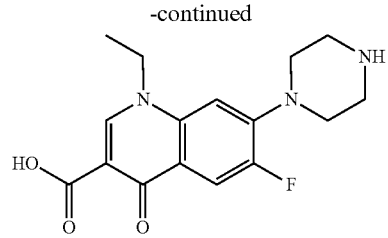
Norfloxacin
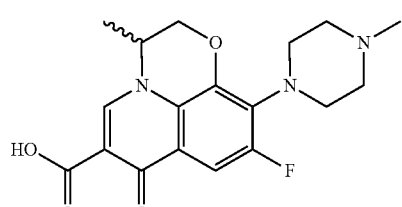
Ofloxacin
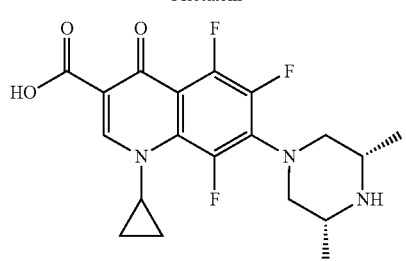
Orbifloxacin
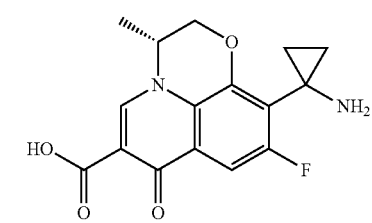
Pazufloxacin
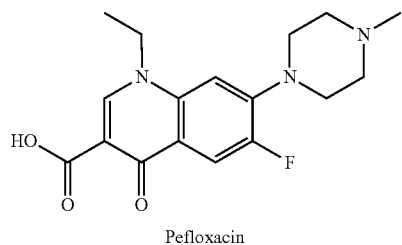
Pefloxacin
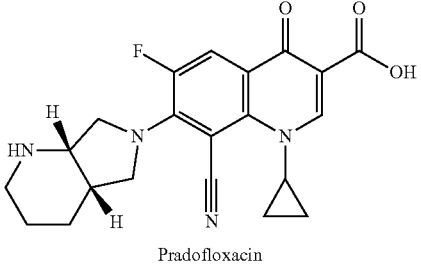
Pradofloxacin

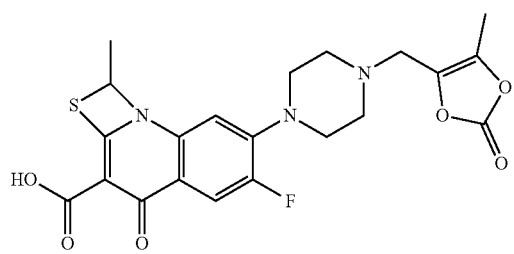
Prulifloxacin
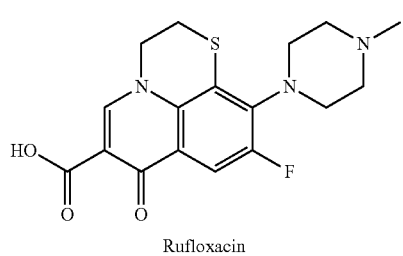
Rufloxacin
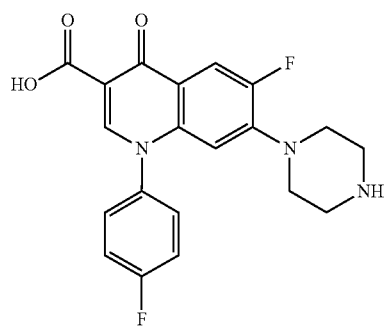
Sarafloxacin
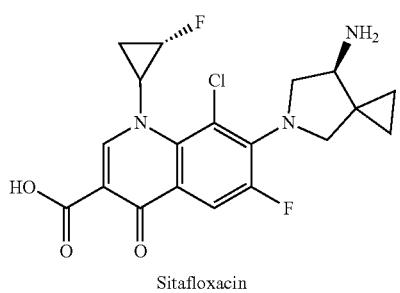
Sitafloxacin
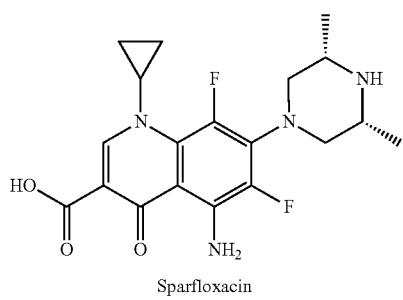
Sparfloxacin
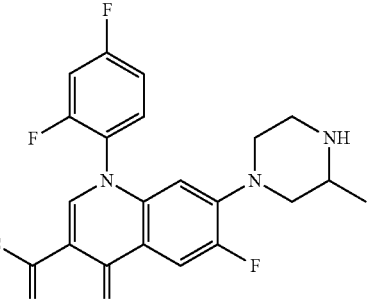
Temafloxacin
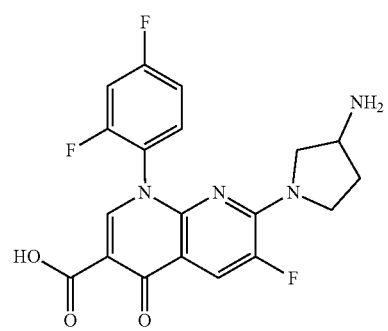
Tosufloxacin
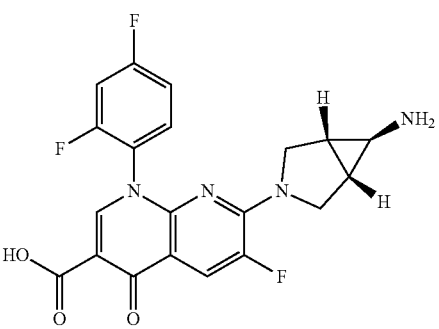
Trovafloxacin
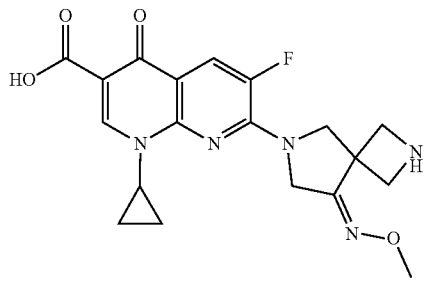
Zabofloxacin
The following is an example of a non-flouronated quinolone.

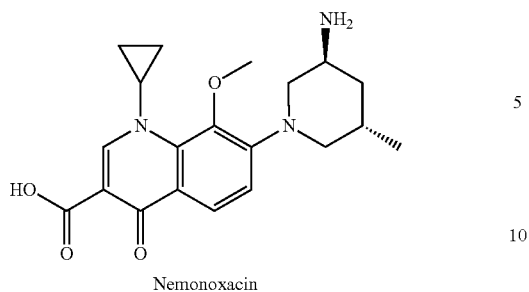
Nemonoxacin
Example 4
The following are non-limiting examples of BP-quinolone conjugates as described herein.
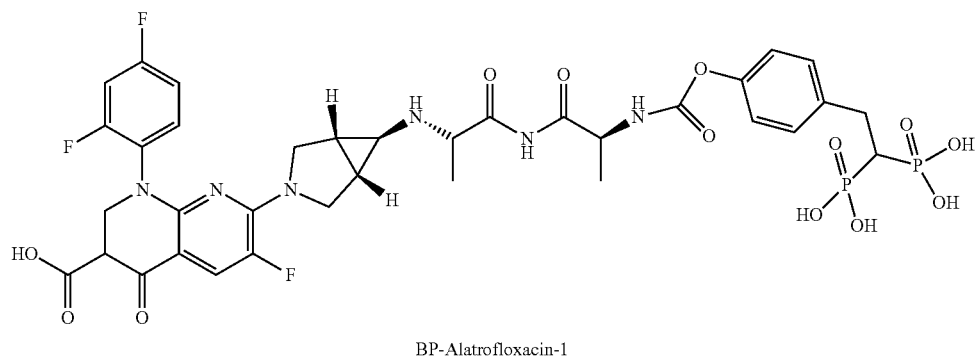
BP-Alatrofloxacin-1
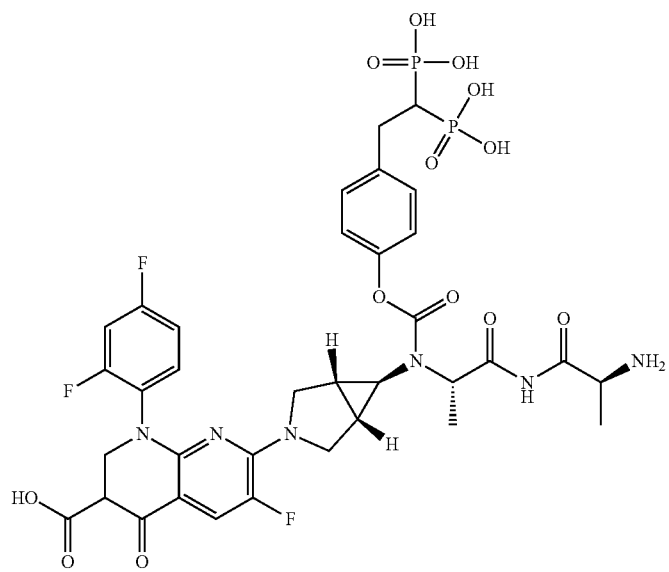
BP-Alatrofloxacin-2

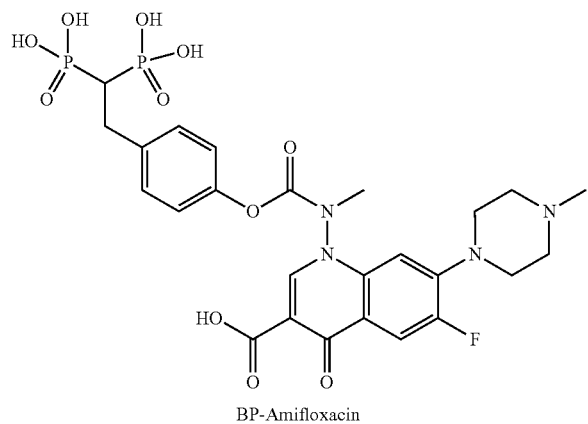
BP-Amifloxacin
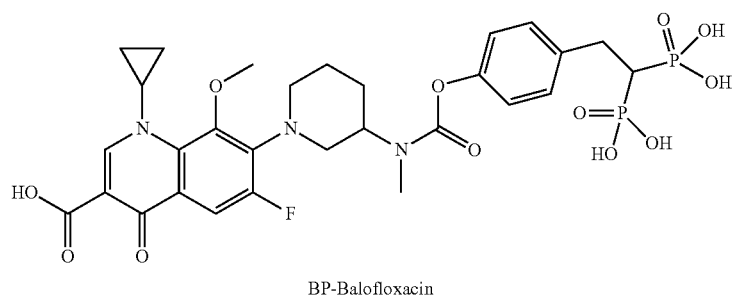
BP-Balofloxacin
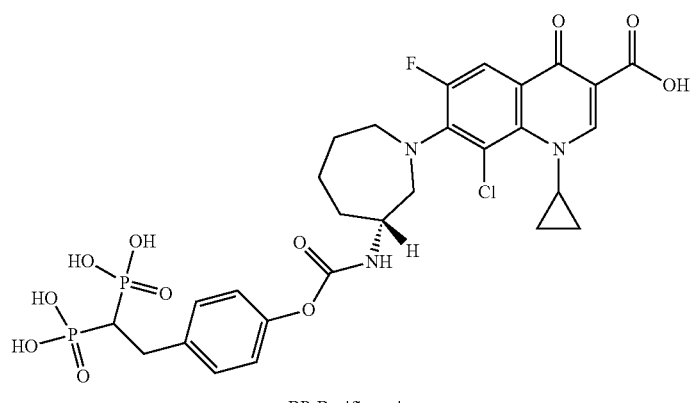
BP-Besifloxacin
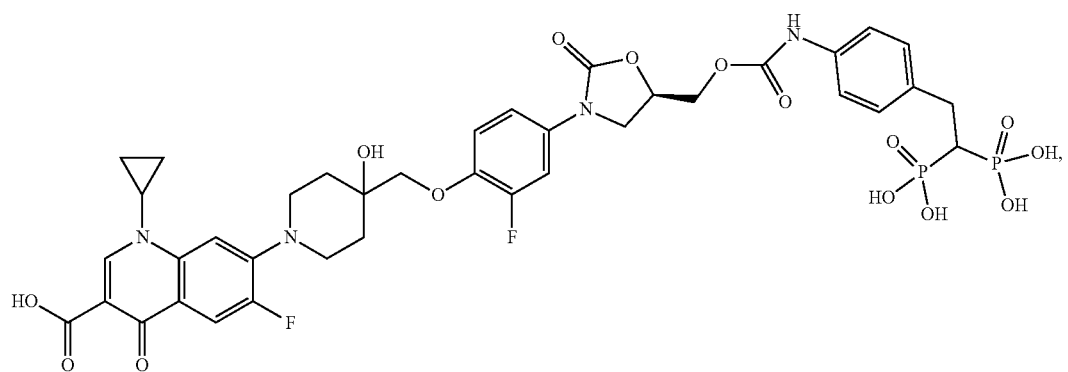
BP-Cadazolid-1

-continued
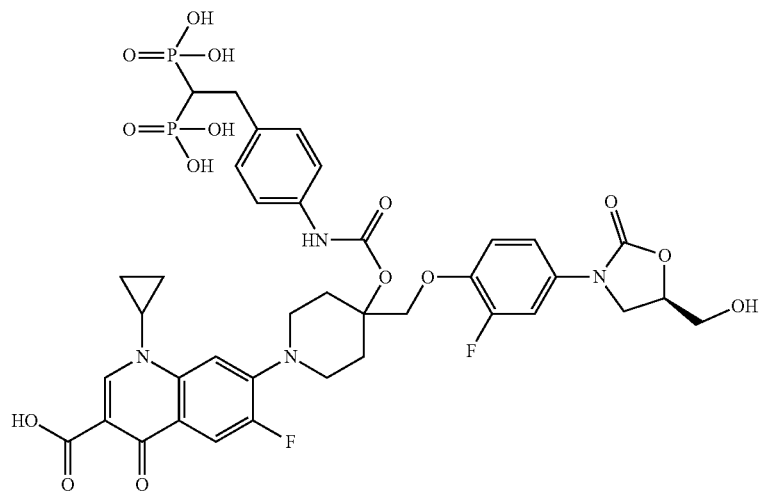
BP-Cadazolid-2
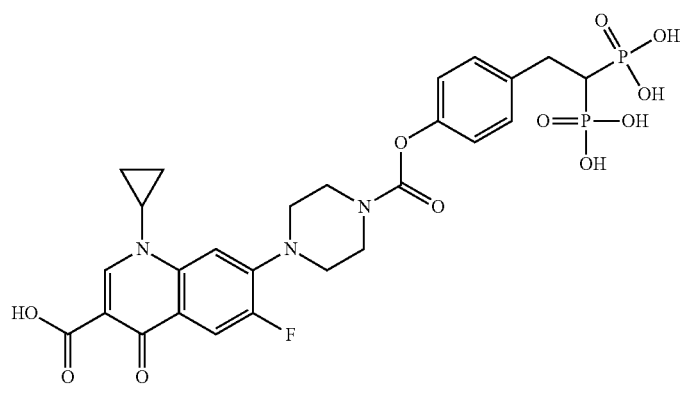
BP-Ciprofloxacin (6)
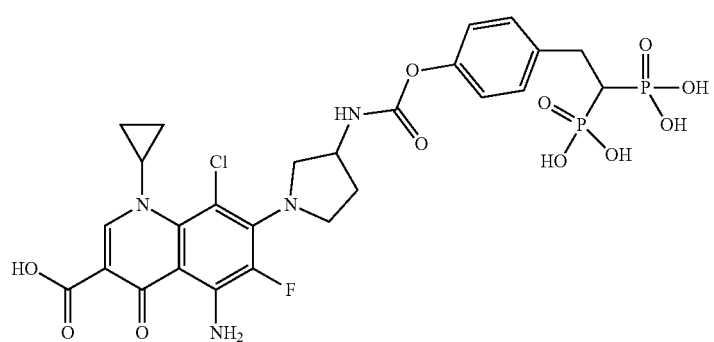
BP-Clinafloxacin-1
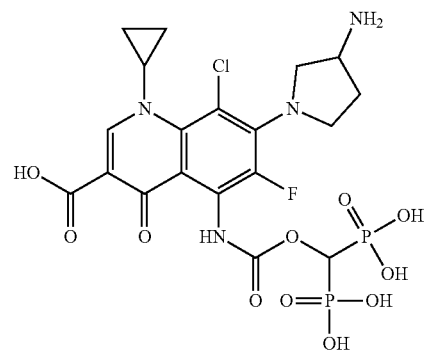
BP-Clinafloxacin-2

-continued
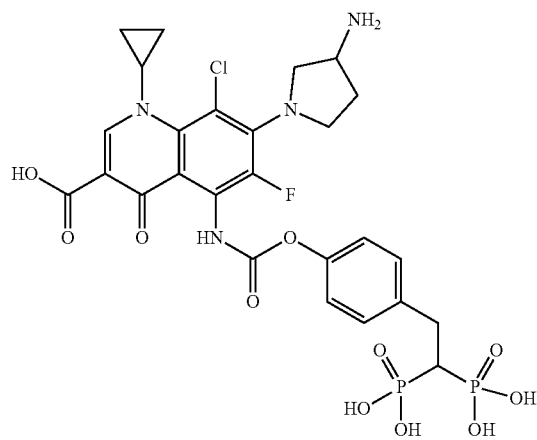
BP-Clinafloxacin-3
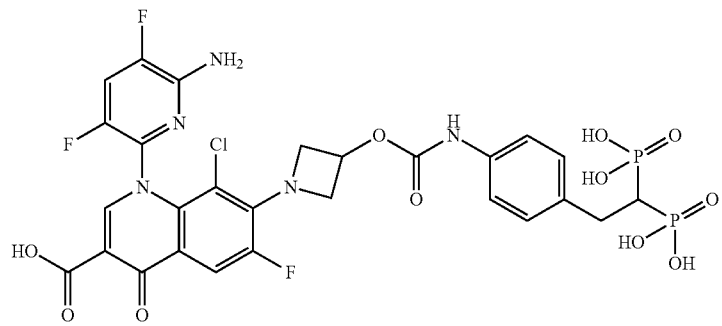
BP-Delafloxacin-1
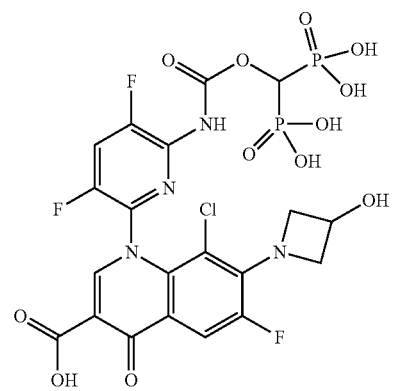
BP-Delafloxacin-2
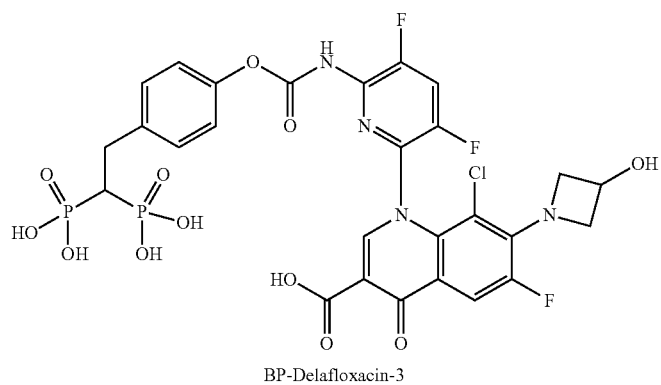
BP-Delafloxacin-3
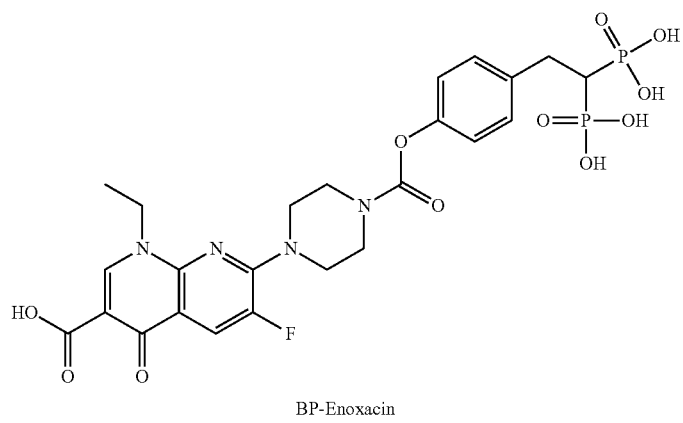
BP-Enoxacin -continued
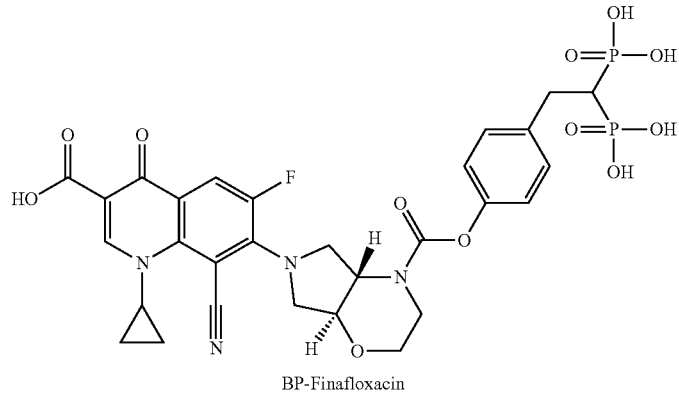
BP-Finafloxacin
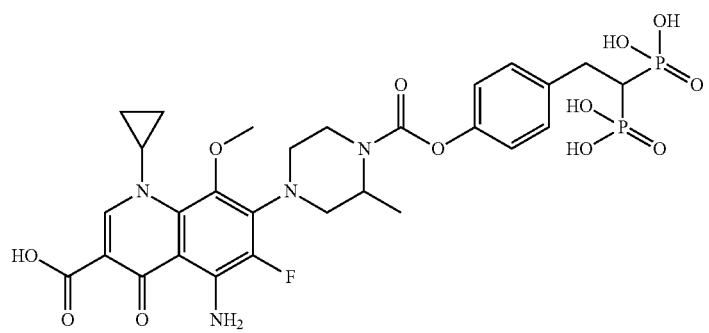
BP-Gatifloxacin-1
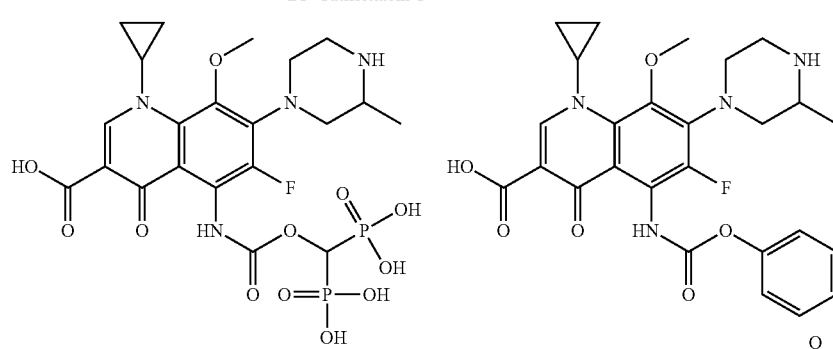
BP-Gatifloxacin-2
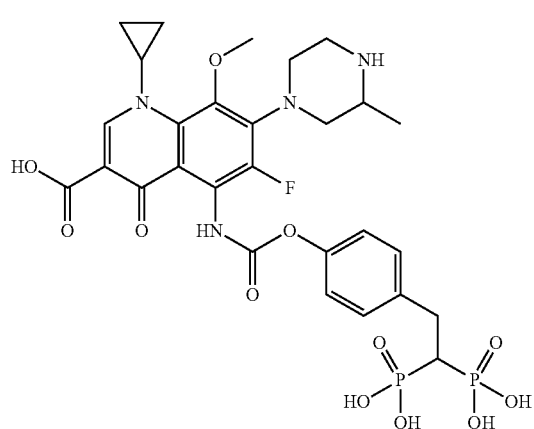
BP-Gatifloxacin-3
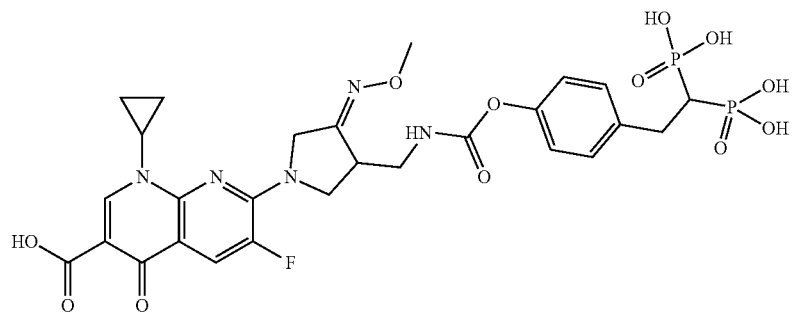
BP-Gemifloxacin -continued
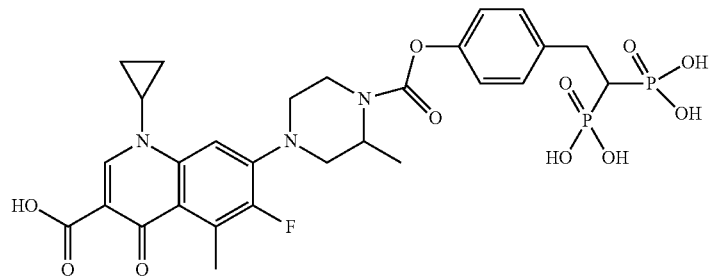
BP-Grepafloxacin
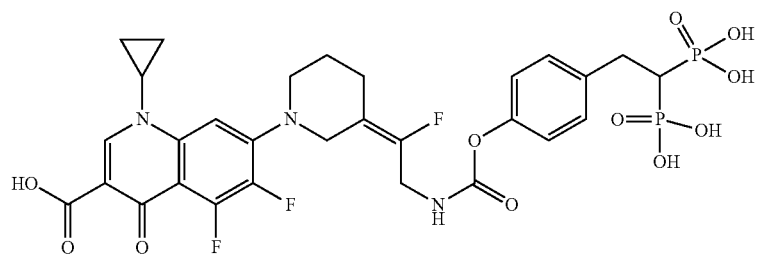
BP-JNJ-Q2
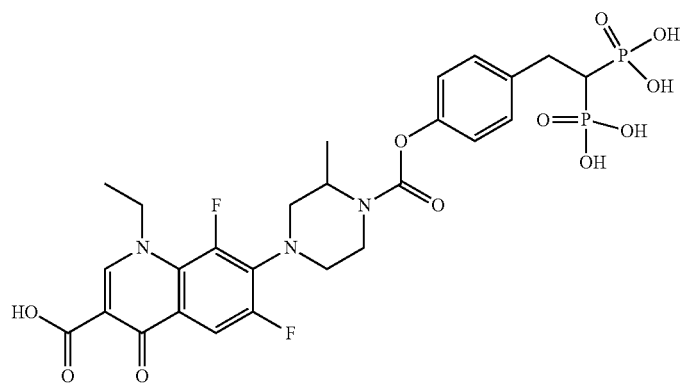
BP-Lomefloxacin
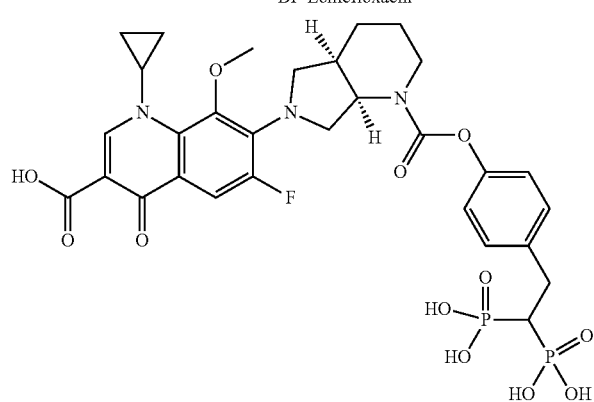
BP-Moxifloxacin
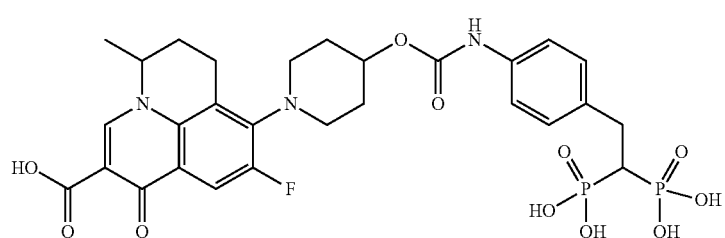
BP-Nadifloxacin -continued
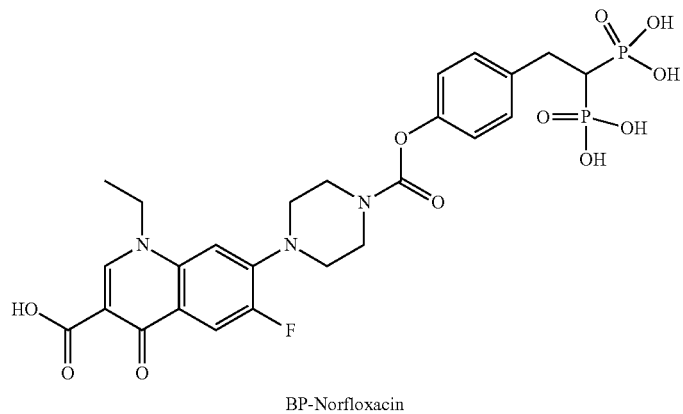
BP-Norfloxacin
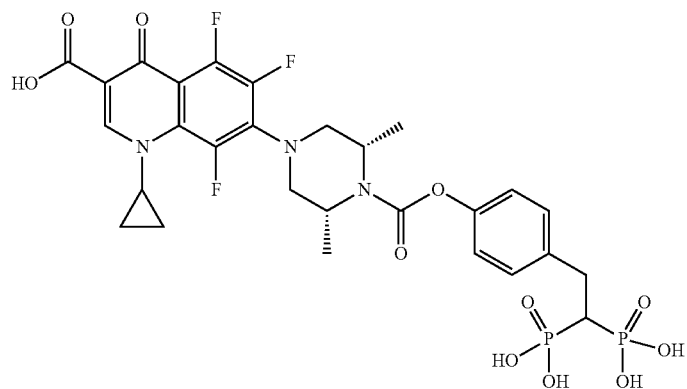
BP-Orbifloxacin
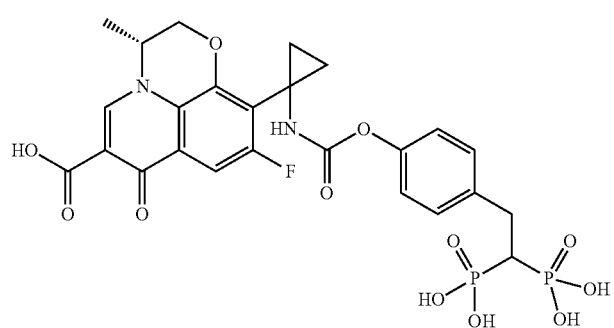
BP-Pazufloxacin
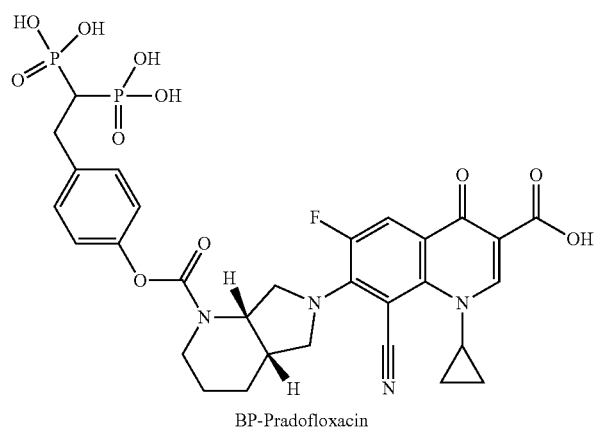
BP-Pradofloxacin -continued
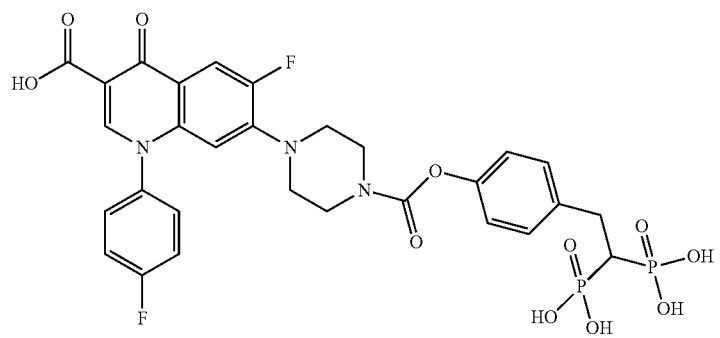
BP-Sarafloxacin
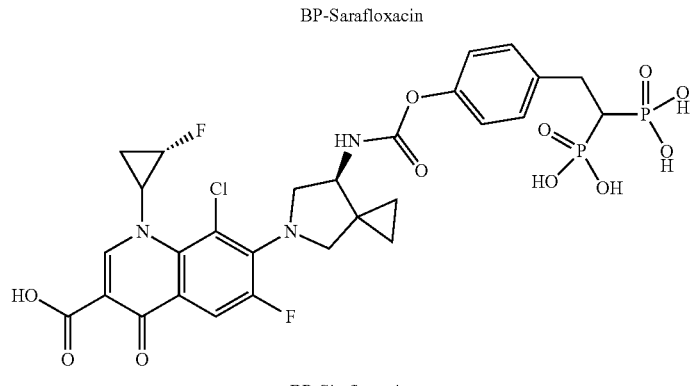
BP-Sitafloxacin
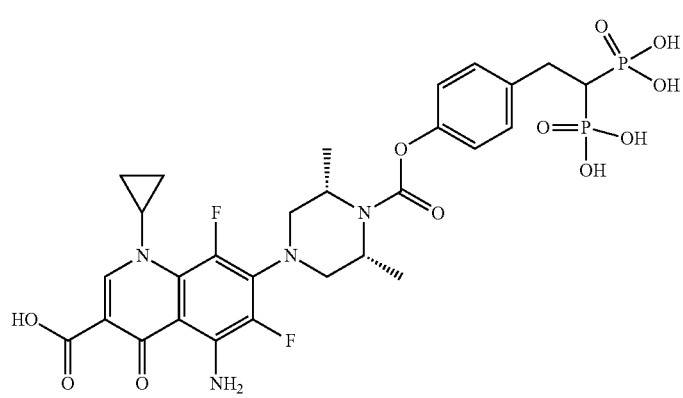
BP-Sparfloxacin-1
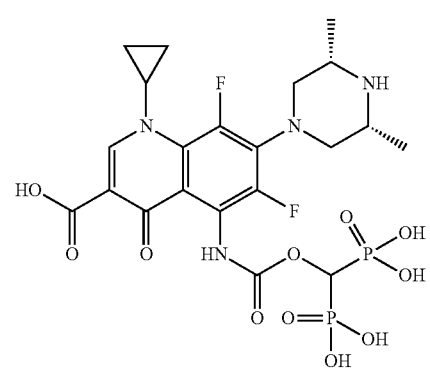
BP-Sparfloxacin-2
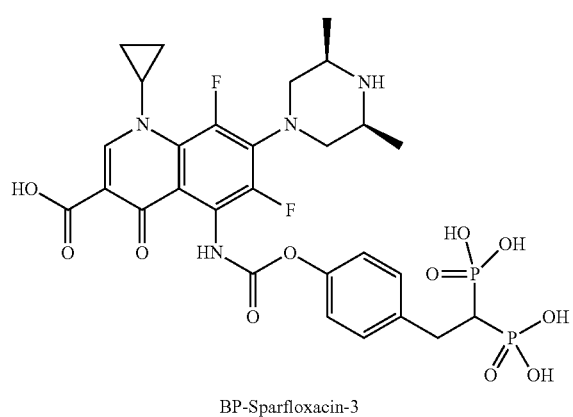
BP-Sparfloxacin-3

-continued
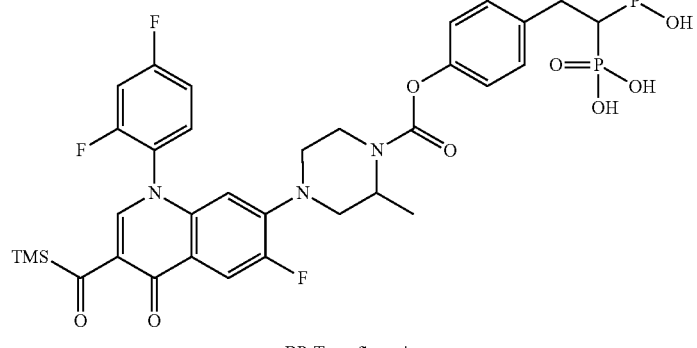
BP-Temafloxacin
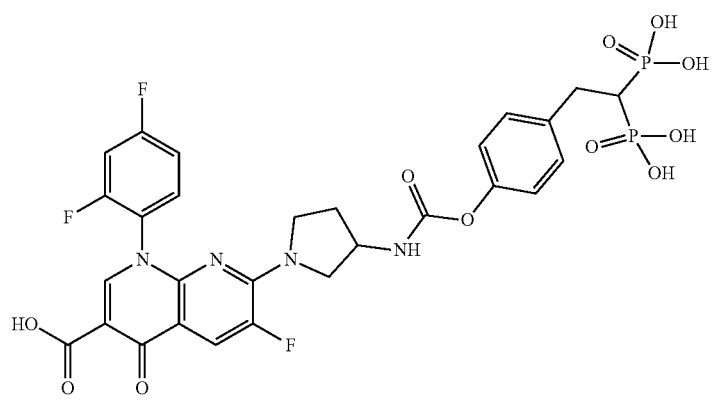
BP-Tosufloxacin
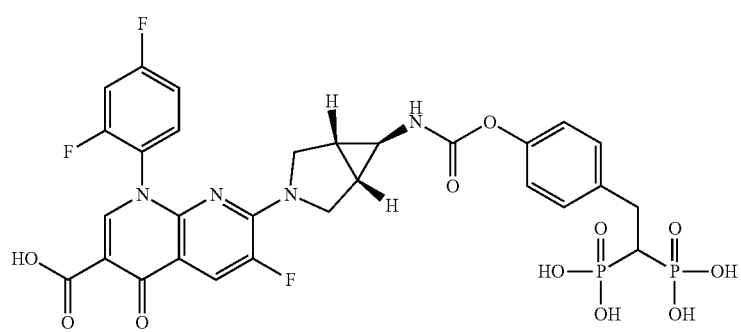
BP-Trovafloxacin
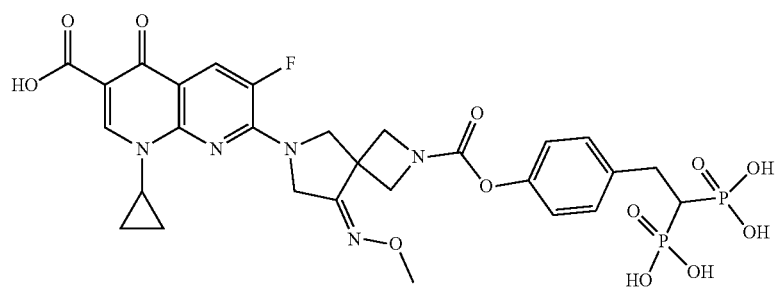
BP-Zabofloxacin

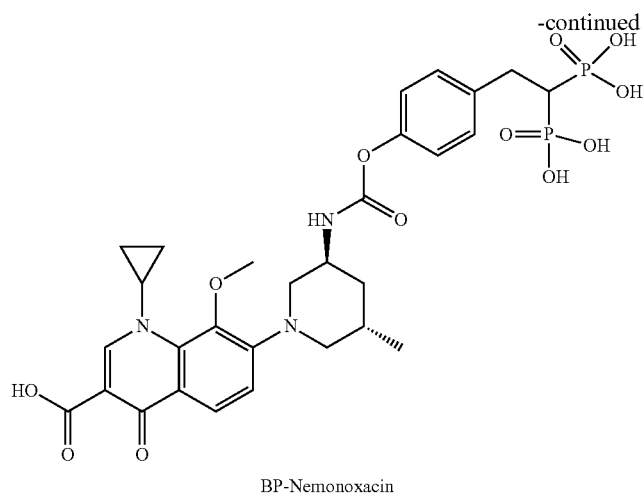

BP-Nemonoxacin

Example 5

Infectious bone disease, or osteomyelitis, is a major problem worldwide in human[1] and veterinary[2] medicine and can be devastating due to the potential for limb-threatening sequelae[3] and mortality.[4] The current approach to treat osteomyelitis is mainly antimicrobial, and often intravenous and long-term, with surgical intervention in many cases to control infection. The causative pathogens in the majority of long bone osteomyelitis cases are biofilms of *Staphylococcus aureus*; these microbes are bound to bone (FIG. 1) in contrast to their planktonic (free-floating) counterparts.[5]

The biofilm-mediated nature of osteomyelitis is important in clinical and experimental settings because many biofilm pathogens are uncultivable and exhibit an altered phenotype with respect to growth rate and antimicrobial resistance.[5, 6] The difficulty in eradicating biofilms with conventional antibiotics partly explains why the high success rates of antimicrobial therapy in general have not yet been realized for orthopedic infections, along with the development of resistant biofilm pathogens, poor penetration of antimicrobial agents into bone, and adverse events related to systemic toxicity.[3]

To overcome the many challenges associated with osteomyelitis treatment,[7] there is increasing interest in drug delivery approaches using bone-targeting conjugates to achieve higher or more sustained local therapeutic concentrations of antibiotic in bone while minimizing systemic exposure.[8] Conjugation of fluoroquinolone antibiotics to osteoadsorptive bisphosphonates (BPs) (FIG. 13) represents a promising approach because of the long clinical track-record of safety of each constituent, and their advantageous biochemical properties.[9, 10] Ciprofloxacin (FIG. 13) has several advantages for repurposing in this context: 1) it can be administered orally or intravenously with relative bioequivalence, 2) it is already FDA approved and indicated for bone and joint infections caused by *Pseudomonas aeruginosa* and several other pathogens, 3) it has broad spectrum antimicrobial activity that includes the most commonly encountered osteomyelitis pathogens like *Staphylococcus aureus* (methicillin-susceptible), *Pseudomonas aeruginosa* for long bone osteomyelitis,[11] and *Aggregatibacter actinomycetemcomitans* for jawbone osteomyelitis,[12] 4) it demonstrates bactericidal activity in clinically achievable doses,[13 and 5]) it is the least expensive drug in the fluoroquinolone family.

However, like most antibiotics, fluoroquinolones suffer from reduced activity against biofilms as compared to the same bacteria in planktonic forms; this has been shown specifically for ciprofloxacin against *S. aureus* in addition to many other bacterial strains and antibiotic classes.[14-17] Such studies have demonstrated that biofilms can be one to several orders of magnitude more resistant to the same antimicrobial agents as compared to their planktonic counterparts. This highlights the importance of a bone-targeted approach for treating osteomyelitis, in order to achieve higher local concentrations of antibiotic against causative biofilms and overcome potential resistance.

The specific bone-targeting properties of the BP family make these drugs ideal carriers for targeting antibiotics to bone in osteomyelitis pharmacotherapy.[18-20] BPs form strong bidentate or tridentate bonds with calcium phosphate mineral, and as a result concentrate in hydroxyapatite (HA), particularly at skeletal sites of active metabolism including sites of infection and inflammation.[21] BPs also exhibit exceptional stability against both chemical and biological degradation.[22] BP-fluoroquinolone antimicrobial activity is complex and is related to the specific strain of pathogen tested, the choice of antibiotic and covalently bound BP moiety, the tether length between the two constituents, the bone binding affinity of the BP, the adsorption-desorption equilibria of the BP, and the stability/lability and kinetics of the linkage moiety used for conjugation.[18-20] Therefore, accumulating evidence suggests that a 'target and release' linker strategy (FIG. 13) where a conjugate is stable in circulation, but labile at the bone surface, may offer more opportunities for optimization and success in this context. We thus hypothesized that conjugation of ciprofloxacin to a phenyl BP moiety, through metabolically hydrolysable carbamate linkers, should mitigate the problems seen with antibiotic dosing in osteomyelitis pharmacotherapy. The cleavable carbamate linkage is a key functionality in many drugs designed for target and release in specific tissues,[23, 24] and confers pharmacokinetic advantages such as stability in serum and lability at infected bone surfaces in the presence of an acidic and enzymatic environment (e.g. inflammation or infection).[25]

A recent apparent success utilizing a bone-targeting and release strategy is provided by Morioka et al.[26] who designed an estradiol analog conjugate using a cleavable variant (carbamate) of the more stable amide peptide bond.

Several versions of this linkage were attempted before the identification of a pharmacologically active variant (aryl carbamate). Importantly, they demonstrated that a single dose of a similarly linked BP-estradiol conjugate (at a dose nearly 5,600 times lower than the total dose of estradiol alone) produced a similar effect on bone to that of the estradiol dosed alone.26 The conjugate also provided an even greater therapeutic index, as there were minimal effects systemically and in uterine tissues compared to the estradiol alone. Pharmacokinetic studies completed by Arns et al.[27] are in agreement with this dramatic enhancement of potency in studies based on a BP-prostaglandin with a more labile linker. Other synthetic examples of this approach in the antimicrobial field are reported for the macrolide class;[28] however, only alkyl carbamates were explored and the lack of further success suggests that target and release strategies are likely chemical class-dependent (taking into consideration compatibilities of the functional groups of each component) as well as biochemical target dependent, and the design for any particular chemical class must be customized for its use.

In this Example the aryl carbamate BP-carbamate-ciprofloxacin conjugate 6 (BV600022) is described and evaluated for its antimicrobial activity against common osteomyelitis pathogens and its in vivo safety and efficacy in an animal model of peri-prosthetic osteomyelitis. The studies in this Example utilize biofilm models and methodology, in addition to planktonic cultures, to provide greater clinical or translational relevance.

At times herein, this compound may be referred to simply as "compound 6," "conjugate 6," or simply "6." Likewise, other compounds or conjugates may similarly be referenced as "compound e.g. 11", "conjugate e.g. 11", "or simply by the compound number designation (e.g. 11).

Results
Chemistry

Figure 16:
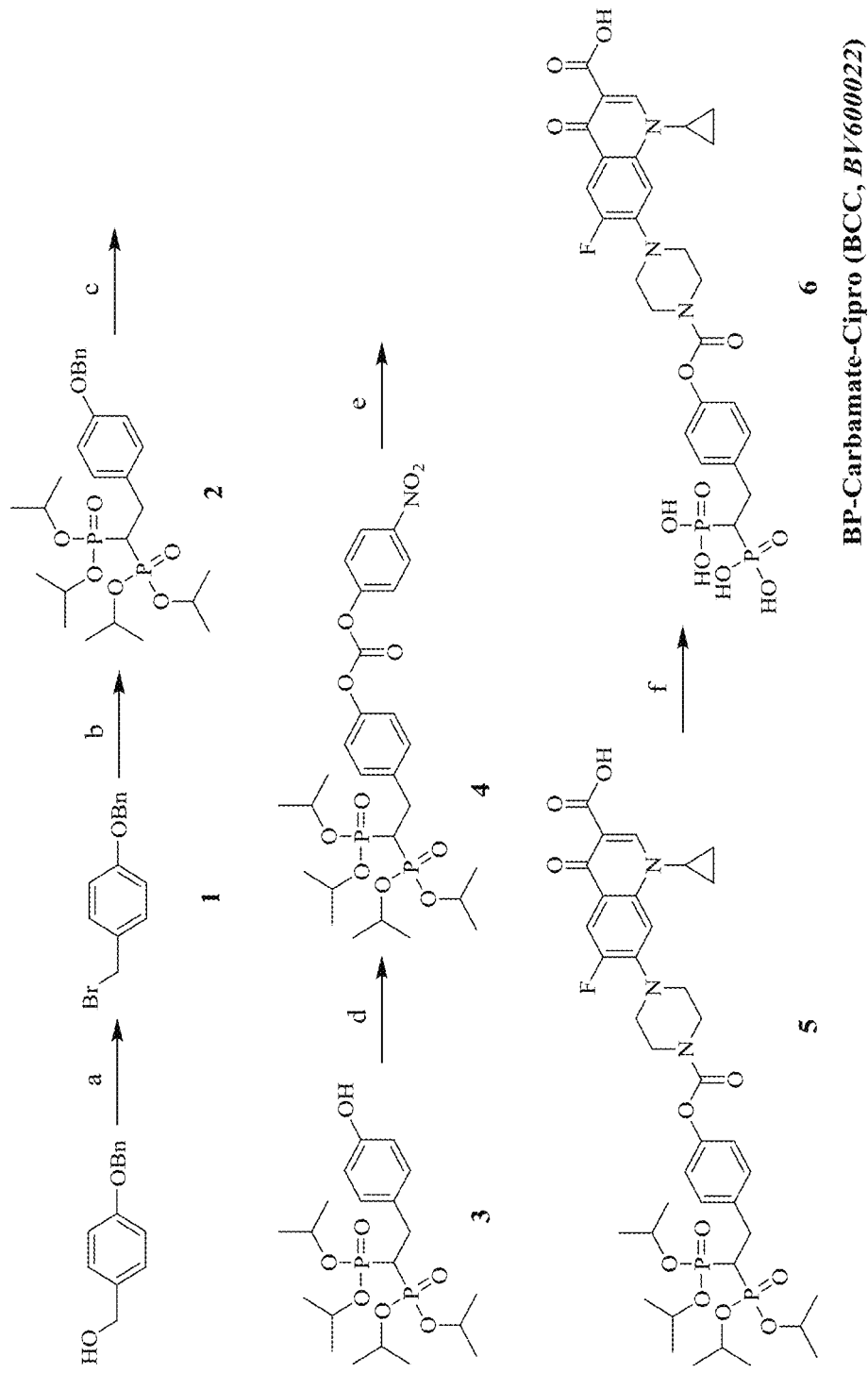
FIG. 16 shows a synthesis scheme for a BP-FQ conjugate.

An overall synthetic Scheme for 6 is shown in FIG. 16, starting from the relatively pharmacologically inert 4-hydroxyphenylethylidene BP (3). The reagents for the Sheme presented in FIG. 16 were as follows: a Reagents and conditions: (a) BTMS (2 equiv), Et2O, 0° C.—rt, 17 h, yield 95%. (b) i) tetraisopropyl methylene bisphosphonate (1 equiv), NaH (1 equiv), THF, rt, 10 min; ii) 1 (1 equiv), rt, 2 h, yield 52%. (c) Pd/C (Catalyst) (0.07 equiv), H2, MeOH, rt, overnight, yield 88%. (d) 4-nitrophenyl chloroformate (1.1 equiv), Et3N (3 equiv), DCM, rt, 2.5 h, yield 44%. (e) Ciprofloxacin (1.2 equiv), water (pH 8.5), THF, 0° C.—rt, overnight, yield 52%. (f) i) BTMS (excess), DCM, 35° C., 24 h, ii) MeOH, rt, overnight, yield 86%.

The rationale for this BP design was to retain the bone-seeking ability of the BP moiety while suppressing its unneeded antiresorptive activity, minimizing confounding factors to focus on evaluating the antimicrobial effect due to the parent ciprofloxacin compound. BP ligands can also be designed to have antiresorptive functionality (of varying potency) if needed to provide a dual-action effect of bone tissue protection in addition to antimicrobial effects at the anatomic site of infection. This phenyl BP was chosen with consideration of bone binding affinity and tether length, as previous studies have demonstrated that weak binding affinity decreases targeting efficiency.[13, 14] It was postulated that the use of an aryl carbamate as a linker might offer optimized stability in plasma and adequate release on bone for this biochemical target as compared to previously derived BP-fluoroquinolone conjugates.

Figure 31:
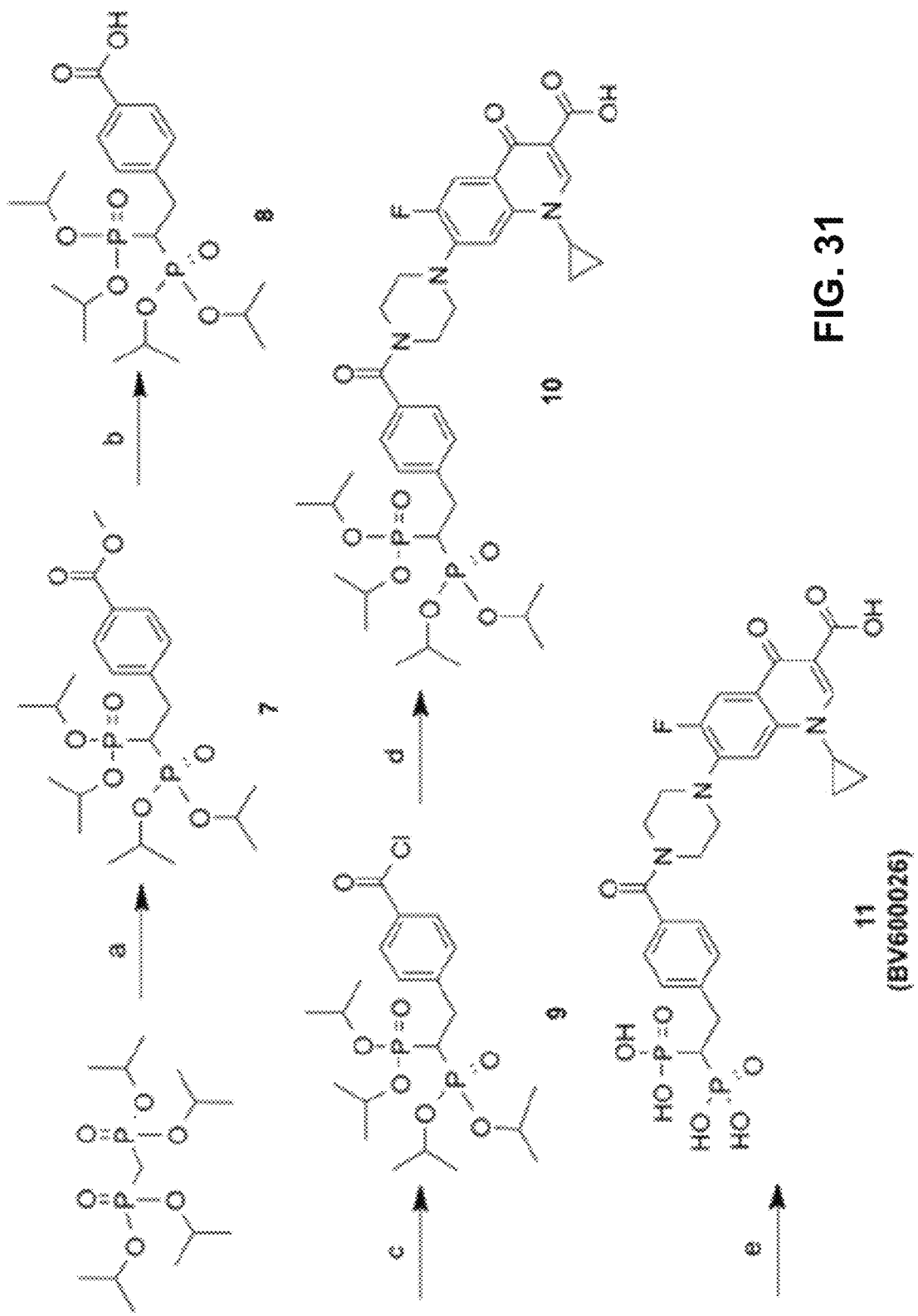
FIG. 31 shows a synthesis scheme for a BP-ciprofloxacin conjugate having an amide linkage (BAC, compound 11) as opposed to a carbamate linkage.

Additionally, a similar BP-ciprofloxacin conjugate having an amide linkage as opposed to a carbamate linkage was synthesized as outlined in the Scheme shown in FIG. 31 as a control conjugate 11 (BV600026). The reagents for the Sheme presented in FIG. 31 were as follows: b Reagents and conditions: (a) i) NaH (1.4 equiv), THF, 0° C.—rt, 1 h; ii) methyl 4-(bromomethyl)benzoate (0.7 equiv), THF, 0° C.—rt, overnight, yield 37%. (b) LiOH.H2O (5 equiv), MeOH, rt, overnight, yield 91%. (c) SOCl2 (2 equiv), DMF (0.05 equiv), DCM, rt, 2 h, yield quantitative. (d) Ciprofloxacin (1 equiv), DIPEA (6 equiv), CHCl3, rt, overnight, yield 65%. (e) i) BTMS (excess), DCM, 35° C., overnight, ii) MeOH, rt, 30 min, yield 82%. Previous investigations have indicated that amide conjugates are not able to release the parent antibiotic and are thus less effective in vitro and in vivo, 11 which it was sought to verify in this instance.

Antibacterial Properties of BP-Ciprofloxacin Conjugates
Minimal Inhibitory Concentration (MIC) Assays:

The antimicrobial activity of both conjugates (6 and 11) and the parent antibiotic ciprofloxacin in standard laboratory planktonic culture systems was evaluated against a panel of *S. aureus* clinical strains associated with bone infections, including methicillin-sensitive *S. aureus* (MSSA) and methicillin-resistant *S. aureus* (MRSA). Following EUCAST (European Committee on Antimicrobial Susceptibility Testing) guidelines[29] results from disc diffusion inhibition zone assays revealed diameters ranging from 25-40 mm (mean 31.5, SD±5), and every strain demonstrated antimicrobial susceptibility to the parent antibiotic ciprofloxacin according to EUCAST clinical breakpoints. Minimal inhibitory concentration (MIC) results for 6 and 11 against eight *S. aureus* strains using microdilution methodology are shown in FIG. 32. MICs for the parent compound ciprofloxacin were determined concurrently for reference (see FIG. 32) and were found to be consistent with established clinical breakpoints.[29]

Figure 18:
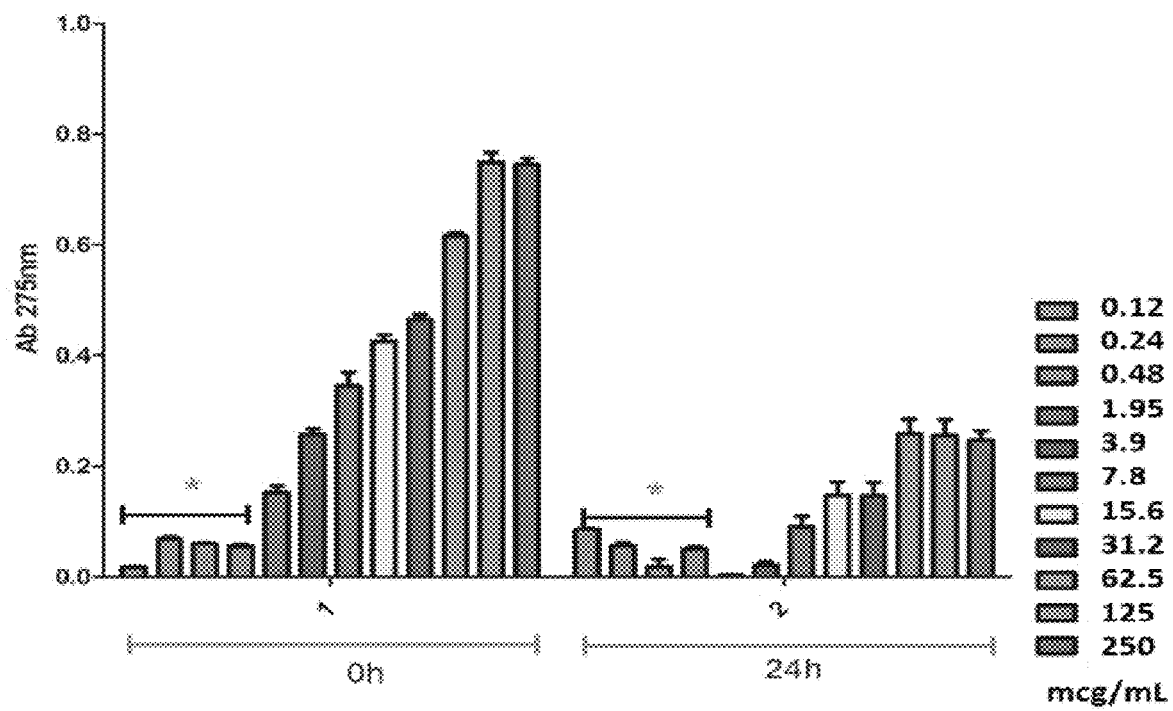
FIG. 18 shows a graph demonstrating results of a spectroscopic analysis of BCC (compound 6) in microbiological media with the addition of HA microspherules confirms adsorption of conjugate to HA, as evidenced by the significant decreases from 0 hr to 24 hrs since only the supernatant is measured absent the HA spherules with adsorbed conjugate. [results for 1.95-250 mcg/mL are all statistically significant: p<0.05, ANOVA; triplicate; *results for 0.12-0.48 mcg/mL (red bars) are inconclusive because of a high value of "blank" measurements.

Hydroxyapatite (HA) Binding Assay:

Having established the antimicrobial efficacy of 6, it was next sought to evaluate HA binding ability. HA spherules were added to the microbiological media and then introduced 6 at various concentrations similar to those used in the antimicrobial testing. Quantitative spectroscopic analysis of supernatant (without HA spherules) confirmed significant adsorption and retention of the conjugate by HA (FIGS. 18 and 5).

pH Effect in Antimicrobial Susceptibility Testing (AST) on Planktonic *S. aureus* Strain ATCC-6538:

*S. aureus* strain ATCC-6538 was selected for further investigation because it demonstrated the lowest MIC profile for both ciprofloxacin and 6 (see FIG. 32) compared to the other strains tested. This ATCC strain is also a well-known and robust biofilm-forming pathogen. Consequently, the conjugates were tested against a challenging pathogen to limit bias and overestimated results, while also facilitating assessment of antimicrobial activity in biofilm based and clinically relevant models. Antimicrobial susceptibility testing (AST) on planktonic *S. aureus* strain ATCC-6538 with 6 under both acidic and physiological pH was performed to assess the effect of pH on conjugate activity. Quantitative results from standard microdilution methodology indicated that under acidic conditions (pH 5) the antimicrobial activity of 6 was improved overall as the MIC50 was reached at half the conjugate concentration required to reach MIC50 under physiological conditions (FIGS. 6 and 4). These results and results presented demonstrated elsewhere herein, the minimum inhibitory concentration terms MIC50 or MIC90 refer to a reduction of 50% or 90% of bacterial load, respectively; and the biofilm-related terms of minimum biofilm inhibitory concentrations (MBIC50 or MBIC90) refer to similar reductions (50% or 90%) but in biofilm bacterial load.

Figure 7:
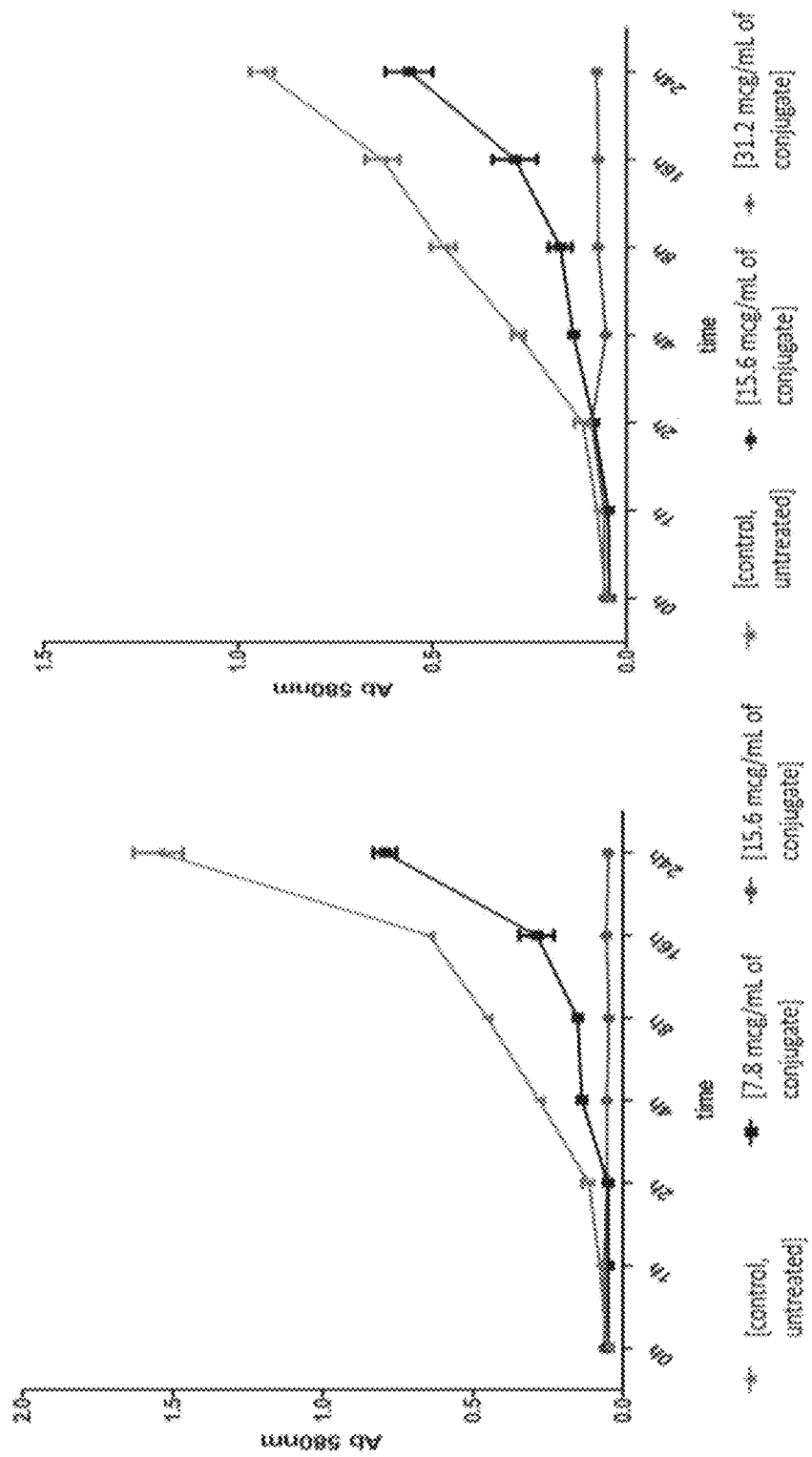
FIG. 7 shows graphs demonstrating the time-kill results for BP-ciprofloxacin (conjugate) against S. aureus strain ATCC-6538 (right graph) and MRSA strain MR4-CIPS (left graph) and at 1× (red line) and ½× (black line) the established MICs showing strong bactericidal activity at 1 hr and up to 24 hrs.

Time-Kill Assays of Compound 6:

Next, kinetic assays were performed with 6 according to CLSI (Clinical Laboratory Standards Institute) methods.[30] Results indicated that this conjugate was bactericidal at the previously established MIC for methicillin-susceptible (ATCC-6538) and methicillinresistant (MR4-CIPS) isolates of planktonic S. aureus within 1 hr and up to 24 hrs, preventing 100% of bacterial growth; these kinetic studies also revealed that at half the MIC value, prevention of bacterial growth became evident after 2 hrs and inhibition was at 50% of control after 24 hrs (e.g. FIG. 7).

Evaluation of Antimicrobial Efficacy of 6 Against Biofilms:

Compound 6 was then tested against pre-formed bacterial biofilms on two different substrates (polystyrene and HA discs) to evaluate antimicrobial efficacy against biofilms, and to also determine if substrate binding-specificity plays any role in the observed antimicrobial efficacy. Biofilms of S. aureus (ATCC-6538), and additionally biofilms of P. aeruginosa (ATCC-15442), were grown on polystyrene or HA as substrates and were subjected to varying concentrations of 6 for assessment of antimicrobial activity. P. aeruginosa here because it is a Gram negative pathogen and the second most common clinical pathogen in osteomyelitis, though less frequent in prevalence than Gram positive S. aureus. E.g. FIG. 8. shows results for polystyrene as the substrate for biofilm growth, and the minimal biofilm inhibitory concentration (MBIC50) of 6 was 15.6-31.2 µg/mL for S. aureus ATCC-6538, which was comparable to the MIC for this strain in planktonic cultures. No MBIC50 was observed for P. aeruginosa ATCC-15442 in the tested range of concentrations and no MBIC90 was observed for either pathogen.

Figure 33:
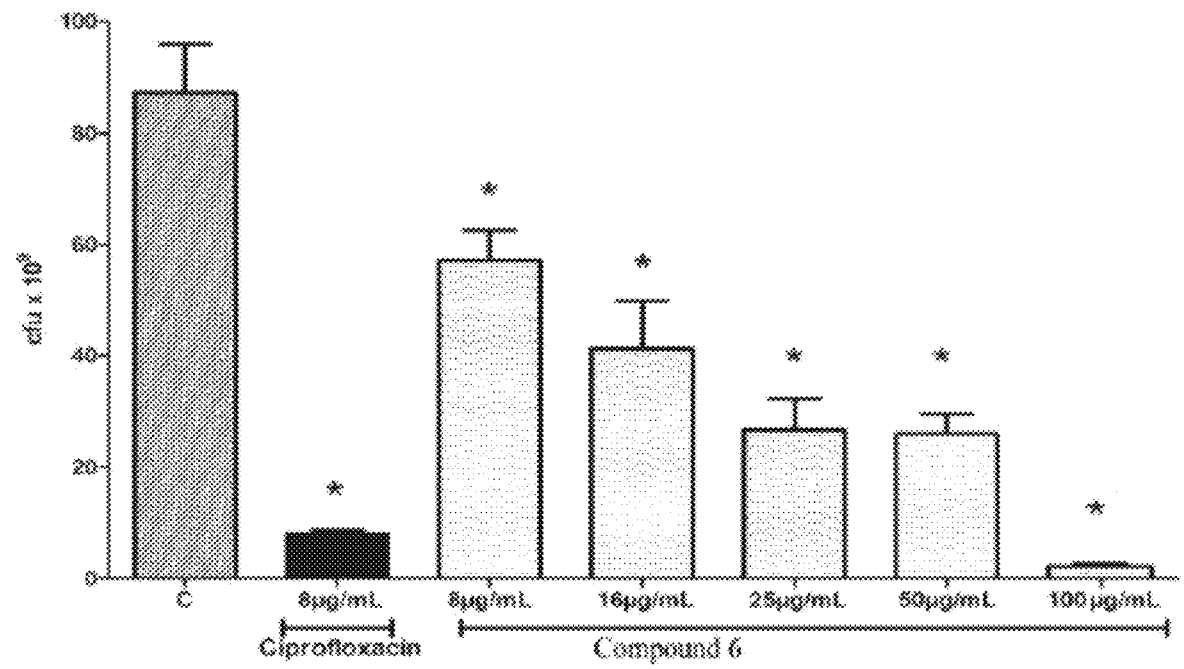
FIG. 33 shows graphs demonstrating antimicrobial susceptibility testing of 6 against biofilms of S. aureus strain ATCC-6538 (top graph) and P. aeruginosa strain ATCC-15442 (bottom graph) formed on HA discs as the substrate. All tested concentrations of 6 (dotted bars top graph) and the parent antibiotic ciprofloxacin resulted in statistically significant bactericidal activity against S. aureus; c=negative control comparator. Against P. aeruginosa, 6 was most effective at physiological pH at 8 µg/mL, and also effective at acidic pH at this concentration, but ciprofloxacin was inactive under either acidic or physiological conditions compared to the controls [*p<0.05, Kruskal-Wallis test; triplicate].
Figure 33:
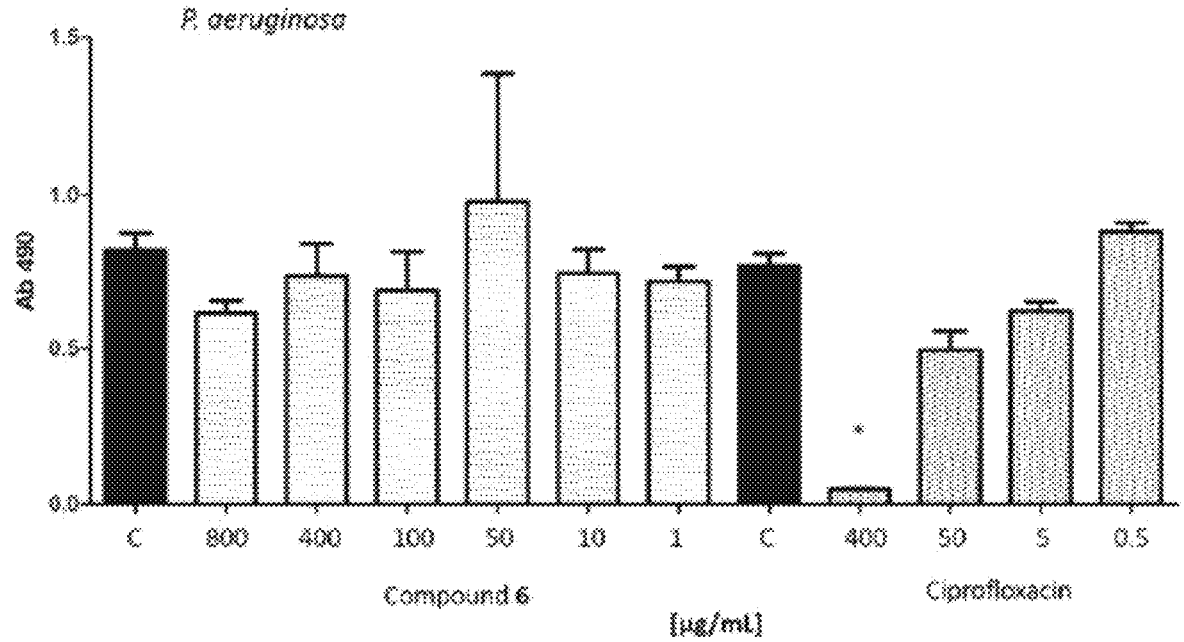

However, when HA discs were used as the biofilm substrate, marked bactericidal activity was observed with 6. As shown in FIG. 33, all tested concentrations of this conjugate resulted in statistically significant ($p<0.05$, Kruskal-Wallis test) bactericidal activity and reduction of colony forming units (CFUs). The MBIC50 of 6 was 16 µg/mL and the MBIC90 was 100 µg/mL against S. aureus strain ATCC-6538; the MBIC90 for the parent drug ciprofloxacin was 8 µg/mL against this pathogen. However, against P. aeruginosa strain ATCC-15442 ciprofloxacin had no inhibitory or bactericidal activity in this setting while the conjugate was bactericidal in acidic and physiological conditions at 50 µg/mL, and showed improved bactericidal activity in physiological conditions as compared to S. aureus where improved antimicrobial activity was observed in acidic conditions.

Preventative Antimicrobial Assays:

Next, antimicrobial tests with κ were performed in a preventative type of experimental setting with planktonic and biofilm cultures, which could also have clinical relevance in antibiotic prophylactic scenarios for osteomyelitis pharmacotherapy. Here HA spherules were introduced to varying concentrations of 6 and then inoculated with S. aureus for 24 hrs, and quantitative assessments indicated no bacterial growth at concentrations as low as 15.6 µg/mL and up to 250 µg/mL of 6, and minimal bacterial growth with strong inhibition at conjugate concentrations ranging from 0.24 to 7.8 µg/mL as shown in e.g. FIG. 10.

Figure 34:
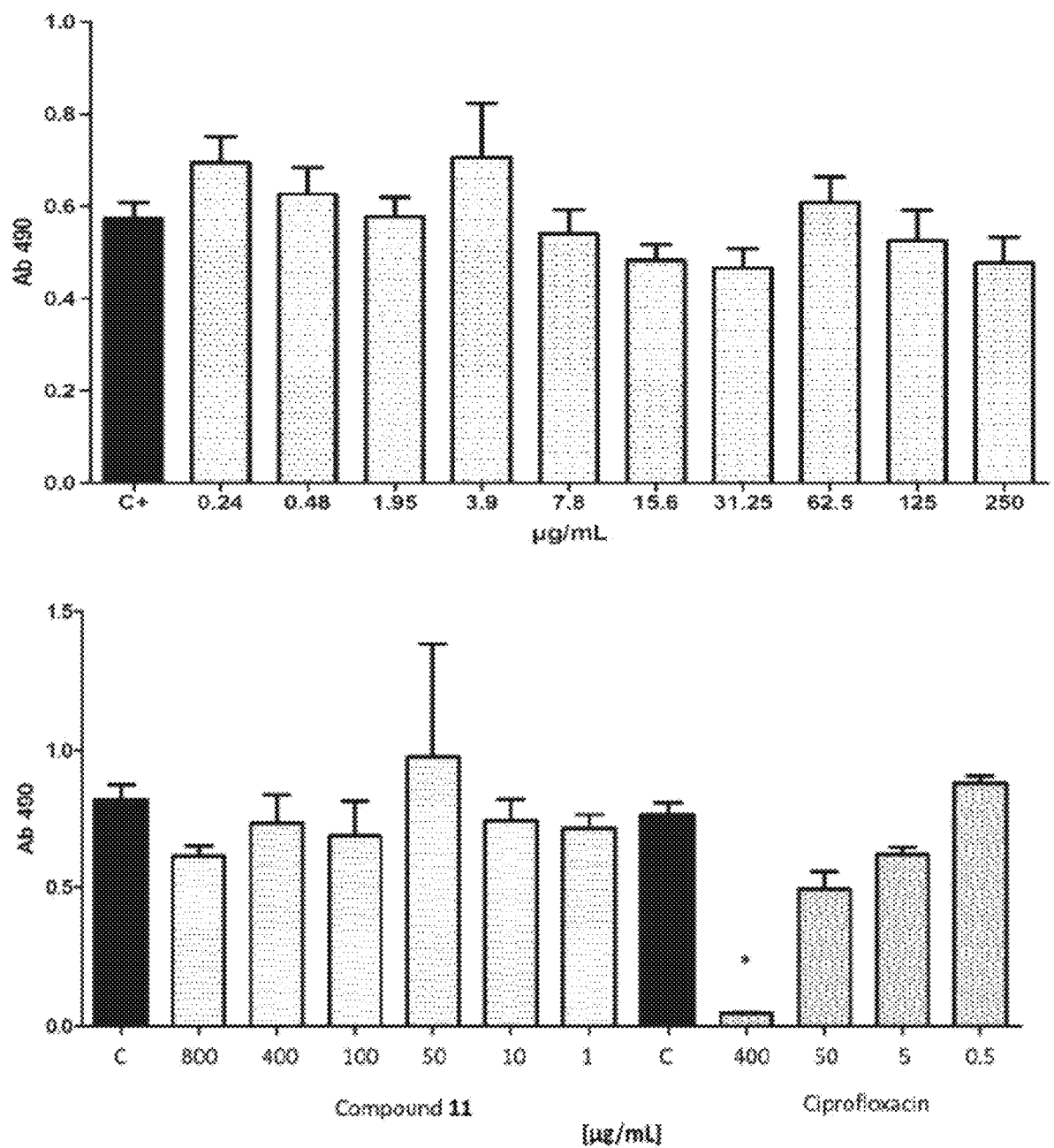
FIG. 34 shows graphs demonstrating the results from Antimicrobial susceptibility testing (top graph) of 11 at increasing concentrations against biofilms of S. aureus strain ATCC-6538 formed on HA as the substrate. No significant activity is observed at any concentration as compared to the control C+[p>0.05, Kruskal-Wallis test; triplicate]. The bottom graph shows results from preventative experiments where HA is pretreated with 11 or the parent antibiotic ciprofloxacin and then inoculated with S. aureus, and again no antimicrobial activity is observed for 11; the only significant reduction is seen with the parent drug at a relatively high dose of 400 µg/mL [*p<0.05, Kruskal-Wallis test; triplicate].

Next, the amide conjugate (11) was tested for ability to treat S. aureus strain ATCC-6538 biofilms in experimental conditions similar to those used to test the carbamate conjugate 6. When evaluating the activity of 11 against established S. aureus biofilms grown on HA, and HA pretreated with 11 prior to biofilm growth in a preventative experimental setting, antimicrobial activity of 11 even at higher doses than those used to test 6, was insignificant in both cases as shown in FIG. 34.

When 6 was tested for ability to prevent S. aureus ATCC-6538 biofilms from forming on pretreated HA, the conjugate showed superior antimicrobial activity as compared the parent antibiotic and in contrast to 11 which showed no significant antimicrobial activity. FIG. 11 shows results of quantitative biofilm cultures and CFU counts after 24 hrs of growth, and at 100 µg/mL the parent drug ciprofloxacin inhibited all biofilm growth whereas at 10 µg/mL, 6 inhibited all growth. Since the molecular mass of ciprofloxacin is approximately half that of 6, 6 was 20 times more active in achieving complete bactericidal action as compared to ciprofloxacin alone.

Figure 35:
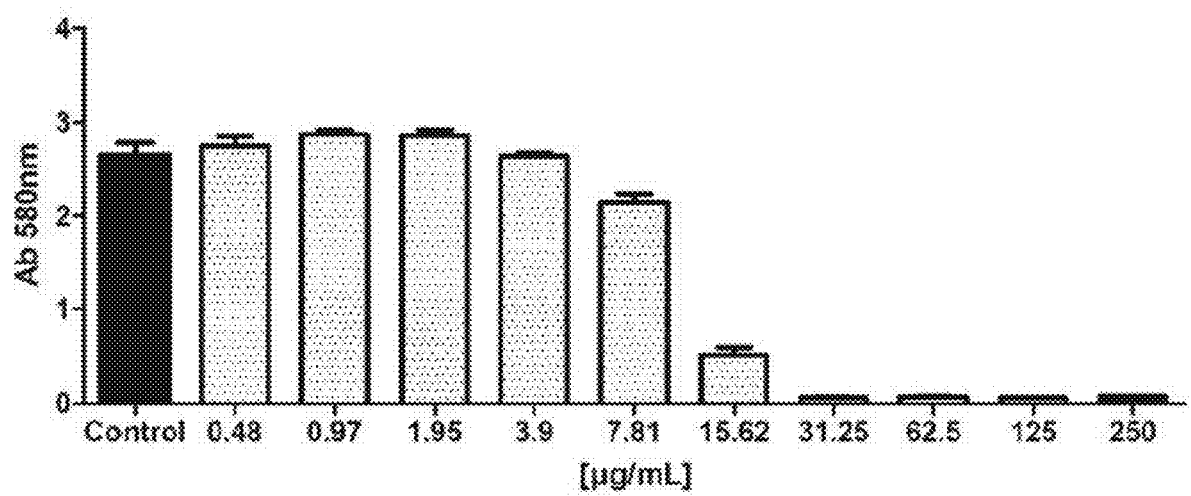
FIG. 35 shows a graph demonstrating antimicrobial susceptibility of 6 against biofilms of *Aggregatibacter actinomycetemcomitans* strain D7S-5 grown on HA shows an effective antimicrobial profile for conjugate 6 at >15 µg/mL.

In Vivo Safety and Efficacy:

Since 6 demonstrated promising activity in vitro, we sought to assess drug safety and efficacy in vivo in an animal model of periprosthetic osteomyelitis. This model is a unique in-house jawbone peri-implant osteomyelitis model that was developed specifically for translational value to study biofilm-mediated disease and host response in vivo.[31] Because a systemic treatment regimen is utilized, this assay also serves to model any infected bone surface, since the resulting osteolysis involved is key to attracting (targeting) high concentrations of a BPconjugate, like any high turnover site on bone, and to subsequently release the active ciprofloxacin component of the conjugate at this diseased bone surface. Briefly, biofilms of the jawbone osteomyelitis pathogen Aggregatibacter actinomycetemcomitans (Aa; wild-type rough strain D7S-1; serotype a), which is not indigenous to rat normal flora and specific to jawbone infections, were pre-inoculated on miniature titanium implants at $10^9$ CFU. To confirm Aa sensitivity to the parent drug ciprofloxacin prior to our animal studies, AST and MIC assays were performed as performed for the long bone osteomyelitis pathogens described previously. Disc diffusion inhibition zone assays revealed diameters >40 mm, and the MIC90 was 2 µg/mL, indicating strong susceptibility of this microbe to the parent drug ciprofloxacin. Aa has also been tested previously for susceptibility to a pH-sensitive biotinylated ciprofloxacin prodrug and was found to be sensitive to the parent antibiotic.[32] As with previous pathogens in this study, Aa biofilm pathogens grown on HA were tested for sensitivity to 6 and found our conjugate displayed effective antimicrobial activity as shown in FIG. 35.

After Aa biofilms are established on implants in vitro, they are surgically transferred to the jawbone of each rat. Animals are anesthetized, the cheeks are retracted and a transmucosal osteotomy is performed so implants can be manually inserted into the osteotomy and secured. Two biofilm-inoculated implants are placed in each rat (n=12 rats, 24 implants total) in the palatal bone bilaterally. This model allows standardized and reproducible quantities of viable bacteria to be formed as well-established biofilms on each implant, which we have previously demonstrated persists in vivo for several weeks after placement and causes infection, inflammation, and bone destruction locally.[31]

Once peri-implant infection was established 1 week postoperatively, the animals were dosed with κ, ciprofloxacin alone as a positive control, and sterile endotoxin-free saline as a negative control at the dosing regimens specified in the experimental section. To determine appropriate dosing concentrations, approximate initial doses were calculated for the conjugate based on previous studies and pharmacokinetic data using similar target and release strategies also in rodents.[13, 26] Increasing doses of 0.1, 1 and 10 mg/kg molar equivalents of 6 can allow for determination of antimicrobial activity in 2 test animals per group based on sample size estimations and previous experience with the animal model.[32] Animals were dosed via intraperitoneal injection under general anesthesia, and all compounds were constituted in sterile physiological injectable saline at appropriate pH. Intraperitoneal injection was used because of the ease of administration in small rodents as compared with other parenteral methods like tail vein injection, and because the pharmacokinetics of ciprofloxacin following gastrointestinal administration shows excellent bioavailability; serum drug levels achieved after such administration are slightly less but comparable to those with intravenous dosing with no substantial loss after first pass metabolism.[33] One week after pharmacotherapy, all animals were sacrificed and en bloc resection of peri-implant hard and soft tissues was performed and homogenized for quantitative assessment of microbial load.

Figure 36:
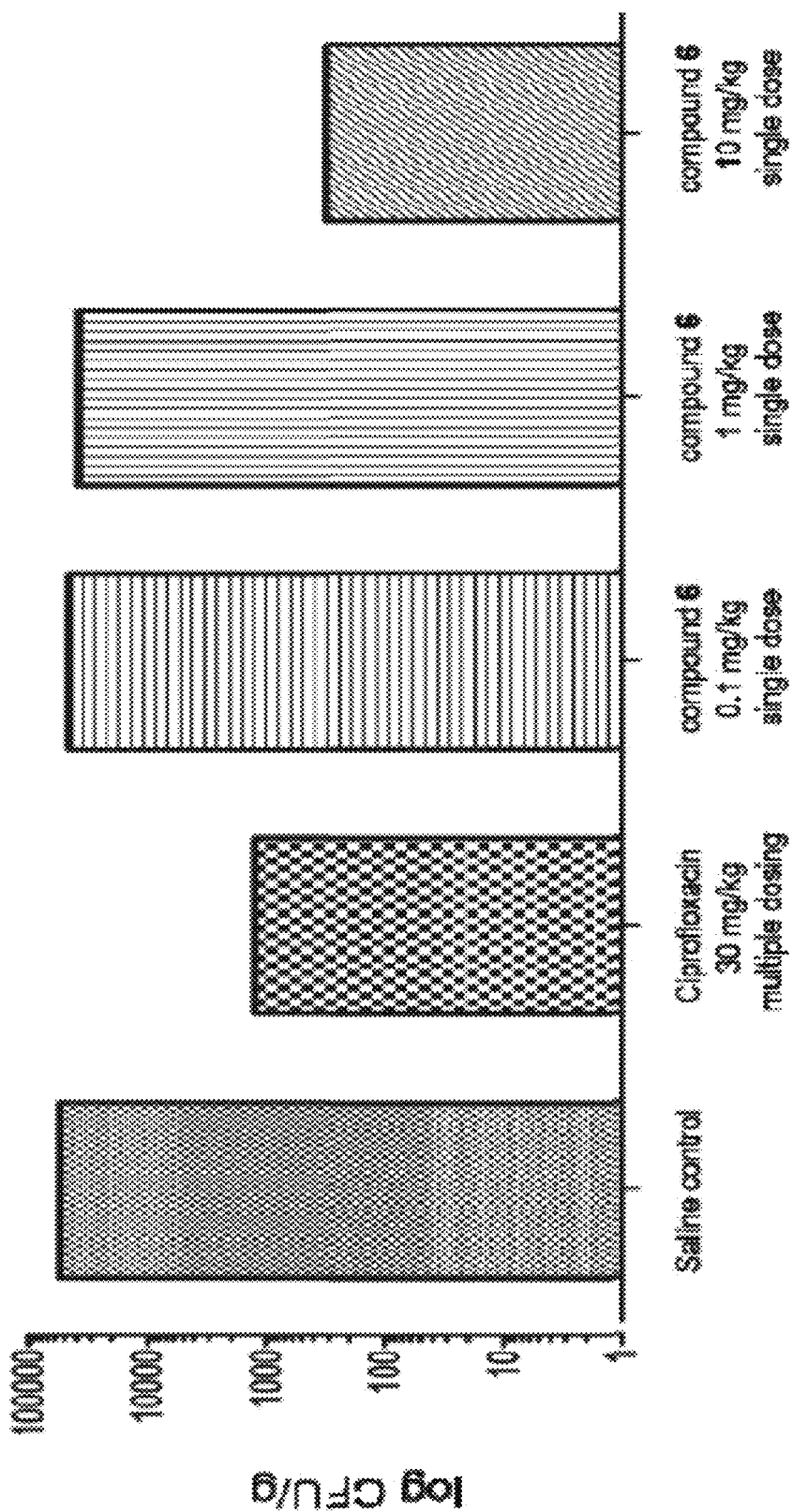
FIG. 36 shows a graph demonstrating antimicrobial results from in vivo animal testing. Data show efficacy of tested compounds for reducing bacterial load. The greatest efficacy was observed at a single high dose (10 mg/kg) of 6 where a 2 log reduction (99% bactericidal activity) was seen as compared to the negative control.

All animals tolerated the pharmacotherapy well with no cutaneous injection-site reactions or inflammation. There were no signs of gross tolerability issues during therapy. Treatment efficacy was quantitatively measured in terms of the logarithmic reduction of the amount of viable bacteria (mean log 10 CFU/gram of tissue) as shown in FIG. 36.

In vivo, the single dose of 6 at 10 mg/kg showed the highest efficacy with a 2 log reduction in bacterial count (99% bacterial killing) and nearly an order of magnitude greater activity than ciprofloxacin alone given at the same per dose concentration (mg/kg) but in multiple doses (30 mg/kg total dose). Thus, given the greater molecular weight of 6 (~2× of ciprofloxacin), the administered single dose of 6 at 10 mg/kg could deliver roughly 5 mg/kg of effective ciprofloxacin assuming full release, which is ⅙th of the ciprofloxacin molar dose of the control ciprofloxacin arm (30 mg/kg total). Ciprofloxacin alone in a multiple dosing regimen resulted in a 1 log reduction in bacterial counts (90% bacterial killing). Concentrations of 6 at 0.1 and 1 mg/kg had little effect, suggesting that a minimum dose is necessary for clinical effect and that further chemistry optimization may be possible in this context.

To validate the animal study findings, and to provide for greater power and larger sample size for statistical analysis, we conducted a second animal experiment nearly identical to the first except for allocation of dosing regimens. Based on dosing data and antimicrobial results from our first animal study described above, we focused this second animal study on three treatment groups: negative control (n=5 rats), 6 at a single high dose of 10 mg/kg (n=5 rats), and 6 at a multiple low dose regimen of 0.3 mg/kg 3×/week (n=2 rats). Dosing groups of 0.1 and 1 mg/kg were excluded as they showed no efficacy previously, and the parent antibiotic alone was also excluded since robust historical data exists for ciprofloxacin efficacy which we also confirmed in our initial animal study. The multiple dosing regimen was utilized again to ascertain whether the lack of recoverable bacteria could be attributed to treatment effect or experimental and sampling error. All other experimental parameters were identical to the first animal experiment, and each animal had two implants placed as before allowing for two results per animal and providing sufficient power for statistical analyses as determined by sample size estimations.

Figure 37:
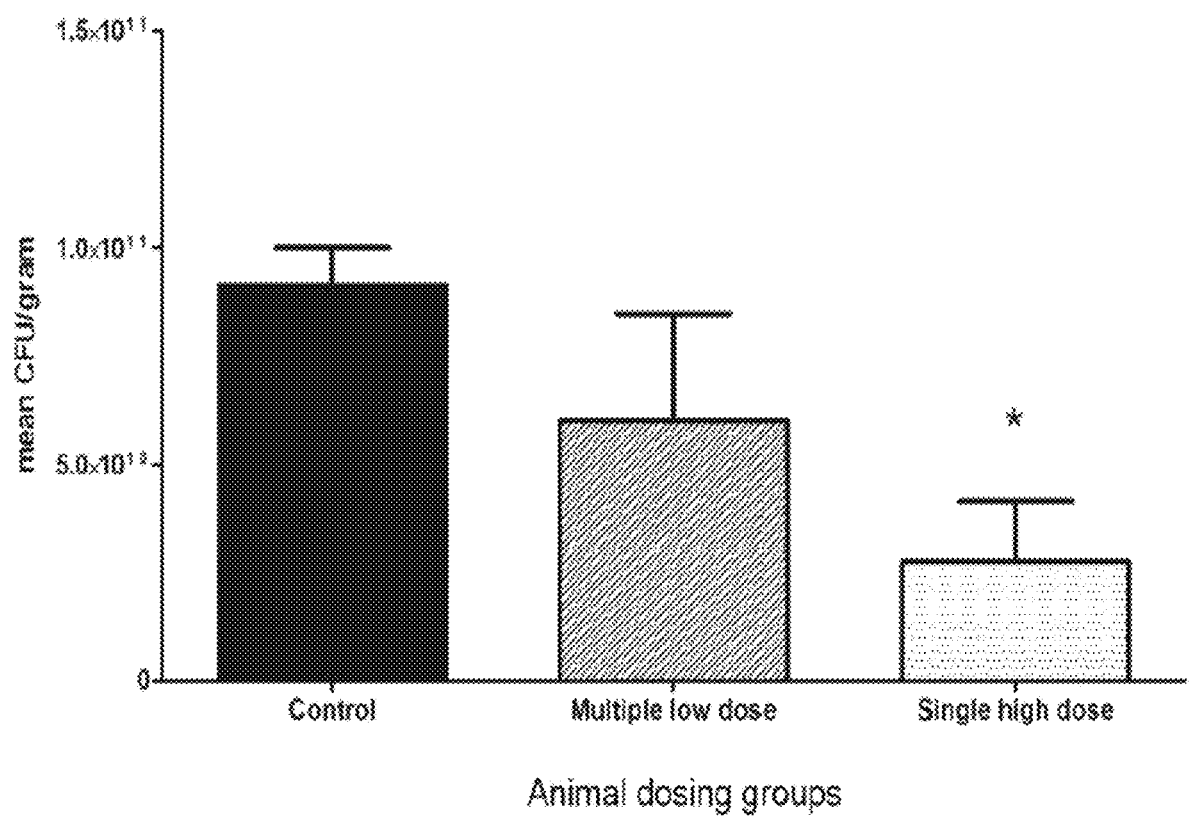
FIG. 37 shows a graph demonstrating Antimicrobial results from the second animal experiment. Data shows efficacy of 6 for reducing bacterial load or mean CFU/gram of tissue (y-axis). The greatest efficacy was observed at a single high dose (10 mg/kg) of the conjugate compared to the control and the multiple low dose group (0.3 mg/kg×3) [*p=0.0005; unpaired t-test, errors bars represent Standard Error].

All animals again tolerated treatment and pharmacotherapy well and there were no signs of gross tolerability issues during therapy. Clinically during euthanasia and surgical resection, it was observed that the majority of the animals in the control group demonstrated evidence of localized peri-prosthetic inflammation as compared to the majority of the animals in the treatment groups which had non-inflamed peri-implant tissues, and implant retention was 23/24 implants (96%) which is a high retention rate and provided robust power for subsequent analyses. Quantitative antimicrobial results from this second animal experiment are shown in FIG. 37. Single factor ANOVA testing (a=0.05) comparing CFUs between treatment groups resulted in a p-value=0.006 for significance between groups, and post-hoc testing utilizing an unpaired t-test (p=0.0005; df=20) and Dunnett's multiple comparisons test (p<0.05) revealed significance for the single high dose of 6 treatment as compared to the control, but not for the multiple low dose group (p>0.05) when compared to the control or to the single high dose treatment group.

Discussion

Targeting antibiotics to bone by conjugation to a BP moiety (via a releasable carbamate linker) is a promising approach for the treatment of osteomyelitis biofilms. Results of AST testing and MIC data presented herein indicate that against planktonic *S. aureus*, ciprofloxacin and 6 have effective bactericidal activity, and that the conjugation linkage impacts antimicrobial activity of the parent drug as evidenced by the weaker activity of 11 (FIG. 32). Higher concentrations of 6 were required to reach MIC, which is anticipated since conjugation is a chemical modification that can alter the biochemical interactions of the antibiotic prior to release from the conjugate. As a result, properties of the parent drug, including its pharmacodynamic effect, can be altered by such modification. MIC results for 6 were consistent with previous literature indicating that conjugates in this class can retain the antibacterial activity of the parent compound, although at slightly lower levels.[9, 10]

Of interest was the wide distribution of MIC values for both conjugates against tested *S. aureus* strains, as compared to ciprofloxacin alone which demonstrated little variance in antimicrobial efficacy against the same strains (FIG. 17). There are several possible explanations for these results. Different strains of bacteria within the same species are known to show significant variance in terms of virulence and antimicrobial susceptibility/resistance to an antibiotic. It is well established that strain-specific variances exist in antibiotic transport and efflux mechanisms, bacterial cell wall density, enzymatic activity levels, resistance mechanisms, and ability to alter pH of the environment.[34] Ciprofloxacin bactericidal activity results from intracellular inhibition of enzymes required for DNA replication—topoisomerase II and IV.[35]

It has been established that intact conjugates in this class generally lack significant intrinsic antibacterial activity,[18, 19] and that any BP-related antimicrobial effect is negligible; therefore, at least partial release of the parent drug is a prerequisite for significant antimicrobial activity, as observed with 6. This is consistent with the low antimicrobial activity of 11 differing in its more stable amide linkage, which resulted in 2-64× the concentration of the more labile carbamate linked conjugate 6 to achieve the same antibacterial effect in the assay.

After evaluating the antimicrobial efficacy of 6, it was sought to assess the bone-binding functionality of the BP moiety and found effective adsorption and retention to HA spherules by the conjugate in a concentration-dependent manner. These results are consistent with previously reported analogs in this class containing BP moieties with similar bone affinities.[13, 19] It was then tested whether activity of 6 would vary in different pH conditions and found a slightly improved profile in acidic conditions, which may be explained at least partially by the fact that the linker is more labile at pH 5 than at pH 7.4 thus releasing more ciprofloxacin at the lower pH. This could be useful for clinical osteomyelitis applications where biofilm pathogens along with host inflammation and osteoclastogenesis produce an acidic local milieu. Other investigators have suggested, however, that although acidic pH brought on by infecting organisms and inflammation could result in some drug release in bone, the efficacy of such a process in providing a significant concentration of the antimicrobial agent is doubtful, and that prodrug design, conjugation scheme, and susceptibility to local enzymatic hydrolysis likely have greater impact on linker cleavability and efficacy.[13] The data in this Example also support such conclusions.

Investigation of time-kill kinetics for 6 demonstrated an efficient rate of bactericidal activity against tested bacteria with sustained bactericidal activity over 24 hrs, supporting cleavage activity of the parent antibiotic with a steadily sustained release profile over time. The antibiotic release kinetics observed here may be different than those observed with currently used biodegradable and non-biodegradable delivery systems for osteomyelitis therapy, which generally demonstrate an initial high bolus of antibiotic release at the site with a smaller percentage of the remaining antibiotic dissipating over an extended period of time.[36, 37]

This Example presents evidence for antimicrobial efficacy of conjugates such as 6 in biofilm-relevant models in vitro and in vivo for osteomyelitis treatment. When osteomyelitis biofilms (S. aureus and P. aeruginosa) were grown in vitro on different substrates such as polystyrene or HA, and then treated with 6, the conjugate was more effective against biofilms in the presence of HA versus polystyrene. This indicates that substrate binding-specificity plays a role in antimicrobial activity in addition to factors like strain of pathogen tested and mode of bacterial growth (planktonic versus biofilm). The fact that 6 was effective against osteomyelitis pathogens on HA, but not effective against the same strains on polystyrene as a substrate, indicates that to effectively treat osteomyelitis biofilms, it is necessary to bind to the substrate (e.g. HA) and release antibiotic directly underneath or within a biofilm rather than just flow the antibiotic along the biofilm surface (as was the case with the parent antibiotic alone or 6 on polystyrene where no substrate binding occurs and no activity was seen against established surface biofilms). The improved activity of 6 found in experimental settings using HA discs in comparison to the setting using polystyrene as a substrate is likely due to the fact that the BP moiety of the conjugate possess high affinity to HA structures, and therefore bacteria adhering to HA were likely subjected to a relatively higher concentration of the parent antibiotic due to localization of 6 to the disc. Also, cleavage of 6 at bone under biofilm bacterial cells may be similar to carbamate cleavage under osteoclast cells as previously shown,22 suggesting that the local environment plays a role in this context and further indicating that the environment under bacteria, that also causes osteolysis, has similarities to the environment under osteoclasts on bone since these environments both seem to be able to cleave the aryl carbamate linkage to release the active ciprofloxacin, probably due to a combination of pH and enzymatic hydrolysis. Previous work by Arns et al.[27] with BP (radiolabeled) prostaglandin conjugates suggest that, as with most BPs,[38] the half-life of the conjugate in the bloodstream is less than 15 minutes. Thus, in that time the conjugate is either bound to bone or excreted. This research study also demonstrates that the half-life of release of the active drug (prostaglandin in this case) from the BP on the bone surface, with linkages related to our carbamate is between 5 and 28 days. The linkage demonstrated herein must release closer to the 5-day half-life to achieve the exciting in vivo result reported here. Arns et al and others27 have speculated that the mechanism of cleavage is most likely enzymatic under bone cells. In the presence of bacteria on mineral surfaces, it is also likely to be an enzymatic-based cleavage. As is already noted in the manuscript during in vitro antimicrobial studies devoid of osteoclasts, our carbamate based conjugate is active, but our non-cleavable amide-based conjugate is far less active.

The conjugates were also tested in osteomyelitis preventative experiments against S. aureus, and found that 6 was 20 times more active in achieving complete bactericidal action as compared to ciprofloxacin alone (FIG. 11), whereas any antimicrobial activity of 11 was not detectable (FIG. 34). These findings support an efficient mechanism of cleavage and release over time of the parent antibiotic from 6 as compared to 11. Efficient binding to HA and release of the parent antibiotic is requisite for conjugates in this class to demonstrate substantial antimicrobial efficacy.

Finally, it was sought to test in vivo safety and efficacy of 6 in a jawbone peri-implant osteomyelitis rat model using the model jawbone pathogen Aa. To confirm Aa sensitivity to the parent drug ciprofloxacin prior to our animal studies, we performed in vitro AST and MIC assays as performed for the long bone osteomyelitis pathogens in this study. Aa demonstrated strong susceptibility to the parent drug ciprofloxacin. Aa biofilms grown on HA (similar to S. aureus and P. aeruginosa) were also tested for sensitivity to 6 and found our conjugate displayed effective antimicrobial activity (FIG. 35). Therefore, two consecutive animal experiments were performed utilizing a peri-implant jawbone osteomyelitis model. In the first in vivo study, a single dose of 6 at 10 mg/kg showed the highest efficacy with 2 log reduction of CFU or 99% bacterial killing and nearly an order of magnitude greater activity than ciprofloxacin alone given at the same per dose concentration (mg/kg) but in multiple doses (FIG. 36), comparable or better than the parent antibiotic alone,[18-20] as was observed with the more labile 6 but not with the more stable 11 even at high doses of exposure, confirming that cleavage contributes and in some instances can be necessary for antimicrobial efficacy. Lower concentrations of 6 in this experiment were ineffective. To validate these results we performed a second larger and more statistically powered in vivo experiment focusing on the efficacious dosing regimen (10 mg/kg) of 6 as compared to control and multiple dosing regimens of 6. Again greatest CFU reduction and efficacy was observed at the single high dose (10 mg/kg) of conjugate.

In vivo experiments confirmed the ability of 6 at a safe and adequate single dose to target infected peri-implant bone and generate a sufficient concentration of the parent antibiotic for bactericidal activity against established Aa biofilms when the activity of the parent antibiotic alone had already diminished. As microbial quantification involved an en bloc resected tissue homogenate, even biofilm bacteria within canaliculi of the 3-dimensional osseous architecture are included for analysis and not just surface pathogens (as the methodology did not involve surface scraping for plating and assessment). This suggests efficacious BP absorption/adsorption to peri-prosthetic bone and antibiotic release as evidence by the considerable reductions in CFU of biofilm bacteria.

These results along with other studies in this field are also indicating that direct comparisons between these conjugates and their parent compound are somewhat arbitrary as conjugates have unique pharmacometric parameters and predominantly localize to bone due to the BP moiety. This is in contrast to the parent antibiotics (the fluoroquinolone class in general) which demonstrate much greater muscle and tendon uptake than bone uptake in humans,[39] and thus correlate with adverse events such as Achilles tendon rupture in susceptible populations. Any future pharmacokinetic modeling and testing for conjugates in this class should include a skeletal compartment of distribution mathematically, which is not generally done with ciprofloxacin and most other antibiotic pharmacokinetic studies. The importance of such an approach in human populations for accurately determining bone pharmacokinetics of BP drugs has been established.[40] Such approaches will provide more accurate and necessary pharmacological data in this context and also inform clinical dosing approaches.

Materials and Methods

All manipulations were performed under nitrogen atmosphere unless stated otherwise. Anhydrous ethyl ether, anhydrous tetrahydrofuran, anhydrous citric acid, chloroform, and magnesium sulfate were purchased from EMD. 4-Benzyloxy benzyl alcohol, bromotrimethylsilane, 4-nitrophenyl chloroformate, hydrochloric acid (37%), anhydrous ethanol, anhydrous N,N-dimethylformamide, and thionyl chloride were purchased from Sigma Aldrich. Sodium sulfate was purchased from Amresco. Sodium hydride (57-63% oil dispersion), tetraisopropyl methylenediphosphonate, 10% Palladium on activated carbon, 4-(bromomethyl)benzoate, lithium hydroxide monohydrate, and N-ethyldiisopropylamine were purchased from Alfa Aesar. Ethyl acetate, hexane, and dichloromethane were purchased from VWR. Anhydrous methyl alcohol, trimethylamine, and sodium carbonate were purchased from Macron. Hydrogen gas was purchased from Airgas. Ciprofloxacin was purchased from Enzo Life Sciences. Acetonitrile (HPLC Grade) was purchased from Spectrum. All reagents were used as received, unless stated otherwise. All solvents were dried using 3 Å molecular sieves (20% m/v).[41] Silica gel was purchased from Silicycle (SilicaFlash P60, 40-63 Å, 40-63 μm, 230-400 mesh).

Nuclear magnetic resonance spectra were recorded on Varian 400-MR 2-Channel NMR Spectrometer with 96-spinner sampler changer and analyzed using TopSpin and MestReNova. Chemical shifts (δ, ppm) for 1H were referenced to residual solvent peaks. Mass spectra were obtained on a Thermo-Finnigan LCQ Deca XP Max mass spectrometer equipped with an ESI source under positive and/or negative modes using Tune Plus version 2.0 software for data acquisition and Xcalibur® 2.0.7 for data processing and reported in m/z. Organic Elemental Analysis was performed on Flash 2000 Elemental Analyzer by Thermo Fisher Scientific.

The purities of the final compounds 6 and 11 as well as commercial ciprofloxacin were ≥95% and were determined using 1H, 31P NMR spectrometry, HPLC and Elemental Analyzer. Analytical HPLC of final compounds were performed on a SHIMADZU HPLC system equipped with diode array detector. LabSolution software was used for both data collection and analysis. HPLC Method A: Phenomenex Luna 5μ C18(2) 100 Å analytical column (250×4.6 mm) operating at a flow rate of 1.0 mL/min was used. The following solvent gradient was employed: (Buffer A=20% ACN in 0.1 M NH4OAc (pH 7.53), Buffer B=70% CAN in 0.1 M NH4OAc (pH 7.16)) 0-7 min 0% B, 7-25 min 100% B, 25-100 min 100% B.

Synthesis. 1-(Benzyloxy)-4-(bromomethyl)benzene (1)

4-Benzyloxy benzyl alcohol (1.00 g, 4.67 mmol) was dissolved in anhydrous diethyl ether (25 mL) in an oven-dried flask under nitrogen. The flask was cooled in an ice bath. Bromotrimethylsilane (BTMS) (1.26 mL, 9.52 mmol, 2 equiv) was added by syringe. The flask was allowed to slowly warm to room temperature. After 17 hrs of stirring, the reaction mixture was poured into water (50 mL) and the organic phase was separated. The aqueous phase was washed with diethyl ether (2×20 mL) and then the combined organic phase was washed with brine (2×20 mL) and dried over sodium sulfate. Evaporation of the solvent afforded compound 1 as a white crystalline solid (1.23 g, 95% yield). 1H NMR (400 MHz, Chloroform-d) δ 7.47-7.28 (m, 7H), 6.98-6.90 (m, 2H), 5.07 (s, 2H), 4.50 (s, 2H).

Tetraisopropyl (2-(4-(benzyloxy)phenyl)ethane-1,1-diyl)bis(phosphonate) (2)

Under nitrogen protection, anhydrous THF (2 mL) was added to sodium hydride (57-63% dispersion in mineral oil) (75 mg, 1.80 mmol, 1 equiv). Tetraisopropyl methylene diphosphonate (570 μL, 1.80 mmol, 1 equiv) was added dropwise with stirring at room temperature. Gas was evolved and the grey suspended solid was consumed leaving a clear solution. The mixture was stirred a further 10 min. Compound 1 (500 mg, 1.80 mmol, 1 equiv) was added in one portion under nitrogen counterflow. The solution remained clear for 1 min and then became turbid. Stirring was maintained for 2 hrs and the reaction progress was monitored by TLC (100% EtOAc visualized by UV and cerium ammonium molybdate (CAM) stain). The reaction mixture was poured into 5% aqueous citric acid (30 mL) and extracted with ether (2×30 mL), washed with brine (30 mL) and evaporated. The residue was purified by flash chromatography using a EtOAc:Hexane gradient (10-100%) to afford 2 as a colorless oil (0.508 g, 52% yield). 1H NMR (400 MHz, Chloroform-d) δ 7.44-7.27 (m, 5H), 7.18 (d, J=8.6 Hz, 2H), 6.87 (d, J=8.7 Hz, 2H), 5.04 (s, 2H), 4.86-4.63 (m, 4H), 3.15 (td J=16.6, 6.1 Hz, 2H), 2.44 (tt, J=24.2, 6.1 Hz, 1H), 1.48-1.01 (m, 24H). 31P NMR (162 MHz, Chloroform-d) δ 21.11.

Tetraisopropyl (2-(4-hydroxyphenyl)ethane-1,1-diyl)bis(phosphonate) (3)

Compound 2 (0.508 g, 0.925 mmol) was dissolved in 13 mL of methanol and 10% palladium on activated carbon (70 mg, 0.066 mmol, 0.07 equiv) was added. The flask was flushed with nitrogen then hydrogen, and stirred overnight with a hydrogen balloon in place. The reaction mixture was filtered through celite with 100 mL of methanol. Evaporation of the filtrate gave the desired compound 3 as a slightly yellow oil (0.368 g, 88% yield) that was used without further purification. 1H NMR (400 MHz, Chloroform-d) δ 7.07 (d, J=8.2 Hz, 2H), 6.69 (d, J=8.2 Hz, 2H), 4.71 (m, 4H), 3.11 (td, J=16.9, 6.0 Hz, 2H), 2.47 (tt, J=24.4, 6.0 Hz, 1H), 1.32-1.21 (m, 24H). 31P NMR (162 MHz, Chloroform-d) δ 21.06.

4-(2,2-Bis(diisopropoxyphosphoryl)ethyl)phenyl (4-nitrophenyl) carbonate (4)

Compound 3 (7.91 g, 15.9 mmol) was dissolved in 150 mL of dichloromethane then triethylamine (6.70 mL, 47.9 mmol, 3 equiv) was added followed by p-nitrophenyl chloroformate (3.54 g, 17.6 mmol, 1.1 equiv) in one portion. Reaction mixture was stirred for 2.5 hrs while being monitored with TLC (5% MeOH in EtOAc, UV visualization). After disappearance of starting material reaction was stopped and the target compound was purified by flash chromatography (1:1 ethyl acetate:hexane) to afford compound 4 (4.33 g, 44% yield). 1H NMR (400 MHz, Chloroform-d) δ 8.29 (d, J=9.1 Hz, 2H), 7.46 (d, J=9.1 Hz, 2H), 7.33 (d, J=8.5 Hz, 2H), 7.15 (d, J=8.6 Hz, 2H), 4.84-4.58 (m, 4H), 3.22 (td, J=16.5, 6.2 Hz, 2H), 2.47 (tt, J=24.1, 6.2 Hz, 1H), 1.33-1.14 (m, 24H).

7-(4-((4-(2,2-Bis(diisopropoxyphosphoryl)ethyl) phenoxy)carbonyl)piperazin-1-yl)-1-cyclopropyl-6-fluoro-4-oxo-1,4-dihydroquinoline-3-carboxylic Acid (5)

Ciprofloxacin (2.76 g, 8.34 mmol, 1.2 equiv) was suspended in 74.7 mL of water in a flask. Then 8.30 mL of 1 M HCl was added and the flask was stirred to dissolve ciprofloxacin, giving a clear colorless solution. $Na_2CO_3$ was added to adjust the pH to 8.5 and a thick white precipitate formed. The flask was placed in an ice bath and Compound 4 (4.28 g, 6.95 mmol, 1 equiv) dissolved in 83 mL of THF was added slowly over about 5 min. The flask was then removed from the ice bath, protected from light and stirred overnight at room temperature. The reaction mixture was concentrated under vacuum to approximately half the original volume and filtered through a fine glass frit funnel. The retained solid was washed with water until no yellow color remained. The solids were then dissolved and washed from the frit with DCM, and the solution was loaded onto a flash silica column and eluted with MeOH:DCM gradient (2-5%) to afford compound 5 (3.47 g, 51.5% yield) as a white solid. 1H NMR (400 MHz, Methanol-d4) δ 8.79 (s, 1H), 7.93 (d, J=13.3 Hz, 1H), 7.54 (s, 1H), 7.30 (d, J=8.4 Hz, 2H), 7.05 (d, J=8.5 Hz, 2H), 4.70 (dpd, J=7.4, 6.2, 1.3 Hz, 4H), 3.90 (m, 4H), 3.65 (s, br, 1H), 3.39 (s, br, 4H), 3.18 (td, J=16.6, 6.4 Hz, 2H), 2.65 (tt, J=24.3, 6.3 Hz, 1H), 1.43-1.34 (m, 2H), 1.34-1.19 (m, 24H), 1.18-1.10 (m, 2H). 31P NMR (162 MHz, Methanol-d4) δ 20.71. MS (ESI+) m/z: 808.2 (M+H), 830.2 (M+Na) calc. for C38H53FN3O11P2+: 808.3.

1-Cyclopropyl-7-(4-((4-(2,2-diphosphonoethyl)phenoxy)carbonyl)piperazin-1-yl)-6-fluoro-4-oxo-1,4-dihydroquinoline-3-carboxylic Acid (6).[42, 43]

Compound 5 (10.0 mg, 1.24 µmol) was dissolved in DCM (200 µL) in a 1.5 ml glass vial and BTMS (200 µL, 1.52 mmol, 122 equiv) was added and the vial was quickly capped and immersed in a 35° C. oil bath. After stirring for 24 hrs, solvent and BTMS were removed under vacuum and 1 mL of MeOH was added and the vial stirred overnight. Solvent was removed under vacuum to afford pure compound 6 as a pale yellow solid with green fluorescence (6.82 mg, 86.1% yield). 1H NMR (400 MHz, Deuterium Oxide) δ 8.51 (s, 1H), 7.92 (d, J=12.2 Hz, 1H), 7.67 (s, 1H), 7.47 (d, J=8.3 Hz, 2H), 7.10 (d, J=8.3 Hz, 2H), 3.98 (s, 2H), 3.79 (s, 2H), 3.67 (s, 1H), 3.42 (s, 4H), 3.16 (td, J=15.5, 6.8 Hz, 2H), 2.21 (tt, J=6.9, 21.6 Hz, 1H), 1.37 (d, J=6.9 Hz, 2H), 1.15 (s, 2H). 31P NMR (162 MHz, Deuterium Oxide) δ 19.16 MS (ESI-) m/z: 638.06 (M-H) calc. for C26H27FN3O11P2-: 638.1. HPLC (Method A, UV 190, 274, 330 nm): tr=11.62 min.

Methyl 4-(2,2-bis(diisopropoxyphosphoryl)ethyl)benzoate (7).[44]

Under nitrogen atmosphere, in a 25 mL round bottom flask, THF (5 mL) was added to 57-63% dispersion of sodium hydride in mineral oil (0.163 g, 4.07 mmol, 1.4 equiv). The suspension was cooled to 0° C., while stirring, and tetraisopropyl methylenediphosphonate (0.926 mL, 2.90 mmol, 1 equiv) was added gradually. The reaction was allowed to reach ambient temperature and once hydrogen gas stopped bubbling out of the reaction mixture, the solution was cooled to 0° C. again. Methyl 4-(bromomethyl) benzoate (0.465 g, 2.03 mmol, 0.7 equiv) was dissolved in THF (2 mL) and added to the reaction dropwise. The resulting solution was stirred overnight while slowly reaching ambient temperature. The reaction mixture was then cooled to 0° C. and quenched with EtOH (1 mL). A 5% aqueous solution of citric acid in water (30 mL) was added and the mixture was extracted with Et2O (3×30 mL), combined organics were washed with brine (50 mL), dried on $Na_2SO_4$, filtered, concentrated under reduced pressure, and purified by silica gel column chromatography using a EtOAc:Hex gradient (10-100%) to afford 7 as a faint yellow oil (0.371 g, 37.0% yield). 1H NMR (400 MHz, Chloroform-d) δ 7.93 (d, J=8.0 Hz, 2H), 7.33 (d, J=8.4 Hz, 2H), 4.79-4.68 (m, 4H), 3.88 (s, 3H), 3.24 (td, J=16.0, 6.4 Hz, 2H), 2.50 (tt, J=24.0, 6.2 Hz, 1H), 1.34-1.24 (m, 24H). 31P NMR (162 MHz, Chloroform-d) δ 20.57.

4-(2,2-Bis(diisopropoxyphosphoryl)ethyl)benzoic Acid (8).[44]

To a solution of 7 (0.131 g, 0.278 mmol) in MeOH (1.5 mL) in a 8 Dram glass vial, LiOH.H2O (0.058 g, 1.39 mmol, 5 equiv) was added and the resulting solution was stirred at room temperature overnight. The reaction mixture was evaporated to dryness, the residue was dissolved in water (30 mL), and HCl(aq) (1 M) was added slowly to reach pH 3. The resulting mixture was extracted with $CHCl_3$ (3×30 mL). Combined organics were dried on MgSO4 and concentrated under reduced pressure to afford 8 as a thick clear oil (0.115 g, 90.6% yield). 1H NMR (400 MHz, Chloroform-d): δ=7.96 (d, J=8.0, 2H), 7.37 (d, J=8.0, 2H), 4.82-4.74 (m, 4H), 3.28 (td, J=16.6, 6.1, 2H), 2.60 (tt, J=24.2, 6.2, 1H), 1.33-1.26 (m, 24H). 31P NMR (162 MHz, Chloroform-d) δ 20.57.

Tetraisopropyl (2-(4-(chlorocarbonyl)phenyl)ethane-1,1-diyl)bis(phosphonate) (9)

Under nitrogen atmosphere, Compound 8 (0.162 g, 0.339 mmol) was dissolved in chloroform (1 mL) an a catalytic amount of DMF (1.30 µL, 0.017 mmol, 0.05 equiv) was added. Thionyl chloride (49.2 µL, 0.678 mmol, 2 equiv) was added slowly and the reaction was allowed to stir for 2 hrs at room temperature. Solvents were removed under vacuum to afford 9 as clear oil. The product was immediately used in the next step without further manipulation (quantitative yield).

7-(4-(4-(2,2-Bis(diisopropoxyphosphoryl)ethyl)benzoyl)piperazin-1-yl)-1-cyclopropyl-6-fluoro-4-oxo-1,4-dihydroquinoline-3-carboxylate (10)

Ciprofloxacin (0.112 g, 0.339 mmol, 1 equiv) was suspended in chloroform (1 mL) and N,N-diisopropylethylamine (DIPEA) (354 µL, 2.03 mmol, 6 equiv) was added. Freshly made compound 9 (168 mg, 0.338 mmol, 1 equiv) was dissolved in chloroform (1 mL) and gradually added to the ciprofloxacin:DIPEA suspension. The reaction mixture was covered with foil and stirred at room temperature overnight. The following day, solvents were removed under vacuum and the resulting crude was dissolved in DCM (5 mL) and filtered through a medium grade frit funnel and washed with more DCM (3×5 mL). The filtrate was concentrated under vacuum and further purified by silica gel column chromatography using a MeOH:DCM gradient (0-10%) to afford 10 as a viscous oil that gradually solidified (0.226 g, 65.1% yield, 1.8 eq DIPEA salt). 1H NMR (400 MHz, Chloroform-d) δ=8.79 (s, 1H), 8.06 (d, J=12.8, 1H), 7.38 (m, 5H), 4.80-4.73 (m, 4H), 4.00 (s, br, 4H), 3.56-3.53 (m, 1H), 3.33-3.20 (m, 6H) 2.50 (m, 1H), 1.45-1.38 (m, 2H), 1.32-1.25 (m, 24H), 1.23-1.19 (m, 2H). 31P NMR (162 MHz, Chloroform-d) δ 20.77.

1-Cyclopropyl-7-(4-(4-(2,2-diphosphonoethyl)benzoyl)piperazin-1-yl)-6-fluoro-4-oxo-1,4-dihydroquinoline-3-carboxylic Acid (11).42, 43

In a 8 Dram glass vial, compound 10 (0.108 g, 0.136 mmol) was dissolved in DCM (700 µL) and BTMS (686 µL, 5.20 mmol, 38 equiv) was added. The vial was capped and heated overnight at 35° C. while covered with foil and stirring. The following day, solvent was removed under vacuum and the crude was quenched with MeOH (2 mL). The resulting solution was stirred at room temperature for 30 min. Solvent was removed under vacuum to afford an orange oil. A few drops of water were added to produce a yellow solid. More MeOH (2 mL) was added and the resulting suspension was filtered using a medium grade fritted glass funnel. The resulting solid was further washed with MeOH to afford 11 as a yellow powder (0.070 g, 82.0% yield). 1H NMR (400 MHz, Deuterium Oxide, pH 7.5): δ=8.54 (s, br, 1H), 7.90-7.87 (m, 1H), 7.65-7.63 (m, 1H), 7.54 (d, J=8.0, 2H), 7.44 (d, J=8.0, 2H), 4.79 (m, overlap with D20, 4H), 4.00 (s, br, 2H), 3.79 (s, br, 2H), 3.47 (s, br, 3H), 3.34 (s, br, 2H), 3.21 (td, J=14.0, 6.4, 2H), 2.30 (tt, J=22.0, 6.6, 1H), 1.38-1.33 (m, 2H), 1.15 (s, br, 2H). 31P NMR (162 MHz, Deuterium Oxide, pH 7.5) δ 19.12. MS (ESI−) m/z: 622.24 (M−H) calc. for $C_{26}H_{27}FN_3O_{10}P_2-$: 622.12. HPLC (Method A, UV 190, 274, 330 nm): tr=4.43 min.

Antibacterial Properties of Bisphosphonate-Ciprofloxacin Conjugates

Experimental Strains:

Seven *S. aureus* clinical osteomyelitis strains of methicillin-susceptible profile and one of methicillin-resistant profile were tested. These pathogens are part of the strain collection of the Department of Pharmaceutical Microbiology and Parasitology Wroclaw Medical University, Poland. Additionally, the following American Type Culture Collection (ATCC) strains were chosen for experimental purposes: *S. aureus* 6538 and *P. aeruginosa* 15442.

Ha Discs:

For custom disc manufacturing, commercially available HA powder was used. Powder pellets of 9.6 mm in diameter were pressed without a binder. Sintering was performed at 900° C. The tablets were compressed using the Universal Testing System for static tensile, compression, and bending tests (Instron model 3384; Instron, Norwood, Mass.). The quality of the manufactured HA discs was checked by means of confocal microscopy and microcomputed tomography (micro-CT) using an LEXT OLS4000 microscope (Olympus, Center Valley, Pa.) and Metrotom 1500 microtomograph (Carl Zeiss, Oberkochen, Germany), respectively.

Disc Diffusion Test to Evaluate Sensitivity of Tested Strains to Ciprofloxacin:

This procedure was performed according to EUCAST guidelines.29 Briefly, 0.5 McFarland (MF) of bacterial dilution was spread on Mueller-Hinton (MH) agar plate. The discs containing 5 mg of ciprofloxacin were introduced and the plate was subjected to incubation at 37° C./24 hrs. Next, inhibition zones were recorded using a ruler. Obtained values (mm) were compared to appropriate values of inhibition zones from EUCAST tables.[29]

Evaluation of the MIC of Tested Compounds Against Planktonic Forms of Clinical Staphylococcal Strains Analyzed:

To assess the impact of parent antibiotic and conjugates on microbial growth, 100 µl of microbial solutions of density 1×105 CFU/ml were placed into wells of 96-well test plates together with appropriate concentrations of tested compounds. Immediately after that, the absorbance of solutions was measured using a spectrometer (Thermo Scientific Multiscan GO) at 580 nm wavelength. Subsequently, plates were incubated for 24 hrs/37° C. in a shaker to obtain optimal conditions for microbial growth and to prevent bacteria from forming biofilms. After incubation, the absorbance was measured once again. The following control samples were established: negative control sample one: sterile medium without microbes; negative control sample two: sterile medium without microbes implemented with DMSO (dimethyl sulfoxide, Sigma-Aldrich) to final concentration of 1% (v/v); positive control sample one: medium+microbes with no compound tested; positive control sample two: medium+microbes with no compound tested but implemented with DMSO to final concentration of 1% (v/v). Rationale for use of 1% DMSO was that ciprofloxacin dissolves efficiently in this solvent, however, concentrations of DMSO>1% could be detrimental for microbial cells. To assess relative number of cells, the following calculations were performed. The value of absorbance of control samples (medium+microbes for conjugate, medium+microbes+DMSO for ciprofloxacin) was estimated at 100%. Next, the relative number of cells subjected to incubation with tested compounds were counted as follows: value of control sample absorbance/value of tested sample*100%.

To confirm results obtained by spectrophotometric assessments, treated bacterial solutions were transferred to 10 mL of fresh medium and left for 48 hrs at 37° C. The occurrence of opacification or lack of opacification of media was proof of pathogen growth or lack of growth, respectively. Additionally, bacterial solutions were cultured on the appropriate stable medium. Growth or lack of growth of bacterial colonies together with above-mentioned results from liquid cultures served as confirmation of results obtained spectrophotometrically.

Spectroscopic Analysis of 6 and 11 in Tryptic Soy Broth (TSB) Microbiological Media with the Addition of HA Spherules:

Various conjugate concentrations were introduced to HA powder (spherules) suspended in TSB microbiological medium. Solutions containing BP-ciprofloxacin an HA spherules were introduced to wells of a 24-well plate. Final concentration of powder was 10 mg/1 mL, while final concentration of conjugates was 0.24-250 mg/L. Immediately afterward the absorbance of solutions was measured using a spectrometer (Thermo Scientific Multisca GO) at 275 nm wavelength. Plates were shaken automatically in the spectrometer prior to assessment. Next, plates were left for 24 hrs/37° C./shaking. After 24 hrs, absorbance was measured once again. To assess the relative concentration of the conjugate at 0 hr and 24 hrs, values of absorbance taken in the beginning and at the end of experiment were compared. The excitation slit, emission slit, integration time, and increment were optimized based on the concentration of samples.

Antimicrobial Susceptibility Testing of 6 Against Planktonic Cultures of S. aureus Strain ATCC-6538 in Acidic Versus Physiological pH:

This experimental setting was performed in the same manner as described previously for disc diffusion testing, but microbiological media was adjusted to pH 7.4 and pH 5 using KOH or HCL solution and measured using a universal pH-indicator (Merck, Poland).

Time-Kill Assay for 6 Against S. aureus Strain ATCC-6538 (MSSA) and Clinical MRSA Strain (MR4-CIPS):

This experiment was performed in the same manner as described previously under the subheading: "Evaluation of MIC of tested compounds against planktonic forms of clinical staphylococcal strains analyzed", but absorbance assays (at 580 nm wavelength) were taken in hour: 0, 1, 2, 4, 8, 16, and 24.

Antimicrobial Susceptibility Testing of 6 Against Preformed Biofilms of S. aureus Strain ATCC-6538 and P. aeruginosa Strain ATCC-15442:

Strains cultured on appropriate agar plates (Columbia agar plate for S. aureus; MacConkey agar plate for P. aeruginosa) were transferred to liquid microbiological media and incubated for 24 hrs/37° C. under aerobic conditions. After incubation, strains were diluted to the density of 1 MF. The microbial dilutions were introduced to wells of 24-well plates containing HA discs as a substrate, or simply to polystyrene wells where the bottom surface of the wells served as the substrate for biofilm development. Strains were incubated at 37° C. for 4 hrs. Next, the microbe-containing solutions were removed from the wells. The surfaces, HA discs and polystyrene plates, were gently rinsed to leave adhered cells and to remove planktonic or loosely-bound microbes. Surfaces prepared in this manner were immersed in fresh TSB medium containing 0.24-125 mg/L of 6 and ciprofloxacin as a control. After 24 hrs of incubation at 37° C. the surfaces were rinsed using physiological saline solution and transferred to 1 mL of 0.5% saponin (Sigma-Aldrich, St Louis, Mo.). The surfaces were vortex-mixed vigorously for 1 minute to detach cells. Subsequently, all microbial suspensions were diluted 10-1 to 10-9 times. Each dilution (100 mL) was cultured on the appropriate stable medium (MacConkey, Columbia for P. aeruginosa and S. aureus, respectively) and incubated at 37° C. for 24 hrs. After this time, the microbial colonies were counted and the number of cells forming biofilm was assessed. Results were presented as the mean number of CFU per square millimeter surface ±standard error of the mean. To calculate the surface area of HA discs, x-ray tomographic analysis was applied. For estimation of the area of test plate bottoms, the equation for circle area: $\pi r^2$ was applied.

Preventative Ability of 6 and 11 to Inhibit S. aureus 6538 Adherence to HA:

Various concentrations of 6 and 11 were introduced to HA powder (spherules) suspended in TSB microbiological medium. Solutions containing 6 and HA spherules were introduced to wells of 24-well plates. Final concentrations of powder were 10 mg/1 mL, while final concentrations of the conjugate were 0.12-250 mg/L. Suspensions were left for 24 hrs/37° C./shaking. After 24 hrs, suspensions were removed from the wells and impulse-centrifuged to precipitate HA powder. Next, supernatant was very gently discarded and a fresh 1 mL of S. aureus of density 105 CFU/mL was introduced to the HA spherules. Subsequently, this solution was shaken, absorbance was measured using 580 nm wavelength and left for 24 hrs/37° C./shaking. After incubation absorbance was measured again and values from 0 hr and 24 hrs were compared to assess reduction of bacterial growth with regard to control sample one (bacterial suspension but no spherules) and control sample two (bacterial suspension+ spherules but with no conjugate added). Additionally, solutions were impulse centrifuged, the supernatant was gently discarded, while bacteria-containing HA spherules were culture plated as before and quantitatively assessed. For testing of 11, solutions containing HA spherules and higher concentrations of 11 ranging from 1-400 µg/mL and ciprofloxacin concentrations ranging from 0.5-400 µg/mL were prepared and again compared to the control sample (bacterial suspension but no HA) for ability to inhibit biofilm formation. Higher concentrations of 11 were tested because of the demonstrated weaker activity of an amide conjugate as compared to the carbamate conjugate.

Survival of S. aureus after 24 Hrs of Incubation on HA Pretreated with 6:

HA discs were immersed in 2 mL of solution containing various concentrations of BP-ciprofloxacin or ciprofloxacin alone and left for 24 hrs/37° C. HA discs incubated in DMSO or phosphate buffer served as control samples. Next, discs were rinsed 3 times with sterile water. After rinsing, 2 mL of 0.5 MF of. S. aureus ATCC6538 were introduced to wells containing HA discs as a substrate for biofilm development and biofilms were formed as before.

Ethics Statement:

All animal protocols and procedures were approved and performed in accordance with the Institutional Animal Care and Use Committee (IACUC) of the University of Southern California (USC), and in accordance with the Panel on Euthanasia of the American Veterinary Medical Association. USC is registered with the United States Department of Agriculture (USDA), has a fully approved Letter of Assurance (#A3518-01) on file with the National Institutes of Health (NIH) and is accredited by the American Association for the Accreditation of Laboratory Animal Care (AAALAC). The title of our IACUC approved protocol is: "Bone targeted antimicrobials for biofilm-mediated osteolytic infection treatment", and the protocol number is 20474. All animal protocols, and investigators and staff involved in the animal studies presented herein, adhered to the Guide for the Care and Use of Laboratory Animals, the USDA Animal Welfare Regulations (CFR 1985) and Public Health Service Policy on Humane Care and Use of Laboratory Animals (1996).

In Vivo Animal Study:

For this study 12 five-month-old, virgin, female Sprague-Dawley rats weighing approximately 200 g each were used in this study. Two to three animals were housed per cage in a vivarium at 22° C. under a 12-hr light/12-hr dark cycle and fed ad libitum with a soft diet (Purina Laboratory Rodent Chow). All animals were treated according to the guidelines and regulations for the use and care of animals at USC. Animals were under the supervision of fulltime veterinarians on call 24 hrs/day who evaluate the animals personally on a daily basis. All animal experiments are described using the ARRIVE45 guidelines for reporting on animal research to ensure the quality, reliability, validity and reproducibility of results.

This animal model is an in-house jawbone peri-implant osteomyelitis model designed specifically to study biofilm-mediated disease and host response in vivo.[31] Biofilms of the jawbone osteomyelitis pathogen Aa were pre-formed on miniature titanium implants at $10^9$ CFU. To confirm Aa sensitivity to the parent drug ciprofloxacin prior to our animal studies, AST and MIC assays were performed against planktonic Aa in addition to the biofilm HA assay as described for the long bone osteomyelitis pathogens. After biofilms were established on the implants in vitro, they were surgically transferred to the jawbone of each rat. For surgery, animals were anesthetized with 4% isoflurane inhalant initially followed by intraperitoneal injection of ketamine (80-90 mg/kg) plus xylazine (5-10 mg/kg). Then local anesthesia was given via infiltration injection of bupivicaine 0.25% at the surgical site. Buprenorphine sustained release (1.0-1.2 mg/kg) was then given subcutaneously as preemptive analgesia before making initial incisions. Once anesthetized, the buccal mucosa of each rat was retracted and a transmucosal osteotomy was performed with a pilot drill into the alveolar ridge in the natural diastema of the anterior palate. Implants were then manually inserted into the osteotomy and secured into the bone until the platform is at mucosal level. Two biofilm-inoculated implants were placed in each rat (n=12 rats) in the palatal bone bilaterally.

One week post-operatively isoflurane 4% was given again to briefly anesthetize the rats and check implant stability and document clinical findings at the implant and infection site, such as presence or absence of inflammation. The animals were then dosed via intraperitoneal injection with BP-ciprofloxacin (6 at 0.1 mg/kg, 1 mg/kg, or 10 mg/kg as a single dose, and at 0.3 mg/kg 3×/week for a multiple dosing group) or ciprofloxacin alone (10 mg/kg 3×/week also as a multiple dosing group) as a positive control, and sterile endotoxin-free saline as a negative control.

Allocation of animals to treatment and control groups was done through a randomization process. The multiple dosing group animals were anesthetized as before prior to each additional injection over the course of the week. All compounds were of pharmacological grade and constituted in sterile physiological injectable saline at appropriate pH. One week after pharmacotherapy, all animals were euthanized in a $CO_2$ chamber (60-70% concentration) for 5 minutes, followed by cervical dislocation. Resection of peri-implant tissues (1 cm2) was performed en bloc and implants were removed. Clinical parameters were noted at surgery and resection, such as presence or absence of peri-prosthetic inflammation. Rat allocations to treatment and control groups were deidentified and concealed from subsequent investigators analyzing the microbial data.

For microbial analysis, resected peri-implant soft tissue and bone was homogenized and processed immediately after surgical resection by placement in 1 mL of 0.5% saponine and vortexed for 1 min before being serially diluted. Serial dilutions at a dilution factor of 10 (e.g. 0.1 mL of saponine solution transferred to 0.9 mL of 0.9% sterile isotonic saline solution) ranging from $10^0$ to $10^{-9}$ were prepared, and 0.1 mL of solution from each of the dilutions was cultured on plates using a spread plate method. The medium for culturing Aa consisted of modified TSB, and frozen stocks were maintained at −80° C. in 20% glycerol, 80% modified TSB. All culturing was performed at 37° C. in 5% CO2 for 48 hrs. The numbers of viable Aa bacteria cultured (number of CFUs per gram of tissue) was counted manually and the reduction in the mean $\log_{10}$ number of CFU per gram as a function of treatment was recorded. In order to confirm Aa bacterial morphotype and also rule out contamination, Gram staining and histologic evaluation was performed by sampling of colonies from plates once CFU counting was completed.

Statistical Analysis

Statistical calculations were performed with SPSS 22.0 (IBM, Armonk, N.Y.) and Excel 2016 (Microsoft Corporation, Redmond, Wash.). Power analyses were performed to determine sample size estimation for in vitro and in vivo studies prior to experimentation using G Power 3 software.[46] Quantitative data from experimental results for each group was analyzed first with descriptive statistics to understand the distribution of the data (parametric or non-parametric) and to generate the mean, standard error, standard deviation, kurtosis and skewness, and 95% confidence levels. The data was then analyzed using the Kruskall-Wallis test or one-way ANOVA as applicable and statistical significance was accepted at $p<0.05$ when comparing treatments to controls. Additionally, for in vivo experiments, post-hoc testing using unpaired t-tests and Dunnett's test for multiple comparisons was performed.

Abbreviations Used

Aa, *Aggregatibacter Actinomycetemcomitans*; AAALAC, American Association for the Accreditation of Laboratory Animal Care; ANOVA, Analysis of variance; ARRIVE, Animal Research: Reporting of In Vivo Experiments; AST, antibiotic sensitivity test; ATCC, American Type Culture Collection; BP, bisphosphonate; BTMS, bromotrimethylsilane; CFU, colony forming units; CLSI, Clinical Laboratory Standards Institute; EUCAST, European Committee on Antimicrobial Susceptibility Testing; HA, hydroxyapatite; IACUC, Institutional Animal Care and Use Committee; MBC, mean bactericidal concentrations; MBIC50, minimal biofilm inhibitory concentration required to inhibit the growth of 50% of organisms; MF, McFarland; MH, Mueller Hinton; MIC50, minimal inhibitory concentration required to inhibit the growth of 50% of organisms; MSSA, methicillin-sensitive *S. aureus*; Pd/C, palladium on activated carbon; SD, standard deviation; BTMS, bromotrimethylsilane; DCM, dichloromethane; $SOCl_2$, thionylchloride; SEM, scanning electron microscopy.

REFERENCES FOR EXAMPLE 5

1. Lew, D. P.; Waldvogel, F. A. Osteomyelitis. *Lancet* 2004, 364, 369-379.
2. Desrochers, A.; St-Jean, G.; Anderson, D. E. Limb amputation and prosthesis. *Vet. Clin. North. Am. Food Anim. Pract.* 2014, 30, 143-155, vi.
3. Stoodley, P.; Ehrlich, G. D.; Sedghizadeh, P. P.; Hall-Stoodley, L.; Baratz, M. E.; Altman, D. T.; Sotereanos, N. G.; Costerton, J. W.; Demeo, P. Orthopaedic biofilm infections. *Curr. Orthop. Pract.* 2011, 22, 558-563.
4. Huang, C. C.; Tsai, K. T.; Weng, S. F.; Lin, H. J.; Huang, H. S.; Wang, J. J.; Guo, H. R.; Hsu, C. C. Chronic osteomyelitis increases long-term mortality risk in the elderly: a nationwide population-based cohort study. *BMC Geriatr.* 2016, 16, 72.
5. Wolcott, R. D.; Ehrlich, G. D. Biofilms and chronic infections. *JAMA* 2008, 299, 2682-2684.
6. Junka, A. F.; Szymczyk, P.; Smutnicka, D.; Kos, M.; Smolina, I.; Bartoszewicz, M.; Chlebus, E.; Turniak, M.; Sedghizadeh, P. P. Microbial biofilms are able to destroy hydroxyapatite in the absence of host immunity in vitro. *J. Oral Maxillofac. Surg.* 2015, 73, 451-464.

7. Panagopoulos, P.; Drosos, G.; Maltezos, E.; Papanas, N. Local antibiotic delivery systems in diabetic foot osteomyelitis: time for one step beyond? *Int. J. Lower Extremity Wounds* 2015, 14, 87-91.
8. Puga, A. M.; Rey-Rico, A.; Magarinos, B.; Alvarez-Lorenzo, C.; Concheiro, A. Hot melt poly-epsilon-caprolactone/poloxamine implantable matrices for sustained delivery of ciprofloxacin. *Acta Biomater.* 2012, 8, 1507-1518.
9. Herczegh, P.; Buxton, T. B.; McPherson, J. C., 3rd; Kovacs-Kulyassa, A.; Brewer, P. D.; Sztaricskai, F.; Stroebel, G. G.; Plowman, K. M.; Farcasiu, D.; Hartmann, J. F. Osteoadsorptive bisphosphonate derivatives of fluoroquinolone antibacterials. *J. Med. Chem.* 2002, 45, 2338-2341.
10. Buxton, T. B.; Walsh, D. S.; Harvey, S. B.; McPherson, J. C., 3rd; Hartmann, J. F.; Plowman, K. M. Bisphosphonate-ciprofloxacin bound to Skelite is a prototype for enhancing experimental local antibiotic delivery to injured bone. *Br. J. Surg.* 2004, 91, 1192-1196.
11. Kim, B. N.; Kim, E. S.; Oh, M. D. Oral antibiotic treatment of staphylococcal bone and joint infections in adults. *J. Antimicrob. Chemother.* 2014, 69, 309-322.
12. Reeves, B. D.; Young, M.; Grieco, P. A.; Suci, P. *Aggregatibacter actinomycetemcomitans* biofilm killing by a targeted ciprofloxacin prodrug. *Biofouling* 2013, 29, 1005-1014.
13. Houghton, T. J.; Tanaka, K. S.; Kang, T.; Dietrich, E.; Lafontaine, Y.; Delorme, D.; Ferreira, S. S.; Viens, F.; Arhin, F. F.; Sarmiento, I.; Lehoux, D.; Fadhil, I.; Laquerre, K.; Liu, J.; Ostiguy, V.; Poirier, H.; Moeck, G.; Parr, T. R., Jr.; Far, A. R. Linking bisphosphonates to the free amino groups in fluoroquinolones: preparation of osteotropic prodrugs for the prevention of osteomyelitis. *J. Med. Chem.* 2008, 51, 6955-6969.
14. Melchior, M. B.; Fink-Gremmels, J.; Gaastra, W. Comparative assessment of the antimicrobial susceptibility of *Staphylococcus aureus* isolates from bovine mastitis in biofilm versus planktonic culture. *J. Vet. Med. B Infect. Dis. Vet. Public Health* 2006, 53, 326-332.
15. Amorena, B.; Gracia, E.; Monzon, M.; Leiva, J.; Oteiza, C.; Perez, M.; Alabart, J. L.; Hernandez-Yago, J. Antibiotic susceptibility assay for *Staphylococcus aureus* in biofilms developed in vitro. *J. Antimicrob. Chemother.* 1999, 44, 43-55.
16. Ceri, H.; Olson, M. E.; Stremick, C.; Read, R. R.; Morck, D.; Buret, A. The Calgary Biofilm Device: new technology for rapid determination of antibiotic susceptibilities of bacterial biofilms. *J. Clin. Microbiol.* 1999, 37, 1771-1776.
17. Olson, M. E.; Ceri, H.; Morck, D. W.; Buret, A. G.; Read, R. R. Biofilm bacteria: formation and comparative susceptibility to antibiotics. *Can. J. Vet. Res.* 2002, 66, 86-92.
18. Zhang, S.; Gangal, G.; Uludag, H. 'Magic bullets' for bone diseases: progress in rational design of bone-seeking medicinal agents. *Chem. Soc. Rev.* 2007, 36, 507-531.
19. Tanaka, K. S.; Houghton, T. J.; Kang, T.; Dietrich, E.; Delorme, D.; Ferreira, S. S.; Caron, L.; Viens, F.; Arhin, F. F.; Sarmiento, I.; Lehoux, D.; Fadhil, I.; Laquerre, K.; Liu, J.; Ostiguy, V.; Poirier, H.; Moeck, G.; Parr, T. R., Jr.; Rafai Far, A. Bisphosphonated fluoroquinolone esters as osteotropic prodrugs for the prevention of osteomyelitis. *Bioorg. Med. Chem.* 2008, 16, 9217-9229.
20. McPherson, J. C., 3rd; Runner, R.; Buxton, T. B.; Hartmann, J. F.; Farcasiu, D.; Bereczki, I.; Roth, E.; Tollas, S.; Ostorhazi, E.; Rozgonyi, F.; Herczegh, P. Synthesis of osteotropic hydroxybisphosphonate derivatives of fluoroquinolone antibacterials. *Eur. J. Med. Chem.* 2012, 47, 615-618.
21. Cheong, S.; Sun, S.; Kang, B.; Bezouglaia, O.; Elashoff, D.; McKenna, C. E.; Aghaloo, T. L.; Tetradis, S. Bisphosphonate uptake in areas of tooth extraction or periapical disease. *J. Oral Maxillofac. Surg.* 2014, 72, 2461-2468.
22. Russell, R. G.; Watts, N. B.; Ebetino, F. H.; Rogers, M. J. Mechanisms of action of bisphosphonates: similarities and differences and their potential influence on clinical efficacy. *Osteoporosis Int.* 2008, 19, 733-759.
23. Guo, X.; Shi, C.; Wang, J.; Di, S.; Zhou, S. pH-triggered intracellular release from actively targeting polymer micelles. *Biomaterials* 2013, 34, 4544-4554.
24. Ghosh, A. K.; Brindisi, M. Organic carbamates in drug design and medicinal chemistry. *J. Med. Chem.* 2015, 58, 2895-2940.
25. Ossipov, D. A. Bisphosphonate-modified biomaterials for drug delivery and bone tissue engineering. *Expert Opin. Drug Delivery* 2015, 12, 1443-1458.
26. Morioka, M.; Kamizono, A.; Takikawa, H.; Mori, A.; Ueno, H.; Kadowaki, S.; Nakao, Y.; Kato, K.; Umezawa, K. Design, synthesis, and biological evaluation of novel estradiolbisphosphonate conjugates as bone-specific estrogens. *Bioorg. Med. Chem.* 2010, 18, 1143-1148.
27. Arns, S.; Gibe, R.; Moreau, A.; Monzur Morshed, M.; Young, R. N. Design and synthesis of novel bone-targeting dual-action pro-drugs for the treatment and reversal of osteoporosis. *Bioorg. Med. Chem.* 2012, 20, 2131-2140.
28. Tanaka, K. S.; Dietrich, E.; Ciblat, S.; Metayer, C.; Arhin, F. F.; Sarmiento, I.; Moeck, G.; Parr, T. R., Jr.; Far, A. R. Synthesis and in vitro evaluation of bisphosphonated glycopeptide prodrugs for the treatment of osteomyelitis. *Bioorg. Med. Chem. Lett.* 2010, 20, 1355-1359.
29. EUCAST: European Committee on Antimicrobial Susceptibility Testing breakpoint tables for interpretation of MICs and zone diameters. http://www.eucast.org/fileadmin/src/media/PDFs/EUC (accessed Jan. 15, 2017).
30. M100-S25 performance standards for antimicrobial susceptibility testing; Twenty-fifth informational supplement. Clinical Laboratory Standards Institute. The Clinical and Laboratory Standards Institute: Wayne, Pa., USA, 2015.
31. Freire, M. O.; Sedghizadeh, P. P.; Schaudinn, C.; Gorur, A.; Downey, J. S.; Choi, J. H.; Chen, W.; Kook, J. K.; Chen, C.; Goodman, S. D.; Zadeh, H. H. Development of an animal model for *Aggregatibacter actinomycetemcomitans* biofilm-mediated oral osteolytic infection: a preliminary study. *J. Periodontol.* 2011, 82, 778-789.
32. Manrique, P.; Freire, M. O.; Chen, C.; Zadeh, H. H.; Young, M.; Suci, P. Perturbation of the indigenous rat oral microbiome by ciprofloxacin dosing. *Mol. Oral. Microbiol.* 2013, 28, 404-414.
33. Oliphant, C. M.; Green, G. M. Quinolones: a comprehensive review. *Am. Fam. Physician* 2002, 65, 455-464.
34. Redgrave, L. S.; Sutton, S. B.; Webber, M. A.; Piddock, L. J. Fluoroquinolone resistance: mechanisms, impact on bacteria, and role in evolutionary success. *Trends Microbiol.* 2014, 22, 438-445.
35. Mustaev, A.; Malik, M.; Zhao, X.; Kurepina, N.; Luan, G.; Oppegard, L. M.; Hiasa, H.; Marks, K. R.; Kerns, R. J.; Berger, J. M.; Drlica, K. Fluoroquinolone-gyrase-DNA complexes: two modes of drug binding. *J. Biol. Chem.* 2014, 289, 12300-12312.

36. Ayre, W. N.; Birchall, J. C.; Evans, S. L.; Denyer, S. P. A novel liposomal drug delivery system for PMMA bone cements. *J. Biomed. Mater. Res. Part B* 2016, 104, 1510-1524.
37. Nandi, S. K.; Bandyopadhyay, S.; Das, P.; Samanta, I.; Mukherjee, P.; Roy, S.; Kundu, B. Understanding osteomyelitis and its treatment through local drug delivery system. *Biotechnol. Adv.* 2016, 34, 1305-1317.
38. Lin, J. H. Bisphosphonates: a review of their pharmacokinetic properties. *Bone* 1996, 18, 75-85.
39. Fong, I. W.; Ledbetter, W. H.; Vandenbroucke, A. C.; Simbul, M.; Rahm, V. Ciprofloxacin concentrations in bone and muscle after oral dosing. *Antimicrob. Agents Chemother.* 1986, 29, 405-408.
40. Sedghizadeh, P. P.; Jones, A. C.; LaVallee, C.; Jelliffe, R. W.; Le, A. D.; Lee, P.; Kiss, A.; Neely, M. Population pharmacokinetic and pharmacodynamic modeling for assessing risk of bisphosphonate-related osteonecrosis of the jaw. *Oral Surg. Oral Med. Oral. Pathol. Oral Radiol.* 2013, 115, 224-232.
41. Williams, D. B.; Lawton, M. Drying of organic solvents: quantitative evaluation of the efficiency of several desiccants. *J. Org. Chem.* 2010, 75, 8351-8354.
42. McKenna, C. E.; Higa, M. T.; Cheung, N. H.; McKenna, M.-C. The facile dealkylation of phosphonic acid dialkyl esters by bromotrimethylsilane. *Tetrahedron Lett.* 1977, 18, 155-158.
43. McKenna, C. E.; Schmidhuser, J. Functional selectivity in phosphonate ester dealkylation with bromotrimethylsilane. *J. Chem. Soc., Chem. Commun.* 1979, 739-739.
44. David, T.; Kotek, J.; Kubicek, V.; Tosner, Z.; Hermann, P.; Lukeš, I. Bis(phosphonate)—building blocks modified with fluorescent dyes. *Heteroat. Chem.* 2013, 24, 413-425.
45. Kilkenny, C.; Browne, W. J.; Cuthi, I.; Emerson, M.; Altman, D. G. Improving bioscience research reporting: the ARRIVE guidelines for reporting animal research. *Vet. Clin. Pathol.* 2012, 41, 27-31.
46. Faul, F.; Erdfelder, E.; Buchner, A.; Lang, A. G. Statistical power analyses using G*Power 3.1: tests for correlation and regression analyses. *Behav. Res. Methods* 2009, 41, 1149-1160.

Example 6

Figure 14:
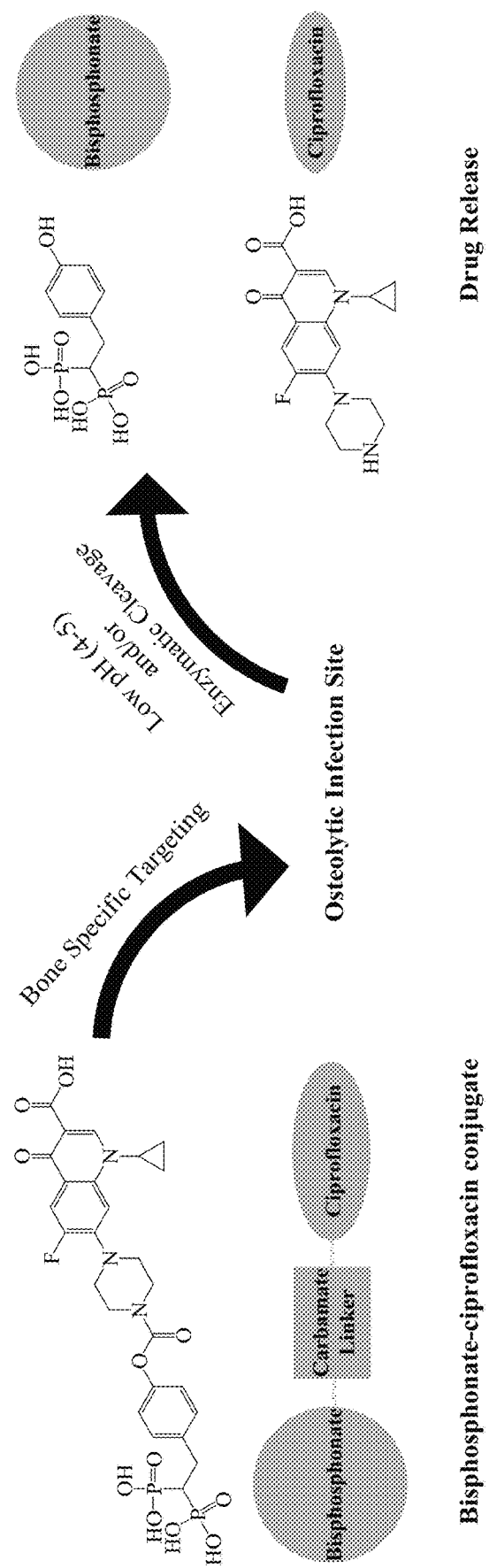
FIG. 14 demonstrates a general strategy of a BP quinolone conjugate capable of targeting and releasing.

Carbamate-linked bisphosphonate-ciprofloxacin is demonstrated herein to be a viable antimicrobial conjugate for, inter alia, targeted therapy of infections bone disease (FIG. 14).

Bisphosphonates (BPs) can form strong bi- and tri-dentate interactions with calcium and thus target bone or hydroxyapatite (HA) surfaces (where biofilm pathogens also reside). The feasibility of a bone-biofilm-targeting antimicrobial approach was demonstrated by successfully designing, synthesizing, and testing a bisphosphonate-carbamate-ciprofloxacin (BCC, compound 6) conjugate in vitro and in vivo against common bone biofilm pathogens. Our results indicated that BCC (compound 6) has a strong bactericidal profile against common long bone and jawbone osteomyelitis organisms in vitro, particularly when biofilm models were used with HA as the substrate for microbial growth and antimicrobial testing. Biofilm growth on HA was inhibited by chemisorbed BCC (compound 6) in an osteomyelitis preventative experimental setting, where the conjugate demonstrated a predictable rate of sustained release and was 20 times more active in achieving complete bactericidal action as compared to the parent drug ciprofloxacin alone. Efficacy and safety of BCC (compound 6) against biofilms of *Aggregatibacter actinomycetemcomitans* was demonstrated in vivo in an animal model of jawbone peri-implantitis. In vivo, a single intraperitoneal dose of 10 mg/kg (15.6 μmol/Kg) of the conjugate produced 99% peri-implant bactericidal efficacy, demonstrating an order of magnitude greater activity than the parent antibiotic ciprofloxacin alone given in multiple doses (90.6 μmol/Kg, totaling a 6-fold higher overall dose of ciprofloxacin). At this single dose of 10 mg/kg, BCC (compound 6) showed greater efficacy and disease resolution than the higher multiply dosed parent antibiotic ciprofloxacin, with no potential systemic toxicity or adverse effects owing to the pharmacokinetic and pharmacodynamic advantages of bone targeting/biodistribution and sustained antibiotic release, respectively, at the site of biofilm infection.

Dental implants are a critical part of modern dental practice and it is estimated that up to 35 million Americans are missing all of their teeth in one or both jaws. The overall market for these implants to replace and reconstruct teeth is expected to reach $4.2 billion by 2022. While the majority of implants are successful, some of these prosthetics fail due to peri-implantitis, leading to supporting bone destruction. Peri-implantitis has a bimodal incidence, including early stage (<12 months) and late stage (>5 years) failures; both of these critical failure points are largely the result of bacterial biofilm infections on and around the implant. Peri-implantitis is a common reason for implant failure. Dental implants failures are generally caused by biomechanical or biological/microbiological reasons. The prevalence of peri-implantitis, the most severe form of microbiological-related implant disease leading to the destruction of supporting bone is difficult to ascertain from the current literature. However, recent studies indicate that peri-implantites is a growing problem with increasing prevalence[4]. A recent study of 150 patients followed 5 to 10 years showed a rate of peri-implantitis of approximately 17% and 30% respectively, indicating that it is a significant issue[5]. Early implant failure or lack of osseointegration is a separate problem and occurs in roughly 9% of implanted jaws[6]. This is more prevalent in the maxilla[6] and is associated with bacterial infection during surgery or from a nearby site (e.g. periodontitis) as well as other well-recognized and modifiable risk factors such as smoking, diabetes, excess cement, and poor oral hygiene[2].

Biofilm infection can be involved in the etiophathogeneiss of peri-implantitis. Biofilm infections represent a unique problem for treatment and are often difficult to diagnose, resistant to standard antibiotic therapy, resistant to host immune responses, and lead to persistent intractable infections[7]. The biofilm hypothesis of infection has been steadily expanded since the early elucidation that bacteria live in matrix supported communities[8,9]. It is now established that over 65% of chronic infections are caused by bacteria living in biofilms[7]. This implies that approximately 12 million people in the US are affected by, and almost half a million people die in the US each year, from these infections. Peri-implantitis and periodontitis are among the most common biofilm infections encountered. Peri-implantitis has been found to be a comparatively simpler infection with less diverse communities (and keystone pathogens) than periodontitis infections[10]. Typically, gram negative species predominate[11]. Other orthopedic or osseous infections including those of the jaw, are also caused by bacterial biofilm communities[12] making the technology developed here amenable for use in these diseases as well.

Currently treatment approaches to peri-implantits have their limitations. While peri-implantitis has several causes, the predominant etiology is bacterial biofilm. There are no universally accepted guidelines or protocols for peri-implantitis therapy, many of the clinical regimens for bacterial peri-implantitis treatment comprise local and systemic antibiotic delivery[13] and surgical debridement of the lesion, including restorative grafting with bone graft substitutes[14,15]. Clinical experience has shown, however, that it is difficult to advance even a local antibiotic delivery device to the bottom of a deep peri-implant pocket and to infected jawbone, or to get systemic antibiotics to penetrate adequately into infected jawbone to kill biofilm pathogens[16], which is largely due to the intrinsic poor bone (and peri-implant) biodistribution or pharmacokinetics of the antibiotics[17]. In previous long-term studies, even when infected implants were cleaned locally with an antiseptic agent and systemic antibiotics were administered, there was additional loss of supporting bone in more than 40% of the advanced peri-implantitis lesions[15].

In addition, longer-term systemic antibiotic therapy could result in systemic toxicity or adverse effects, and also resistance. Therefore it has become common practice by clinicians to use local delivery systems for achieving higher therapeutic antibacterial concentrations in bone. For example, dentists use chairside mixing of minocycline or doxycycline powder (e.g. Arestin®), or chlorhexidine solution (e.g. PerioChip®), with bone graft material for local delivery[18]. Such approaches are merely a slurry and do not represent a strong binding between the antibiotic and the bone substitute as in the BioVinc approach, and thus suffer from comparatively earlier washout and less efficient pharmacokinetics as previously discussed. In addition, investigators have also used several biodegradable and non-biodegradable local antibiotic delivery systems[19]. However, these approaches have several limitations, e.g., non-biodegradable approaches (e.g. polymethylmethacrylate cements) require a second surgery to remove the antibiotic loaded device, are incompatible with certain antibiotics, and suffer from inefficient release kinetics; in some cases, <10% of the total delivered antibiotic is released[17]. Biodegradable materials including fibers, gels, and beads are receiving increasing interest, however, their clinical efficacy for the treatment of peri-implantitis is not well-documented[3]. Even when effective antimicrobials/antiseptics are used to treat peri-implantitis in the jaw, such as local chlorhexidine delivery, there is minor influence on treatment outcomes as demonstrated in prospective animal and human studies[15,17]. These data taken together further support the poor pharmacokinetics of antibiotics in bone as previously mentioned, and highlight the need for bone-binding/bone-targeted and sustained antibiotic release strategies.

BP-Conjugates

Figure 15:
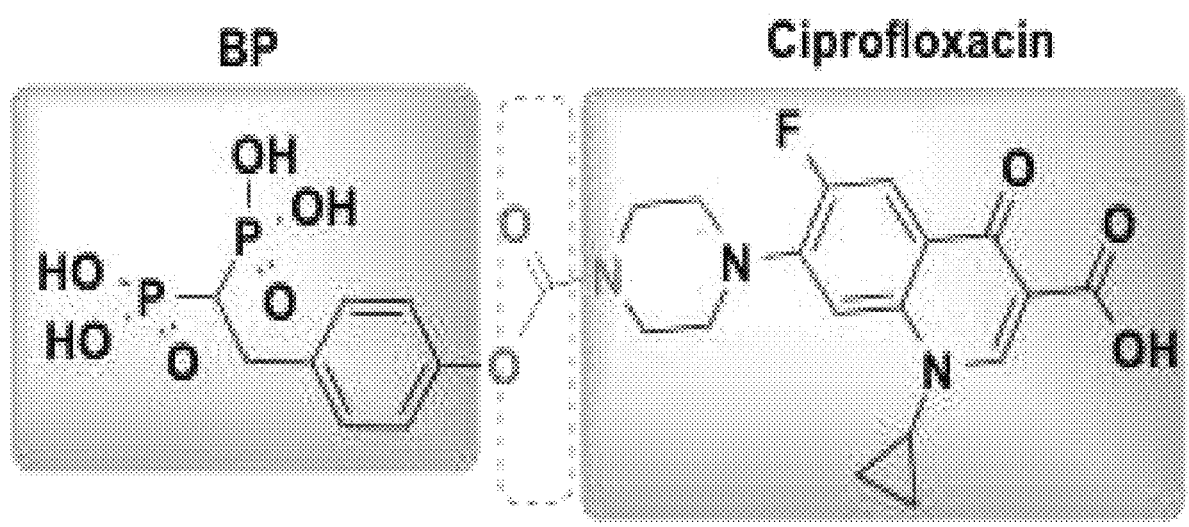
FIG. 15 shows an embodiment of a BP-FQ conjugate.

Considering the limitations of current treatment approaches, it is a significant advance in the field to develop a bone/biofilm-targeting antimicrobial agent. The BP-antibiotic (BP-Ab) conjugates provided herein can overcome many challenges associated with poor antibiotic pharmacokinetics or bioavailability in bone and within bone-bound biofilms. These compounds can reduce infection via a "targeting and release approach," which can reduce concern with systemic toxicity and/or drug exposure in other (e.g. non-infected) tissues. The BP-Ab conjugates can be integrated into a bone graft substitute. The BP-Ab can be a BP-fluoroquinolone conjugate. In some instances, the BP-Ab can be a bisphosphonate-carbamate-ciprofloxacin (BCC, compound 6), as shown in FIG. 15. The exemplary structure of FIG. 15 is also referred to herein as BCC (compound 6). When integrated into a bone graft the BP-Ab bone graft material can also be referred to as a BP-Ab-bone graft. For example, when the antibiotic is a fluoroquinolone, it can be referred to as a BP-FQ-bone graft. These compound(s) can effectively adsorb to hydroxyapatite (HA)/bone, and can achieve a sustained release and antimicrobial efficacy against biofilm pathogens over time. The compounds and graft material integrating the compound(s) provided herein can be used as an anti-infective bone graft substitute for adjunct treatment or prevention of peri-implantitis. The conjugate will be released locally from the graft material with sustained release kinetics and cleaved in the presence of bacterial or osteoclastic activity as we have previously demonstrated, in vitro and in vivo, in other results provided elsewhere herein. In this way the grafts can provide greater local concentrations of the FQ, such as ciprofloxacin, as compared to current delivery routes. In sum the compounds and bone-graft materials provided herein can contain an antibiotic that is conjugated to a safe or pharmacologically inactive (non-antiresorptive) BP moiety bound to calcium/HA in the graft material via strong polydentate electrostatic interactions, and the antibiotic releases over time; it does not simply represent a topical antibiotic that is merely mixed in as a slurry with existing bone graft material as some current clinical approaches in this context. This chemisorbed drug attached to calcium phosphate mineral (HA) is therefore a major advance in the field and overcomes many of the limitations in antibiotic delivery to peri-implant bone for effective bactericidal activity against biofilm pathogens.

The general concept of targeting bone by linking active drug molecules to BPs has been discussed in a review[30]. However, as of this time no FDA approved drugs have been developed, as early attempts led to either systemically unstable prodrugs or non-cleavable conjugates that were found mostly to inactivate either component of the conjugate by interfering with the pharmacophoric requirements. In the quinolone field a prominent example was described by Herczegh where antibacterial properties of the fluoroquinolone were diminished upon conjugation with a stable BP-linked congener[31-32]. Therefore, a target and release linker strategy is needed.

Recently, medicinal chemistry strategies exploiting less stable linking techniques start to emerge. Others have linked fluoroquinolones via the carboxylic acid group to several different BP moieties. They found that glycolamide ester prodrugs of the antibiotics moxifloxacin and gatifloxacin reduced infection when used prophylactically in a rat osteomyelitis model[33]. This same group has used acyloxycarbamate and phenylpropanone based linkers to tether the same antibiotics via amine functionality to simple BP systems[34]. They show using the same prophylactic rat model that these conjugates are also better than the parent antibiotic at inhibiting the establishment of infection. The Targanta team[33] has carried several of these prodrug strategies on into use with the glycopeptide antibiotic oritavancin[35]. This dual function drug seems to be somewhat effective in preventing infection. However, to date they have not published studies showing that they can treat an established infection and they also have not published pharmacokinetics of the prodrug. It is believed that these analogs are too labile in the bloodstream to fully realize success with this therapeutic approach as their drug candidate selection was based in part on plasma instability. Thus it is believed that these compounds developed by these groups fail to achieve effective local concentrations of the antibiotic.

The BCC compound(s) (FIG. 15) can incorporate the phenyl moiety of the phenyl carbamate linker directly into the BP portion of the molecule. Release kinetics can be modified or tuned via modification of the phenyl ring with electron withdrawing or donating groups, which can alter the liability of the linker. Additionally, the BP core lacks effectiveness as an antiresorptive agent, and thus, does not carry the risk of medication-related osteonecrosis of the jaw like the more potent nitrogen-containing BP drugs (e.g., zoledronate[39,40]. It is demonstrate herein and in other Examples herein that this target and release strategy using the phenyl carbamate linker very likely releases the active drug directly into the bacterial biofilm in the bone milieu. The bone targeting is so effective that it works better than ciprofloxacin against biofilms grown on HA bone matrix surrogate than on planktonic cultures grown in plastic vessels. An analog conjugate made with a non-cleavable amide linkage (bisphosphonate-amide-ciprofloxacin, BAC, compound 11), leaving out the phenolic oxygen of the carbamate, was found to have very little effect on bacterial growth under any circumstances, demonstrating that active cleavage of the conjugate is required for antimicrobial activity.

A synthesis scheme for BCC (compound 6) is demonstrated in FIG. 16. The compound was characterized by $^1$H, $^{13}$C and $^{31}$P NMR as well as by mass spectrometry. In order to help determine if antimicrobial activity is primarily due to the released ciprofloxacin we decided to synthesize an amide linked conjugate that was designed not to release ciprofloxacin from the conjugate as well. The synthesis of this compound went smoothly (FIG. 31), and afforded the control compound BAC (compound 11) with reasonable yield.

A series of assays were performed to determine the minimum inhibitory concentrations (MIC) of BCC (compound 6) (also referred to as "BCC (6)"), BAC (compound 11) (also referred to as "BAC (11)") and the parent drug ciprofloxacin against a group of Staphylococcus aureus (SA) strains. These experiments were carried out using dilution assays according to the European Committee on Antimicrobial Susceptibility Testing guidelines (ref. 43). Testing of the three compounds (FIG. 17) demonstrates that the BCC (compound 6) conjugate retains significant bactericidal activity against these pathogens while the BAC (compound 11) has lost most of the activity. These antibiotic susceptibility testing (AST) and MIC data indicate that against planktonic and clinically relevant SA pathogens, ciprofloxacin and BCC (compound 6) have strong bactericidal activity, and that the conjugation linking impacts antimicrobial activity of the parent drug as evidenced by the weak activity of the BAC (compound 11). Our testing of ciprofloxacin against these strains was consistent with established clinical breakpoints.

The compounds were tested for adsorption to suspended HA beads as a surrogate for bone binding since HA is the main inorganic constituent in bone. Our BCC (compound 6) is indeed taken up by the HA beads as indicated by the measurement of residual conjugate in the supernatant after bead removal (FIG. 18). Conjugate in the supernatant was measured at 0 and 24 hrs by spectrophotometry using the absorbance at 275 nM the determined $\lambda_{max}$ for BCC (compound 6). This clearly indicates that BCC (6) is bound to this bone surrogate. We did not measure the binding of the BAC (compound 11) as the data for BCC (compound 6) was consistent with binding of this type of BP which would drive the BAC (compound 11) binding as well (ref. 35, 44).

The next in vitro test was to combine the bone surrogate targeting activity of the BCC (6) with the ready release of ciprofloxacin that is indicated by the MIC activity against SA strains. For this experiment HA discs were pretreated with solutions of the conjugates or ciprofloxacin at the designated concentrations followed by rinsing to remove the compound solution. Biofilms of SA (strain ATCC-6538) were allowed to grow according to our published procedures. Quantitative counts of colony forming units (CFUs) were carried out after 24 hrs of growth. Discs pretreated with DMSO and PBS were used as controls. The results demonstrated that BCC (6) inhibits all bacterial growth at 10 µg/mL (FIG. 11) whereas the pure ciprofloxacin was completely inhibitory at 100 µg/mL. Because the molecular weight of the conjugate is approximately half that of the pure ciprofloxacin, this indicated that the BCC (compound 6) is roughly 20 times more potent at completely inhibiting the growth of bacterial biofilms than the parent drug. This supports the release of drug from the conjugate over time in the milieu of bone matrix. The amide conjugate BAC (11) did not inhibit the growth of biofilms on bone substitute even at very high concentrations (data not shown) indicating that the release of ciprofloxacin was crucial to this activity and consistent with earlier literature and the planktonic culture studies (FIG. 18)[30, 34, 35, 44].

With the aforementioned results showing that our BCC (6) has bactericidal activity, we were ready to test its activity against a biofilm infection in an animal model. Briefly, Aggregatibacter actinomycetemcomitans (Aa; wild-type rough strain D7S-1; serotype a), which is not indigenous to rat normal flora and specific to jawbone infections, are pre-inoculated on miniature titanium implants at $10^9$ CFU. To confirm Aa sensitivity to the parent drug ciprofloxacin prior to our animal studies, we performed AST and MIC assays with Aa, as performed for the long bone osteomyelitis pathogens described previously. Disc diffusion inhibition zone assays revealed diameters >40 mm, and the MIC[90] was 2 mg/mL, indicating strong susceptibility of Aa to the parent drug ciprofloxacin. Inoculated implants, bearing the Aa biofilms, were placed into 12 rats (2 implants per animal). This model reliably forms well-characterized biofilm infections on surrounding jawbone, causing inflammation and associated peri-implantitis disease. (ref. 45) After allowing biofilms to develop the animals were randomized into three treatment groups (BCC (6) 10 mg/kg single dose in 5 animals, BCC (6) 0.3 mg/kg 3× weekly in 2 animals, and control treatment with sterile saline in 5 animals). A pilot experiment (2 animals/group) demonstrated that the BCC (6) single dose at 10 mg/kg was approximately as effective as ciprofloxacin given at 30 mg/kg total dose administered in a 3×10 mg per week regimen (not shown). Therefore, we decided not to include the ciprofloxacin control in the larger experiment to reduce animal usage. All animals tolerated treatment and pharmacotherapy well with no adverse events. Clinically, during euthanasia and surgical resection, we observed that the majority of the animals in the control group demonstrated evidence of localized peri-prosthetic inflammation as compared to the majority of the animals in the treatment groups which had non-inflamed peri-implant tissues, and implant retention was 23/24 implants (96%) overall providing for robust statistical analyses.

Figure 19:
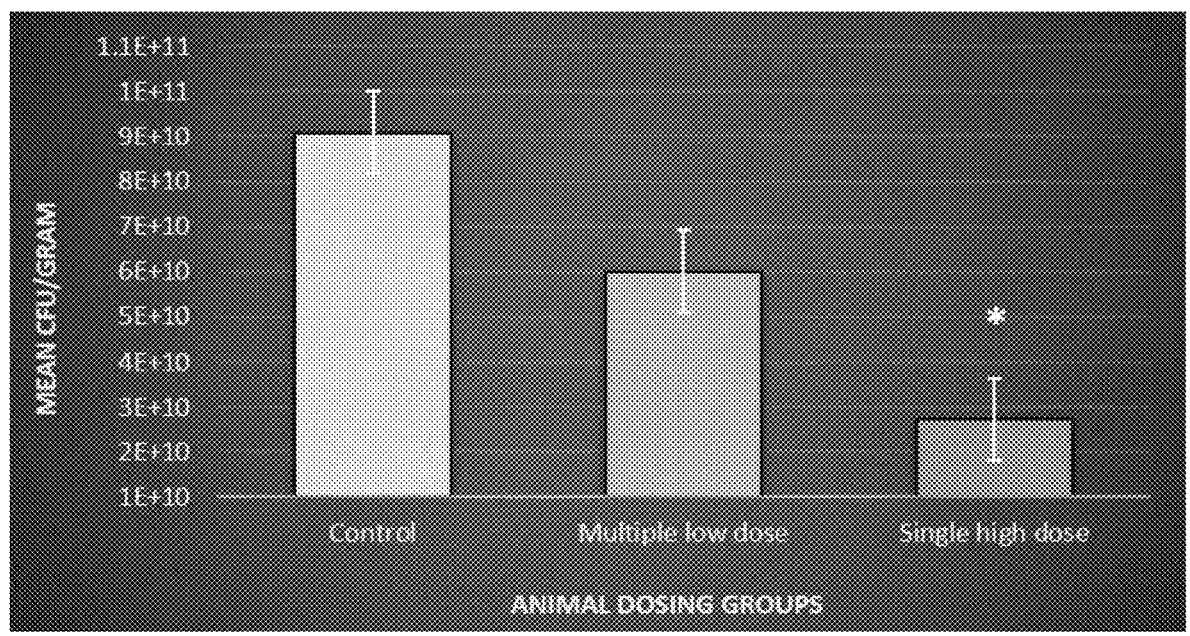
FIG. 19 shows a graph demonstrating efficacy of the BCC (compound 6) for reducing bacterial load or mean CFU/gram of tissue. The greatest efficacy was again observed at a single high dose (10 mg/kg) of the conjugate as compared to the control [*p=0.0005; unpaired t-test, error bars represent Standard Error].

Quantitative determination of the CFU of Aa from resected peri-implant tissue (23/24 implants) post-euthanasia was carried out and results are shown in FIG. 19 where the single dose of 10 mg/kg BCC (6) demonstrated approximately 6 log units of kill and even the low multiple dose showed 2-3 (99% to 99.9%) log kill in this experiment. With this experiment the single dose of 10 mg/kg BCC (6) showed the greatest efficacy and was highly statistically significant (p=0.0005) as compared to the control arm.

In both of these animal models the BCC (6) was delivered by intraperitoneal injection to assure exposure to the compound since there is relative bioequivalence with intravenous or gastrointestinal routes of administration of fluoroquinolones. We believe these results in total demonstrate the feasibility of using releasable BP-antibiotic (BP-Ab) conjugate as a drug for the treatment of peri-implant disease and related osteomyelitis. Here we propose to build on these results to incorporate the BP-Ab conjugate into a dental bone graft substitute material for local oral delivery and release.

Example 7

Figure 20:
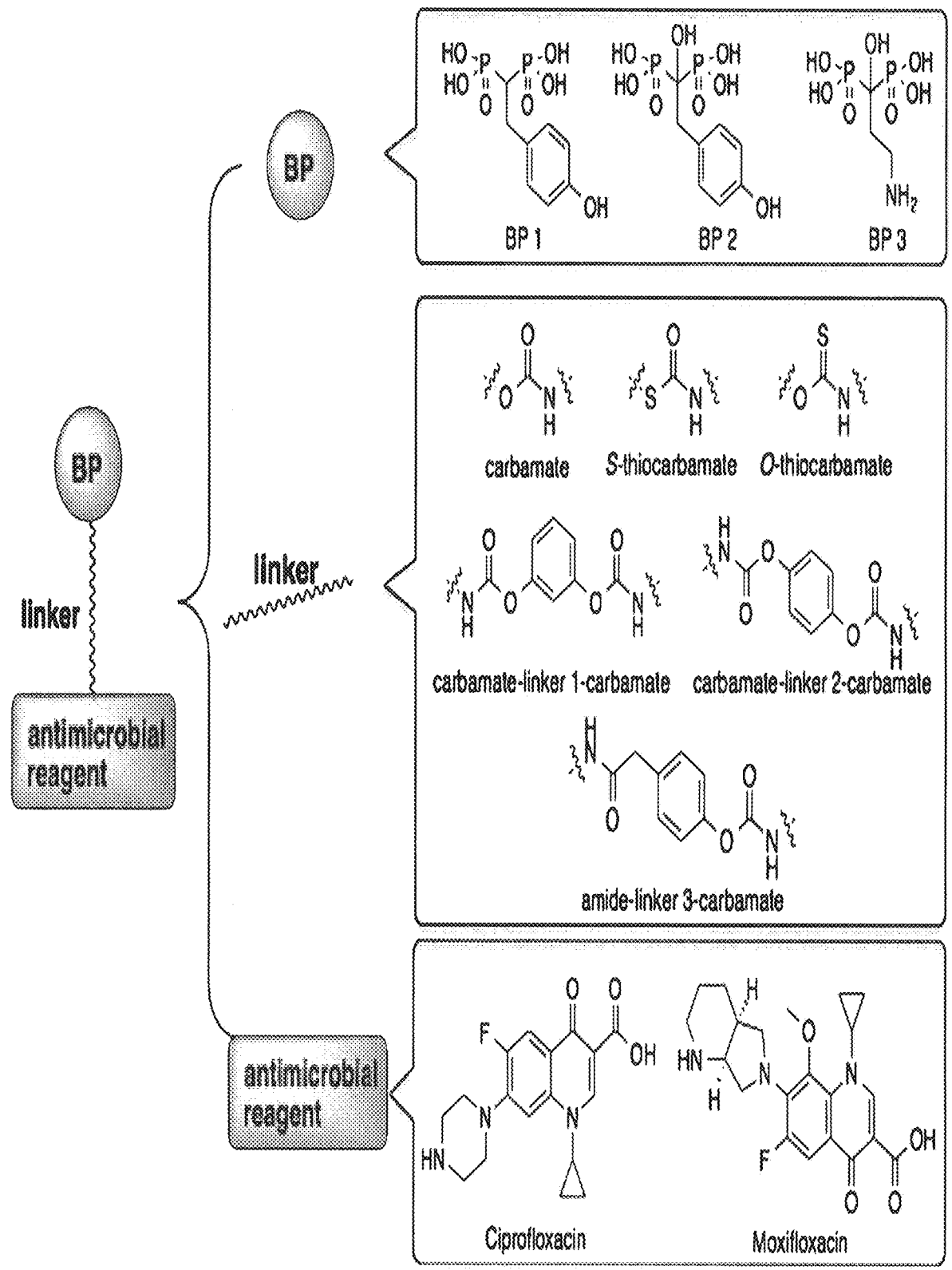
FIG. 20 shows additional BP-Ab conjugate design.
Figure 21:
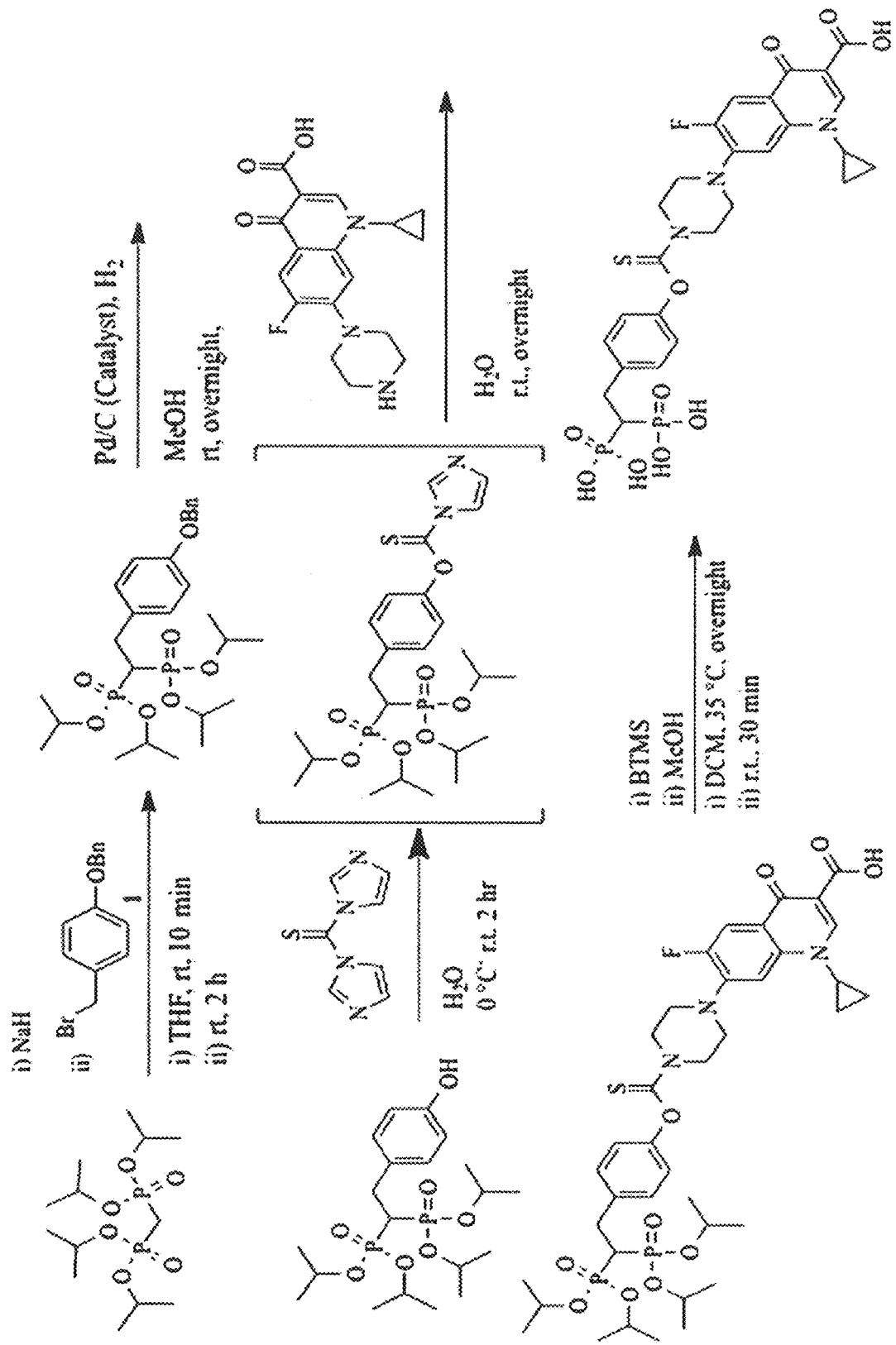
FIG. 21 shows an embodiment of a synthesis scheme for synthesis of BP-Ab conjugates with an O-thiocarbamate linker.
Figure 22:
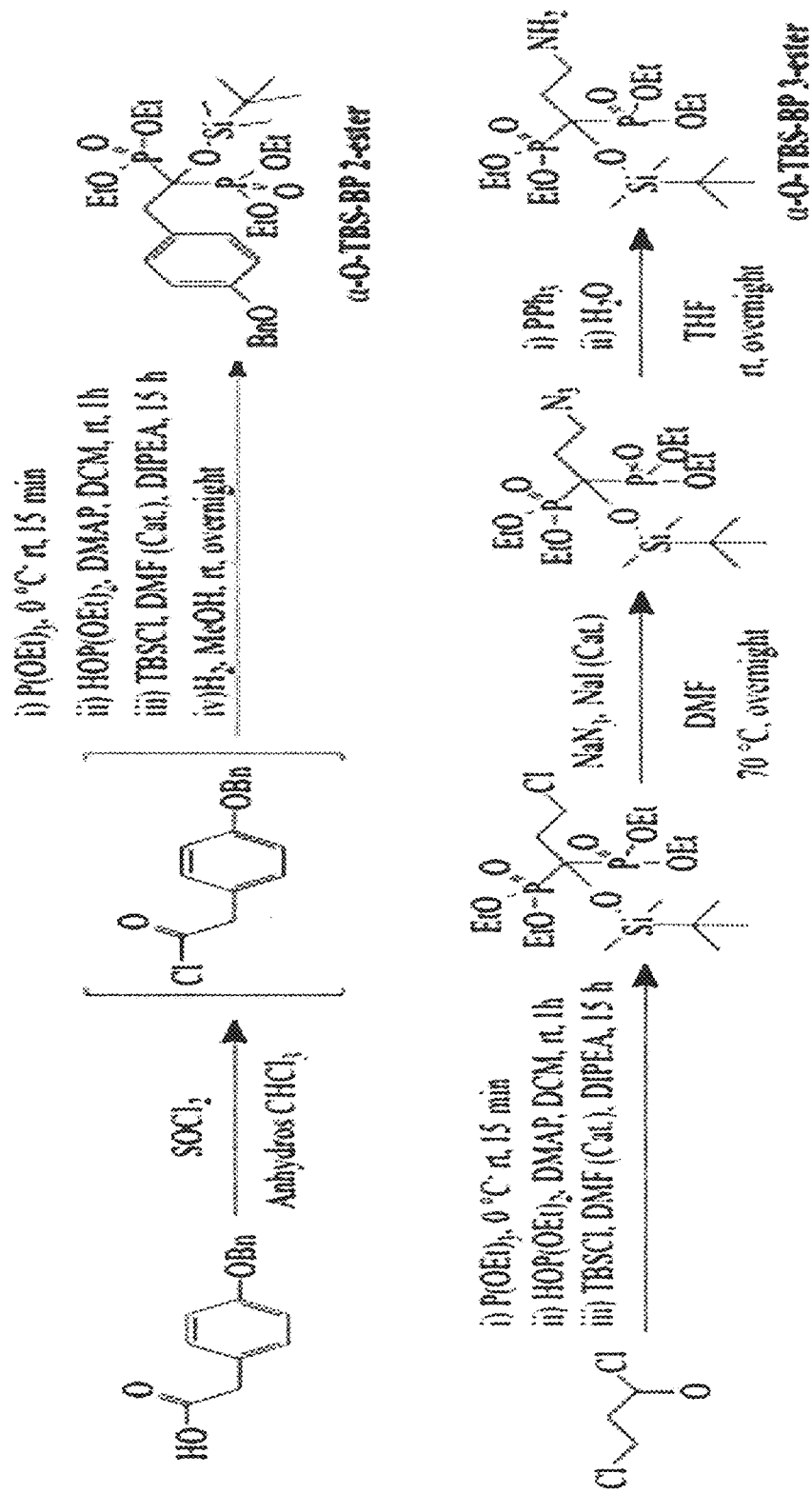
FIG. 22 shows an embodiment of a scheme for synthesis of Q-OH protected BP esters.
Figure 23:
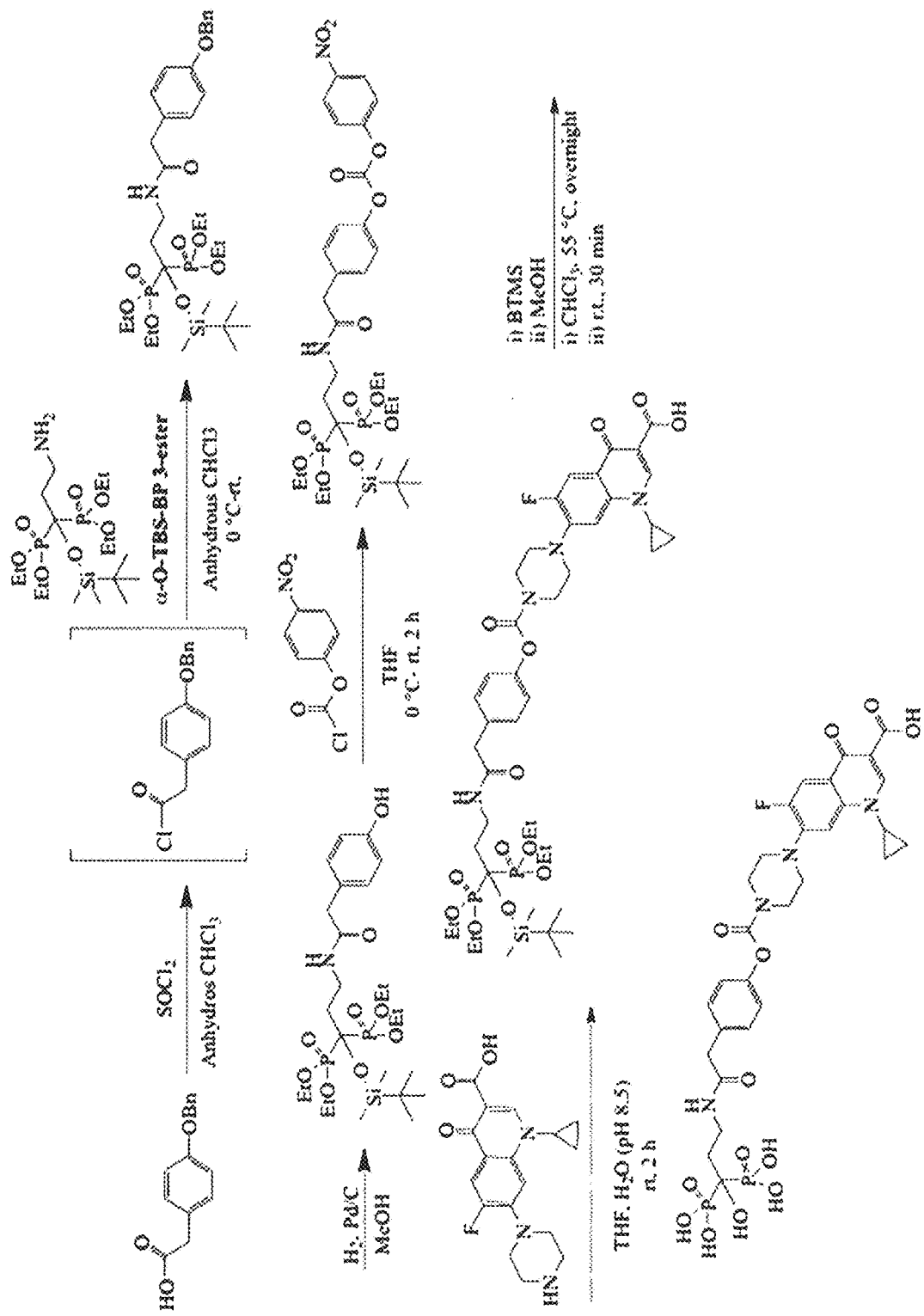
FIG. 23 shows an embodiment of a scheme for synthesis of BP 3-linker 3-ciprofloxacin.

Design and synthesis of additional BP-Ab conjugates (FIG. 20). Additional BP-Ab conjugates can be designed using, for example, ciprofloxacin and moxifloxacin conjugated to BPs (e.g. 4-hydroxyphenylethylidene BP (BP 1, FIG. 20), its hydroxy-containing analog (BP 2, FIG. 20, with higher bone affinity) and pamidronate (BP 3, FIG. 20), via carbamate based linkers (e.g. carbamate, S-thiocarbamate, and O-thiocarbamate). FIG. 21 shows an exemplary synthesis scheme for synthesis of BP-Ab conjugates with an O-thiocarbamate linker. Conjugates with S-thiocarbamate linkage (slightly more labile) can be obtained by isomerization of conjugates with O-thiocarbamate linkage via the Newman-Kwart rearrangement (ref. 47, 48). Preliminary chemistry has already been conducted to demonstrate the feasibility of the quick synthesis of these targets. Adding bone affinity is therefore well demonstrated using the α-OH containing BPs (49). Added bone affinity will enhance concentrations of the conjugate at the bone surface and facilitate higher local concentrations of drug short term and long term. For the synthesis of conjugates with α-OH containing BPs (BP 2 and pamidronate, FIG. 20), since the α-OH bisphosphonate ester is prone to rearrangement to a phosphonophosphate, the α-OH can be protected with the tert-butyldimethylsilyl (TBS) group (Scheme 2, FIG. 22) (50). Then the α-O-TBS BP 2 ester are activated by 4-nitrophenyl chloroformate and reacted with ciprofloxacin or moxifloxacin similarly as in FIG. 21. For α-O-TBS BP 3 ester, a linker with phenol group (e.g., linker 1 (resorcinol), linker 2 (hydroquinone), linker 3 (4-hydroxyphenylacetic acid), FIG. 20) are used to tether BP and antimicrobial agents, and the synthesis route using linker 3 is illustrated as an example here (Scheme 3, FIG. 23). All BP-Ab conjugates are characterized by 1H, 31P, 13C NMR, MS, HPLC, and elemental analysis to assure identity.

The mineral binding affinity of the BP-Ab conjugates can be determined. Briefly, Anorganic bovine bone large particle size (uniformly 1-2 mm) can be accurately weighed (1.4-1.6 mg) and suspended in a 4 mL clear vial containing the appropriate volume of assay buffer [0.05% (wt/vol) Tween20, 10 µM EDTA and 100 mM HEPES pH=7.4] for 3 hr. This bone material can then be incubated with increasing amounts of BP-Ab (0, 25, 50, 100, 200 and 300 µM). Samples can be gently shaken for 3 h at 37° C. in the assay buffer. Subsequent to the equilibrium period, the vials can be centrifuged at 10,000 rpm for 5 min to separate solids and supernatant. The supernatant (0.3 mL) can be collected and the concentration of the equilibrium solution are measured using a Shimadzu UV-VIS spectrometer (275 nm wavelength). Fluorescent emission can also be used to calculate binding parameters. Nonspecific binding can be measured with a similar procedure in the absence of HA as control. The amount of parent drug/BP-Ab conjugates bound to HA is deduced from the difference between the input amount and the amount recovered in the supernatants after binding. Binding parameters ($K_d$ and Bmax represent the equilibrium dissociation constant and maximum number of binding sites, respectively) can be calculated using the PRISM program (Graphpad, USA) and measured in 5 independent experiments. Compounds with an equilibrium dissociation constant ($K_d$) lower than 20 µM (~2× $K_d$ of parent BPs) can be preferred. A two-sample t-test can be used to evaluate the binding parameters of the BP-Abs. The sample size (n=5) in each group can be used to detect the effect size 1.72 for this hypothesis at a power of 80% and a one-side Type I error of 0.05.

The linkage-stability of the BP-Ab conjugates can be determined. Briefly, the linker stability of each BP-Ab conjugate can be tested in PBS buffers with different pH (pH=1, 4, 7.4, 10) and human or canine serum. BP-Ab can be suspended in 400 µL of above-mentioned PBS or in 400 µL of 50% (v/v in PBS) human or canine serum. The suspension/solution can be incubated for 24 h at 37° C. and centrifuged at 13000 rpm for 2 min, and the supernatant can be recovered. Methanol (5× volume relative to supernatant) can be added to each supernatant, and the mixture can be vortexed for 15 min to extract released fluoroquinolone. The mixture can be then centrifuged at 10000 rpm for 15 min to pellet the insoluble material. The supernatant containing the extracted fluoroquinolone can be recovered and evaporated to dryness. The dried pellets can be resuspended in PBS, and the amount of released fluoroquinolone can be determined by UV-VIS measurements as described previously. The percentage of fluoroquinolone drug released can then be calculated based on the input amount and the measured amount of released drug. The identity of released drug can be confirmed by LC-MS analysis and/or NMR if the concentrations are sufficient.

The in vitro inhibition of biofilm growth on HA discs can be determined. Briefly, for custom disc manufacturing, commercially available HA powder can be used. Powder pellets of 9.6 mm in diameter can be pressed without a binder. Sintering can be performed at 900° C. The tablets can be compressed using the Universal Testing System for static tensile, compression, and bending tests (Instron model 3384; Instron, Norwood, Mass.). The quality of the manufactured HA discs can be checked by means of confocal microscopy and microcomputed tomography (micro-CT) using an LEXT OLS4000 microscope (Olympus, Center Valley, Pa.) and Metrotom 1500 microtomograph (Carl Zeiss, Oberkochen, Germany), respectively. HA discs can then be introduced to the following concentrations [mg/mL] of each BP-Ab conjugate and ciprofloxacin/moxifloxacin: 800, 400, 200, 100, 50, 25, 10, 5, 1 and left for 24 h/37° C. After incubation, HA discs can be removed and introduced to 1 mL of PBS and left for 5 min in gentle rocker shaker; 3 subsequent rinsings are performed this way. After rinsing, 1 mL of Aa suspension can be introduced to discs and left for 24 h/37° C. Discs can then be rinsed to remove non-bound bacteria and subjected to vortex shaking. The serial dilutions of suspension obtained can then be culture plated on modified TSB agar plates and colony growth is counted after 24 h.

The oseeointegration effect of the BP-FQ-bone grafts on critical size can be evaluated in supra-alveolar peri-implant defect model for bone grafting. Briefly, in this split mouth design, mandibular PM2-PM4 are bilaterally extracted in 6 beagle dogs (3 males, 3 females) and are allowed to heal for 12 weeks. Crestal incision are made followed by mucoperiosteal flap reflection. Ostectomy are performed to create a 6 mm supra-alveolar defect. Implant site osteotomy preparations are made in each of the premolar regions by sequential cutting with internally irrigated drills in graduated diameters under copious irrigation. Implants (Astra Tech Osseospeed Tx® 3×11 mm) are placed in the position of PM2-PM4 on each side in such manner that the implants are positioned 4 mm supracrestally in relation to the created defect and at the same distance from the buccal cortical bone plate. Dogs are divided randomly into 3 different groups (2 dogs per group):

1. Anorganic bovine bone (1 g large particle size 1-2 mm) chemisorbed with BP-fluoroquinolone are used on the right side and collagen plugs (negative control) are used on the left side.

2. Anorganic bovine bone (1 g large particle size 1-2 mm, positive control) are used on the right side and collagen plugs (negative control) are used on the left side.

3. Bio-Oss® (1 g large particle size 1-2 mm) chemisorbed with BP-fluoroquinolone are used on the right side and Bio-Oss® (1 g large particle size 1-2 mm, positive control) are used on the left side.

Chemistry and antimicrobial assay results from experiments described above can inform calculations of the ideal standardized quantity of the conjugate for adsorption to graft material for use in all in vivo experiments described here. Early calculations predicated based on the preliminary results indicate that 5 mg or less of conjugate adsorbed to 1 g of graft material will provide 2-3 orders of magnitude bactericidal activity above the MIC of tested pathogens. Our BP-fluoroquinolone conjugate can be applied in a range of bone graft materials including commercially available ones, e.g., Bio-Oss®; thus we choose house-made an organic bovine bone and BioOss as a positive control in the study for a demonstration of wide applications of the conjugate. All defects are filled (depending on the groups above) with a standardized amount of biomaterial up to the platform of each implant on both sides, and Bio-Gide® membranes are used to cover the graft and the implants for improved stability. The flaps are closed in a tension free manner with the use of periosteal releasing incisions, internal mattress and finally marginal single interrupted sutures (PTFE 4,0, Cytoplast, USA). MicroCT are acquired at this point and animals are monitored clinically for inflammation and adverse events. Additionally, as described in the experiments to follow, these animals undergo PK studies to assess for any systemic exposure to the components within the graft material (e.g. intact conjugate, BP, antibiotic, or linker). Animals are sacrificed after 12 weeks and the mandibles are resected and examined by micro-CT followed by histologic preparation. Baseline micro-CT scans of the jaws are taken for comparison to post-experimental scans. Quantitative 3D volumetric micro-CT and histomorphometric analyses are performed to examine the volume of new bone present in peri-implant sites, as well as first bone-to-implant contact, total defect area, regenerated area, regenerated area within total defect area, regenerated bone, residual bone substitute material, percentage of mineralized tissue, soft tissue, and void. Finally, necropsy are performed for post-mortem evaluation of organs and systems for gross and microscopic signs of tolerability issues from local oral therapy.

Antimicrobial efficacy of the BP-FQ-bone grafts can be evaluated in a canine peri-implantitis model. Briefly, in this split mouth design, mandibular PM2-PM4 are extracted bilaterally in 8 beagle dogs (4 males, 4 females; 48 teeth total) using minimally traumatic technique. After 3 months of healing mucoperiosteal flaps are elevated on both sides of the jaw and osteotomy preparations are made in each of the premolar regions by sequential cutting with internally irrigated drills in graduated diameters under copious external irrigation. Using a non-submerged technique, implants (Astra Tech Osseospeed Tx® 3×11 mm) are installed at each site. The sequence of implant placement are identical in both sides but randomized with a computer generated randomization scheme between dogs. Healing abutments are connected to the implants and flaps approximated with resorbable sutures. A plaque control regimen comprising brushing with dentifrice is then initiated four times a week. Twelve weeks after implant placement just prior to initiation of experimental peri-implantitis, microbiological samples are obtained from all peri-implant sites with sterile paper points (Dentsply, Maillefer, size 35, Ballaigues, Switzerland) and placed immediately in Eppendorf tubes (Starlab, Ahrensburg, Germany) for microbiological analysis. Microbiologic analysis are performed as we have previously detailed via DNA extraction and 16S rRNA PCR amplification. (55) PCR amplicons are sequenced using the Roche 454 GS FLX platform and data analyzed with the Quantitative Insights into Microbial Ecology (QIIME) software package (56). Colony forming unit counts (CFU/mL) are determined from samples as in our Phase I study as described earlier. At this point experimental peri-implantitis are initiated as follows. *Aggregatibacter actinomycetemcomitans* (Aa) biofilm, a keystone periodontal pathogen, which is not endogenous to canine flora, are initiated on the healing abutments in vitro as performed in our previous experiment in a rat animal model and also in our previous animal peri-implantitis study. The biofilm inoculated healing abutments are placed on the implants and cotton ligatures are placed in a submarginal position around the neck of implants. After 10 weeks of bacterial infection, microbial sampling and analysis are done again as before and micro-CT scans are taken as the baseline for the peri-implantitis defect. Treatment of this experimental peri-implantitis model are initiated by surgical debridement of all implant sites by raising full-thickness buccolingual flaps, removing any existing calculus from implant surfaces using an air-powder abrasion device, and wiping of the implant surfaces with gauze soaked in chlorhexidine gluconate 0.12%. The animals are divided into 4 groups as follows (2 dogs per group):

1. Anorganic bovine bone (1 g large particle size 1-2 mm) with chemisorbed BP-fluoroquinolone are used on the right side and collagen plugs (negative control) are used on the left side.

2. Anorganic bovine bone (1 g large particle size 1-2 mm, positive control) are used on the right side and collagen plugs (negative control) are used on the left side.

3. Anorganic bovine bone (1 g large particle size 1-2 mm) with chemisorbed BP-fluoroquinolone are used on the right side and an antimicrobial releasing device (100 mg topical minocycline, positive control) are used on the left side.

4. Bio-Oss® (1 g large particle size 1-2 mm) with chemisorbed BP-fluoroquinolone (positive control) are used on the right side and an antimicrobial releasing device (100 mg topical minocycline, positive control) are used on the left side.

Treatment group assignments are blinded to future investigators for data analysis. Standardized and comparable amounts of antimicrobials are used in treatment groups. After treatment, flaps are repositioned and sutured (PTFE 4,0, Cytoplast, USA) and oral hygiene measures reinstituted after 1 week following suture removal. Clinical and micro-CT scan examinations are performed again at 3 months after surgery and also microbiological samples are acquired at this time point for analysis as described above. Six months after peri-implantitis surgery animals are euthanized and micro-CT scans are performed, and the jaws are resected for assessment of histopathologic parameters as detailed in the section "critical size supra-alveolar peri-implant defect model." An inflammatory score are determined from histologic sections as previously detailed (ref. 57) for correlation with clinical and radiologic findings.

Statistical analysis: Statistical calculations are performed with SPSS 22.0 (IBM, Armonk, N.Y.) and Excel 2016 (Microsoft Corporation, Redmond, Wash.). Power analyses were performed to determine sample size estimations for all animal studies using G Power 3 software[58]. Following data collection from these animal studies, quantitative outcomes are analyzed first with descriptive statistics to understand the distribution of the data (parametric or non-parametric) and to generate the mean, standard error, standard deviation, kurtosis and skewness, and 95% confidence levels. The data are analyzed using the Kruskall-Wallis test, ANOVA, or mixed linear models as applicable and statistical significance are carried out at a=0.05 level when comparing groups. Post-hoc testing using unpaired t-tests and Dunnett's test for multiple comparisons are also performed to further validate findings. All animal experiments are described using the ARRIVE guidelines for reporting on animal research to ensure the quality, reliability, validity, and reproducibility of results[59].

The drug compound and component stability and in vitro ADME of BCC (6) can be evaluated. This data can help establish if there is likely to be any large differences in human metabolism vs. experimental animals. Incubation of 6 with human, rat, and dog liver microsomes and hepatocytes followed by LC/MS analysis of the metabolite mixture are performed. The metabolic profile of ciprofloxacin is known[62,63], and so our focus are on any metabolites of the BP portion of the molecule and of the parent (e.g. piperazine ring cleavage as is known for ciprofloxacin). Once metabolites have been determined in vitro, plasma samples from other in vivo experiments described above are used to determine these compounds at steady state in vivo.

The toxicology of the BCC (6) can be evaluated in rat and dog to determine NOAEL. In order to determine the NOAEL and maximum tolerated dosage (MTD) in rat and dog we first carry out dose ranging studies. Groups of 6 rats (3 males, 3 females), are given a single intravenous dose of 10 mg/kg for 6, or based on our best assessment at the time. The dose are escalated by doubling until acute toxicity is noted (MTD) then this dose are reduced by 20% sequentially until no effects are seen, this will be the NOAEL for the compound. Toxicity are assessed as mild, moderate or substantial, and moderate toxicity in ≥2 or substantial toxicity in ≥1 animal define the MTD[64]. Animals are followed for body weight and clinical observations for 5 days. After 5 days, animals are euthanized and necropsy performed to assess for organ weight and histology (15 sections to include liver and kidney based on clinical BP toxicology). A similar dose range study are carried out in dogs (1/sex, starting at the equivalent dose as determined from allometric scaling 4 mg/kg assuming 250 g rats and 10 kg dogs) and include hematology and clinical chemistry in addition to identical terminal studies as in rat. This can use a total of 4-6 cohorts.

An expanded acute toxicity testing in groups of animals including toxicokinetics and recovery testing at the NOAEL and the MTD can be performed. Groups of 48 rats including 10/sex can be used for each dose for assessment of toxicity and 9/sex for toxicokinetics and 5/sex for recovery. Toxicokinetics are determined at 6 time points (3 rats/time point chosen randomly from male or female) following administration of each dose. Time points are 5, 30, 60, 120 mins, 12 hrs, and 24 hrs post dosing. Recovery animals are observed for 14 days followed by assessment of organ weight and histology as in the above study. From the toxicokinetic study, PK parameters are determined by non-compartmental analysis (NCA) including Cmax, AUC and half-life. An identical experiment are carried out in canines but include 10 total animals (3/sex for dosing and 2/sex for recovery) with multiple blood draws from each animal at the same time points as for the rats. The AUC at the NOAEL for canines are used to calculate the maximum allowable exposure from the bone graft/BP-fluoroquinolone conjugate as described in aim 2 and PK experiments in canines are used to determine if there is systemic exposure above $\frac{1}{100}$ of this level.

For population modeling, a unique 3-compartment (blood/urine/bone) mathematical model of BP pharmacokinetics which has been validated clinically and are applied to the current project[65]. From the canine study, in each animal at the time of euthanasia, we sample bone (jaw and femur), tendon (gastrocnemius) for determination of BP and fluoroquinolone concentrations. We combine these data and our model to describe the time course in dogs. From this model we can simulate the expected exposure of bone and cartilage to both BP and fluoroquinolone with alternative dosing or repeated dosing. This can inform subsequent human dosing. The nonparametric adaptive grid (NPAG) algorithm with adaptive gamma implemented within the Pmetrics package for R (Laboratory of Applied Pharmacokinetics and Bioinformatics, Los Angeles, Calif.) are used for all PK modelfitting procedures as previously described[66-68]. Assay error (SD) is accounted for using an error polynomial as a function of the measured concentration, and comparative performance evaluation are completed using Akaike's information criterion, a regression of observed versus predicted concentrations, visual plots of PK parameter-covariate regressions, and the rule of parsimony.

Example 8

The BP-Ab conjugates can be integrated into grafts and grafting devices. In embodiments, one or more of the BP-Ab conjugates can be integrated into an already approved bone graft product, such as the bovine bone materials from BioOss® (Geistlich Pharma AG, Switzerland) or MinerOss® (BioHorizons, Birmingham, Ala.) to name a few. The BP-Ab conjugate(s) can be admixed with a support material for use as a dental bone graft substitute. The product will comprise the conjugate adsorbed to an organic bovine bone material. This material will allow the local delivery of antibiotic to the region of bone graft implantation to reduce bacterial infection rates and associated dental pathology such as peri-implantitis and other infections. The dental applications for our product could include not only peri-implantitis treatment, but also socket preservation after tooth extraction, ridge or sinus augmentation, periodontitis prevention or treatment, osteomyelitis or osteonecrosis treatment or prevention, or other oral and periodontal surgery applications where such a bone graft could be beneficial. The BP-fluoroquinolone conjugate material will be intimately adsorbed on the bone graft substitute and our preliminary data show sustained release into the area of bone destruction in the case of infections, which allows our product to more effectively deliver antibiotic to the site of infection with negligible to no systemic exposure to either component of the conjugate compound.

The grafting material can also be beneficial for non-dental grafting procedures, such as sinus grafting procedures.

REFERENCES FOR EXAMPLES 6-8

1. http://www.aaid.com/about/press_room/dental_implants_faq.html
2. Quirynen M, De Soete M, van Steenberghe D. Infectious risks for oral implants: a review of the literature. Clinical Oral Implants Research. 2002; 13(1):1-19. doi: 10.1034/j.1600-0501.2002.130101.x. PubMed PMID: 12005139.
3. Norowski P A, Jr., Bumgardner J D. Biomaterial and antibiotic strategies for peri-implantitis: a review. J Biomed Mater Res B Appl Biomater. 2009; 88(2):530-43. doi: 10.1002/jbm.b.31152. PubMed PMID: 18698626.
4. Salvi G E, Cosgarea R, Sculean A. Prevalence and Mechanisms of Peri-implant Diseases. J Dent Res. 2016. doi: 10.1177/0022034516667484. PubMed PMID: 27680028.
5. Meijer H J A, Raghoebar G M, de Waal Y C M, Vissink A. Incidence of peri-implant mucositis and peri-implantitis in edentulous patients with an implant-retained mandibular overdenture during a 10-year follow-up period. Journal of Clinical Periodontology. 2014; 41(12):1178-83. doi: 10.1111/jcpe.12311. PubMed PMID: 25229397.
6. Jemt T, Olsson M, Stenport V F. Incidence of First Implant Failure: A Retroprospective Study of 27 Years of Implant Operations at One Specialist Clinic. Clinical Implant Dentistry and Related Research. 2015; 17:E501-E10. doi: 10.1111/cid.12277. PubMed PMID: 25536273.
7. Wolcott R D, Ehrlich G D. Biofilms and chronic infections. Jama-Journal of the American Medical Association. 2008; 299(22):2682-4. doi: 10.1001/jama.299.22.2682. PubMed PMID: 18544729.
8. Costerton J W, Cheng K J, Geesey G G, Ladd T I, Nickel J C, Dasgupta M, Marrie T J. Bacterial biofilms in nature and disease. Annual Review of Microbiology. 1987; 41:435-64. PubMed PMID: 3318676.
9. Costerton J W, Geesey G G, Cheng K J. How bacteria stick. Scientific American. 1978; 238(1):86-95. PubMed PMID: 635520.
10. Kumar P S, Mason M R, Brooker M R, O'Brien K. Pyrosequencing reveals unique microbial signatures associated with healthy and failing dental implants. J Clin Periodontol 2012; 39(5):425-33. doi: 10.1111/j.1600-051X.2012.01856.x. PubMed PMID: 22417294; PubMed Central PMCID: PMC3323747.
11. Shibli J A, Melo L, Ferrari D S, Figueiredo L C, Faveri M, Feres M. Composition of supra and subgingival biofilm of subjects with healthy and diseased implants. Clin Oral Implants Res. 2008; 19(10):975-82. doi: 10.1111/j.1600-0501.2008.01566.x. PubMed PMID: 18828812.
12. Stoodley P, Ehrlich G D, Sedghizadeh P P, Hall-Stoodley L, Baratz M E, Altman D T, Sotereanos N G, Costerton J W, DeMeo P. Orthopaedic Biofilm Infections. Curr Orthop Pract. 2011; 22(6):558-63. PubMed PMID: 22323927; PubMed Central PMCID: PMC3272669.
13. Javed F, AlGhamdi A S T, Ahmed A, Mikami T, Ahmed H B, Tenenbaum H C. Clinical efficacy of antibiotics in the treatment of peri-implantitis. International Dental Journal. 2013; 63(4):169-76. doi: 10.1111/idj.12034. PubMed PMID: 23879251.
14. Smeets R, Henningsen A, Jung O, Heiland M, Hammacher C, Stein J M. Definition, etiology, prevention and treatment of peri-implantitis—a review. Head Face Med. 2014; 10. doi: 10.1186/1746-160x-10-34. PubMed PMID: 25185675; PubMed Central PMCID: PMC4164121.
15. Leonhardt A, Dahlen G, Renvert S. Five-year clinical, microbiological, and radiological outcome following treatment of peri-implantitis in man. J Periodontol. 2003; 74(10):1415-22. doi: 10.1902/jop.2003.74.10.1415. PubMed PMID: 14653386.
16. Mombelli A. Microbiology and antimicrobial therapy of peri-implantitis. Periodontol 2000. 2002; 28:177-89. PubMed PMID: 12013341.
17. Levison M E, Levison J H. Pharmacokinetics and Pharmacodynamics of Antibacterial Agents. Infect Dis Clin North Am. 2009; 23(4):75-89. doi: 10.1016/j.idc.2009.06.008. PubMed PMID: 24484576; PubMed Central PMCID: PMC4079031
18. Kaur K, Sikri P. Evaluation of the effect of allograft with doxycycline versus the allograft alone in the treatment of infrabony defects: A controlled clinical and radiographical study. Dent Res J (Isfahan). 2013; 10(2):238-46. PubMed PMID: 23946743; PubMed Central PMCID: PMC3731967.
19. Inzana J A, Schwarz E M, Kates S L, Awad H A. Biomaterials approaches to treating implant-associated osteomyelitis. Biomaterials. 2016; 81:58-71. doi: 10.1016/j.biomaterials.2015.12.012. PubMed PMID: 26724454.
20. Schmitt C M, Moest T, Lutz R, Neukam F W, Schlegel K A. Anorganic bovine bone (ABB) vs. autologous bone (AB) plus ABB in maxillary sinus grafting. A prospective non-randomized clinical and histomorphometrical trial. Clin Oral Implants Res. 2015; 26(9):1043-50. doi: 10.1111/clr.12396. PubMed PMID: 24730602.
21. Kluin O S, van der Mei H C, Busscher H J, Neut D. Biodegradable vs non-biodegradable antibiotic delivery devices in the treatment of osteomyelitis. Expert Opin Drug Deliv. 2013; 10(3):341-51. doi: 10.1517/17425247.2013.751371. PubMed PMID: 23289645.
22. https://www.accessdata.fda.gov/drugsatfda_docs/label/2009/019537s073, 020780s030lbl.pdf
23. Nancollas G H, Tang R, Phipps R J, Henneman Z, Guide S, Wu W, Mangood A, Russell R G G, Ebetino F H. Novel insights into actions of bisphosphonates on bone: Differences in interactions with hydroxyapatite. Bone. 2006; 38(5):617-27. doi: 10.1016/j.bone.2005.05.003. PubMed PMID: 16046206.
24. Russell R G G, Watts N B, Ebetino F H, Rogers M J. Mechanisms of action of bisphosphonates: similarities and differences and their potential influence on clinical efficacy. Osteoporos Int 2008; 19(6):733-59. doi: 10.1007/s00198-007-0540-8. PubMed PMID: 18214569.
25. Kavanagh K L, Guo K D, Dunford J E, Wu X Q, Knapp S, Ebetino F H, Rogers M J, Russell R G G, Oppermann U. The molecular mechanism of nitrogen-containing bisphosphonates as anti osteoporosis drugs. Proc Natl Acad Sci USA. 2006; 103(20):7829-34. doi: 10.1073/pnas.0601643103. PubMed PMID: 16684881; PubMed Central PMCID: PMC1472530.
26. Kashemirov B A, Bala J L F, Chen X, Ebetino F H, Xia Z, Russell R G G, Coxon F P, Roelofs A J, Rogers M J, McKenna C E. Fluorescently labeled risedronate and related analogues: "magic linker" synthesis. Bioconjug Chem. 2008; 19(12):2308-10. doi: 10.1021/bc800369c. PubMed PMID: 19032080.
27. Junka A F, Szymczyk P, Smutnicka D, Kos M, Smolina I, Bartoszewicz M, Chlebus E, Turniak M, Sedghizadeh P P. Microbial biofilms are able to destroy hydroxyapatite in the absence of host immunity in vitro. J Oral Maxillofac Surg. 2015; 73(3):451-64. doi: 10.1016/j.joms.2014.09.019. PubMed PMID: 25544303.

28. Sedghizadeh P P, Kumar S K S, Gorur A, Schaudinn C, Shuler C F, Costerton J W. Identification of microbial biofilms in osteonecrosis of the jaws secondary to bisphosphonate therapy. J Oral Maxillofac Surg 2008; 66(4): 767-75. doi: 10.1016/j.joms.2007.11.035. PubMed PMID: 18355603.
29. Sedghizadeh P P, Kumar S K S, Gorur A, Schaudinn C, Shuler C F, Costerton J W. Microbial biofilms in osteomyelitis of the jaw and osteonecrosis of the jaw secondary to bisphosphonate therapy. J Am Dent Assoc. 2009; 140(10):1259-65. PubMed PMID: 19797556.
30. Zhang S F, Gangal G, Uludag H. 'Magic bullets' for bone diseases: progress in rational design of bone-seeking medicinal agents. Chem Soc Rev 2007; 36(3):507-31. doi: 10.1039/b512310k. PubMed PMID: 17325789.
31. Herczegh P, Buxton T B, McPherson J C, Kovacs-Kulyassa A, Brewer P D, Sztaricskai F, Stroebel G G, Plowman K M, Farcasiu D, Hartmann J F. Osteoadsorptive bisphosphonate derivatives of fluoroquinolone antibacterials. J Med Chem. 2002; 45(11):2338-41. doi: 10.1021/jm0105326. PubMed PMID: 12014972.
32. Buxton T B, Walsh D S, Harvey S B, McPherson J C, Hartmann J F, Plowman K M. Bisphosphonate-ciprofloxacin bound to Skelite™ is a prototype for enhancing experimental local antibiotic delivery to injured bone. British Journal of Surgery. 2004; 91(9):1192-6. doi: 10.1002/bjs.4644. PubMed PMID: 15449273.
33. Tanaka K S E, Houghton T J, Kang T, Dietrich E, Delorme D, Ferreira S S, Caron L, Viens F, Arhin F F, Sarmiento I, Lehoux D, Fadhil I, Laquerre K, Liu J, Ostiguy V, Poirier H, Moeck G, Parr T R, Far A R. Bisphosphonated fluoroquinolone esters as osteotropic prodrugs for the prevention of osteomyelitis. Bioorg Med Chem. 2008; 16(20):9217-29. doi: 10.1016/j.bmc.2008.09.010. PubMed PMID: 18815051.
34. Houghton T J, Tanaka K S E, Kang T, Dietrich E, Lafontaine Y, Delorme D, Ferreira S S, Viens F, Arhin F F, Sarmiento I, Lehoux D, Fadhil I, Laquerre K, Liu J, Ostiguy V, Poirier H, Moeck G, Parr T R, Far A R. Linking Bisphosphonates to the Free Amino Groups in Fluoroquinolones: Preparation of Osteotropic Prodrugs for the Prevention of Osteomyelitis. J Med Chem. 2008; 51(21):6955-69. doi: 10.1021/jm801007z. PubMed PMID: 18834106.
35. Tanaka K S E, Dietrich E, Ciblat S, Metayer C, Arhin F F, Sarmiento I, Moeck G, Parr T R, Far A R. Synthesis and in vitro evaluation of bisphosphonated glycopeptide prodrugs for the treatment of osteomyelitis. Bioorg Med Chem Lett. 2010; 20(4):1355-9. doi: 10.1016/j.bmcl.2010.01.006. PubMed PMID: 20097069.
36. Arns S, Gibe R, Moreau A, Morshed M M, Young R N. Design and synthesis of novel bone-targeting dual-action pro-drugs for the treatment and reversal of osteoporosis. Bioorganic & Medicinal Chemistry. 2012; 20(6):2131-40. doi: 10.1016/j.bmc.2012.01.024. PubMed PMID: 22341574.
37. Liu C C, Hu S, Chen G, Georgiou J, Arns S, Kumar N S, Young R N, Grynpas M D. Novel EP4 Receptor Agonist-Bisphosphonate Conjugate Drug (C1) Promotes Bone Formation and Improves Vertebral Mechanical Properties in the Ovariectomized Rat Model of Postmenopausal Bone Loss. J Bone Miner Res. 2015; 30(4):670-80. doi: 10.1002/jbmr.2382. PubMed PMID: 25284325.
38. Morioka M, Kamizono A, Takikawa H, Mori A, Ueno H, Kadowaki S I, Nakao Y, Kato K, Umezawa K. Design, synthesis, and biological evaluation of novel estradiol-bisphosphonate conjugates as bone-specific estrogens. Bioorg Med Chem. 2010; 18(3):1143-8. doi: 10.1016/j.bmc.2009.12.041. PubMed PMID: 20071185
39. Katsarelis H, Shah N P, Dhariwal D K, Pazianas M. Infection and Medication-related Osteonecrosis of the Jaw. J Dent Res. 2015; 94(4):534-9. doi: 10.1177/0022034515572021. PubMed PMID: 25710950.
40. Lee S H, Chan R C, Chang S S, Tan Y L, Chang K H, Lee M C, Chang H E, Lee C C. Use of bisphosphonates and the risk of osteonecrosis among cancer patients: a systemic review and meta-analysis of the observational studies. Support Care Cancer. 2014; 22(2):553-60. doi: 10.1007/s00520-013-2017-y. PubMed PMID: 24203085.
41. Moura L A, Ribeiro F V, Aiello T B, Duek E A D, Sallum E A, Nociti F H, Casati M Z, Sallum A W. Characterization of the release profile of doxycycline by PLGA microspheres adjunct to non-surgical periodontal therapy. J Biomater Sci Polym Ed 2015; 26(10):573-84. doi: 10.1080/09205063.2015.1045249. PubMed PMID: 25917501
42. https://www.govtrack.us/congress/bills/114/hr34/text
43. EUCAST breakpoint tables for interpretation of MICs and zone diameters. 2015. http://www.eucast.org/
44. McPherson J C, Runner R, Buxton T B, Hartmann J F, Farcasiu D, Bereczki I, Roth E, Tollas S, Ostorhazi E, Rozgonyi F, Herczegh P. Synthesis of osteotropic hydroxybisphosphonate derivatives of fluoroquinolone antibacterials. Eur J Med Chem. 2012; 47:615-8. doi: 10.1016/j.ejmech.2011.10.049. PubMed PMID: 22093760.
45. Freire M O, Sedghizadeh P P, Schaudinn C, Gorur A, Downey J S, Choi J H, Chen W, Kook J K, Chen C, Goodman S D, Zadeh H H. Development of an Animal Model for *Aggregatibacter Actinomycetemcomitans* Biofilm-Mediated Oral Osteolytic Infection: A Preliminary Study. J Periodontol. 2011; 82(5):778-89. doi: 10.1902/jop.2010.100263. PubMed PMID: 21222546.
46. Vacondio F, Silva C, Lodola A, Fioni A, Rivara S, Duranti A, Tontini A, Sanchini S, Clapper J R, Piomelli D, Mor M, Tarzia G. Structure-property relationships of a class of carbamate-based fatty acid amide hydrolase (FAAH) inhibitors: chemical and biological stability. Chem Med Chem. 2009; 4(9):1495-504. doi: 10.1002/cmdc.200900120. PubMed PMID: 19554599; PubMed Central PMCID: PMCPMC3517974.
47. Lloyd-Jones G C, Moseley J D, Renny J S. Mechanism and application of the Newman-Kwart O→S rearrangement of O-aryl thiocarbamates. Synthesis-Stuttgart. 2008 (5):661-89. doi: 10.1055/s-2008-1032179.
48. Moseley J D, Sankey R F, Tang O N, Gilday J P. The Newman-Kwart rearrangement re-evaluated by microwave synthesis. Tetrahedron. 2006; 62(19):4685-9. doi: 10. 1016/j.tet.2005.12.063.
49. Ebetino F H, Hogan A M, Sun S, Tsoumpra M K, Duan X, Triffitt J T, Kwaasi A A, Dunford J E, Barnett B L, Oppermann U, Lundy M W, Boyde A, Kashemirov B A, McKenna C E, Russell R G. The relationship between the chemistry and biological activity of the bisphosphonates. Bone. 2011; 49(1):20-33. doi: 10.1016/j.bone.2011.03.774. PubMed PMID: 21497677.
50. Vachal P, Hale J J, Lu Z, Streckfuss E C, Mills S G, MacCoss M, Yin D H, Algayer K, Manser K, Kesisoglou F, Ghosh S, Alani L L. Synthesis and study of alendronate derivatives as potential prodrugs of alendronate sodium for the treatment of low bone density and osteoporosis. J Med Chem. 2006; 49(11):3060-3. doi: 10.1021/jm060398v. PubMed PMID: 16722624.

51. Lopez-Piriz R, Sola-Linares E, Rodriguez-Portugal M, Malpica B, Diaz-Gumes I, Enciso S, Esteban-Tejeda L, Cabal B, Granizo J J, Moya J S, Torrecillas R. Evaluation in a Dog Model of Three Antimicrobial Glassy Coatings: Prevention of Bone Loss around Implants and Microbial Assessments. Plos One. 2015; 10(10). doi: 10.1371/journal.pone.0140374. PubMed PMID: 26489088; PubMed Central PMCID: PMC4619200

52. Orti V, Bousquet P, Tramini P, Gaitan C, Mertens B, Cuisinier F. Benefits of mineralized bone cortical allograft for immediate implant placement in extraction sites: an in vivo study in dogs. J Periodontal Implant Sci. 2016; 46(5):291-302. doi: 10.5051/jpis.2016.46.5.291. PubMed PMID: 27800212; PubMed Central PMCID: PMC5083813.

53. Reizner W, Hunter J G, O'Malley N T, Southgate R D, Schwarz E M, Kates S L. A systematic review of animal models for Staphylococcus aureus osteomyelitis. European Cells & Materials. 2014; 27:196-212. PubMed PMID: 24668594; PubMed Central PMCID: PMC4322679.

54. Wancket L M. Animal Models for Evaluation of Bone Implants and Devices: Comparative Bone Structure and Common Model Uses. Vet Pathol 2015; 52(5):842-50. doi: 10.1177/0300985815593124. PubMed PMID: 26163303.

55. Saber M H, Schwarzberg K, Alonaizan F A, Kelley S T, Sedghizadeh P P, Furlan M, Levy T A, Simon J H, Slots J. Bacterial Flora of Dental Periradicular Lesions Analyzed by the 454-Pyrosequencing Technology. J Endod. 2012; 38(11):1484-8. doi: 10.1016/j.joen.2012.06.037. PubMed PMID: 23063222.

56. Caporaso J G, Kuczynski J, Stombaugh J, Bittinger K, Bushman F D, Costello E K, Fierer N, Pena A G, Goodrich J K, Gordon J I, Huttley G A, Kelley S T, Knights D, Koenig J E, Ley R E, Lozupone C A, McDonald D, Muegge B D, Pirrung M, Reeder J, Sevinsky J R, Tumbaugh P J, Walters W A, Widmann J, Yatsunenko T, Zaneveld J, Knight R. QIIME allows analysis of high-throughput community sequencing data. Nature Methods. 2010; 7(5):335-6. doi: 10.1038/nmeth.f.303. PubMed PMID: 20383131.

57. Battula S, Lee J W, Wen H B, Papanicolaou S, Collins M, Romanos G E. Evaluation of Different Implant Designs in a Ligature-Induced Peri-implantitis Model: A Canine Study. International Journal of Oral & Maxillofacial Implants. 2015; 30(3):534-45. doi: 10.11607/jomi.3737. PubMed PMID: 26009904.

58. Faul F, Erdfelder E, Buchner A, Lang A G. Statistical power analyses using G*Power 3.1: Tests for correlation and regression analyses. Behav Res Methods. 2009; 41(4):1149-60. doi: 10.3758/brm.41.4.1149. PubMed PMID: 19897823.

59. Kilkenny C, Browne W, Cuthill I C, Emerson M, Altman D G. Animal research: Reporting in vivo experiments: The ARRIVE guidelines. Br J Pharmacol. 2010; 160(7): 1577-9. doi: 10.1111/j.1476-5381.2010.00872.x. PubMed PMID: 20649561; PubMed Central PMCID: PMC2936830.

60. Salvi G E, Lang N P. Diagnostic parameters for monitoring peri-implant conditions. Int J Oral Maxillofac Implants. 2004; 19:116-27. PubMed PMID: 15635952.

61. http://www.fda.gov/downloads/Drugs/GuidanceComplianceRegulatoryInformation/Guidances/UCM072193.pdf 62. Jaehde U, Zurcher J, Sorgel F, Naber K, Schunack W. Metabolism of Ciprofloxacin in Humans following Oral and Intravenous Administration. Reviews of Infectious Diseases. 1989; 11:S1135.

63. Vancebryan K, Guay D R P, Rotschafer J C. Clinical pharmacokinetics of ciprofloxacin. Clin Pharmacokinet 1990; 19(6):434-61. PubMed PMID: 2292168.

64. Baumans V, Brain P F, Brugere H, Clausing P, Jeneskog T, Perretta G. Pain and distress in laboratory rodents and lagomorphs. Report of the Federation of European Laboratory Animal Science Associations (FELASA) Working Group on Pain and Distress accepted by the FELASA Board of Management November 1992. Laboratory Animals. 1994; 28(2):97-112. doi: 10.1258/002367794780745308. PubMed PMID: 8035572.

65. Sedghizadeh P P, Jones A C, LaVallee C, Jelliffe R W, Le A D, Lee P, Kiss A, Neely M. Population pharmacokinetic and pharmacodynamic modeling for assessing risk of bisphosphonate-related osteonecrosis of the jaw. Oral Surg Oral Med Oral Pathol Oral Radiol 2013; 115(2): 224-32. doi: 10.1016/j.oooo.2012.08.455. PubMed PMID: 23246224; PubMed Central PMCID: PMC3545087.

66. O'Donnell J N, Gulati A, Lavhale M S, Sharma S S, Patel A J, Rhodes N J, Scheetz M H. Pharmacokinetics of centhaquin citrate in a rat model. J Pharm Pharmacol. 2016; 68(1):56-62. doi: 10.1111/jphp.12498. PubMed PMID: 26725913.

67. Neely M N, van Guilder M G, Yamada W M, Schumitzky A, Jelliffe R W. Accurate Detection of Outliers and Subpopulations With Pmetrics, a Nonparametric and Parametric Pharmacometric Modeling and Simulation Package for R. Ther Drug Monit. 2012; 34(4):467-76. doi: 10.1097/FTD.0b013e31825c4ba6. PubMed PMID: 22722776 PubMed Central PMCID: PMC3394880

68. Tatarinova T, Neely M, Bartroff J, van Guilder M, Yamada W, Bayard D, Jelliffe R, Leary R, Chubatiuk A, Schumitzky A. Two general methods for population pharmacokinetic modeling: non-parametric adaptive grid and non-parametric Bayesian. J Pharmacokinet Pharmacodyn. 2013; 40(2):189-99. doi: 10.1007/s10928-013-9302-8. PubMed PMID: 23404393; PubMed Central PMCID: PMC3630269.

69. Wacha H, Wagner D, Schafer V, Knothe H. Concentration of ciprofloxacin in bone tissue after single parenteral administration to patients older than 70 years. Infection. 1990; 18(3):173-6. PubMed PMID: 2365470.

Example 9

Figure 38:
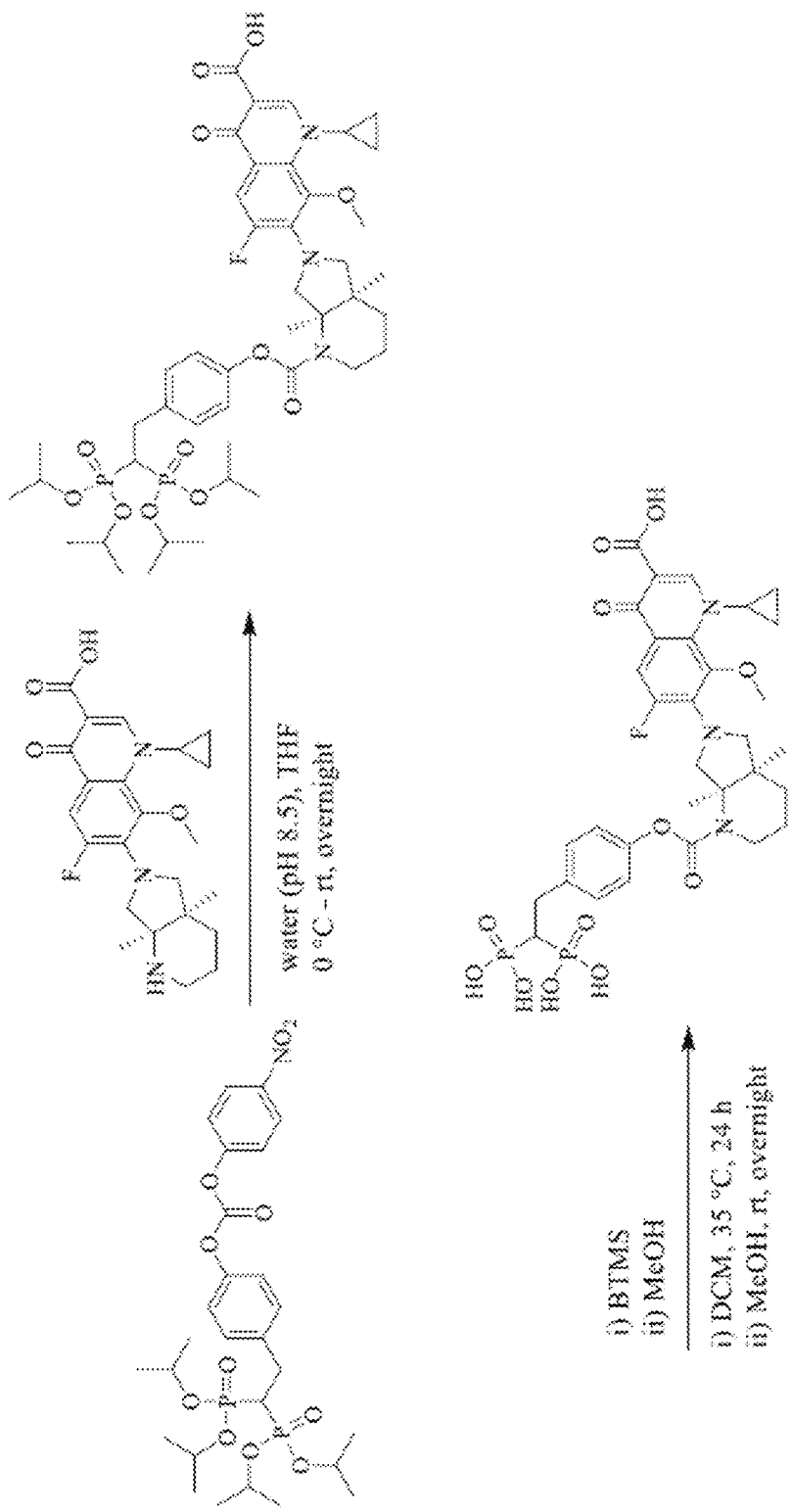
FIG. 38 shows a BP-carbamate-moxifloxacin BP conjugate and synthesis scheme.
Figure 39:
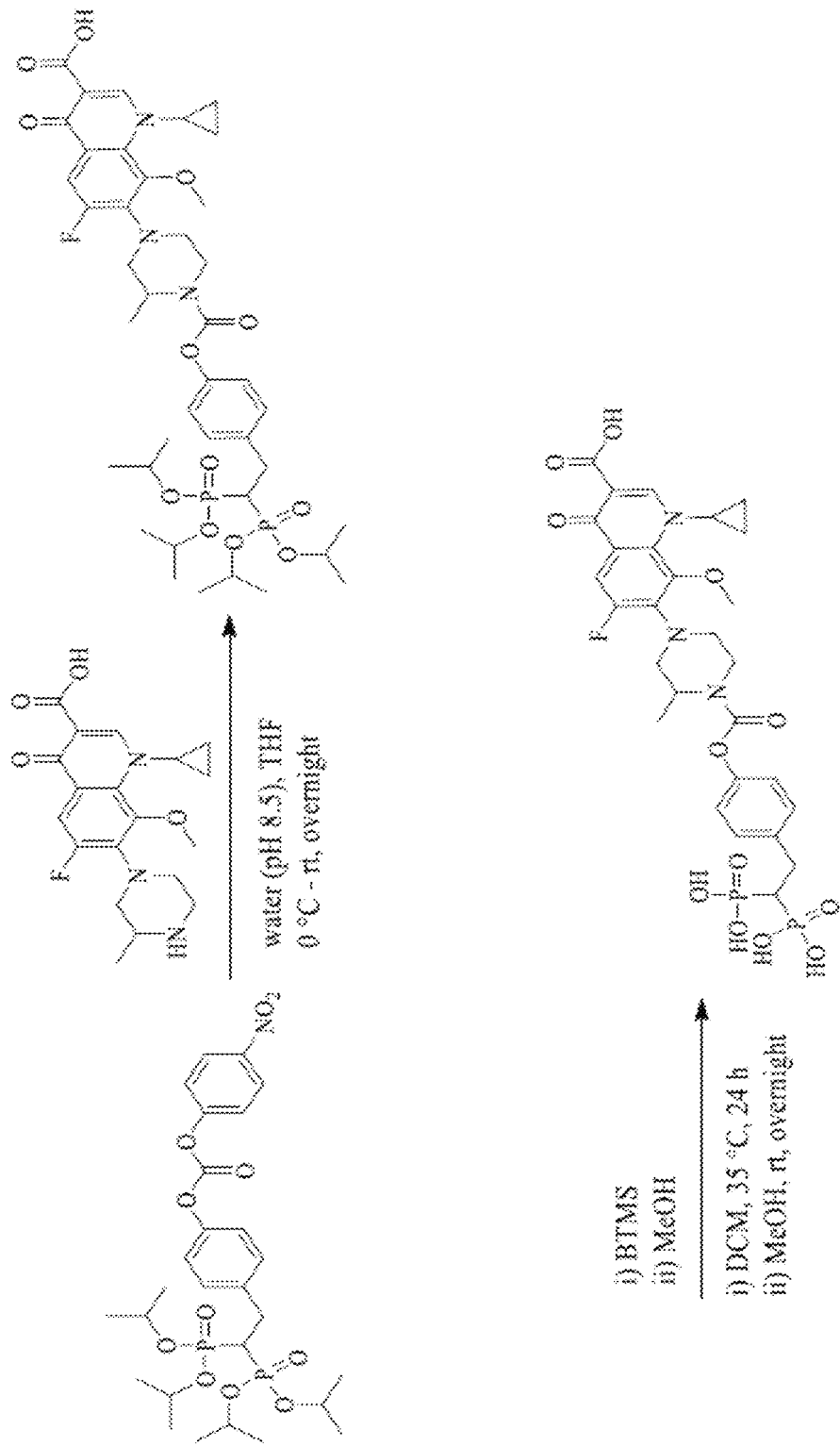
FIG. 39 shows a BP-carbamate-gatifloxacin BP conjugate and synthesis scheme.
Figure 40:
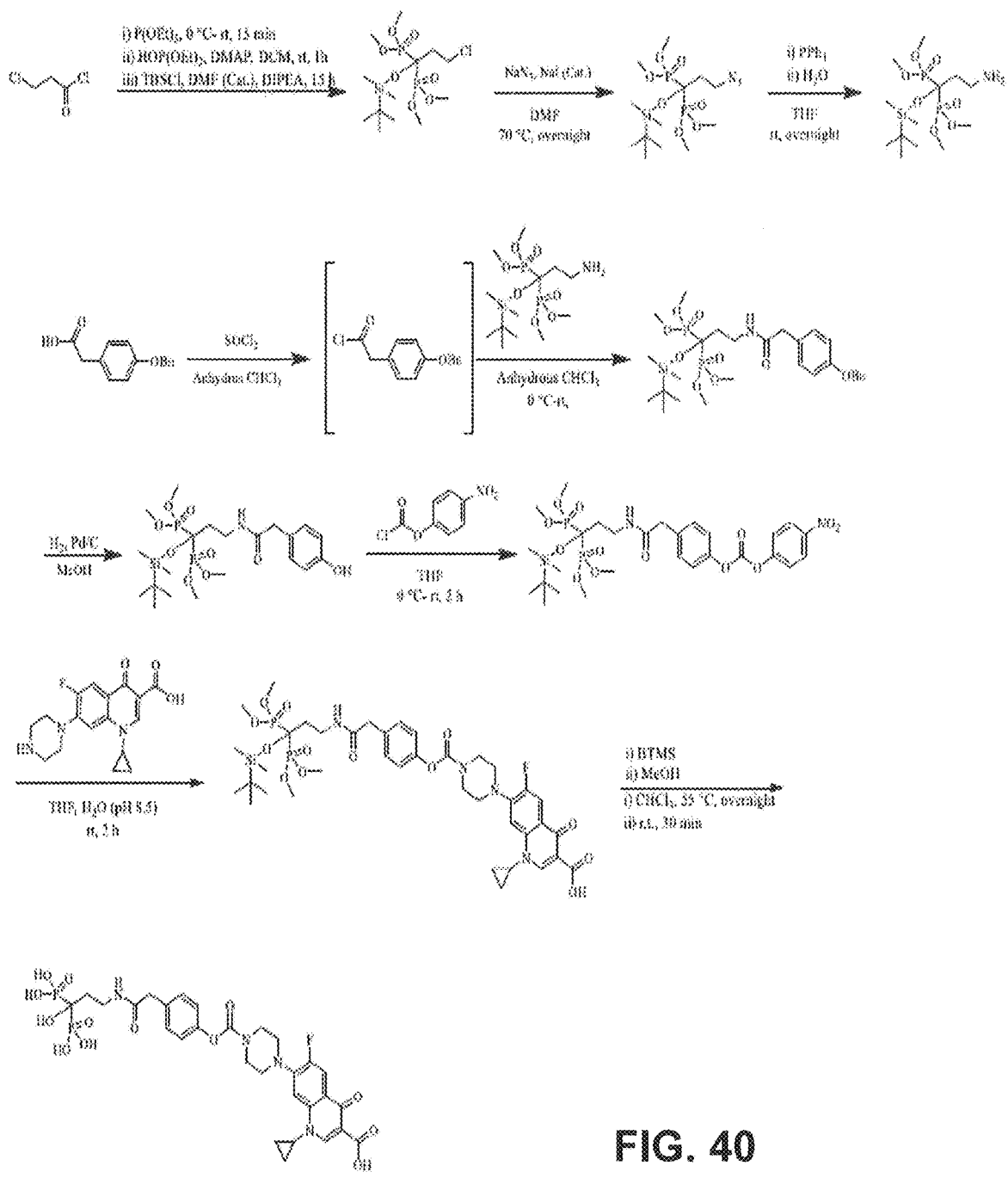
FIG. 40 shows a BP-p-Hydroxyphenyl Acetic Acid-ciprofloxacin BP conjugate and synthesis scheme.
Figure 41:
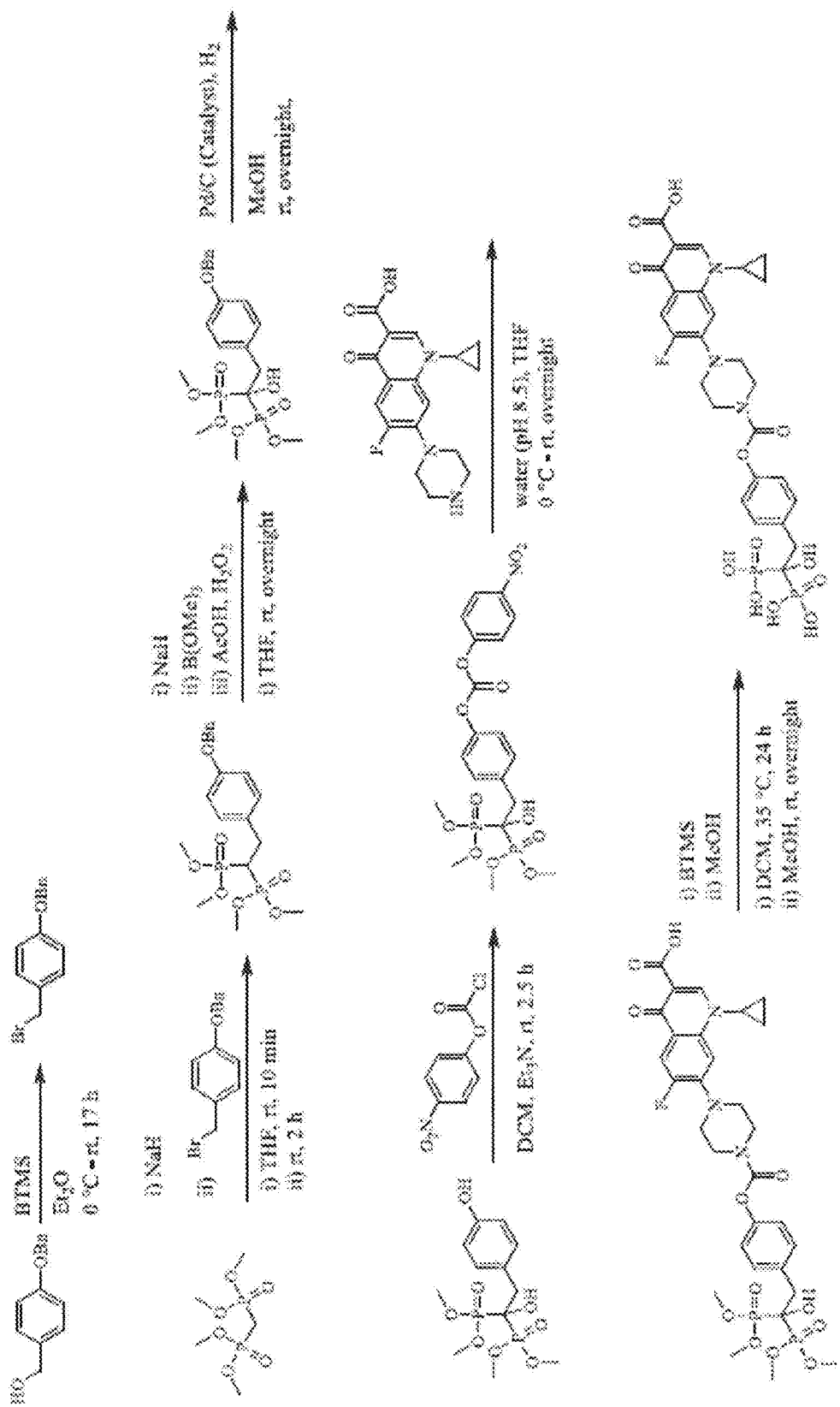
FIG. 41 shows a BP-OH-ciprofloxacin BP conjugate and synthesis scheme.
Figure 42:
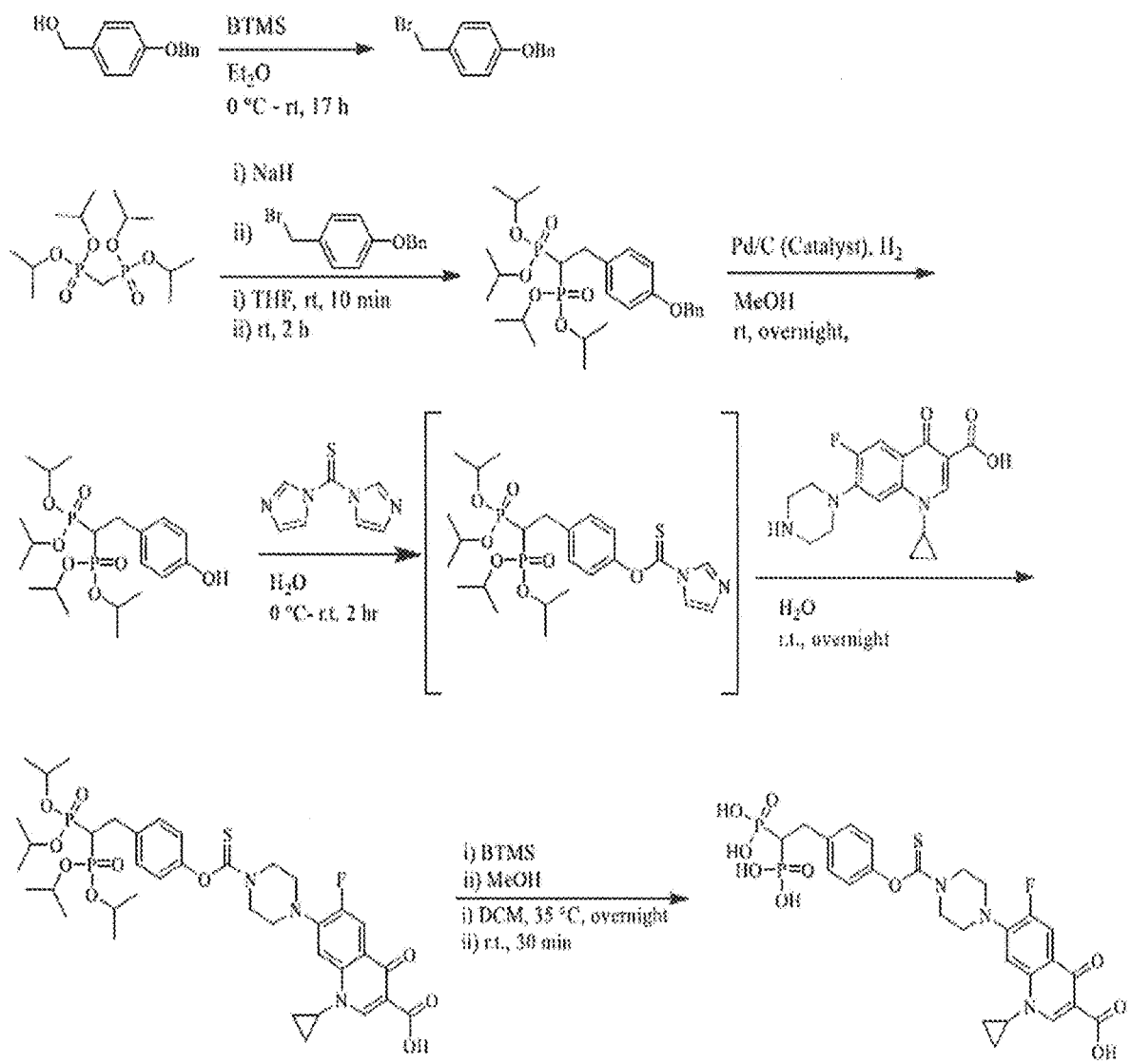
FIG. 42 shows a BP-O-Thiocarbamate-ciprofloxacin BP conjugate and synthesis scheme.
Figure 43:
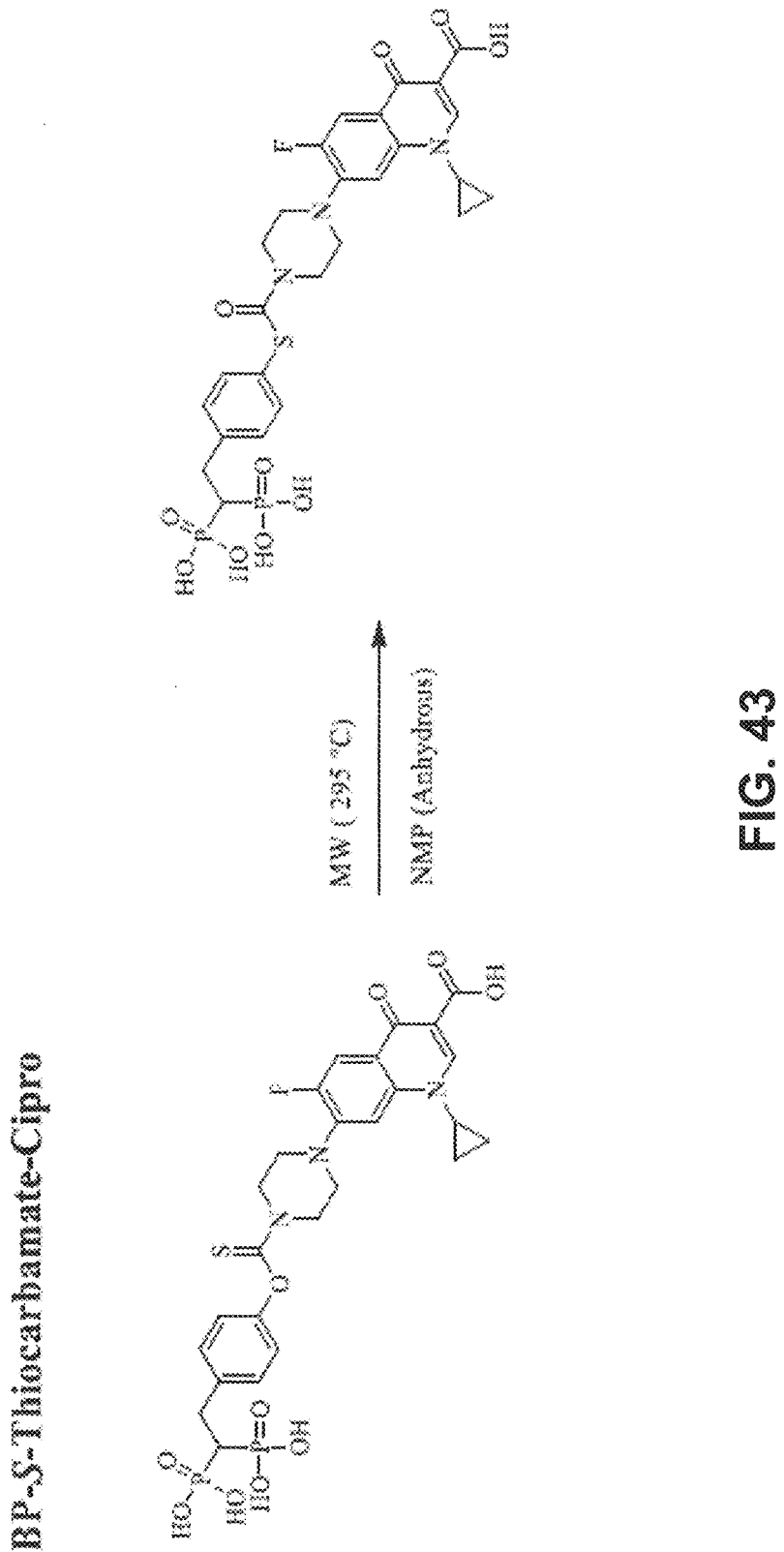
FIG. 43 shows a BP-S-Thiocarbamate-ciprofloxacin BP conjugate and synthesis scheme.
Figure 44:
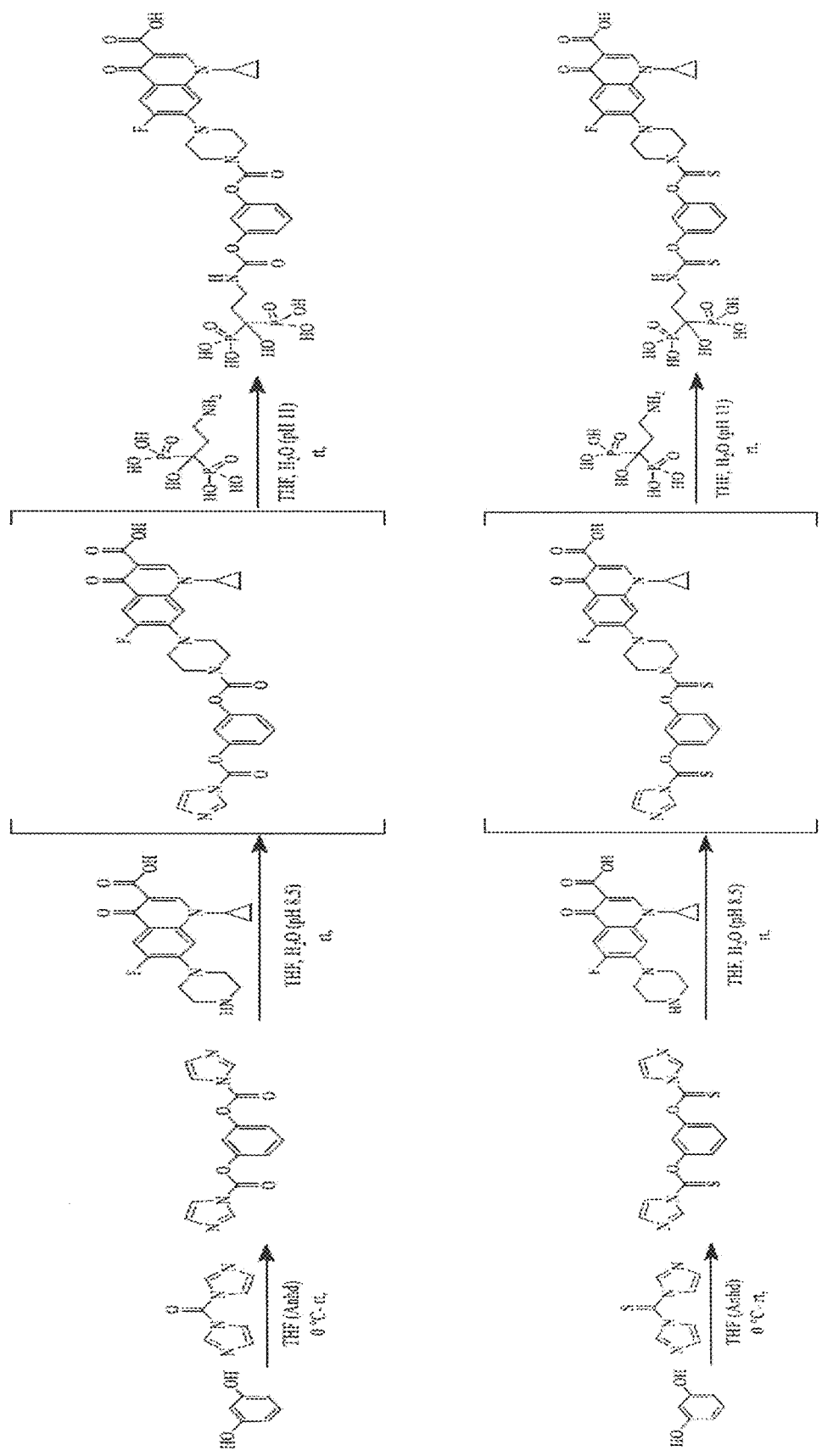
FIG. 44 shows a BP-Resorcinol-ciprofloxacin BP conjugate and synthesis scheme.
Figure 45:
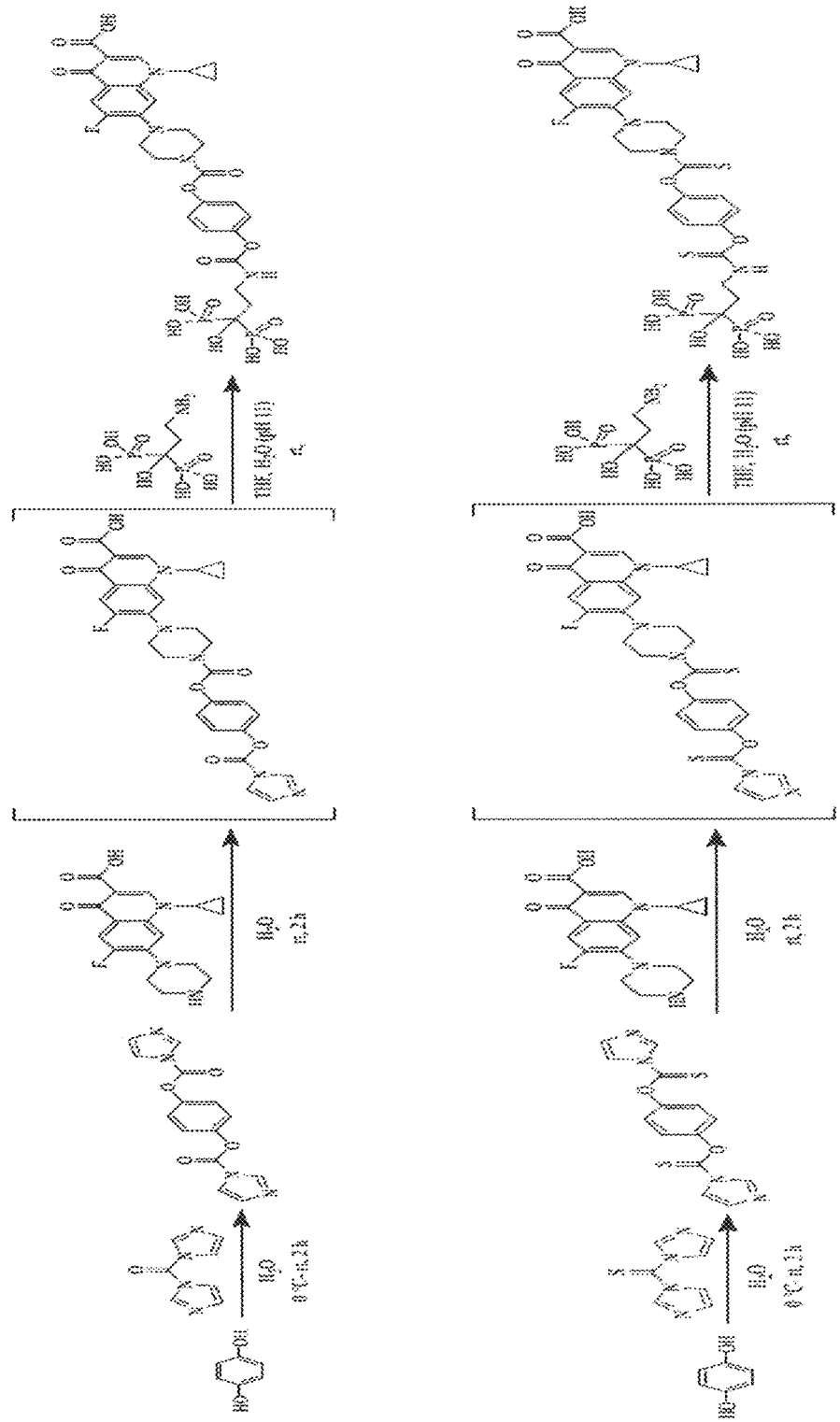
FIG. 45 shows a BP-Hydroquinone-ciprofloxacin BP conjugate and synthesis scheme.

This Example demonstrates various BP conjugate compounds and synthesis schemes. BP-carbamate-ciprofloxacin BP conjugate and synthesis scheme is demonstrated in FIG. 16 and related descriptions. BP-carbamate-moxifloxacin BP conjugate and synthesis scheme is demonstrated in FIG. 38. FIG. 39 shows a BP-carbamate-gatifloxacin BP conjugate and synthesis scheme. FIG. 40 shows a BP-p-Hydroxyphenyl Acetic Acid-ciprofloxacin BP conjugate and synthesis scheme. FIG. 41 shows a BP-OH-ciprofloxacin BP conjugate and synthesis scheme. FIG. 42 shows a BP-O-Thiocarbamate-ciprofloxacin BP conjugate and synthesis scheme. FIG. 43 shows a BP-S-Thiocarbamate-ciprofloxacin BP conjugate and synthesis scheme. FIG. 44 shows a BP-Resorcinol-ciprofloxacin BP conjugate and synthesis scheme. FIG. 45 shows a BP-Hydroquinone-ciprofloxacin BP conjugate and synthesis scheme.

Figure 46:
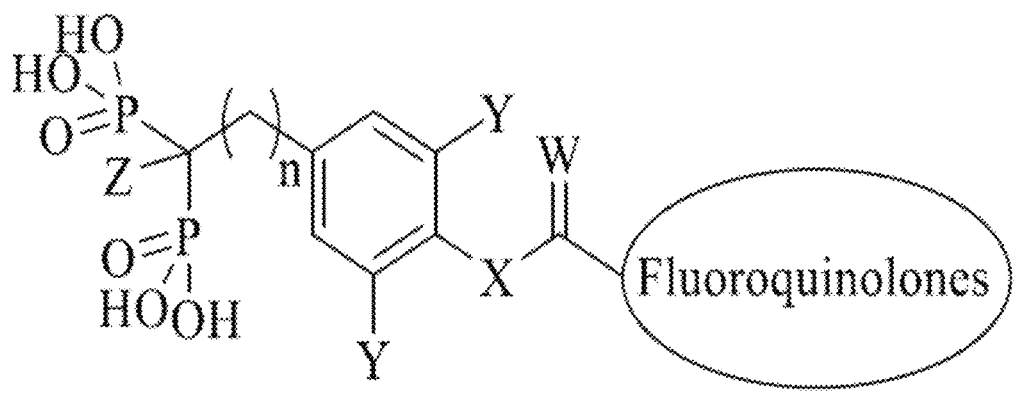
FIG. 46 shows one embodiment of a genus structure for a genus of BP-Fluoroquinolones.
Figure 47:
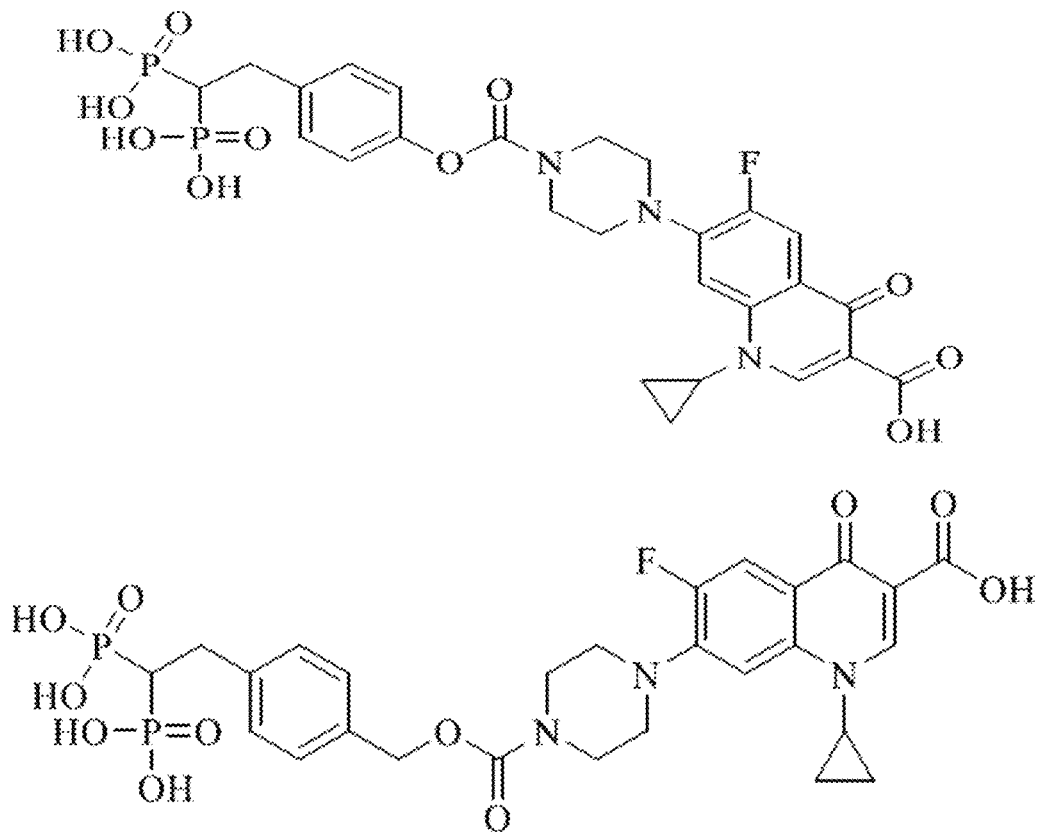
FIG. 47 shows various BP-fluoroquinolone conjugates.

FIG. 46 shows one embodiment of a genus structure for a BP-fluoroquinolone conjugate, where W can be O or S or N, X can be O, S, N, $CH_2O$, $CH_2N$, or $CH_2S$, Y can be H, $CH_3$, $NO_2$, F, Cl, Br, I, or $CO_2H$, Z can be H, $CH_3$, OH, $NH_2$, SH, F, Cl, Br, or I, and n can be 1-5. FIG. 47 shows various BP-fluoroquinolone conjugates.

Figure 48:
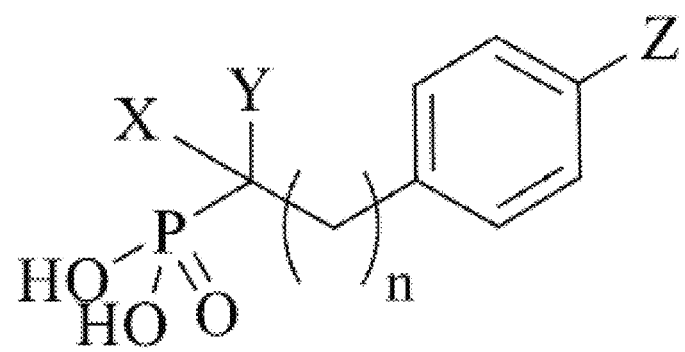
FIG. 48 shows one embodiment of a genus structure for a genus of a phosphonate containing an aryl group.
Figure 49:
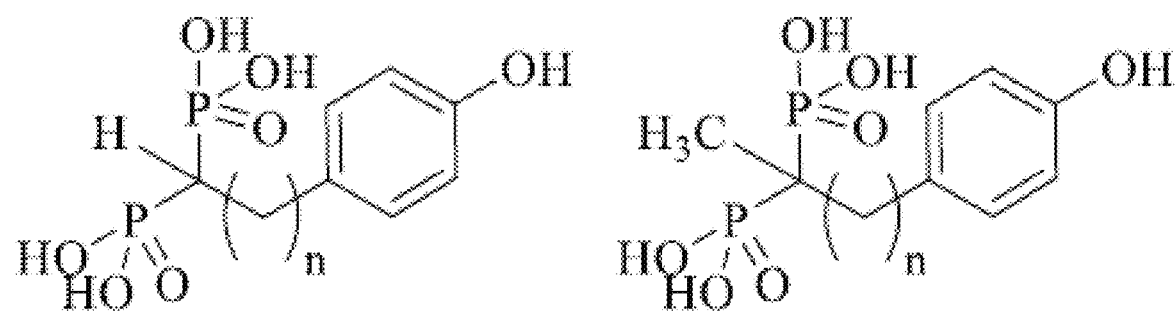
FIG. 49 shows various BPs, where X can be F, Cl, Br, or I.
Figure 49:
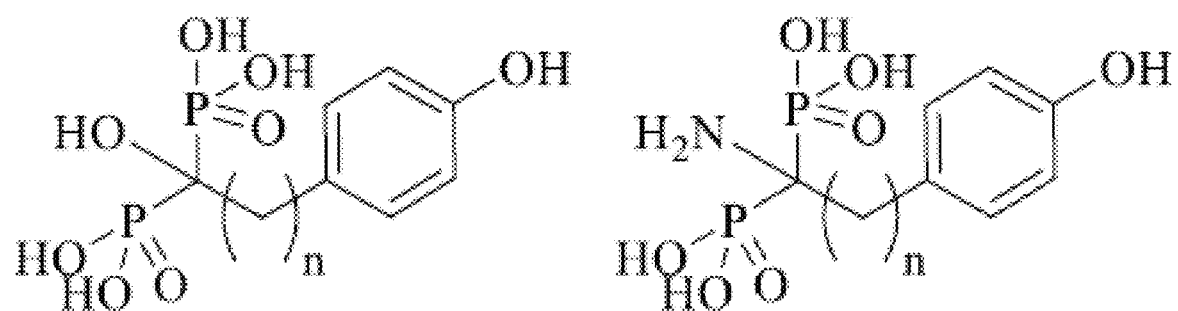

FIG. 48 shows one embodiment of a genus structure for a genus of a phosphonate containing an aryl group, where X can be H, $CH_3$, OH, $NH_2$, SH, F, Cl, Br, or I, Y can be $PO_3H_2$, or $CO_2H$. Z can be OH, $NH_2$, SH, or $N_3$, and n can be 1 or 2. FIG. 49 shows various BPs, where X can be F, Cl, Br, or I and n can be 1 or 2.

Figure 52:
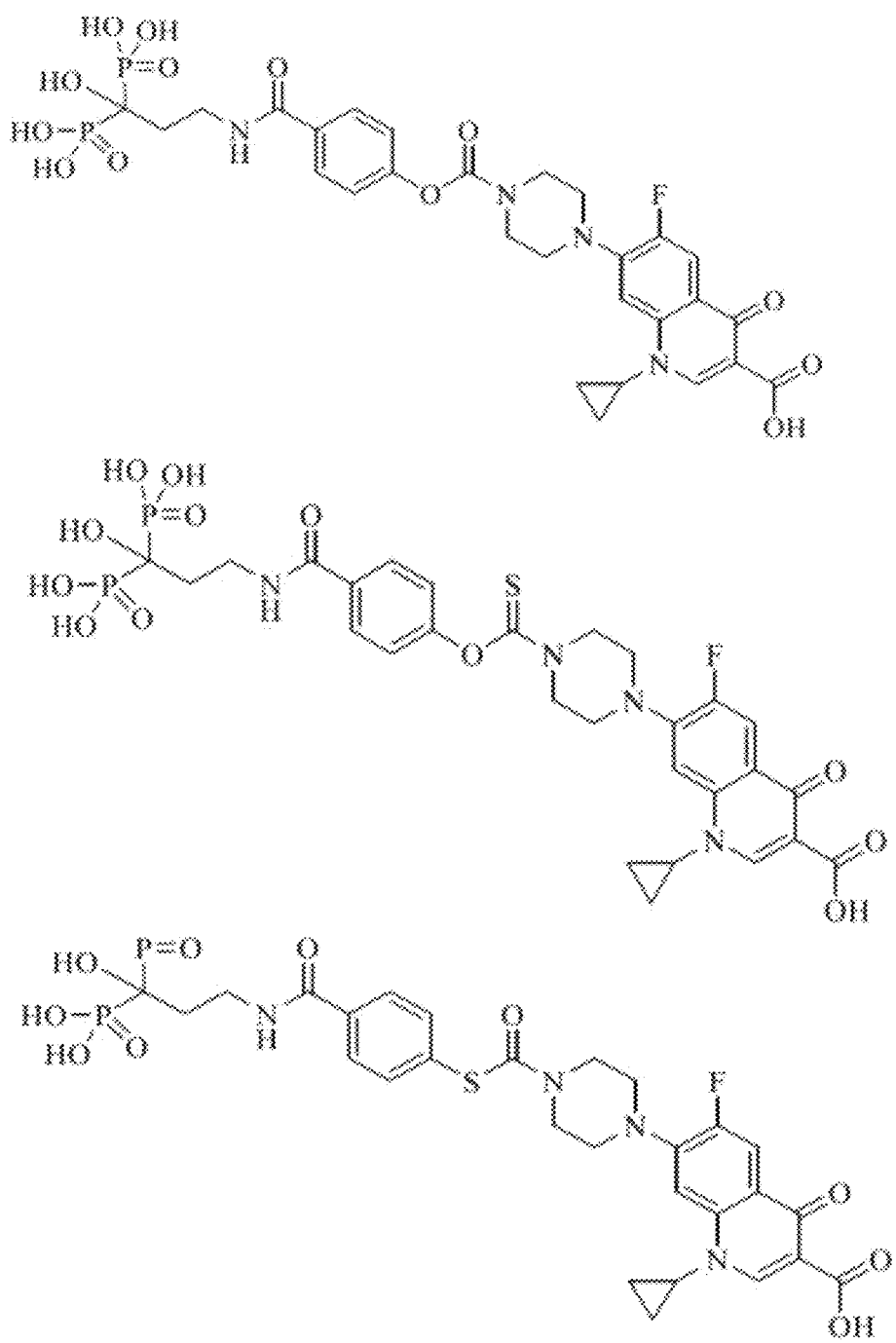
FIG. 52 shows various BP-pamidronate-ciprofloxacin conjugates.
Figure 53:
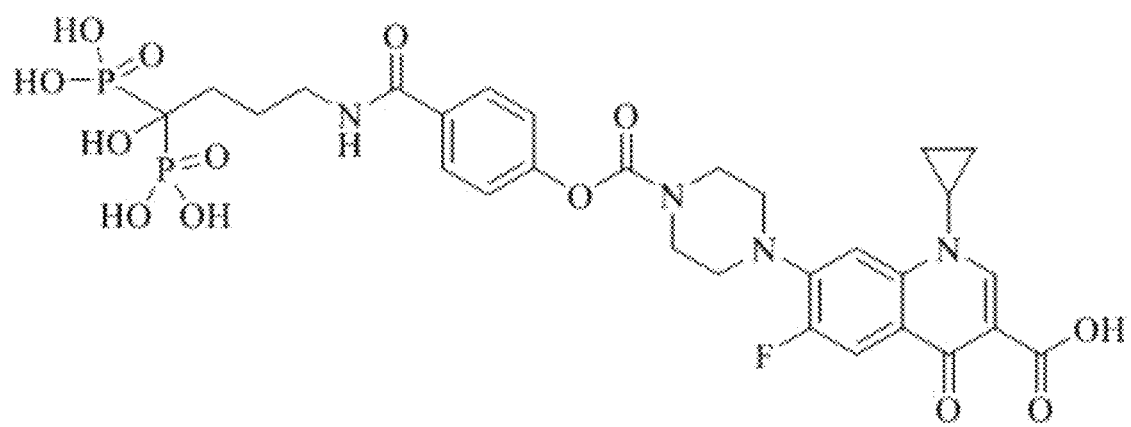
FIG. 53 shows various BP-Alendronate-ciprofloxacin conjugates.
Figure 53:
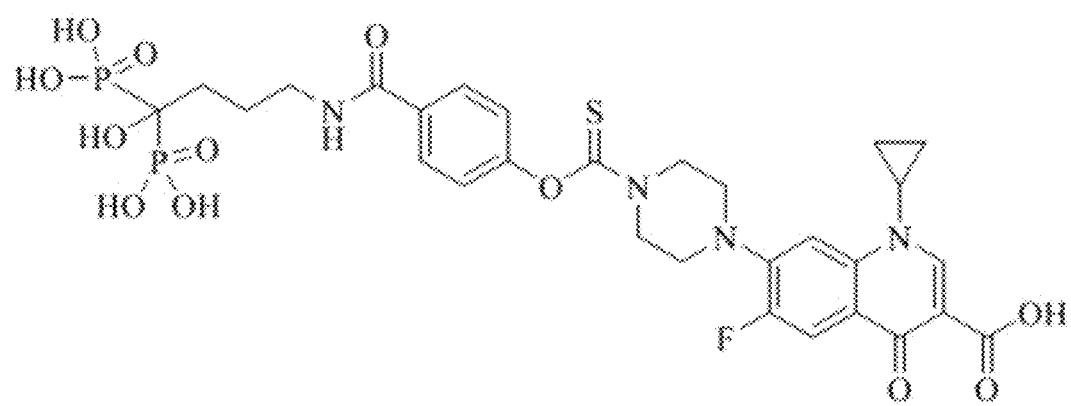
Figure 53:
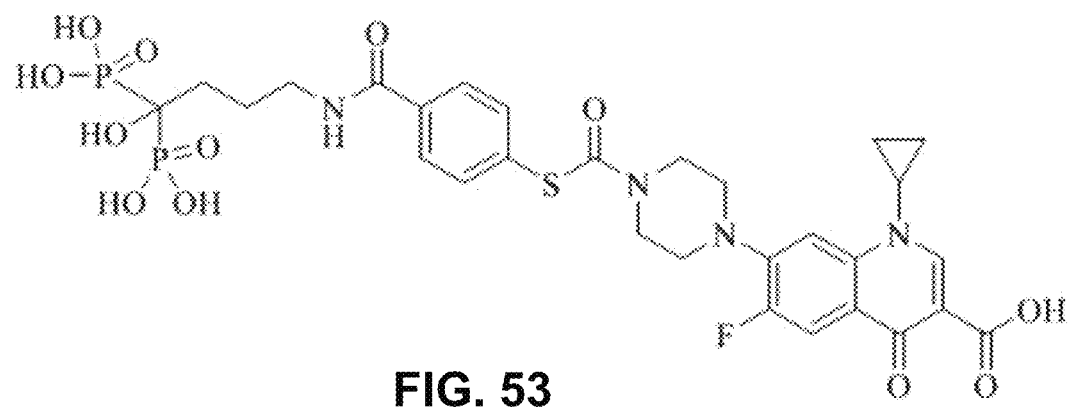

FIG. 50 shows various BP's with terminal primary amines. FIG. 51 shows various BPs coupled to a linker containing a terminal hydroxyl and amine functional groups where R can be Risedronate, Zoledronate, Minodronate, Pamidronate, or Alendronate. FIG. 52 shows various BP-pamidronate-ciprofloxacin conjugates. FIG. 53 shows various BP-Alendronate-ciprofloxacin conjugates.

Example 10

The antimicrobial properties of a thiocarbamate BP conjugate (13) was evaluated.

Compound 13 (an O-thiocarbamate BP Conjugate)

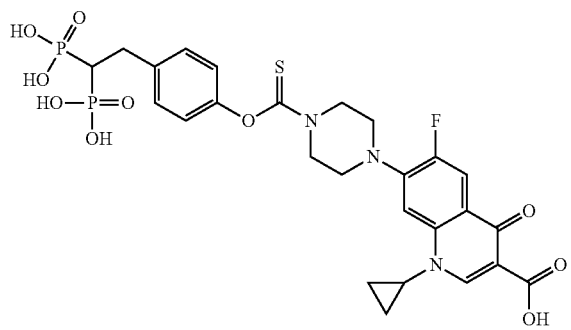

Compound 13 can also be referred to as 1-cyclopropyl-7-(4-((4-(2,2-diphosphonoethyl)phenoxy)carbonothioyl) piperazin-1-yl)-6-fluoro-4-oxo-1,4-dihydroquinoline-3-carboxylic acid. Compound 13 was synthesized as follows. Tetraisopropyl (2-(4-hydroxyphenyl)ethane-1,1-diyl)bis (phosphonate) (0.10 mmol) was emulsified in water and cooled in an ice bath while stirring vigorously. 1,1'-Thiocarbonyldiimidazole (0.12 mmol) was added and allowed to stir for 1 hour. The ice bath was then removed and stirring continued at room temperature for 1 more hour. Ciprofloxacin (0.12 mmol) was then added and the reaction was stirred overnight at room temperature while covered with foil to avoid light. The next day, the white paste was filtered using a frit funnel and the solids were washed with water and then ether. The solids were collected and purified by silica column chromatography using a $MeOH:CHCl_3$ gradient to afford an off white solid. The solid was dissolved in DCM and bromotrimethylsilane (BTMS) (4.00 mmol) was added and heated at 35° C. in an oil bath overnight. Solvent and BTMS were removed by evaporation and MeOH was added and allowed to stir at room temperature for 30 minutes. Solvent was removed on rotavapor and the product was precipitated in chilled MeOH. The suspension was filtered using a frit funnel and washed with additional MeOH. The solid was collected and excess solvent evaporated to afford the target compound.

Figure 24:
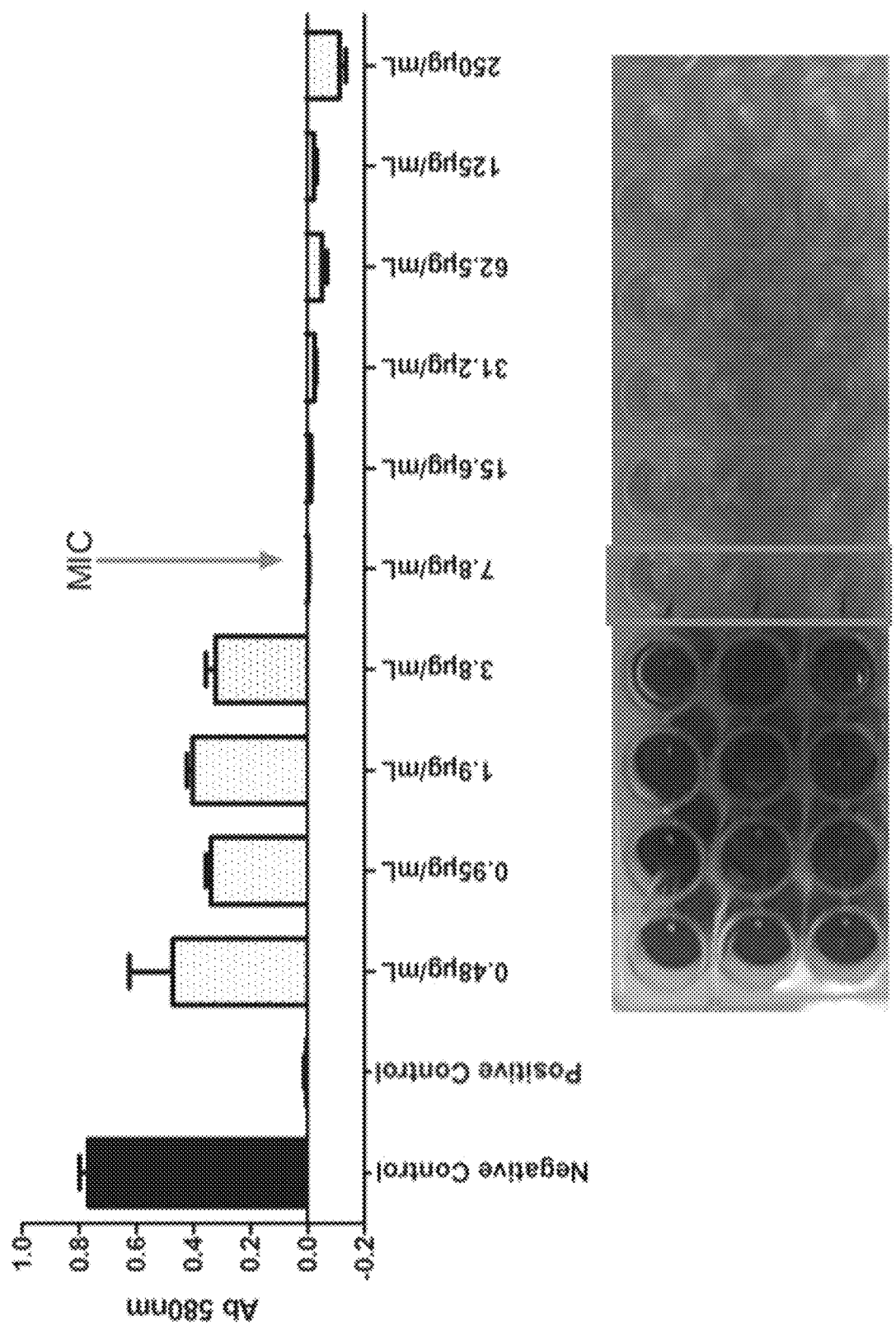
FIG. 24 shows a graph and image demonstrating results from an evaluation of the MIC of an O-thiocarbamate BP conjugate against planktonic S. aureus strain ATCC 6538: negative control=medium+microbes without conjugate treatment; positive control=sterile medium without microbes.

FIG. 24 shows a graph and image demonstrating results from an evaluation of the MIC of an O-thiocarbamate BP conjugate against planktonic *S. aureus* strain ATCC 6538: negative control=medium+microbes without conjugate treatment; positive control=sterile medium without microbes.

Figure 25:
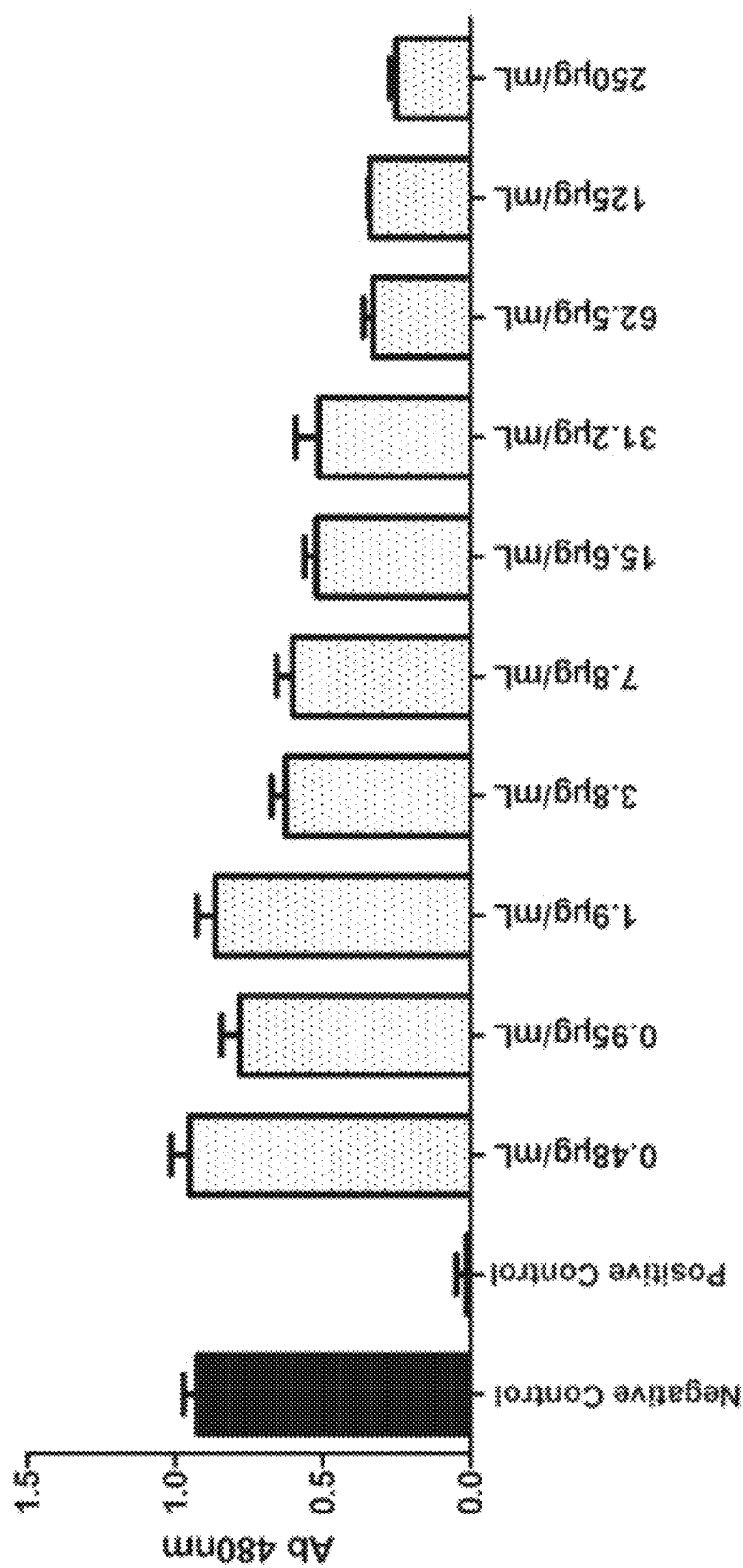
FIG. 25 shows a graph demonstrating results from an evaluation of the antimicrobial activity or bacterial load reduction of the thiocarbamate conjugate against biofilms of S. aureus strain ATCC 6538 formed on polystyrene as the substrate: negative control=microbial dilution without conjugate treatment; positive control=sterile dilution without microbes.

FIG. 25 shows a graph demonstrating results from an evaluation of the antimicrobial activity or bacterial load reduction of the thiocarbamate conjugate against biofilms of *S. aureus* strain ATCC 6538 formed on polystyrene as the substrate: negative control=microbial dilution without conjugate treatment; positive control=sterile dilution without microbes.

Figure 26:
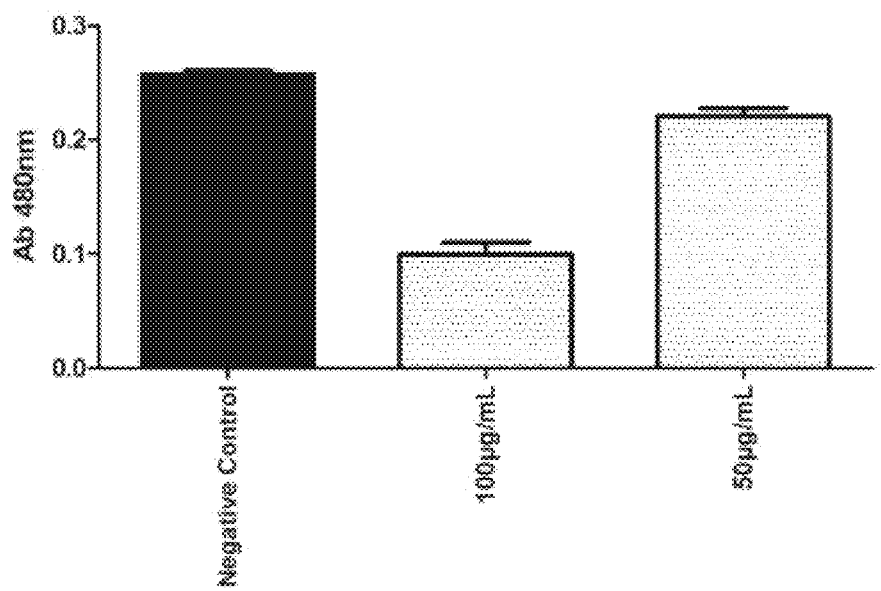
FIG. 26 shows a graph demonstrating results from an evaluation of the antimicrobial activity of the O-thiocarbamate BP conjugate tested against preformed biofilms of S. aureus ATCC 6538 on hydroxyapatite as the substrate; negative control=microbial dilution without conjugate treatment. (*p<0.05, Kruskal-Wallis test; triplicate; comparator=control).

FIG. 26 shows a graph demonstrating results from an evaluation of the antimicrobial activity of the O-thiocarbamate BP conjugate tested against preformed biofilms of *S. aureus* ATCC 6538 on hydroxyapatite as the substrate; negative control=microbial dilution without conjugate treatment. (*$p<0.05$, Kruskal-Wallis test; triplicate; comparator=control).

Figure 27:
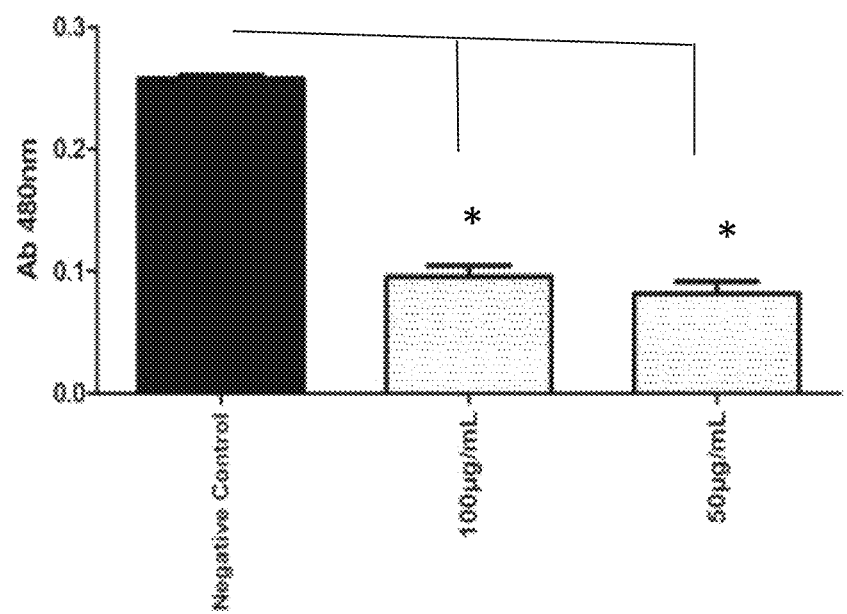
FIG. 27 shows a graph demonstrating results from a study using O-thiocarbamate BP conjugate-treated hydroxyapatite discs evaluating the ability to prevent biofilm formation of S. aureus ATCC 6538; negative control=microbial dilution without conjugate treatment. (*p<0.05, Kruskal-Wallis test; triplicate; comparator=control).

FIG. 27 shows a graph demonstrating results from a study using O-thiocarbamate BP conjugate-treated hydroxyapatite discs evaluating the ability to prevent biofilm formation of *S. aureus* ATCC 6538; negative control=microbial dilution without conjugate treatment. (*$p<0.05$, Kruskal-Wallis test; triplicate; comparator=control).

Figure 28:
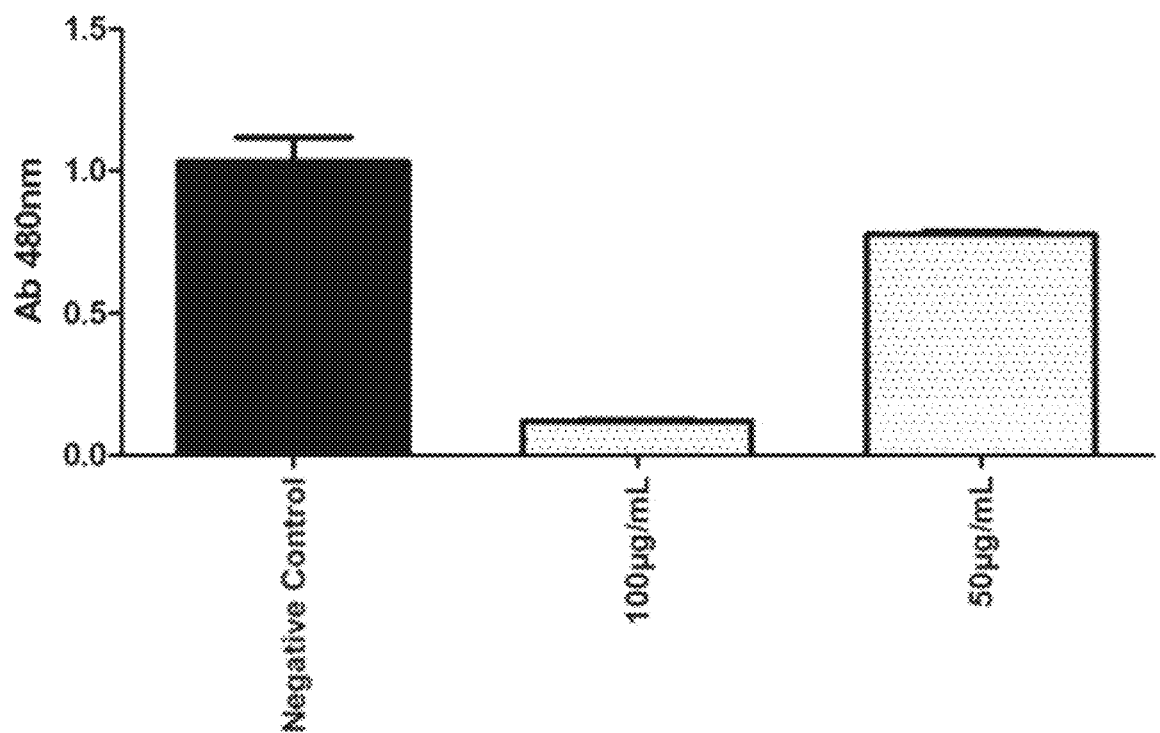
FIG. 28 shows a graph demonstrating results from a study using O-thiocarbamate BP conjugate-treated hydroxyapatite powder evaluating the ability to prevent biofilm formation of S. aureus ATCC 6538; negative control=microbial dilution without conjugate treatment. (*p<0.05, Kruskal-Wallis test; triplicate; comparator=control).

FIG. 28 shows a graph demonstrating results from a study using O-thiocarbamate BP conjugate-treated hydroxyapatite powder evaluating the ability to prevent biofilm formation of *S. aureus* ATCC 6538; negative control=microbial dilution without conjugate treatment. (*$p<0.05$, Kruskal-Wallis test; triplicate; comparator=control).

Example 11

Described in this example are additional exemplary BP-conjugates and their synthesis.

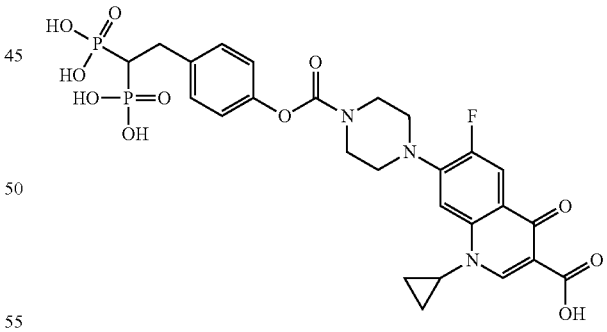

1-cyclopropyl-7-(4-((4-(2,2-diphosphonoethyl)phenoxy)carbonyl)piperazin-1-yl)-6-fluoro-4-oxo-1,4-dihydroquinoline-3-carboxylic Acid (6)

Ciprofloxacin (0.12 mmol) was suspended in water and the pH was adjusted to 8.5 using $Na_2CO_3$. The suspension was cooled in an ice bath and 4-(2,2-bis(diisopropoxyphosphoryl)ethyl)phenyl (4-nitrophenyl) carbonate (0.10 mmol) dissolved in THF was added dropwise. Reaction mixture was then removed from ice bath, protected from light and stirred overnight at room temperature. The following day, reaction mixture was diluted with water and filtered through a fine glass frit funnel. The retained solid was washed with water until no yellow color remained. The solid was then dissolved and washed from the frit funnel using DCM. The recovered crude was further purified on a silica column using a MeOH:DCM gradient. Title compound was afforded as a white solid which was dissolved in DCM and bromotrimethylsilane (BTMS) (4.00 mmol) was added and heated at 35° C. in an oil bath overnight. Solvent and BTMS were removed by evaporation and MeOH was added and allowed to stir at room temperature for 30 minutes. Solvent was removed on rotavapor and the product was precipitated in chilled MeOH. The suspension was filtered using a frit funnel and washed with additional MeOH. The solid was collected and excess solvent removed evaporated to afford the target compound.

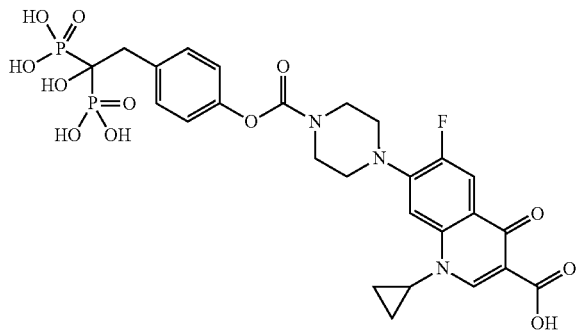 [SMILES: O=C(O)c1cn(C2CC2)c2cc(N3CCN(C(=O)Oc4ccc(CC(O)(P(=O)(O)O)P(=O)(O)O)cc4)CC3)c(F)cc2c1=O]

1-cyclopropyl-6-fluoro-7-(4-((4-(2-hydroxy-2,2-diphosphonoethyl)phenoxy)carbonyl)piperazin-1-yl)-4-oxo-1,4-dihydroquinoline-3-carboxylic Acid (12)

(1-hydroxy-2-(4-hydroxyphenyl)ethane-1,1-diyl)bis(phosphonic acid) (0.10 mmol) was dissolved in water and cooled in an ice bath while stirring vigorously. 1,1'-Carbonyldiimidazole (0.12 mmol) was added and allowed to stir for 1 hour. The ice bath was then removed and stirring continued at room temperature for 1 more hour. Ciprofloxacin (0.12 mmol) was then added and the reaction was stirred overnight at room temperature while covered with foil to avoid light. The next day, solvent was removed by evaporation and MeOH was added to precipitate the product. The suspension was filtered using a frit funnel and washed with additional MeOH. The solid was collected and excess solvent evaporated to afford the target compound.

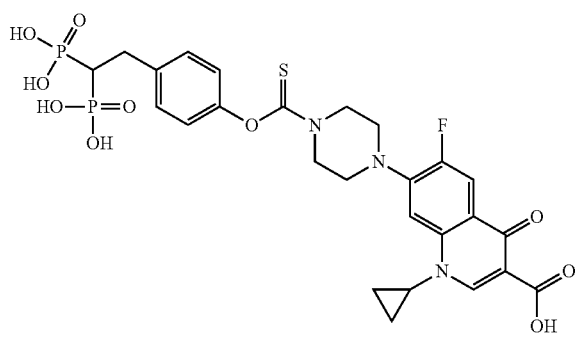 [SMILES: O=C(O)c1cn(C2CC2)c2cc(N3CCN(C(=O)Sc4ccc(CC(P(=O)(O)O)P(=O)(O)O)cc4)CC3)c(F)cc2c1=O]

1-cyclopropyl-7-(4-((4-(2,2-diphosphonoethyl)phenoxy)carbonothioyl)piperazin-1-yl)-6-fluoro-4-oxo-1,4-dihydroquinoline-3-carboxylic Acid (13)

Tetraisopropyl (2-(4-hydroxyphenyl)ethane-1,1-diyl)bis(phosphonate) (0.10 mmol) was emulsified in water and cooled in an ice bath while stirring vigorously. 1,1'-Thiocarbonyldiimidazole (0.12 mmol) was added and allowed to stir for 1 hour. The ice bath was then removed and stirring continued at room temperature for 1 more hour. Ciprofloxacin (0.12 mmol) was then added and the reaction was stirred overnight at room temperature while covered with foil to avoid light. The next day, the white paste was filtered using a frit funnel and the solids were washed with water and then ether. The solids were collected and purified by silica column chromatography using a MeOH:CHCl$_3$ gradient to afford an off white solid. The solid was dissolved in DCM and bromotrimethylsilane (BTMS) (4.00 mmol) was added and heated at 35° C. in an oil bath overnight. Solvent and BTMS were removed by evaporation and MeOH was added and allowed to stir at room temperature for 30 minutes. Solvent was removed on rotavapor and the product was precipitated in chilled MeOH. The suspension was filtered using a frit funnel and washed with additional MeOH. The solid was collected and excess solvent evaporated to afford the target compound.

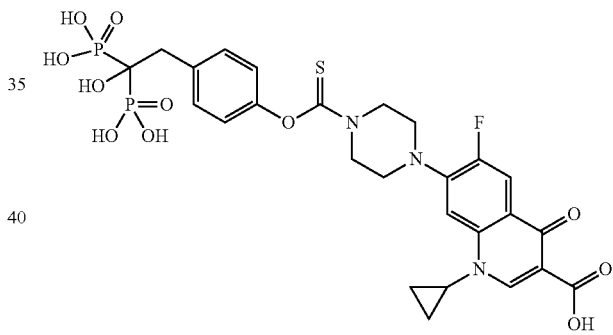

1-cyclopropyl-6-fluoro-7-(4-((4-(2-hydroxy-2,2-diphosphonoethyl)phenoxy)carbonothioyl)piperazin-1-yl)-4-oxo-1,4-dihydroquinoline-3-carboxylic Acid (14)

(1-hydroxy-2-(4-hydroxyphenyl)ethane-1,1-diyl)bis(phosphonic acid) (0.10 mmol) was dissolved in water and cooled in an ice bath while stirring vigorously. 1,1'-Thiocarbonyldiimidazole (0.12 mmol) was added and allowed to stir for 1 hour. The ice bath was then removed and stirring continued at room temperature for 1 more hour. Ciprofloxacin (0.12 mmol) was then added and the reaction was stirred overnight at room temperature while covered with foil to avoid light. The next day, solvent was removed by evaporation and MeOH was added to precipitate the product. The suspension was filtered using a frit funnel and washed with additional MeOH. The solid was collected and excess solvent evaporated to afford the target compound.

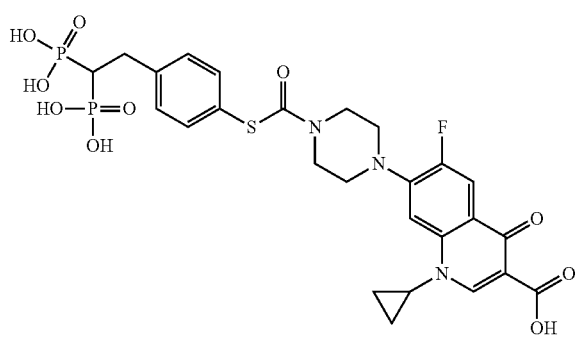

1-cyclopropyl-7-(4-(((4-(2,2-diphosphonoethyl)phenyl)thio)carbonyl) piperazin-1-yl)-6-fluoro-4-oxo-1,4-dihydroquinoline-3-carboxylic Acid (15)

In a microwave vial, compound 13 was suspended on NMP and heated at 290° C. in a microwave reactor for 20 minutes. The suspension was filtered and washed with MeOH to afford the target compound.

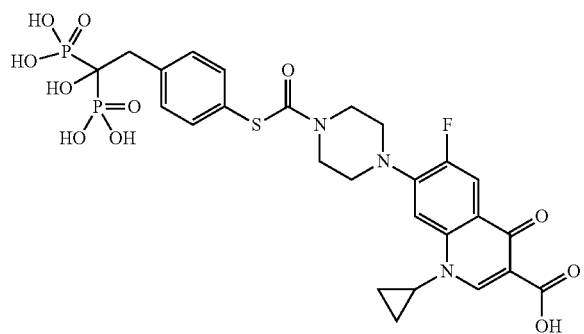 [SMILES: O=C(O)c1cn(C2CC2)c2cc(N3CCN(C(=O)Sc4ccc(CC(O)(P(=O)(O)O)P(=O)(O)O)cc4)CC3)c(F)cc2c1=O]

1-cyclopropyl-6-fluoro-7-(4-(((4-(2-hydroxy-2,2-diphosphonoethyl)phenyl)thio)carbonyl)piperazin-1-yl)-4-oxo-1,4-dihydroquinoline-3-carboxylic Acid (16)

In a microwave vial, compound 14 was suspended on NMP and heated at 290° C. in a microwave reactor for 20 minutes. The suspension was filtered and washed with MeOH to afford the target compound.

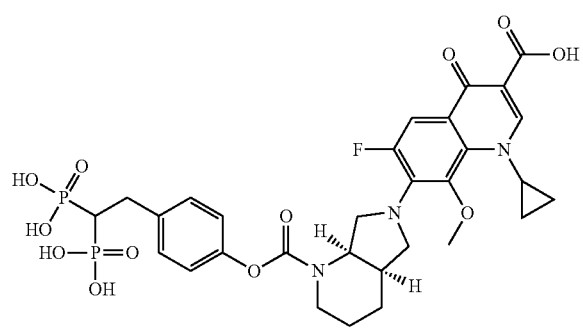 [SMILES: COc1c(N2C[C@H]3CCCN(C(=O)Oc4ccc(CC(P(=O)(O)O)P(=O)(O)O)cc4)[C@H]3C2)c(F)cc2c(=O)c(C(=O)O)cn(C3CC3)c12]

1-cyclopropyl-7-((4aR,7aR)-1-((4-(2,2-diphosphonoethyl)phenoxy)carbonyl)octahydro-6H-pyrrolo[3,4-b]pyridin-6-yl)-6-fluoro-8-methoxy-4-oxo-1,4-dihydroquinoline-3-carboxylic Acid (17)

Compound 17 was synthesized according to the procedure described for compound 6, replacing ciprofloxacin with moxifloxacin.

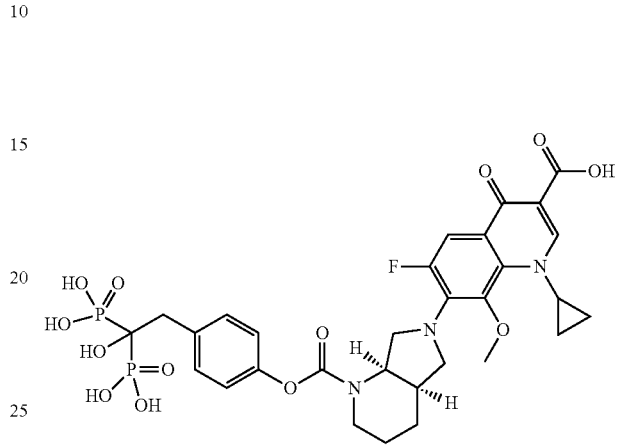

1-cyclopropyl-6-fluoro-7-((4aR,7aR)-1-((4-(2-hydroxy-2,2-diphosphonoethyl)phenoxy)carbonyl)octahydro-6H-pyrrolo[3,4-b]pyridin-6-yl)-8-methoxy-4-oxo-1,4-dihydroquinoline-3-carboxylic Acid (18)

Compound 18 was synthesized according to the procedure described for compound 12, replacing ciprofloxacin with moxifloxacin.

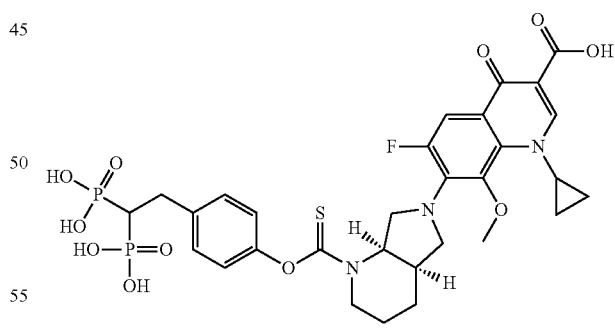

1-cyclopropyl-7-((4aR,7aR)-1-((4-(2,2-diphosphonoethyl)phenoxy)carbonothioyl)octahydro-6H-pyrrolo[3,4-b]pyridin-6-yl)-6-fluoro-8-methoxy-4-oxo-1,4-dihydroquinoline-3-carboxylic Acid (19)

Compound 19 was synthesized according to the procedure described for compound 13, replacing ciprofloxacin with moxifloxacin.

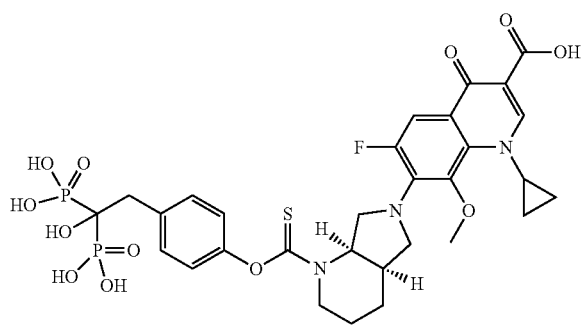 [SMILES: COc1c(N2C[C@H]3CCCN(C(=S)Oc4ccc(CC(O)(P(=O)(O)O)P(=O)(O)O)cc4)[C@H]3C2)c(F)cc2c(=O)c(C(=O)O)cn(C3CC3)c12]

1-cyclopropyl-6-fluoro-7-((4aR,7aR)-1-((4-(2-hydroxy-2,2-diphosphonoethyl)phenoxy)carbonothioyl)octahydro-6H-pyrrolo[3,4-b]pyridin-6-yl)-8-methoxy-4-oxo-1,4-dihydroquinoline-3-carboxylic Acid (20)

Compound 20 was synthesized according to the procedure described for compound 14, replacing ciprofloxacin with moxifloxacin.

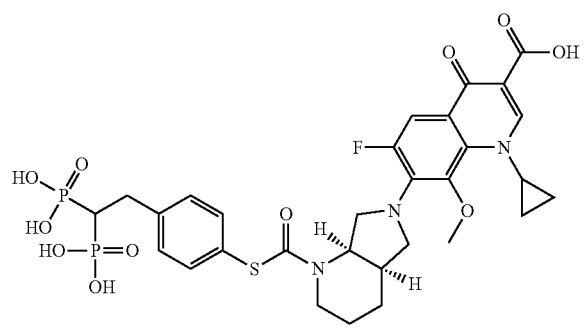

1-cyclopropyl-7-((4aR,7aR)-1-(((4-(2,2-diphosphonoethyl)phenyl)thio)carbonyl)octahydro-6H-pyrrolo[3,4-b]pyridin-6-yl)-6-fluoro-8-methoxy-4-oxo-1,4-dihydroquinoline-3-carboxylic Acid (21)

In a microwave vial, compound 19 was suspended on NMP and heated at 290° C. for 20 minutes. The suspension was filtered and washed with MeOH to afford the target compound.

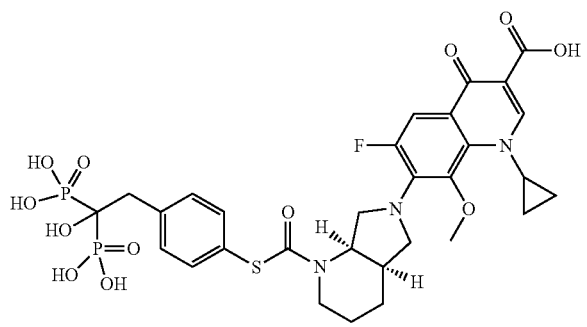 [SMILES: COc1c(N2C[C@H]3CCCN(C(=O)Sc4ccc(CC(O)(P(=O)(O)O)P(=O)(O)O)cc4)[C@H]3C2)c(F)cc2c(=O)c(C(=O)O)cn(C3CC3)c12]

1-cyclopropyl-6-fluoro-7-((4aR,7aR)-1-(((4-(2-hydroxy-2,2-diphosphonoethyl)phenyl)thio)carbonyl)octahydro-6H-pyrrolo[3,4-b]pyridin-6-yl)-8-methoxy-4-oxo-1,4-dihydroquinoline-3-carboxylic Acid (22)

In a microwave vial, compound 20 was suspended on NMP and heated at 290° C. for 20 minutes. The suspension was filtered and washed with MeOH to afford the target compound.

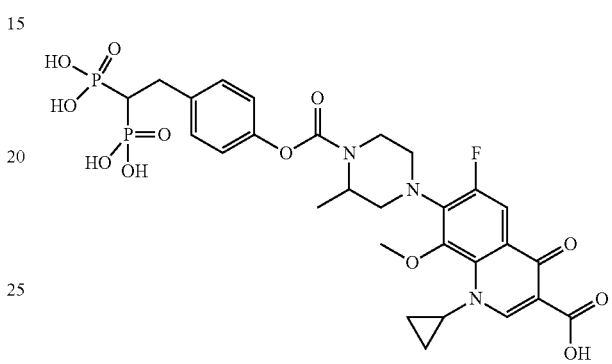

1-cyclopropyl-7-(4-((4-(2,2-diphosphonoethyl)phenoxy)carbonyl)-3-methylpiperazin-1-yl)-6-fluoro-8-methoxy-4-oxo-1,4-dihydroquinoline-3-carboxylic Acid (23)

Compound 23 was synthesized according to the procedure described for compound 6, replacing ciprofloxacin with gatifloxacin.

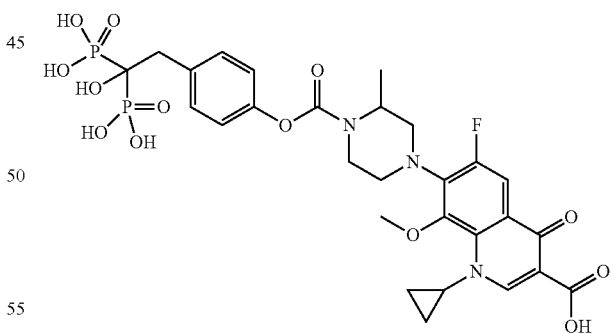

1-cyclopropyl-6-fluoro-7-(4-((4-(2-hydroxy-2,2-diphosphonoethyl)phenoxy)carbonyl)-3-methylpiperazin-1-yl)-8-methoxy-4-oxo-1,4-dihydroquinoline-3-carboxylic Acid (24)

Compound 24 was synthesized according to the procedure described for compound 12, replacing ciprofloxacin with gatifloxacin.

131

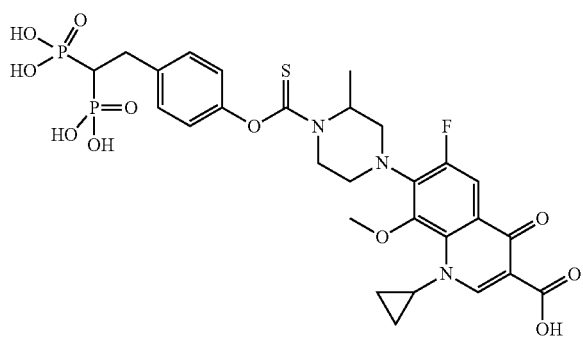

1-cyclopropyl-7-(4-((4-(2,2-diphosphonoethyl)phe-
noxy)carbonothioyl)-3-methylpiperazin-1-yl)-6-
fluoro-8-methoxy-4-oxo-1,4-dihydroquinoline-3-
carboxylic Acid (25)

Compound 25 was synthesized according to the procedure described for compound 13, replacing ciprofloxacin with gatifloxacin.

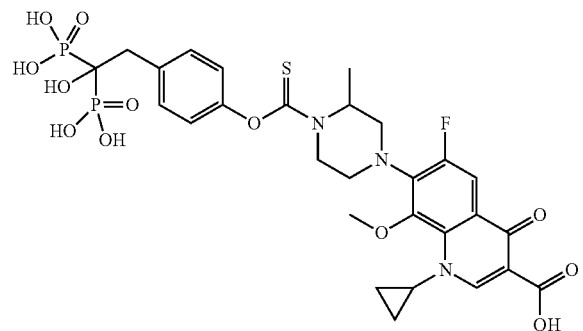 [SMILES: COc1c(N2CCN(C(=O)Oc3ccc(CC(O)(P(=O)(O)O)P(=O)(O)O)cc3)C(C)C2)c(F)cc2c(=O)c(C(=O)O)cn(C3CC3)c12]

1-cyclopropyl-6-fluoro-7-(4-((4-(2-hydroxy-2,2-di
phosphonoethyl)phenoxy)carbonothioyl)-3-meth-
ylpiperazin-1-yl)-8-methoxy-4-oxo-1,4-dihydroqui-
noline-3-carboxylic Acid (26)

Compound 26 was synthesized according to the procedure described for compound 14, replacing ciprofloxacin with gatifloxacin.

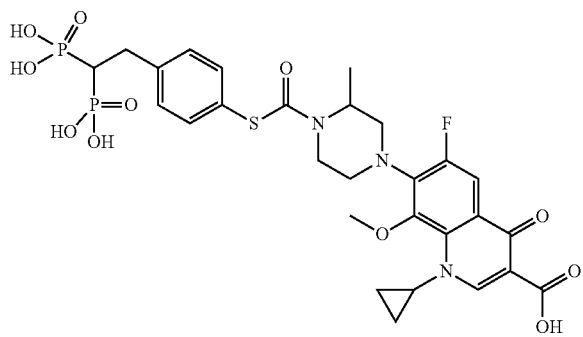 [SMILES: COc1c(N2CCN(C(=O)Sc3ccc(CC(P(=O)(O)O)P(=O)(O)O)cc3)C(C)C2)c(F)cc2c(=O)c(C(=O)O)cn(C3CC3)c12]

132

1-cyclopropyl-7-(4-(((4-(2,2-diphosphonoethyl)phe-
nyl)thio)carbonyl)-3-methylpiperazin-1-yl)-6-fluoro-
8-methoxy-4-oxo-1,4-dihydroquinoline-3-carboxylic
Acid (27)

In a microwave vial, compound 25 was suspended on NMP and heated at 290° C. for 20 minutes. The suspension was filtered and washed with MeOH to afford the target compound.

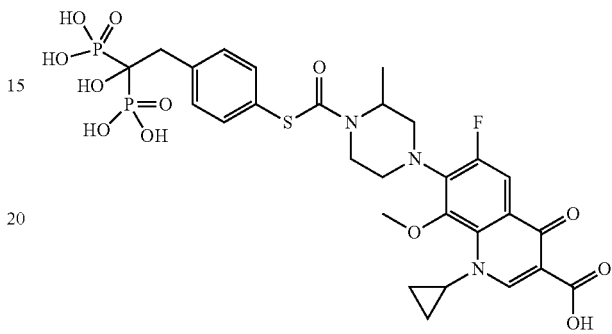

1-cyclopropyl-6-fluoro-7-(4-(((4-(2-hydroxy-2,2-
diphosphonoethyl)phenyl)thio)carbonyl)-3-meth-
ylpiperazin-1-yl)-8-methoxy-4-oxo-1,4-dihydroqui-
noline-3-carboxylic Acid (28)

In a microwave vial, compound 26 was suspended on NMP and heated at 290° C. for 20 minutes. The suspension was filtered and washed with MeOH to afford the target compound.

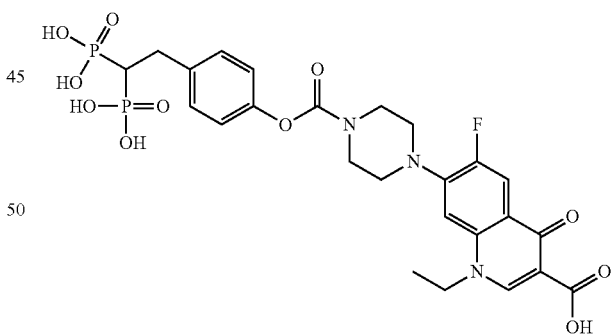

7-(4-((4-(2,2-diphosphonoethyl)phenoxy)carbonyl)
piperazin-1-yl)-1-ethyl-6-fluoro-4-oxo-1,4-dihydro-
quinoline-3-carboxylic Acid (29)

Compound 29 was synthesized according to the procedure described for compound 6, replacing ciprofloxacin with norfloxacin.

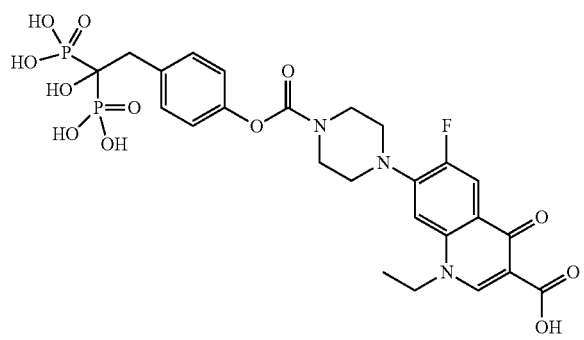

1-ethyl-6-fluoro-7-(4-((4-(2-hydroxy-2,2-di-phosphonoethyl)phenoxy)carbonyl)piperazin-1-yl)-4-oxo-1,4-dihydroquinoline-3-carboxylic Acid (30)

Compound 30 was synthesized according to the procedure described for compound 12, replacing ciprofloxacin with norfloxacin.

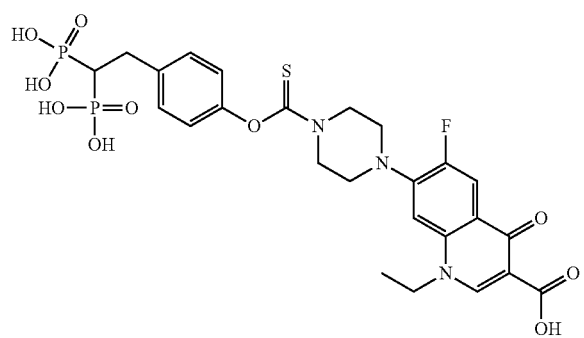 [SMILES: CCn1cc(C(=O)O)c(=O)c2cc(F)c(N3CCN(C(=O)Oc4ccc(CC(P(=O)(O)O)P(=O)(O)O)cc4)CC3)cc21]

7-(4-((4-(2,2-diphosphonoethyl)phenoxy)carbonothioyl)piperazin-1-yl)-1-ethyl-6-fluoro-4-oxo-1,4-dihydroquinoline-3-carboxylic Acid (31)

Compound 31 was synthesized according to the procedure described for compound 13, replacing ciprofloxacin with norfloxacin.

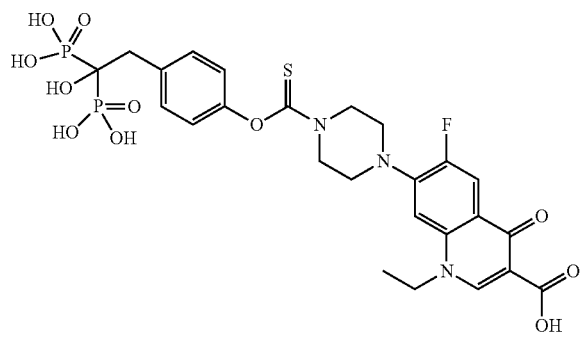 [SMILES: CCn1cc(C(=O)O)c(=O)c2cc(F)c(N3CCN(C(=S)Oc4ccc(CC(O)(P(=O)(O)O)P(=O)(O)O)cc4)CC3)cc21]

1-ethyl-6-fluoro-7-(4-((4-(2-hydroxy-2,2-di-phosphonoethyl)phenoxy)carbonothioyl)piperazin-1-yl)-4-oxo-1,4-dihydroquinoline-3-carboxylic Acid (32)

Compound 32 was synthesized according to the procedure described for compound 14, replacing ciprofloxacin with norfloxacin.

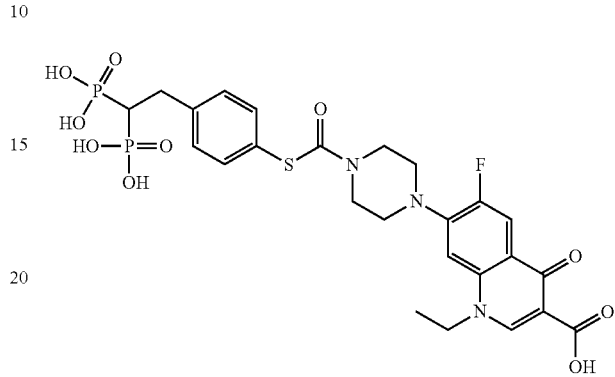

7-(4-(((4-(2,2-diphosphonoethyl)phenyl)thio)carbonyl)piperazin-1-yl)-1-ethyl-6-fluoro-4-oxo-1,4-dihydroquinoline-3-carboxylic Acid (33)

In a microwave vial, compound 31 was suspended on NMP and heated at 290° C. for 20 minutes. The suspension was filtered and washed with MeOH to afford the target compound.

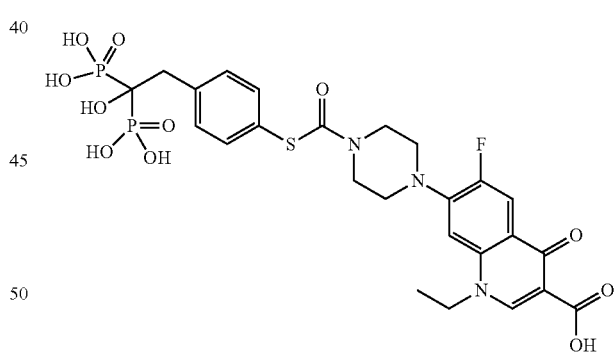

1-ethyl-6-fluoro-7-(4-(((4-(2-hydroxy-2,2-di-phosphonoethyl)phenyl)thio)carbonyl)piperazin-1-yl)-4-oxo-1,4-dihydroquinoline-3-carboxylic Acid (34)

In a microwave vial, compound 32 was suspended on NMP and heated at 290° C. for 20 minutes. The suspension was filtered and washed with MeOH to afford the target compound.

135
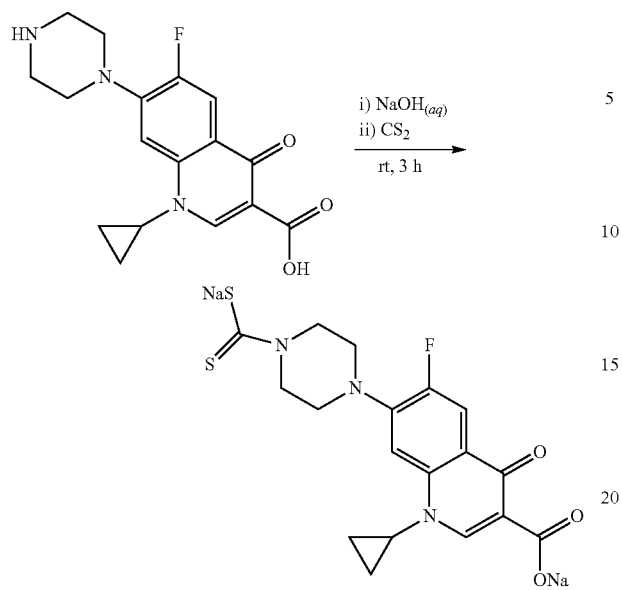
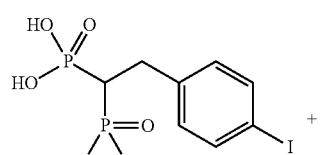
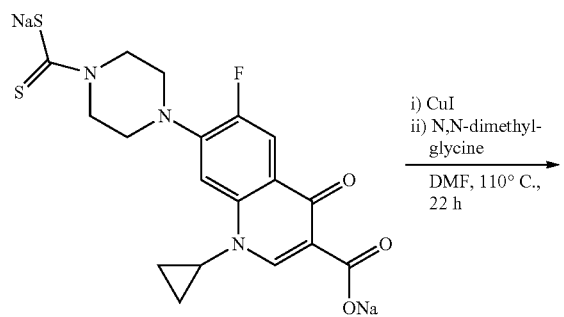
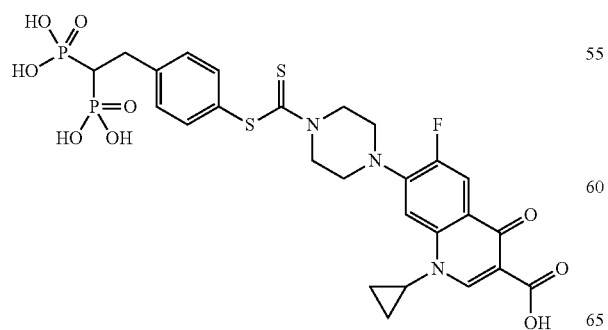
136
1-cyclopropyl-7-(4-(((4-(2,2-diphosphonoethyl)phenyl)thio)carbonothioyl)piperazin-1-yl)-6-fluoro-4-oxo-1,4-dihydroquinoline-3-carboxylic Acid (35)
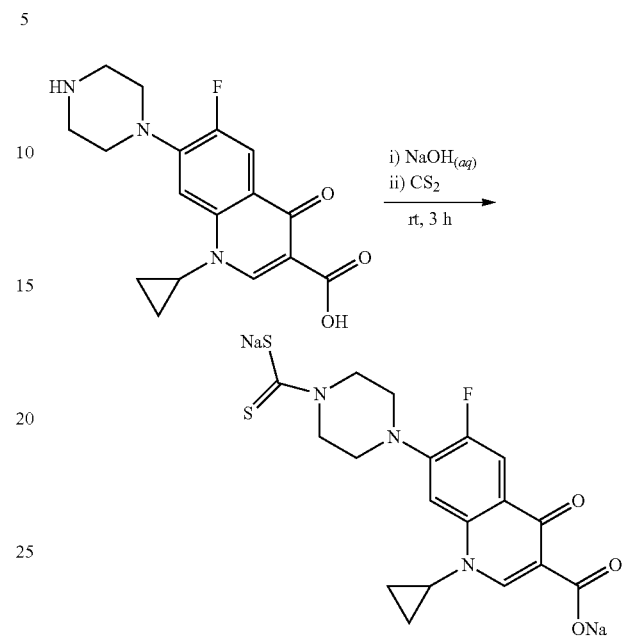
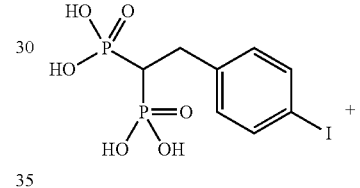
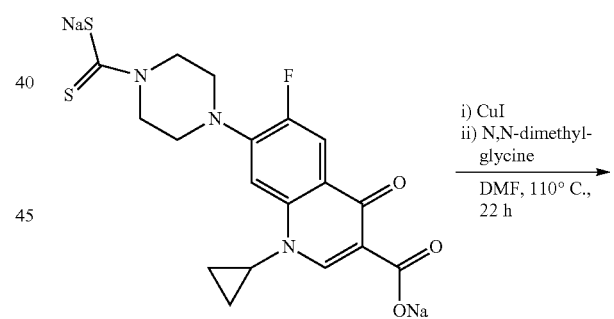
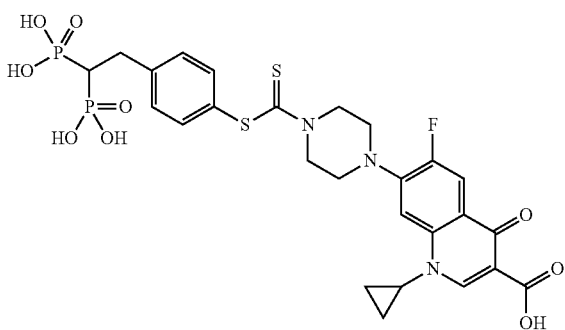

1-cyclopropyl-6-fluoro-7-(4-(((4-(2-hydroxy-2,2-diphosphonoethyl)phenyl)thio)carbonothioyl)piperazin-1-yl)-4-oxo-1,4-dihydroquinoline-3-carboxylic Acid (36)

Example 12

1. Dimethyl acetylphosphonate (XV-PC-055) (37)

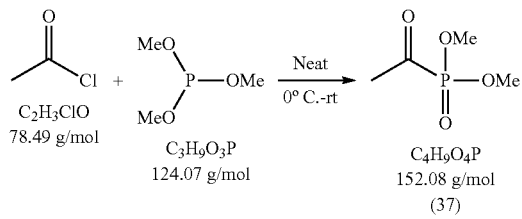

Trimethyl phosphite (2.36 mL, 20 mmol) was added to ice-cold acetyl chloride (1.44 mL, 20.2 mmol) under N$_2$ over a period of 20 mins. The colorless solution was warmed to room temperature, stirred for 30 mins, and concentrated under vacuum to afford 2.89 g (94%) product as colorless oil which was used in next reaction as is. $^1$HNMR (300 MHz, CDCl3): δ 3.84 (d, J=12 Hz, 6H), 2.46 (d, J=5.4 Hz, 3H). $^{31}$PNMR (121 MHz, CDCl$_3$): δ −1.10.

2. Tetramethyl(1-hydroxyethylidene)-bisphosphonate (XV-PC-057) (38)

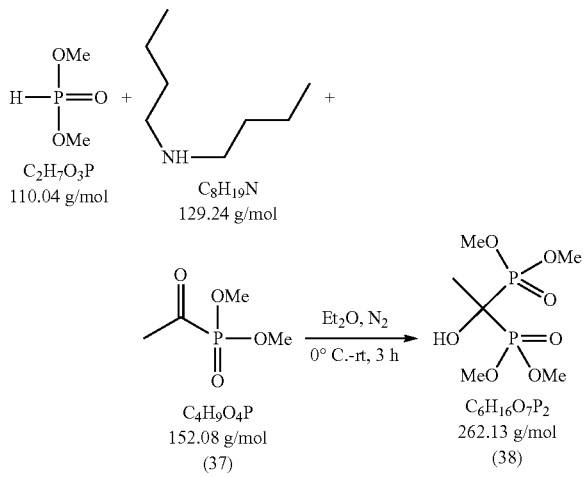

Dimethyl acetylphosphate (37) (2.2 g, 14.44 mmol) was added dropwisely to an ice-cold solution of dimethyl phosphite (1.63 mL, 15.91 mmol) and dibutylamine (0.767 mL, 1.44 mmol) in dry ether (30 mL) under N$_2$. The ice bath was removed, and the mixture was stirred at room temperature for 3 h. The resulting precipitate was filtered, washed with ether, and dried under vacuum overnight to afford 3.24 g (85%) of product as white solid. $^1$HNMR (300 MHz, CDCl$_3$): δ 3.94-3.82 (m, 12H), 3.44 (t, J=8.4 Hz, 1H), 1.68 (t, J=16.2 Hz, 3H). $^{31}$PNMR (121 MHz, CDCl$_3$): δ 22.21. MS-ESI: 263.1 [M+H]+.

3. Tetramethyl (1-{[(4-nitrophenoxy)carbonyl]oxy}ethane-1,1-diyl)bis(phosphonate) (XV-PC-099) (39)

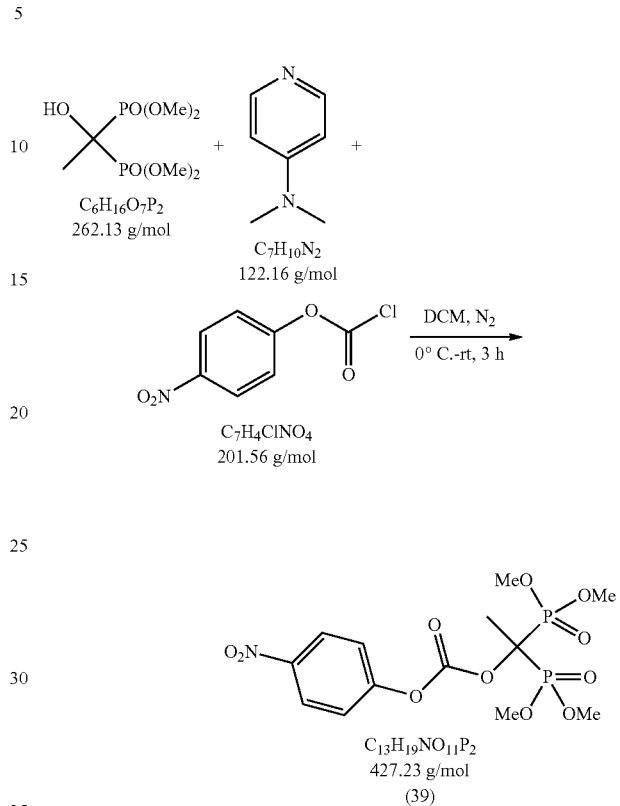

p-nitrophenyl chloroformate (768 mg, 3.81 mmol) was added to an ice-cold solution of DMAP (466 mg, 3.81 mmol) in DCM (20 mL) under N$_2$. After stirring for 10 mins, the tetramethyl(1-hydroxyethylidene)-bisphosphonate (1 g, 3.81 mmol) was added in one portion. The ice-bath was removed, and the mixture was stirred at room temperature for 3 h. Next, the reaction mixture was extracted with 20 mL each of cold aqueous 0.1 N HCl (2×), water, brine, dried over MgSO$_4$, and concentrated. The crude mixture was separated by column chromatography using EtOAc/MeOH (1-3%) to afford 1.16 g (71%) light-yellow oil. $^1$HNMR (300 MHz, CDCl3): δ 8.27 (d, J=9 Hz, 2H), 7.40 (d, J=9 Hz, 2H), 3.97-3.87 (m, 12H), 2.02 (t, J=15.6 Hz, 3H). $^{31}$PNMR (121 MHz, CDCl$_3$): δ 17.98. MS-ESI: 445.3 [M+NH4]+.

4: Ciprofloxacin carbamoyl etidronate tetramethyl Ester (XV-PC-101) (40)

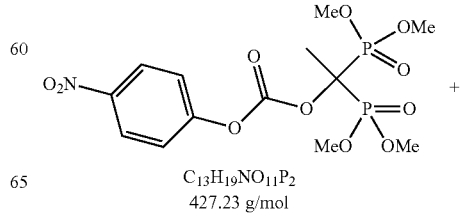

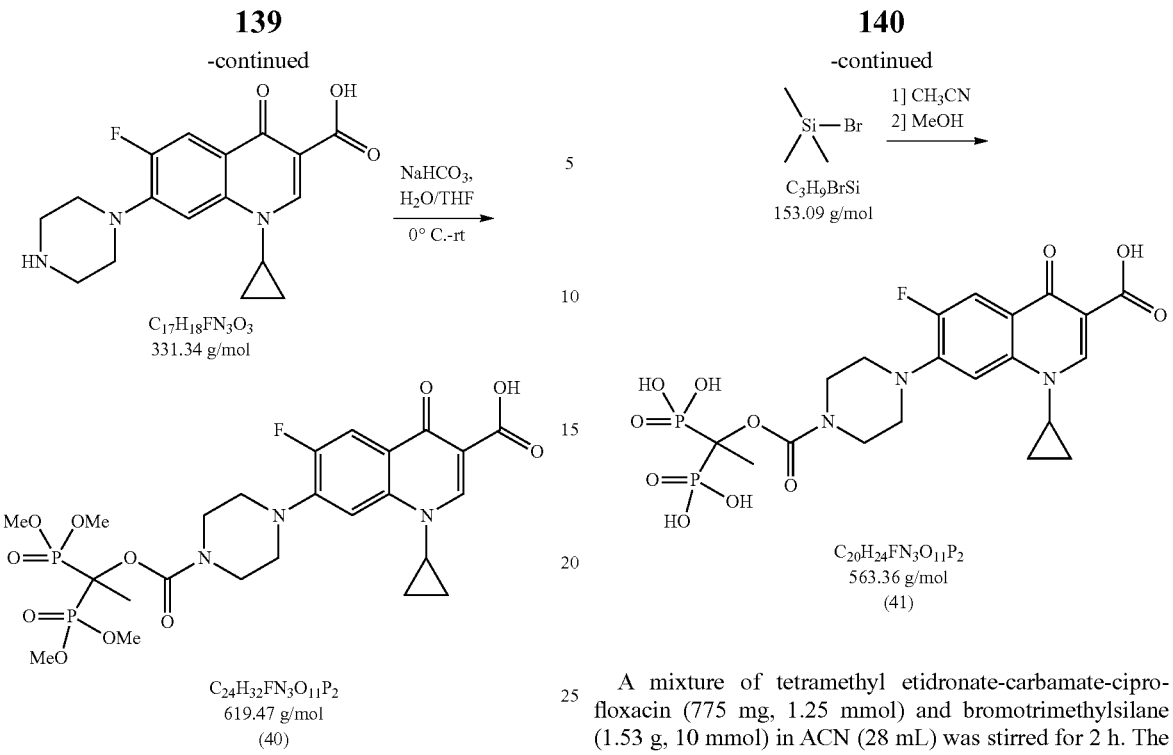

To a solution of NaHCO$_3$ (239.5 mg, 2.85 mmol) in H$_2$O (20 mL) was added ciprofloxacin (899.6 mg, 2.71 mmol) and the suspension was cooled in ice-bath. Next, the tetramethyl (1-{[(4-nitrophenoxy)carbonyl]oxy}ethane-1,1-diyl)bis(phosphonate) dissolved in THF (20 mL) was added dropwisely over a period of 20 mins. The yellow suspension was stirred overnight (14 h) at room temperature. The reaction mixture was concentrated, and the crude mixture was separated by column chromatography using DCM/MeOH (1-5%) to provide 832 mg (49%) of light-yellow solid. $^1$HNMR (300 MHz, CDCl$_3$): δ 8.77 (s, 1H), 8.03 (d, J=12.6 Hz, 1H), 7.36 (d, J=6.9 Hz, 1H) 3.98-3.80 (m, 12H), 3.79-3.68 (br s, 4H), 3.58-3.50 (m, 1H), 3.30 (t, J=9.6 Hz, 4H), 1.95 (t, J=15.6 Hz, 3H), 1.40 (q, J=6.8 Hz, 2H), 1.23-1.16 (m, 2H). $^{31}$PNMR (121 MHz, CDCl3): δ 20.19. MS-ESI: 620.3 [M+H]+.

5. Etidronate-carbamate-Ciprofloxacin (XV-PC-105) (41)

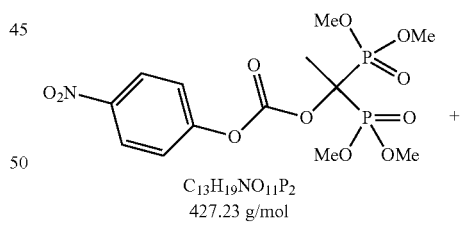

A mixture of tetramethyl etidronate-carbamate-ciprofloxacin (775 mg, 1.25 mmol) and bromotrimethylsilane (1.53 g, 10 mmol) in ACN (28 mL) was stirred for 2 h. The volatiles were evaporated under vacuum and MeOH (28 mL) was added to the residue. After stirring for 30 mins the resulting suspension was filtered, washed with MeOH (10 mL×2), and dried under vacuum overnight to afford 662 mg (93%) off-white solid. $^1$H NMR (300 MHz, 20% CD$_3$CN in DMSO-d6) δ 8.66 (s, 1H), 7.92 (d, J=13.2 Hz, 1H), 7.57 (d, J=7.4 Hz, 1H), 3.78 (p, J=3.1 Hz, 1H), 3.64 (br d, J=32.1 Hz, 4H), 3.32 (br s, 4H), 1.82 (t, J=15.1 Hz, 3H), 1.32 (d, J=6.5 Hz, 2H), 1.16 (s, 2H). $^{31}$PNMR (121 MHz, 20% CD3CN in DMSO-d6): δ 15.57. MS-ESI: 564.2 [M+H]+.

6. Moxifloxacin carbamoyl etidronate tetramethyl Ester (XVI-PC-029) (42)

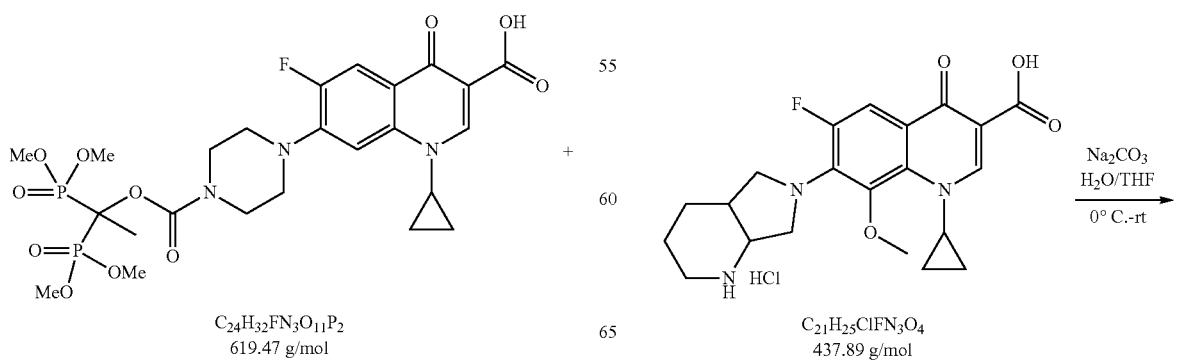

-continued

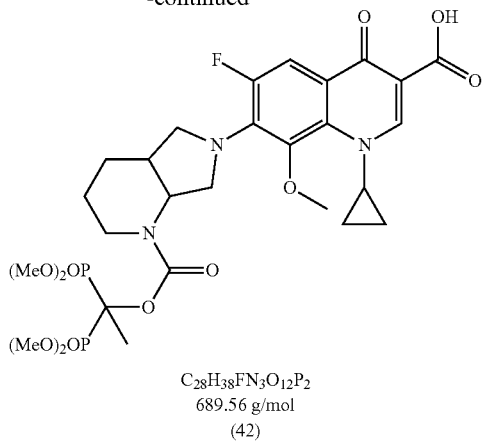

C<sub>28</sub>H<sub>38</sub>FN<sub>3</sub>O<sub>12</sub>P<sub>2</sub>
689.56 g/mol
(42)

Moxifloxacin HCl was added to a solution of Na2CO3 in H2O (20 mL) and the solution was cooled in ice bath. Next, the tetramethyl (1-{[(4-nitrophenoxy)carbonyl]oxy}ethane-1,1-diyl)bis(phosphonate) dissolved in THF (20 mL) was added dropwisely over 30 min. The ice bath was removed, the flask was covered with aluminum foil, and the reaction was stirred for 20 h at room temperature. Next, the reaction mixture was concentrated, and the crude purified by column chromatography using DCM/MeOH (1-5%) to afford 624 mg (29%) of product as off-white foam. $^{1}$H NMR (300 MHz, Chloroform-d) δ 8.78 (s, 1H), 7.81 (d, J=13.8 Hz, 1H), 4.82 (br s, 1H), 4.16-4.04 (m, 2H), 4.02-3.92 (m, 2H), 3.92-3.80 (m, 12H), 3.56 (s, 3H), 3.48 (t, J=10.5 Hz, 1H), 3.24 (d, J=10.5 Hz, 1H), 3.00 (br s, 1H), 2.40-2.24 (m, 1H), 1.94 (t, J=15.9 Hz, 3H), 1.87-1.74 (m, 2H), 1.60-1.44 (m, 2H), 1.35-1.21 (m, 1H), 1.17-1.01 (m, 2H), 0.88-0.75 (m, 1H). $^{31}$PNMR (121 MHz, CDCl3): δ 20.36. MS-ESI: 690.4 [M+H]+

7. Etidronate-carbamate-Moxifloxacin (XVI-PC-033) (43)

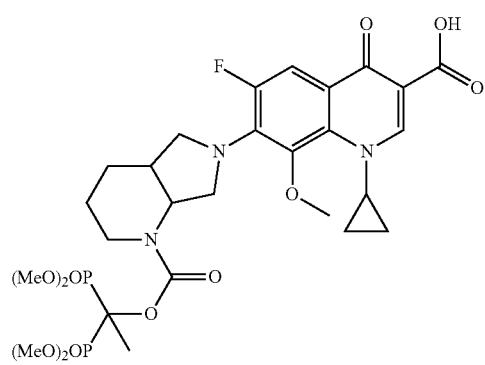

C<sub>28</sub>H<sub>38</sub>FN<sub>3</sub>O<sub>12</sub>P<sub>2</sub>
689.56 g/mol

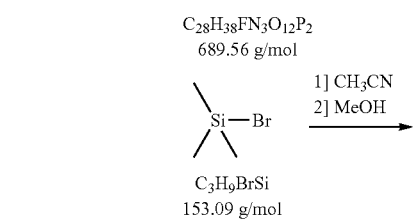

1] CH<sub>3</sub>CN
2] MeOH

C<sub>3</sub>H<sub>9</sub>BrSi
153.09 g/mol

-continued

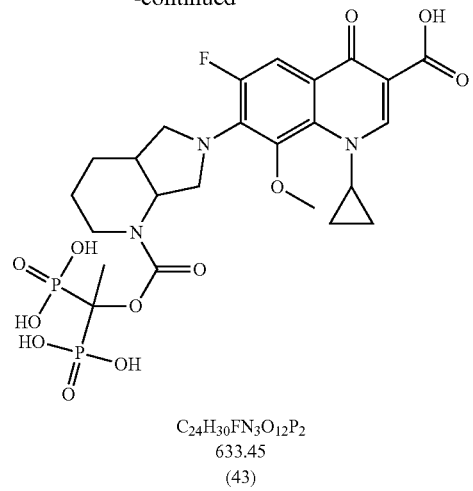

C<sub>24</sub>H<sub>30</sub>FN<sub>3</sub>O<sub>12</sub>P<sub>2</sub>
633.45
(43)

A mixture of tetramethyl etidronate-carbamate-moxifloxacin tetramethyl ester (764 mg, 1.10 mmol) and bromotrimethylsilane (1.35 g, 8.86 mmol) in ACN (25 mL) was stirred for 2 h. The volatiles were evaporated under vacuum and MeOH (25 mL) was added to the residue. After stirring for 30 mins, the solvent was evaporated, and the residue was triturated with minimum volume of DCM for 30 mins. The solid was filtered, and dried under high vacuum to afford 757 mg of product (quantitative yield). $^{1}$H NMR (300 MHz, Methanol-d4) δ 8.98 (s, 1H), 7.79 (d, J=14.5 Hz, 1H), 4.39-4.25 (m, 1H), 4.24-4.07 (m, 2H), 4.01 (t, J=10.3 Hz, 1H), 3.65 (s, 3H), 3.61-3.51 (m, 2H), 3.41 (d, J=10.7 Hz, 1H), 3.04 (br s, 1H), 2.43-2.27 (m, 1H), 1.90 (t, J=15.2 Hz, 3H), 1.83-1.71 (m, 2H), 1.55 (q, J=10.8 Hz, 2H), 1.43-1.32 (m, 1H), 1.30-1.18 (m, 1H), 1.17-1.03 (m, 1H), 1.01-0.83 (m, 1H). $^{31}$PNMR (121 MHz, Methanol-d4): δ 16.60. MS-ESI: 634.2 [M+H]+.

Example 13

The following is a general structure of BP-quinolone as can be described in one or more aspects herein.

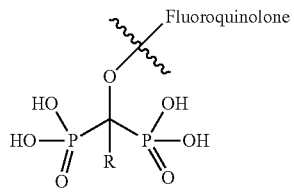

conjugates between alpha-OH containing BP and fluoroquinolone

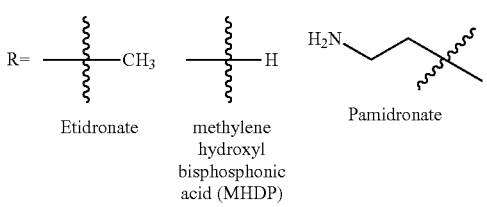

Etidronate    methylene hydroxyl bisphosphonic acid (MHDP)    Pamidronate

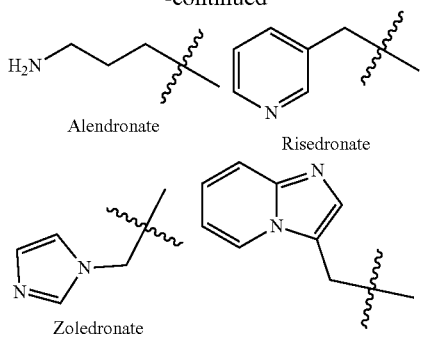
Example 14
The following are non-limiting examples of BP-quinolone conjugates as described in one or more aspects herein.
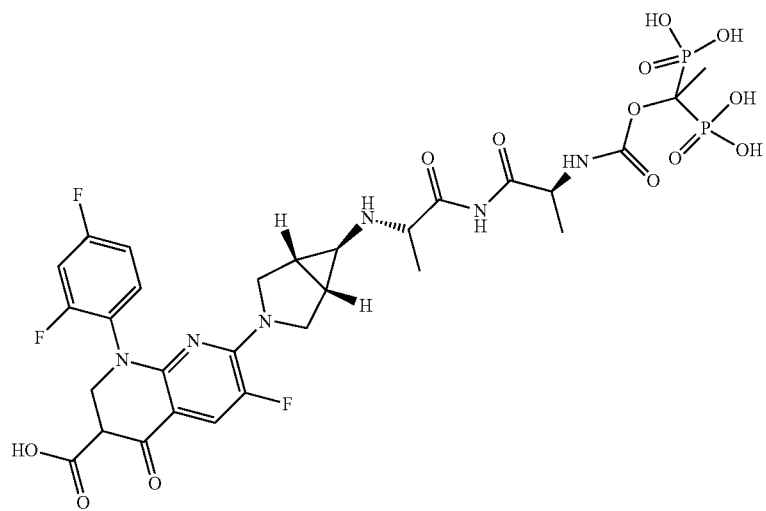
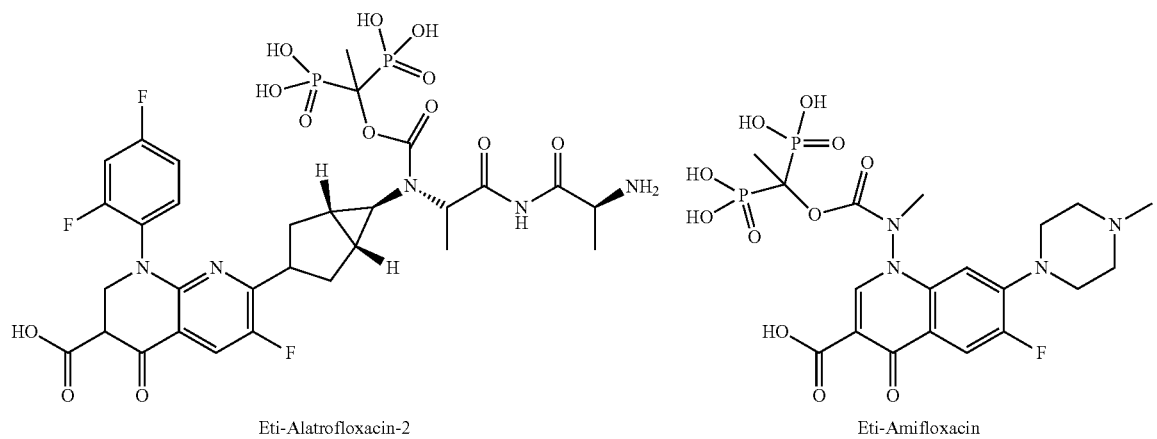

-continued
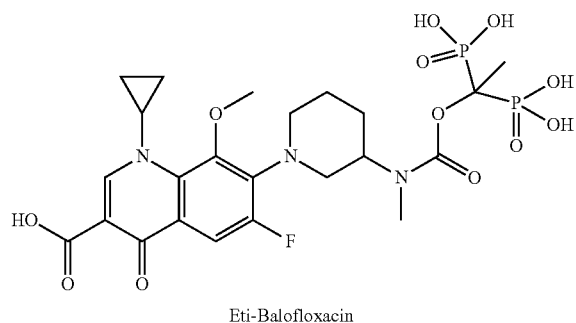
Eti-Balofloxacin
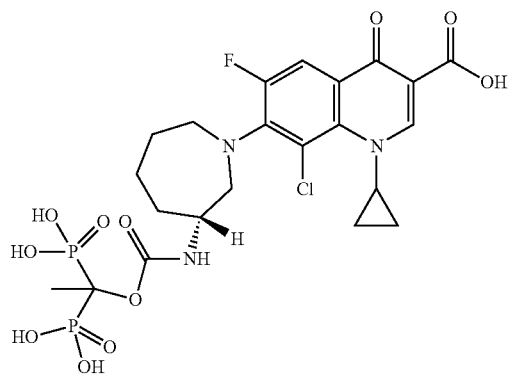
Eti-Besifloxacin
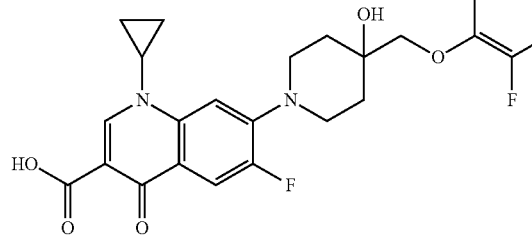
Eti-Cadazolid-1
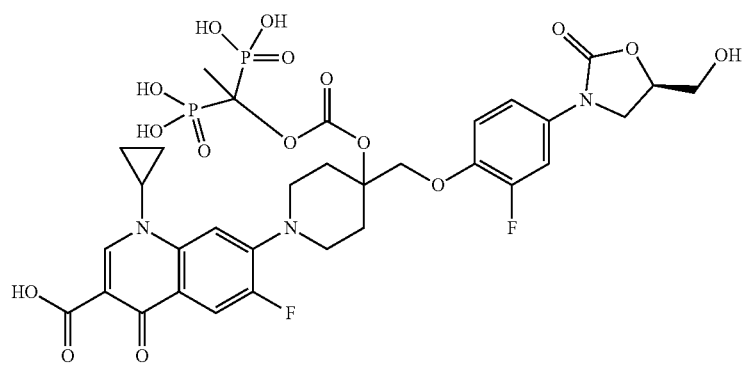
Eti-Cadazolid-2
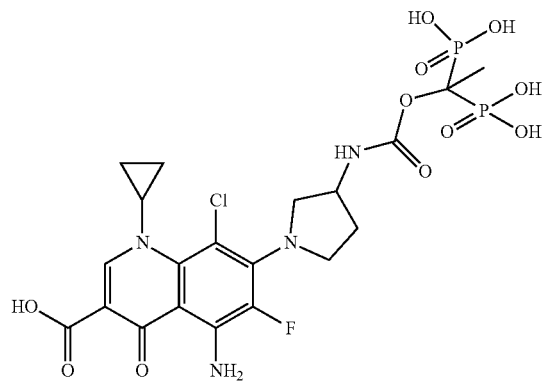
Eti-Clinafloxacin-1
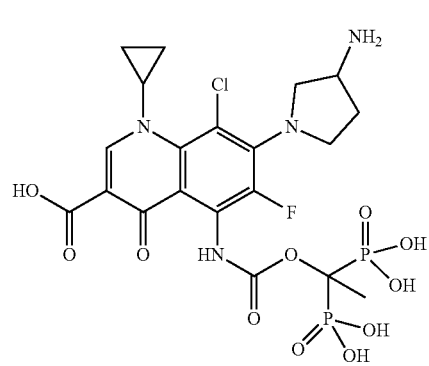
Eti-Clinafloxacin-2

-continued
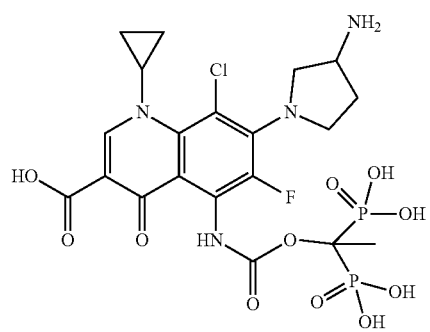
Eti-Clinafloxacin-3
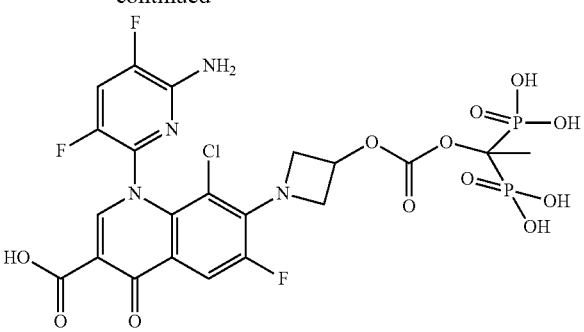
Eti-Delafloxacin-1
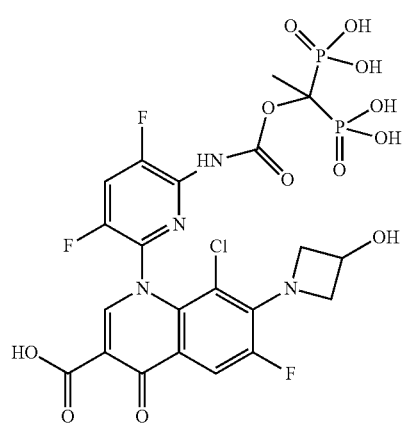
Eti-Delafloxacin-2
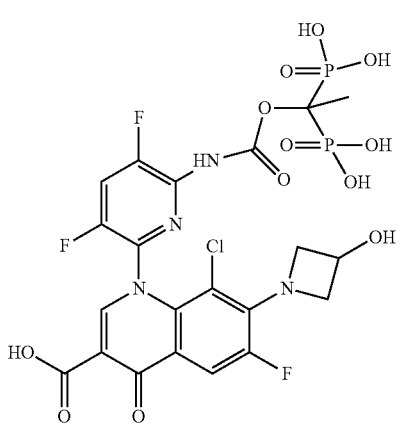
Eti-Delafloxacin-3
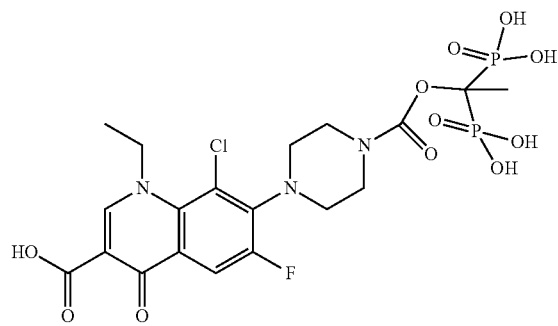
Eti-Enoxacin
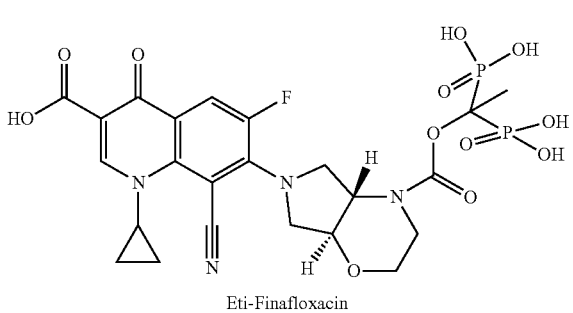
Eti-Finafloxacin
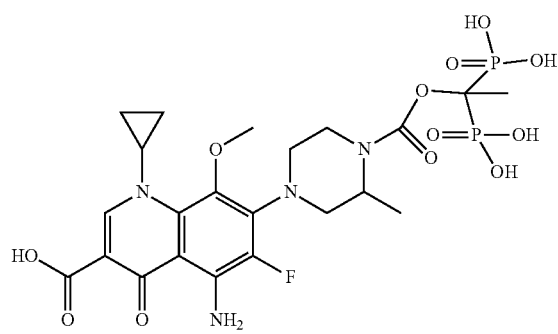
Eti-Gatifloxacin-1
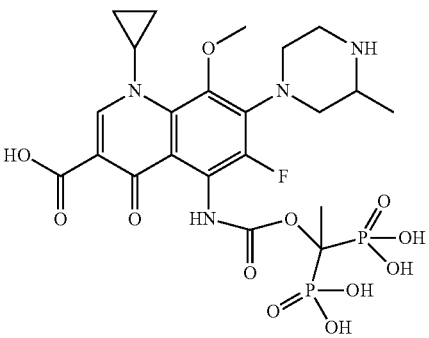
Eti-Gatifloxacin-2

-continued
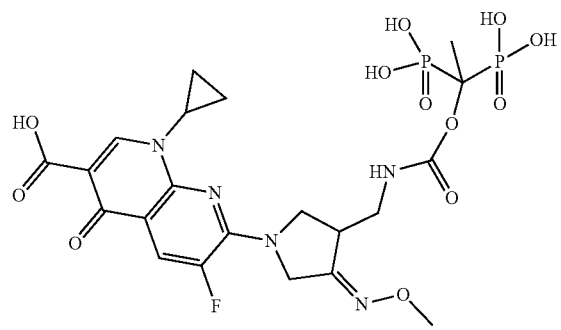
Eti-Gemifloxacin
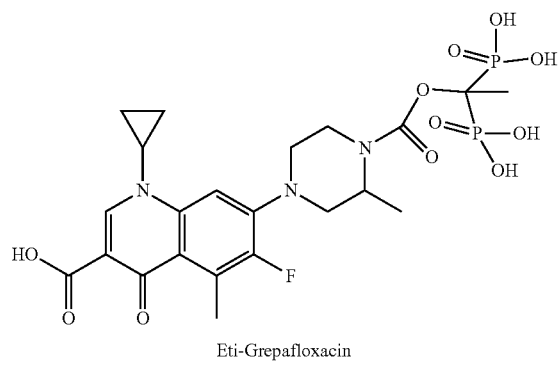
Eti-Grepafloxacin
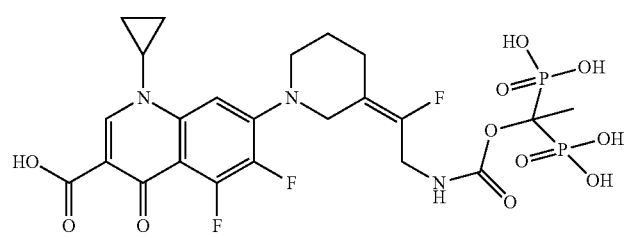
Eti-JNJ-Q2
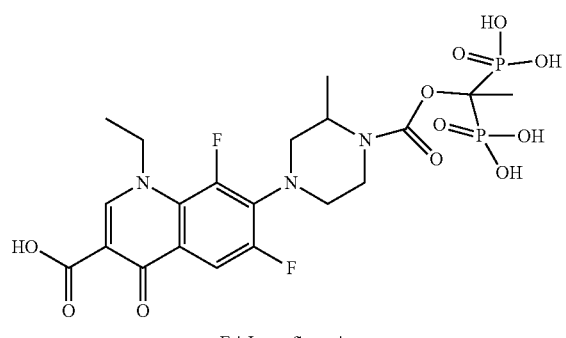
Eti-Lomefloxacin
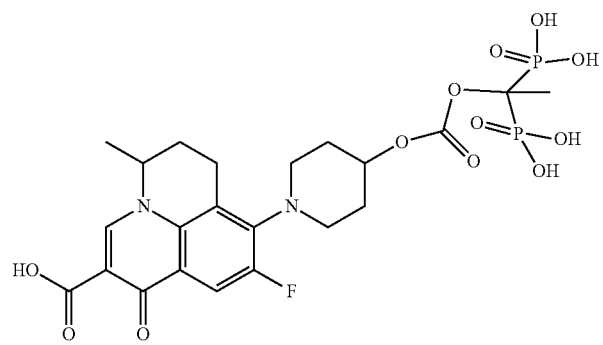
Eti-Nadifloxacin
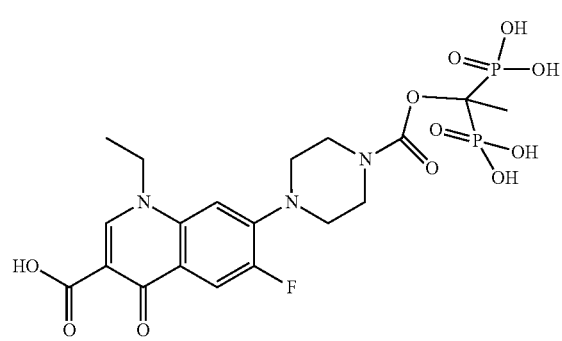
Eti-Norfloxacin
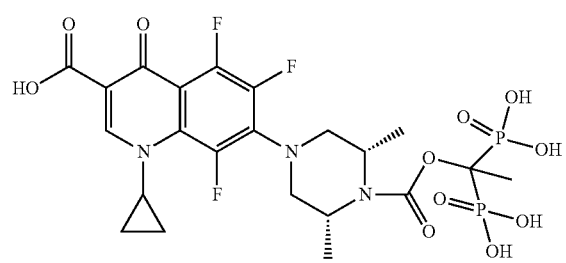
Eti-Orbifloxacin
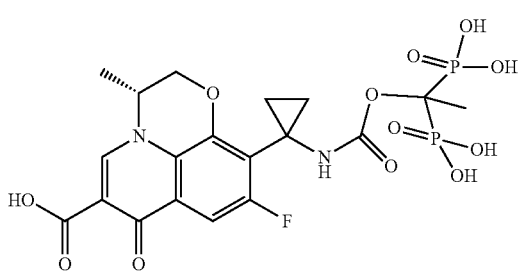
Eti-Pazufloxacin -continued
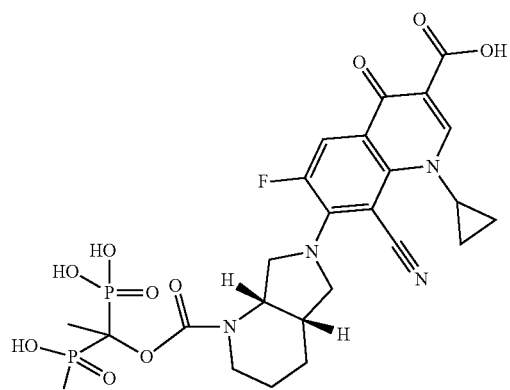
Eti-Pradofloxacin
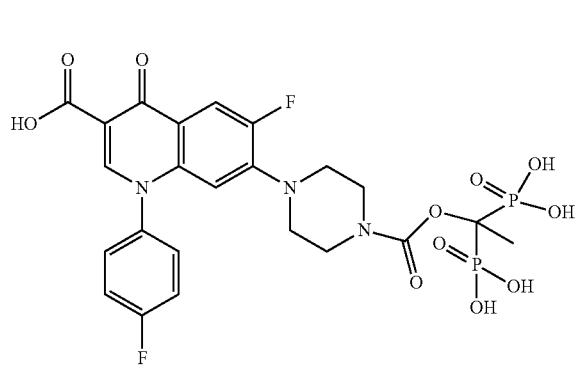
Eti-Sarafloxacin
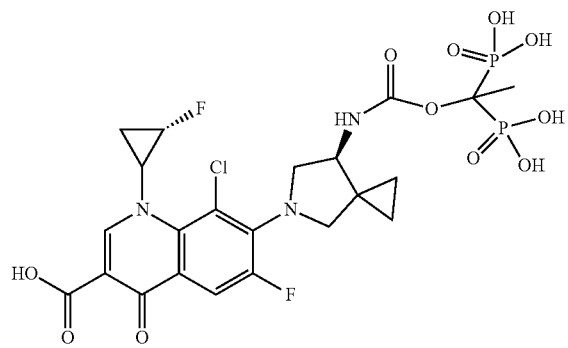
Eti-Sitafloxacin
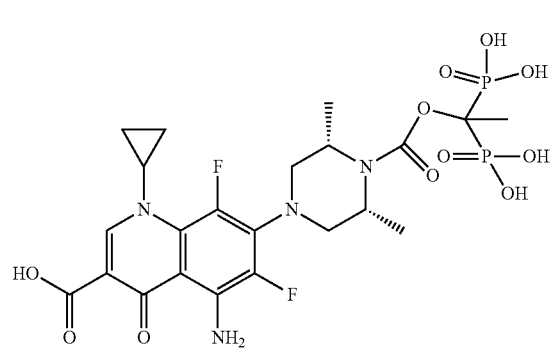
Eti-Sparfloxacin-1
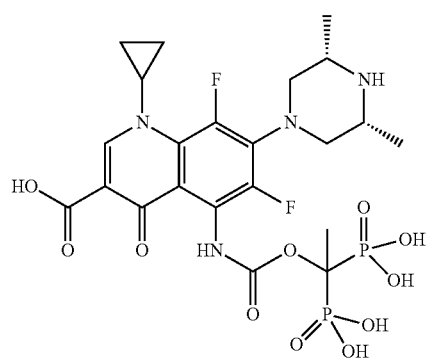
Eti-Sparfloxacin-2
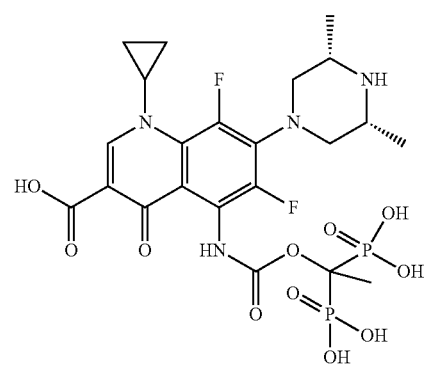
Eti-Sparfloxacin-3
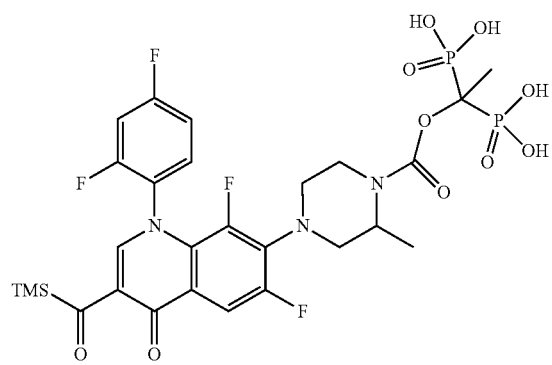
Eti-Temafloxacin
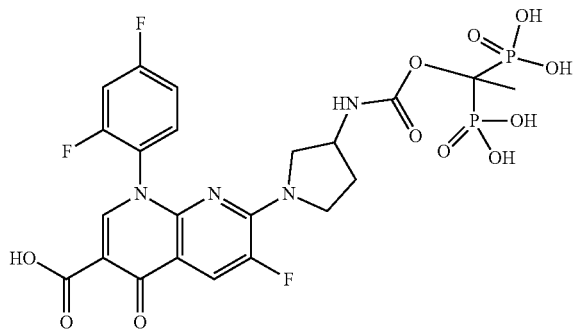
Eti-Tosufloxacin -continued
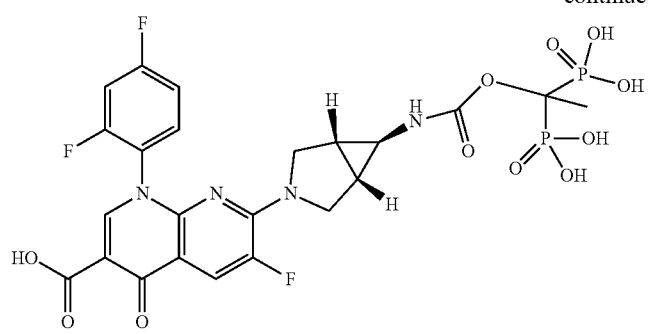
Eti-Trovafloxacin
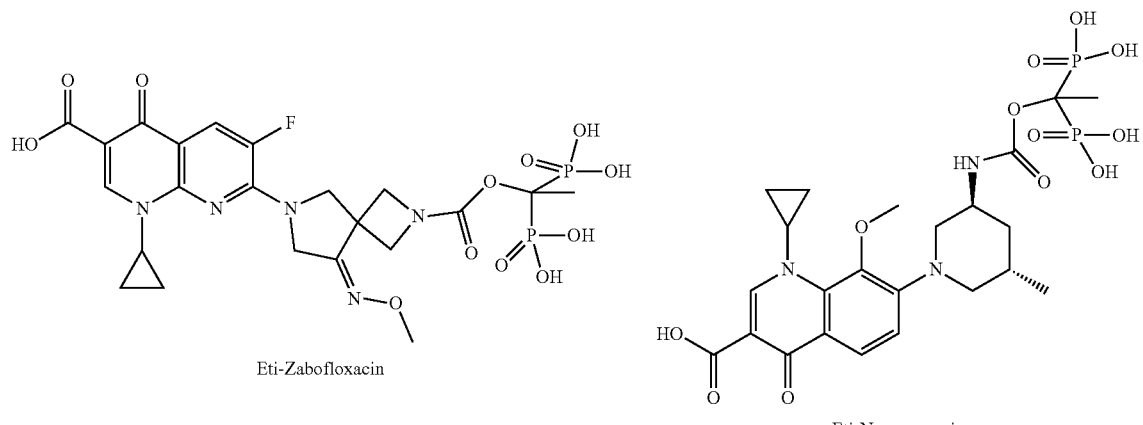
Eti-Zabofloxacin
Eti-Nemonoxacin
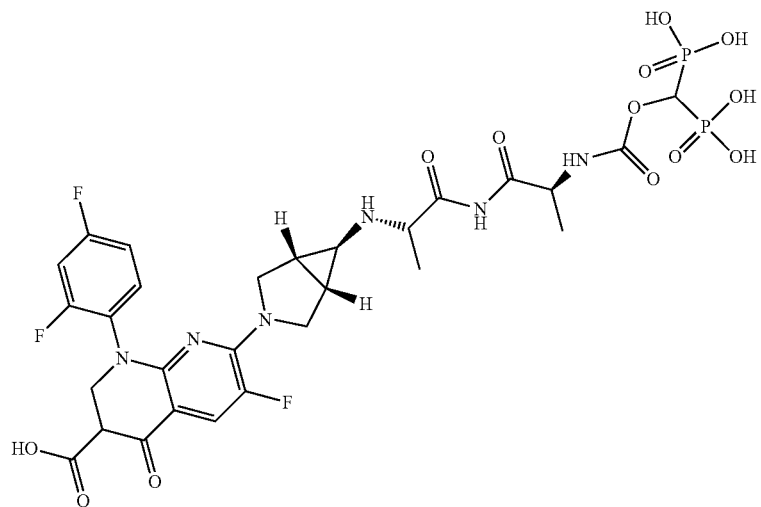
MHDP-Alatrofloxacin-1

-continued
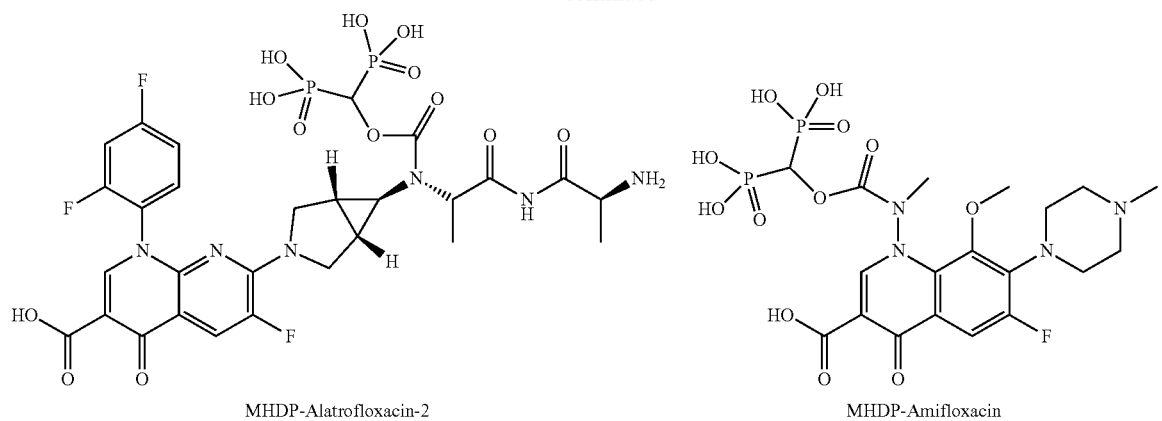
MHDP-Alatrofloxacin-2
MHDP-Amifloxacin
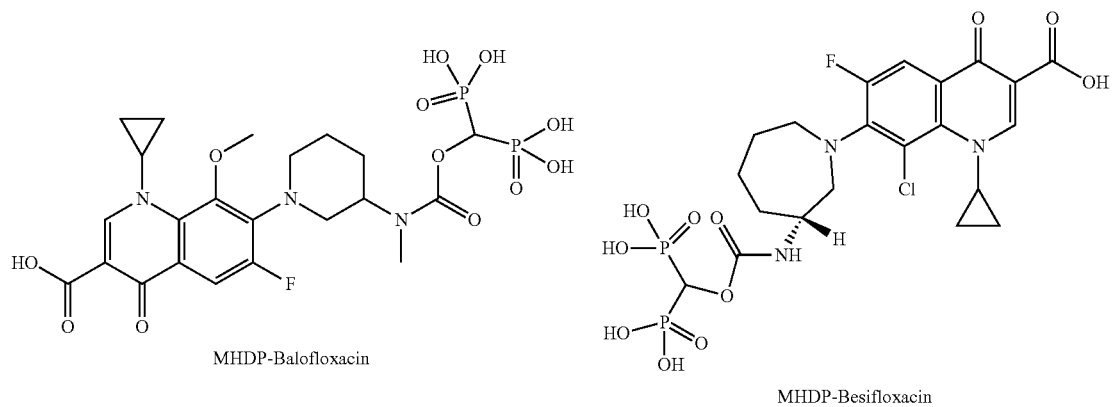
MHDP-Balofloxacin
MHDP-Besifloxacin
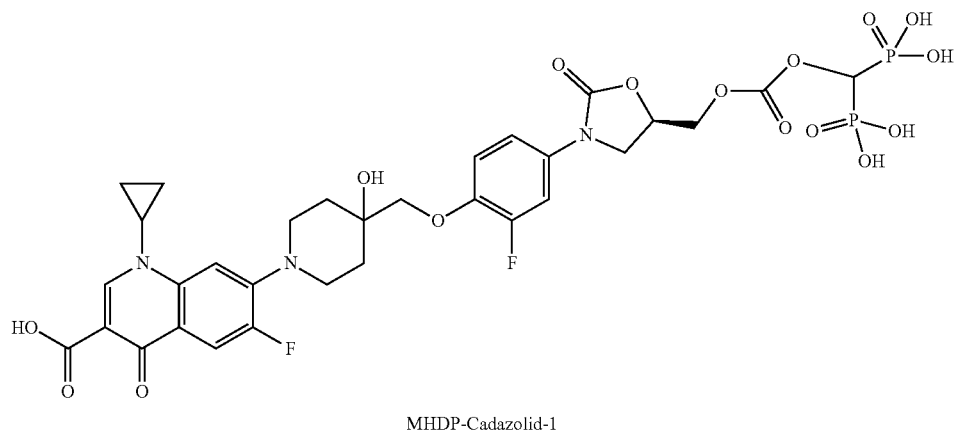
MHDP-Cadazolid-1
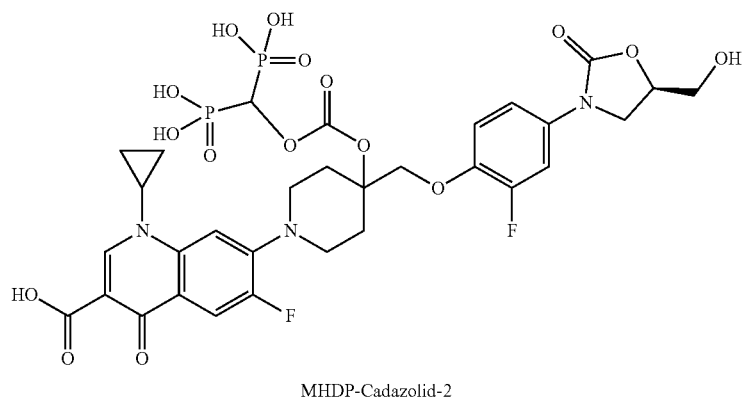
MHDP-Cadazolid-2

-continued
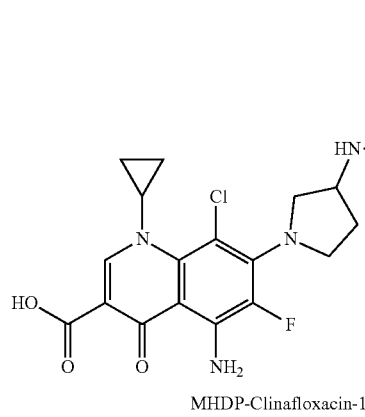
MHDP-Clinafloxacin-1
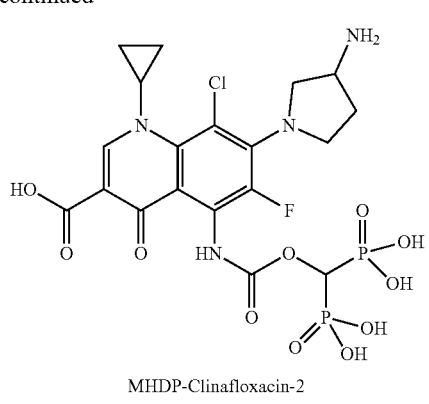
MHDP-Clinafloxacin-2
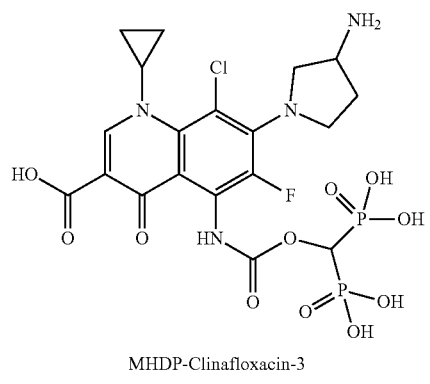
MHDP-Clinafloxacin-3
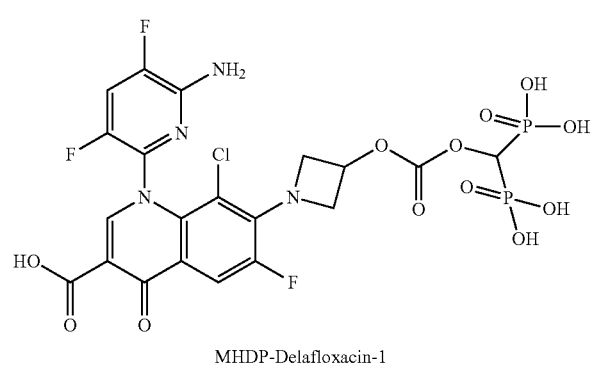
MHDP-Delafloxacin-1
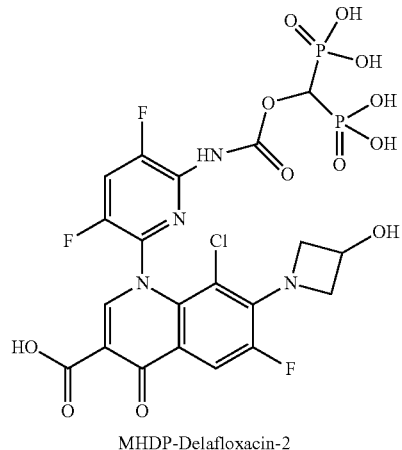
MHDP-Delafloxacin-2
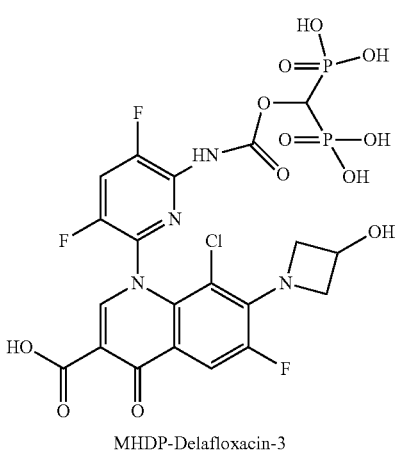
MHDP-Delafloxacin-3
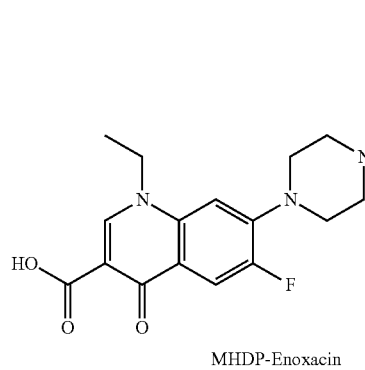
MHDP-Enoxacin
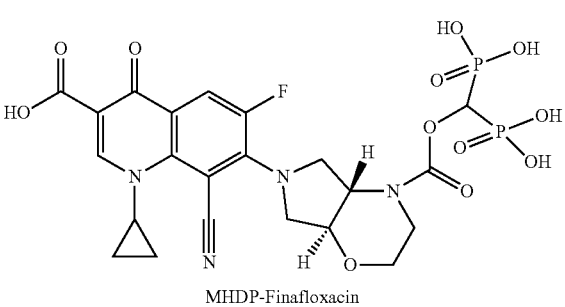
MHDP-Finafloxacin -continued
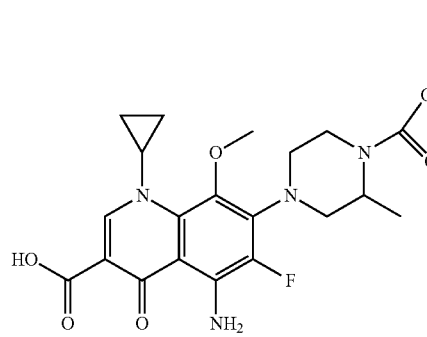
MHDP-Gatifloxacin-1
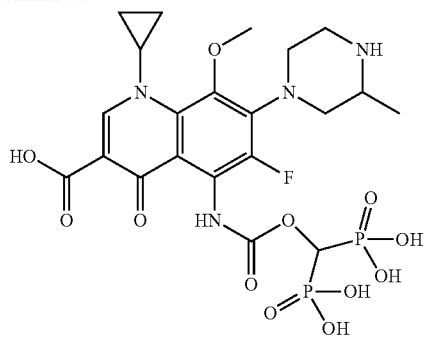
MHDP-Gatifloxacin-2
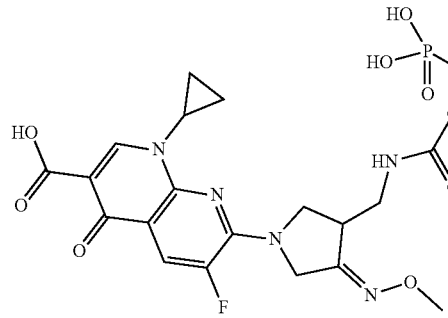
MHDP-Gemifloxacin
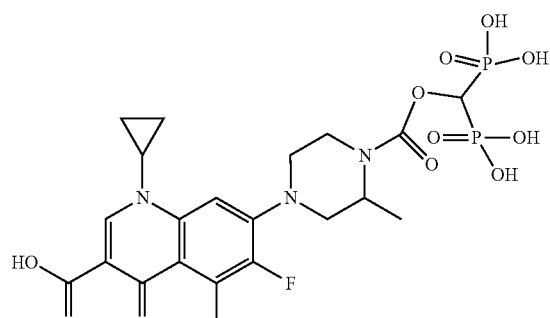
MHDP-Grepafloxacin
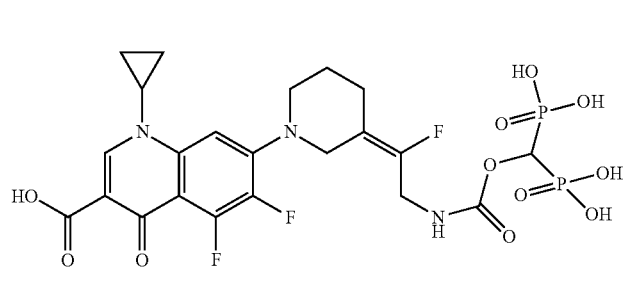
MHDP-JNJ-Q2
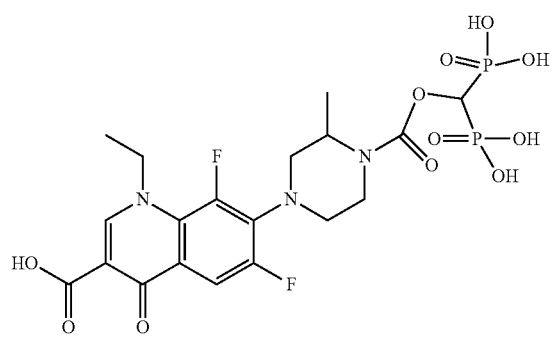
MHDP-Lomefloxacin
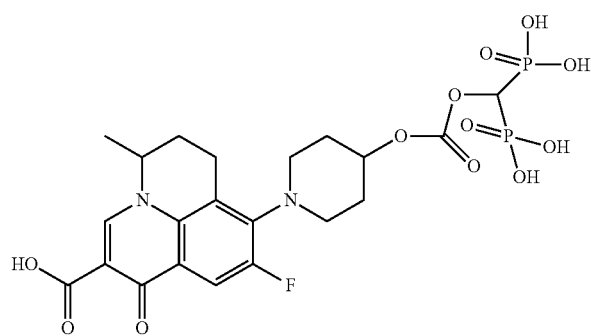
MHDP-Nadifloxacin
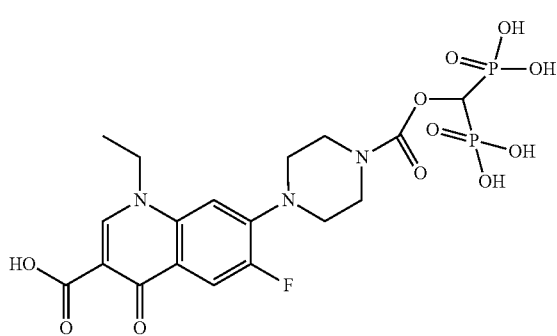
MHDP-Norfloxacin -continued
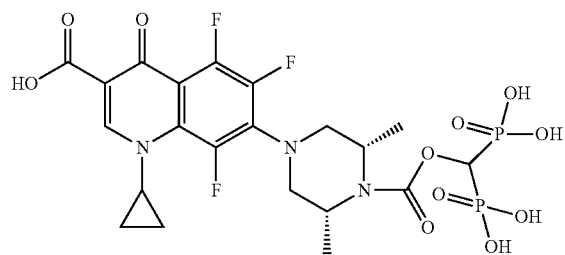
MHDP-Orbifloxacin
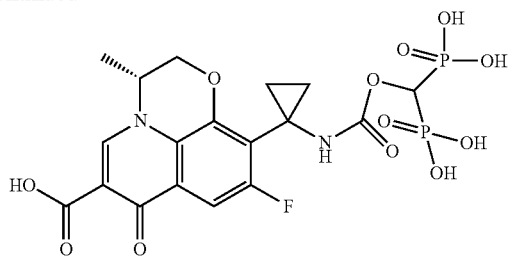
MHDP-Pazufloxacin
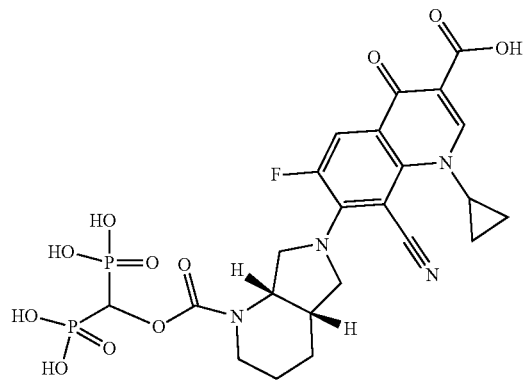
MHDP-Pradofloxacin
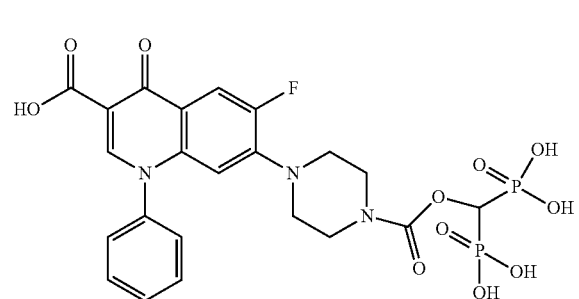
MHDP-Sarafloxacin
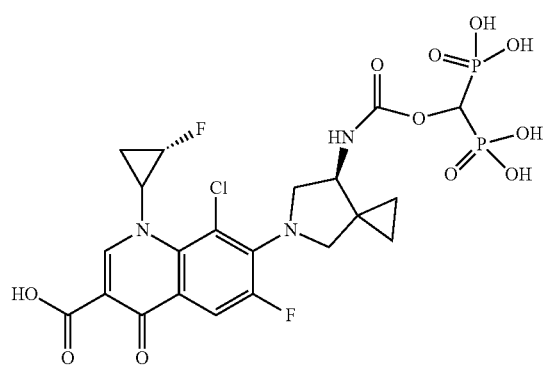
MHDP-Sitafloxacin
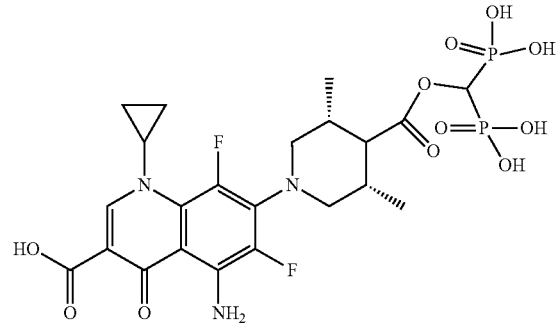
MHDP-Sparfloxacin-1
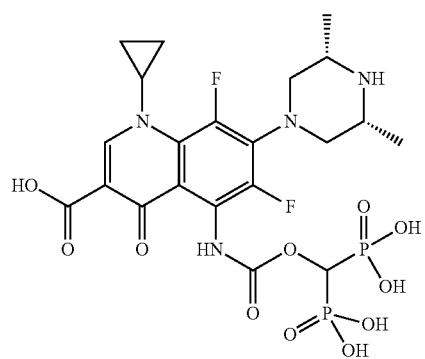
MHDP-Sparfloxacin-2
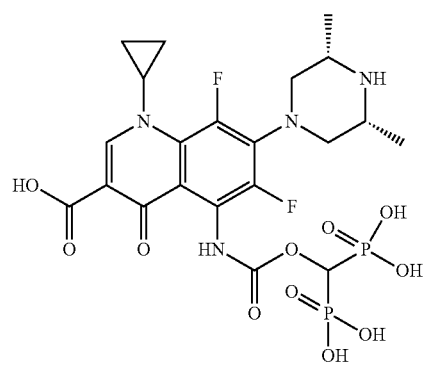
MHDP-Sparfloxacin-3

163 164
-continued
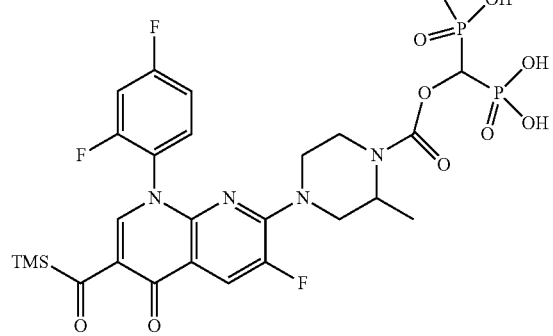
MHDP-Temafloxacin
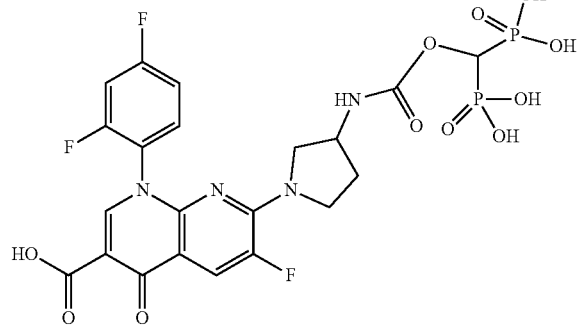
MHDP-Tosufloxacin
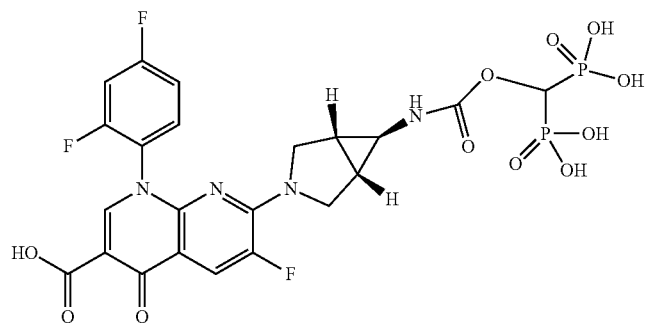
MHDP-Trovafloxacin
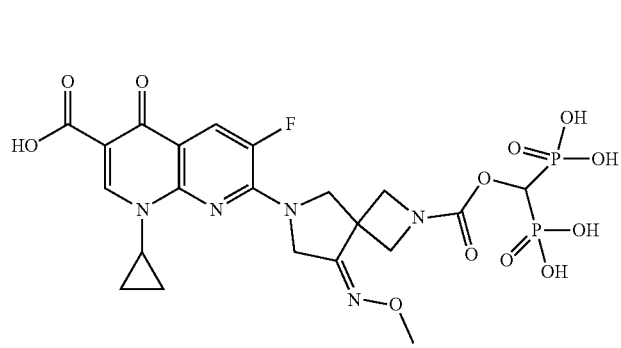
MHDP-Zabofloxacin
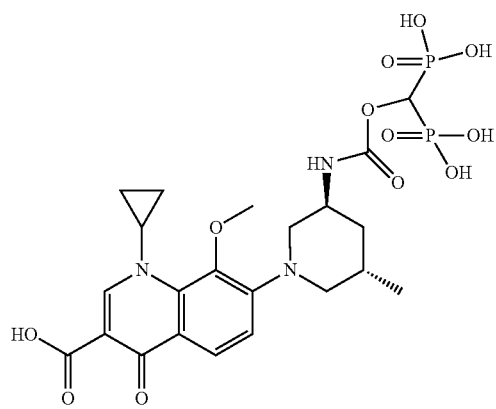
MHDP-Nemonoxacin
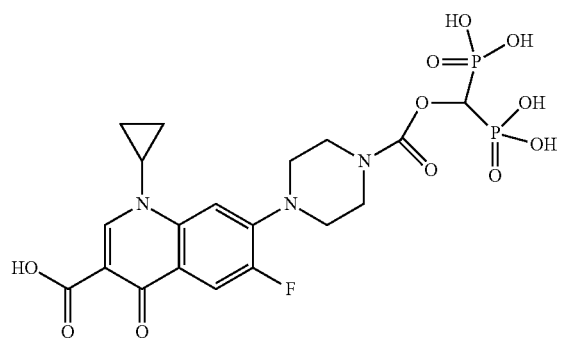
MHDP-Ciprofloxacin
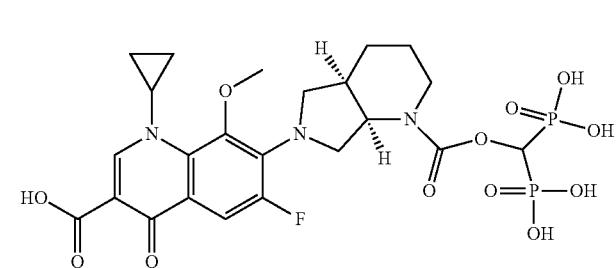
MHDP-Moxifloxacin -continued
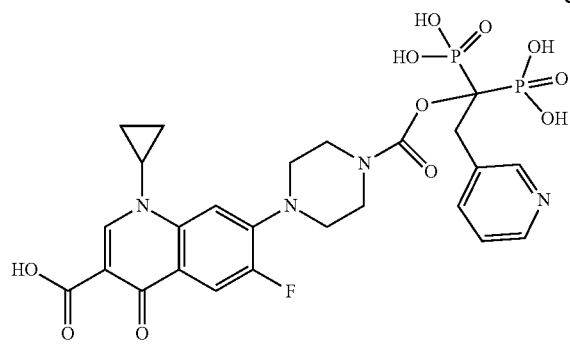
RIS-Ciprofloxacin
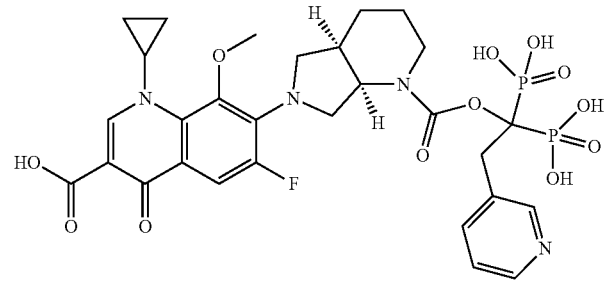
RIS-Moxifloxacin
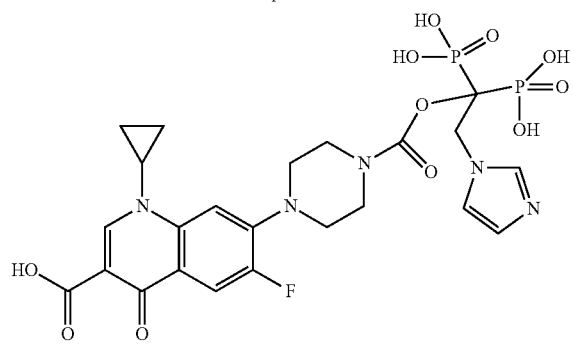
ZOL-Ciprofloxacin
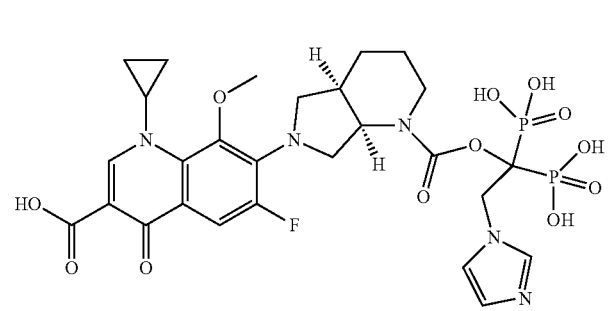
ZOL-Moxifloxacin
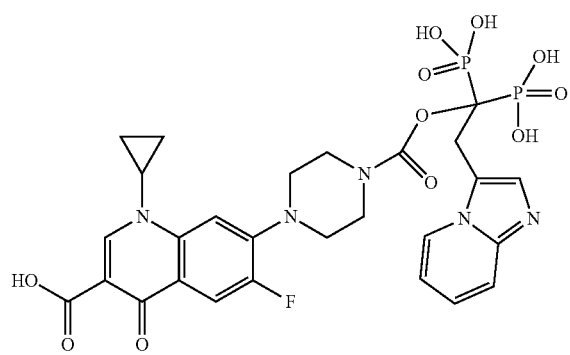
MIN-Ciprofloxacin
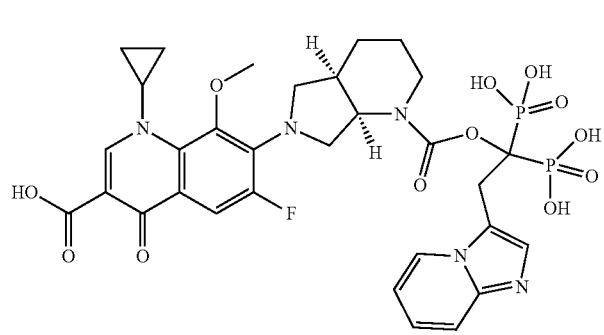
MIN-Moxifloxacin
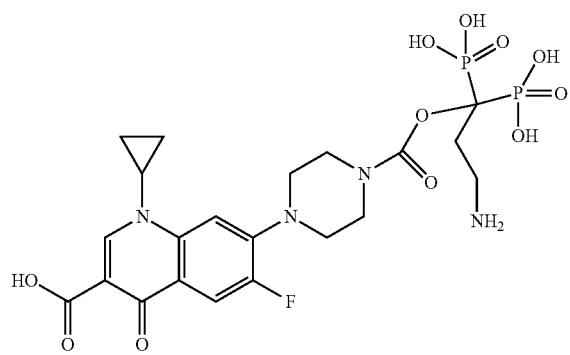
PAM-Ciprofloxacin
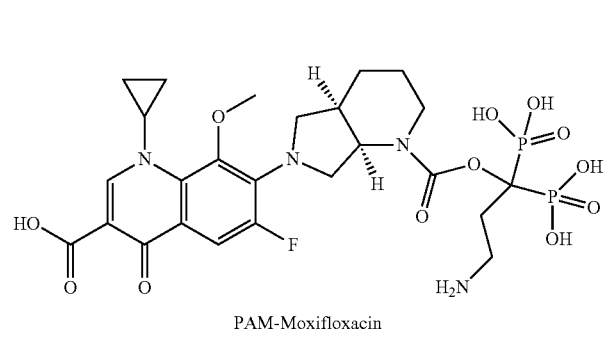
PAM-Moxifloxacin -continued

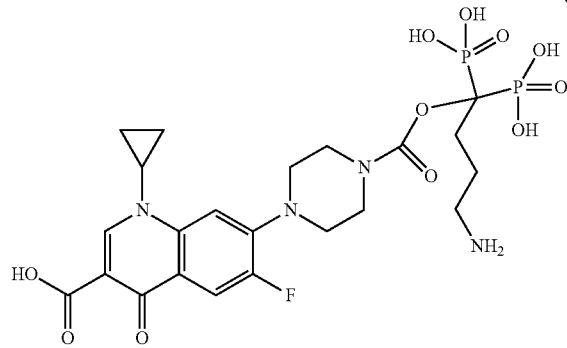
ALN-Ciprofloxacin

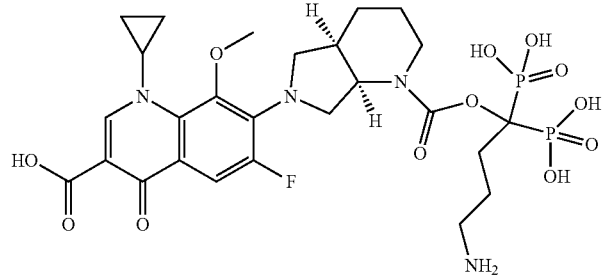
ALN-Moxifloxacin

We claim:
1. A compound comprising:
a bisphosphonate; and
a quinolone compound;
wherein the quinolone compound is releasably coupled to the bisphosphonate via a linker, wherein the linker is a carbamate linker and, wherein the compound is according to Formula (6)

Formula (6)

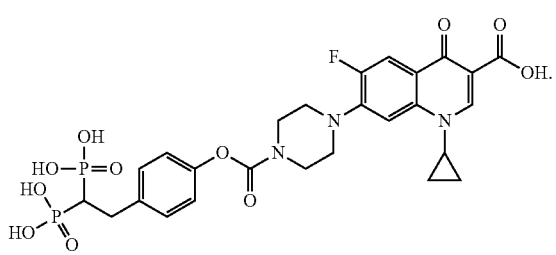

2. A pharmaceutical formulation, comprising an amount of a compound comprising a bisphosphonate, and a quinolone compound, wherein the quinolone compound is releasably coupled to the bisphosphonate via a linker, wherein the linker is a carbamate linker, and wherein the compound is according to Formula (6)

Formula (6)

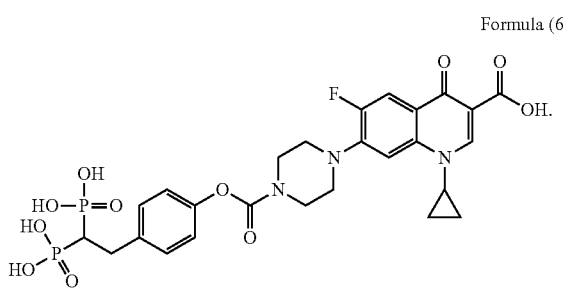

3. A compound comprising:
a bisphosphonate; and
a quinolone compound;
wherein the quinolone compound is releasably coupled to the bisphosphonate via a linker, wherein the linker is a carbamate linker and, wherein the compound has a formula according to Formula (12):

Formula (12)

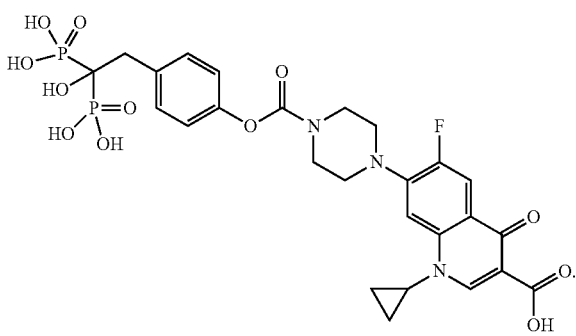

4. A compound comprising:
a bisphosphonate; and
a quinolone compound;
wherein the quinolone compound is releasably coupled to the bisphosphonate via a linker, wherein the linker is a carbamate linker and, wherein the compound has a formula according to Formula (13):

Formula (13)

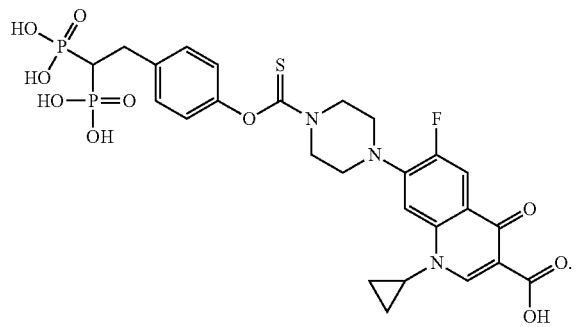

5. A compound comprising:
a bisphosphonate; and
a quinolone compound;
wherein the quinolone compound is releasably coupled to the bisphosphonate via a linker, wherein the linker is a carbamate linker and, wherein the compound has a formula according to Formula (15):

Formula (15)

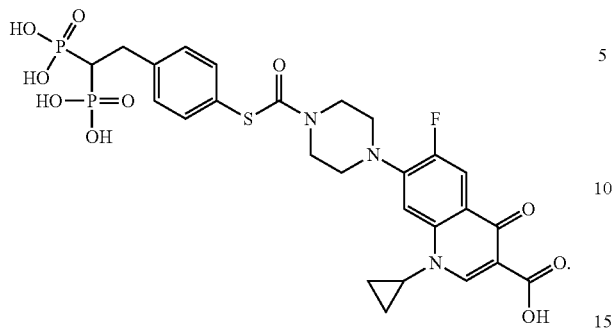

6. A compound comprising:
a bisphosphonate; and
a quinolone compound;
wherein the quinolone compound is releasably coupled to the bisphosphonate via a linker, wherein the linker is a carbamate linker and, wherein the compound has a formula according to Formula (41):

Formula (41)

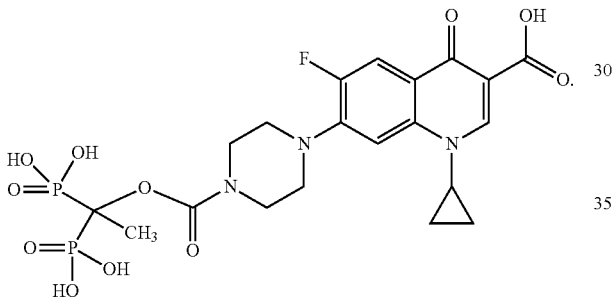

7. A compound comprising:
a bisphosphonate; and
a quinolone compound;
wherein the quinolone compound is releasably coupled to the bisphosphonate via a linker, wherein the linker is a carbamate linker and, wherein the compound has a formula according to Formula (43):

Formula (43)

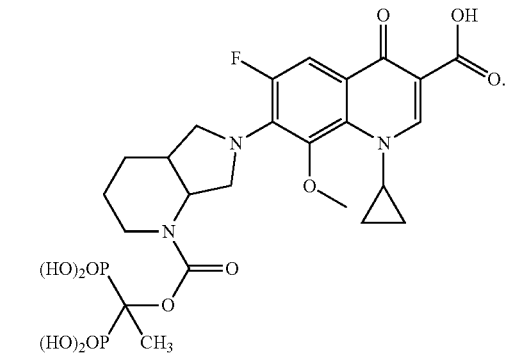

8. A compound comprising:
a bisphosphonate; and
a quinolone compound;
wherein the quinolone compound is releasably coupled to the bisphosphonate via a linker, wherein the linker is a carbamate linker, and
wherein the compound has the formula:

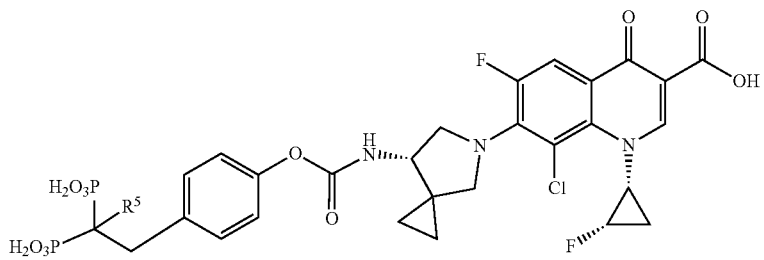

where $R^5$ is H or OH.

9. A compound comprising:
a bisphosphonate; and
a quinolone compound;
wherein the quinolone compound is releasably coupled to the bisphosphonate via a linker, wherein the linker is a carbamate linker, and
wherein the compound has the formula:

where $R^5$ is H or OH.

10. A compound comprising:
a bisphosphonate; and
a quinolone compound;
  wherein the quinolone compound is releasably coupled to the bisphosphonate via a linker, wherein the linker is a carbamate linker, and
wherein the compound has the formula:
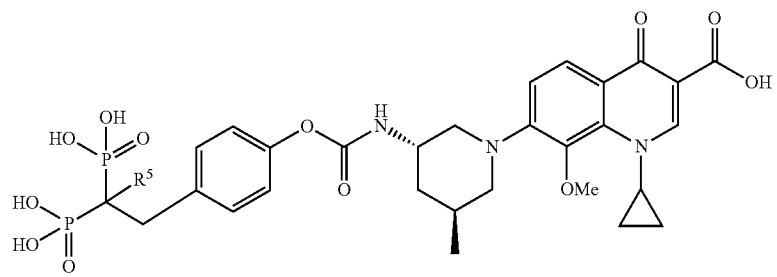
where $R^5$ is H or OH.
* * * * *